US012004514B2

(12) United States Patent
Smith et al.

(10) Patent No.: US 12,004,514 B2
(45) Date of Patent: *Jun. 11, 2024

(54) ENGINEERING THE PRODUCTION OF A CONFORMATIONAL VARIANT OF OCCIDIOFUNGIN THAT HAS ENHANCED INHIBITORY ACTIVITY AGAINST FUNGAL SPECIES

(71) Applicants: Mississippi State University, Starkville, MS (US); The Texas A&M University System, College Station, TX (US)

(72) Inventors: James Leif Smith, College Station, TX (US); Akshaya Ravichandran, College Station, TX (US); Shien Lu, Starkville, MS (US); Ganyu Gu, Painter, VA (US)

(73) Assignees: The Texas A&M University System, College Station, TX (US); Mississippi State University, Starkville, MS (US)

( * ) Notice: Subject to any disclaimer, the term of this patent is extended or adjusted under 35 U.S.C. 154(b) by 604 days.

This patent is subject to a terminal disclaimer.

(21) Appl. No.: 17/113,764

(22) Filed: Dec. 7, 2020

(65) Prior Publication Data

US 2022/0007652 A1    Jan. 13, 2022

Related U.S. Application Data

(63) Continuation of application No. 16/403,123, filed on May 3, 2019, now abandoned, which is a continuation of application No. 15/438,934, filed on Feb. 22, 2017, now abandoned, which is a continuation of application No. 14/090,679, filed on Nov. 26, 2013, now Pat. No. 9,624,270.

(60) Provisional application No. 61/731,105, filed on Nov. 29, 2012.

(51) Int. Cl.
| | |
|---|---|
| *A01N 63/50* | (2020.01) |
| *A01N 43/713* | (2006.01) |
| *A61K 38/12* | (2006.01) |
| *C07K 7/54* | (2006.01) |
| *C07K 7/56* | (2006.01) |
| *C12N 9/16* | (2006.01) |

(52) U.S. Cl.
CPC .......... *A01N 63/50* (2020.01); *A01N 43/713* (2013.01); *A61K 38/12* (2013.01); *C07K 7/54* (2013.01); *C07K 7/56* (2013.01); *C12N 9/16* (2013.01); *C12Y 301/02* (2013.01)

(58) Field of Classification Search
CPC ........ A01N 43/713; A61K 38/12; C07K 7/54; C07K 7/56; C12N 9/16; C12Y 301/02
See application file for complete search history.

(56) References Cited

U.S. PATENT DOCUMENTS

| | | |
|---|---|---|
| 7,560,252 B2 | 7/2009 | Salas et al. |
| 8,785,376 B2 | 7/2014 | Schmidt et al. |
| 9,139,616 B2 | 9/2015 | Schmidt et al. |
| 9,624,270 B2 | 4/2017 | Smith et al. |
| 9,879,048 B2 | 1/2018 | Schmidt et al. |
| 2003/0130121 A1 | 7/2003 | Gerhardson et al. |
| 2004/0209325 A1 | 10/2004 | Yang et al. |
| 2005/0026819 A1 | 2/2005 | Kaniga |
| 2006/0003944 A1 | 1/2006 | Glinka et al. |
| 2006/0229432 A1 | 10/2006 | Danishefsky et al. |
| 2007/0202051 A1 | 8/2007 | Schuschnig |
| 2011/0002983 A1 | 1/2011 | Hipler et al. |
| 2011/0136729 A1 | 6/2011 | Lu et al. |
| 2015/0024998 A1 | 1/2015 | Schmidt et al. |

FOREIGN PATENT DOCUMENTS

| | | |
|---|---|---|
| EP | 2925774 B1 | 1/2018 |
| WO | WO2013096697 A3 | 6/2013 |
| WO | WO2014085419 A1 | 6/2014 |
| WO | WO2016040940 A1 | 3/2016 |

OTHER PUBLICATIONS

Brewster, Marcus E., and Thorsteinn Loftsson. "Cyclodextrins as pharmaceutical solubilizers." Advanced drug delivery reviews 59.7 (2007): 645-666.

Hing, Steven Lai, et al. "Toxicological evaluation of occidiofungin against mice and human cancer cell lines." Pharmacology & Pharmacy 5.11 (2014): 1085-1093.

Lu, S.E. et al., "Isolation and identification and genetic analysis of rhizobacteria antagonistic to plant soilborne fungal pathogens." Phytopathology 95 (2005): 62-63.

Gu, G. et al., "AmbR1 is a key transcriptional regulator for production of antifungal activity of Burkholderia contaminans strain MS14". FEMS Microbiology Letters 297 (2009): 54-60.

Gu, G.Y. et al., "Biosynthesis of an antifungal oligopeptide in Burkholderia contaminans strain MS14." Biochem. Biophys. Res. Commun. 380 (2009): 328-332.

Ghannoum, M. G. et al., "Antifungal Agents: Mode of Action, Mechanisms of Resistance, and Correlation of these Mechanisms with Bacterial Resistance." Clin. Microbiol. Rev. 12.4 (1999): 501-517.

Gu G. et al. "Genetic and Biochemical map for the Biosynthesis of Occidiofungin, an Antifungal Produced by Burkholderia contaminans Strain MS14" Applied Env. Microbiology 77.17 (2011): 6189-6198.

(Continued)

*Primary Examiner* — Paul J Holland
(74) *Attorney, Agent, or Firm* — Mendelsohn Dunleavy, P.C.

(57) ABSTRACT

Occidiofungin is a cyclic nonribosomally synthesized antifungal peptide with submicromolar activity. This invention is directed to compositions enriched for particular occidiofungin diastereomers/conformers, methods of making compositions enriched for particular diastereomers/conformers and microorganisms suitable for producing enriched compositions of particular diastereomers/conformers. Methods of treating fungal infections or plants infected by fungi are also provided.

8 Claims, 15 Drawing Sheets

Figure 1:
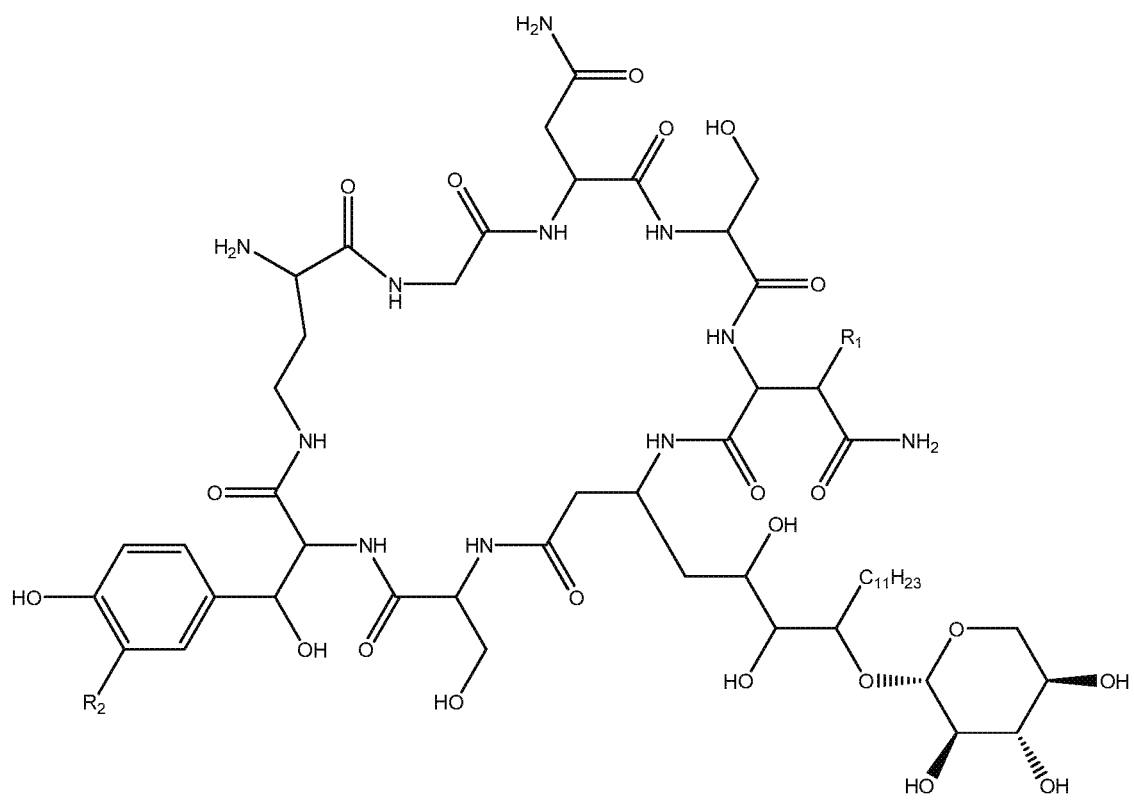

Specification includes a Sequence Listing.

(56) References Cited

OTHER PUBLICATIONS

Baysal, C. et al. "Free Energy Based Populations of Interconverting Microstates of a Cyclic Peptide Lead to the Experimental NMR Data," Biopolymers, Feb. 1999, pp. 329-344, vol. 50.

Boddy, C. N. "Sweetening Cyclic Peptide Libraries," Chemistry & Biology, Dec. 2004, pp. 1599-1606, vol. 11, No. 15.

Boguslavsky, V. et al. "Effect of peptide conformation on membrane permeability," J. Peptide Res., 2003, pp. 287-297, vol. 61.

Delagio, F. et al. "NMRPipe: A multidimensional spectral processing system based on UNIX pipes," Journal of Biomolecular NMR, 1995, pp. 277-293, vol. 6.

Ellis, D. et a/. "Occidiofungin's Chemical Stability and In Vitro Potency against Candida Species," Antimicrobial Agents and Chemotherapy, Nov. 2011, pp. 765-769, vol. 56, No. 2.

Fernandez-Lopez, S. et al. "Antibacterial agents based on the cyclic D,L-a-peptide architecture," Nature, Jul. 26, 2001, pp. 452-455, vol. 412.

Fischbach, M. A. et al. "Assembly-Line Enzymology for Polyketide and Nonribosomal Peptide Antibiotics: Logic, Machinery, and Mechanisms," Chem. Rev., Jul. 7, 2006, pp. 3468-3496, vol. 106, No. 8.

Fridkin, G. et al. "Azo cyclization: peptide cyclization via azo bridge formation," The Journal of Peptide Research, 2002, pp. 104-111, vol. 60.

Heikkinen, S. et al. "Quantitative 20 HSQC (Q-HSQC) via Suppression of J-Dependence of Polarization Transfer in NMR Spectroscopy: Application to Wood Lignin," J. Am. Chem. Soc., 2003, pp. 4362-4367, vol. 125, No. 14.

Jelokhani-Niaraki, M. et al. "Conformation and other biophysical properties of cyclic antimicrobial peptides in aqueous solutions," J. Peptide Res., 2001, pp. 293-306, vol. 58.

Jelokhani-Niaraki, M. et a/. "Interaction of Gramicidin S and its Aromatic Amino-Acid Analog with Phospholipid Membranes," Biophysical Journal, Oct. 2008, pp. 3306-3321, vol. 95, No. 7.

Johnson, B. A. et a/. "NMR View: A computer program for the visualization and analysis of NMR data," Journal of Biomolecular NMR, 1994, pp. 603-614, vol. 4.

Koglin, A. et al. "Conformational Switches Modulate Protein Interactions in Peptide Antibiotic Synthetases," Science, Apr. 14, 2006, pp. 273-276, vol. 312, No. 5571.

Koglin, A. et al. "Structural basis for the selectivity of the external thioesterase of the surfactin synthetase," Nature, Aug. 14, 2008, pp. 907-912, vol. 454.

Kohli, R. M. et a/. "The thioesterase domain from a nonribosomal peptide synthetase as a cyclization catalyst for integrin binding peptides," PNAS, Feb. 5, 2002, pp. 1247-1252, 18 vol. 99, No. 3.

Kohli, R. M. et a/. "Biomimetic synthesis and optimization of cyclic peptide antibiotics," Nature, Aug. 8, 2002, pp. 658-661, vol. 418.

Lautru, S. et al. "Substrate recognition by nonribosomal peptide synthetase multi-enzymes," Microbiology, 2004, pp. 1629-1636, vol. 150.

Lin, Z. et al. "Burkholdines from Burkholderia ambifaria: Antifungal Agents and Possible Virulence Factors," Journal of Natural Products, Sep. 18, 2012, pp. 1518-1523, vol. 75, No. 9.

Liao, G. et al. "Regulation Mechanisms Underlying the Biosynthesis of Daptomycin and Related Lipopeptides," Journal of Cellular Biochemistry, 2012, pp. 735-741, vol. 113.

Lu, S. et al "Occidiofungin, a Unique Antifungal Glycopeptide Produced by a Strain of Burkholderia contaminans," Biochemistry, 2009, pp. 8312-8321, vol. 48, No. 35.

Lu, S. et al. "Characterization of the salA, syrF, and syrG Regulatory Genes Located at the Right Border of the Syringomycin Gene Cluster of Pseudomonas syringae pv. syringae," MPMI, 2002, pp. 43-53, vol. 15, No. 1.

NCBI, GenBank accession No. ADT64850.1, "putatitve thioesterase [Burkholderia contaminans]," Dec. 13, 2010.

NCBI, GenBank accession No. ACL81527.1, "putative nonribosomal peptide synthetase [Burkholderia contaminans]," Dec. 13, 2010.

Prentki, P. et al. "The Plasmid cloning vector pBR325 contains a 482 base-pair-long inverted duplication," Gene, 1981, pp. 289-299, vol. 14.

Rai, R. K. et al. "Quantification of Metabolites from Two-Dimensional Nuclear Magnetic Resonance Spectroscopy: Application to Human Urine Samples," Analytical Chemistry, Dec. 15, 2009, pp. 10232-10238, vol. 81, No. 24.

Rayan, A. et al. "Exploring the conformational space of cyclic peptides by a stochastic search method," Journal of Molecular Graphics and Modeling, 2004, pp. 319-333, vol. 22.

Ravichandran, A. et al. "The Presence of Two Cyclase Thioesterases Expands the Conformational Freedom of the Cyclic Peptide Occidiofungin," Journal of Natural Products, Feb. 8, 2013, pp. 150-156, vol. 76. No. 2.

Samel, S. A. et al. "The Thioesterase Domain of the Fengycin Biosynthesis Cluster: A Structural Base for the Macrocyclization of a Non-ribosomal Lipopeptide," J. Mol. Biol., 2006, pp. 876-899, vol. 359.

Schwarzer, D. et al. "Exploring the impact of different thioesterase domains for the design of hybrid peptide synthetases," Chemistry & Biology, 2001, pp. 997-1010, vol. 8, No. 10.

Sieber, S. A. et al. "Learning from Nature's Drug Factories: Nonribosomal Synthesis of Macrocyclic Peptides," Journal of Bacteriology, Dec. 2003, pp. 7036-7043, vol. 185, No. 24.

Tan, W. et a/. "Nonclinical Toxicological Evaluation of Occidiofungin, a Unique Glycolipopeptide Antifungal," International Journal of Toxicology, Jun. 11, 2012, pp. 326-336, vol. 31, No. 4.

Thomson, E. L. S. et al. "A Burhholderia cepacia complex non-ribosomal peptide-synthesized toxin is hemolytic and required for full virulence," Virulence, May/Jun. 2012, pp. 286-298, vol. 3, No. 3.

Tseng, C. C. et al. "Characterization of the Surfactin Synthetase C-Terminal Thioesterase Domain as a Cyclic Depsipeptide Synthase," Biochemistry, 2002, pp. 13350-13359, vol. 41, No. 45.

Walsh, C. T. "Polyketide and Nonribosomal Peptide Antibiotics: Modularity and Versatility," Science, Mar. 19, 2004, pp. 1805-1810, vol. 303, No. 5665.

White, C. J. et al. "Contemporary strategies for peptide macrocyclization," Nature Chemistry, Jul. 23, 2011, pp. 509-524, vol. 3.

Yeh, E. et a/. "Type II Thioesterase Restores Activity of a NRPS Module Stalled with an Aminoacyl-S-enzyme that Cannot Be Elongated," ChemBioChem, 2004, pp. 1290-1293, vol. 5.

Bonmatin, J.-M. et al. "Diversity Among Microbial Cyclic Lipopeptides: Iturins and Surfactins. Activity-Structure Relationships to Design New Bioactive Agents" Combinatorial Chemistry & High Throughput Screening, 2003, pp. 541-556, vol. 6, No. 6.

Alexeyev, M. F. et al. "Three Kanamycin Resistance Gene Cassettes with Different Polylinkers" Biotechniques, 1995, pp. 52 and 54, vol. 18, No. 1.

Vilhena, C. et al. "Daptomycin: A Review of Properties, Clinical Use, Drug Delivery and Resistance" Mini-Reviews in Medicinal Chemistry, 2012, pp. 202-209, vol. 12.

Thomson, E.L. et al. "A Burkholderia cepacia complex non-ribosomal peptide-synthesized toxin in hemolytic and required for full virulence", Virulence, May 2012, vol. 3, pp. 286-298.

Communication pursuant to Article 94(3) EPC for European Application No. 15840420.2; dated May 16, 2019.

Occidiofungin: R1 (-H or -OH); R2 (-H or -Cl)

Occidiofungin: (R1,-H or -OH); (R2,-H or -Cl)

Occidiofungin: (R1,-H or -OH); (R2,-H or -Cl)

Occidiofungin: (R1,-H or -OH); (R2,-H or -Cl)

ENGINEERING THE PRODUCTION OF A CONFORMATIONAL VARIANT OF OCCIDIOFUNGIN THAT HAS ENHANCED INHIBITORY ACTIVITY AGAINST FUNGAL SPECIES

CROSS-REFERENCE TO RELATED APPLICATION

This application is a continuation of U.S. patent application Ser. No. 16/403,123, filed on May 3, 2019, now abandoned, which, in turn, is a continuation of U.S. patent application Ser. No. 15/438,934, filed on Feb. 22, 2017, now abandoned, which, in turn, is a continuation of U.S. patent application Ser. No. 14/090,679, filed on Nov. 26, 2013 (now issued as U.S. Pat. No. 9,624,270), which claims the benefit of U.S. Provisional Application No. 61/731,105 filed Nov. 29, 2012, the disclosures of which are hereby incorporated by reference in their entirety, including all figures, tables, and amino acid or nucleic acid sequences.

GOVERNMENT SUPPORT STATEMENT

This invention was made with government support under 0204332 awarded by the National Institute of Food and Agriculture, USDA. The government has certain rights in the invention.

BACKGROUND OF THE INVENTION

Nonribosomal peptide synthetases (NRPSs) produce a wide array of small and structurally complex peptides that have therapeutic potential. The system enables the incorporation of nonproteinogenic amino acids into the polypeptide. Polyketide synthetases (PKSs) are a family of enzymes or enzyme complexes that produce polyketides. Integration of PKSs into the NRPSs system further increases the variety of polypeptides that can be produced by these systems. Recent studies are aimed at exploiting NRPSs for producing peptide libraries that can be screened for therapeutic applications.[1-9]

Unlike linear peptides, cyclic peptides are restrained to fewer conformations that facilitate their interaction with their molecular target.[10-18] These structural constraints provide resistance to proteases, extreme pH, and temperature.[10, 19] These attributes make them one of the most promising scaffolds for pharmacophores. Synthetic design of cyclic peptides is hindered by regioselectivity.

Classical total synthesis of peptides by solid phase or solution phase peptide synthesis followed by subsequent cyclization reactions requires the addition and removal of protecting groups at the right stages to drive the cyclization among the correct residues.[8] Even with these considerations, proper cyclization is hindered by intermolecular interactions and entropically disfavoured pre-cyclization conformations resulting in a vast mixture of compounds or low yields. Microorganisms ensure the formation of a functional cyclic peptide conformation by enzymatically catalyzing the cyclization and release of the peptide with regioselectivity using a cyclase thioesterase.[1, 7] The cyclase thioesterase is often located at the C-terminal end of the last NRPS involved in the synthesis of the peptide and is referred to as the TE (Thioesterase) domain.

The TE domain can hydrolyze the bound peptide as a linear peptide or it can catalyze an intramolecular reaction resulting in the formation of a cyclic peptide. At present, very little is known about the cyclization mechanism of peptides. The crystal structure of the surfactin peptide cyclase provided the first basic understanding of its mechanism of action.[20, 21] The peptidyl chain bound to 4-phosphopantetheine cofactor (ppan) that is attached to the thiolation (T)-domain is transferred to a serine in the adjacent TE domain. Ser80 is part of a catalytic triad of residues (His 207 and Asp107) in the surfactin cyclase. His207 and Asp107 activate the Ser80, facilitating the transfer of the peptidyl chain to the TE domain. Once the peptide is transferred to the TE domain, the cyclase binding pocket enables proper orientation and cyclization of the peptide substrate. The enzyme was found to share structural homology to α,β-hydrolase family. The lack of water in the binding cleft of the cyclase, which prevents hydrolysis, is the significant alteration from the hydrolase family that gives the cyclase thioesterase its ability to form cyclic peptides.

Occidiofungin is a broad spectrum nonribosomally synthesized cyclic antifungal peptide that has submicro/nanomolar activity and low toxicity.[19, 22-26] An interesting feature in occidiofungin's biosynthetic pathway is the presence of two putative thioesterases. One is present as an independently expressed thioesterase, OcfN, and the other is a C-terminal TE domain of OcfD. There remains a need for the production of anti-fungal agents that have increased cidal activity against various fungi.

BRIEF SUMMARY OF THE INVENTION

This invention relates to antifungal compounds and their therapeutic use in the prevention or treatment of fungal infections and diseases. Particularly, various aspects of the invention provide compositions enriched for occidiofungin diastereomers/conformers that have higher activity against fungal infections or diseases (in mammals or plants).

Other aspects of the invention provide for compositions enriched for particular diastereomers/conformers produced by genetic modification of occidiofungin producing microorganisms such that the production of a particular occidiofungin diastereoomer/conformer is favored. Thus, the invention relates to methods of making such occidiofungin diastereomers/conformers, compositions enriched for such diastereomers/conformers and methods of using compositions comprising occidiofungin diastereomers/conformers disclosed herein as fungicides for animals and plants. The invention further relates to the microorganisms that produce compositions enriched for occidiofungin enriched for occidiofungin diastereomers/conformers corresponding to diastereomers/conformers having the TOCSY fingerprint identified in FIG. 5C (the grey NH correlations). Methods of increasing the production of occidiofungin diastereomers/ conformers corresponding to diastereomers/conformers having the TOCSY fingerprint identified in FIG. 5C (the grey NH correlations) in microorganisms and productions systems are also provided.

Figure 5A:
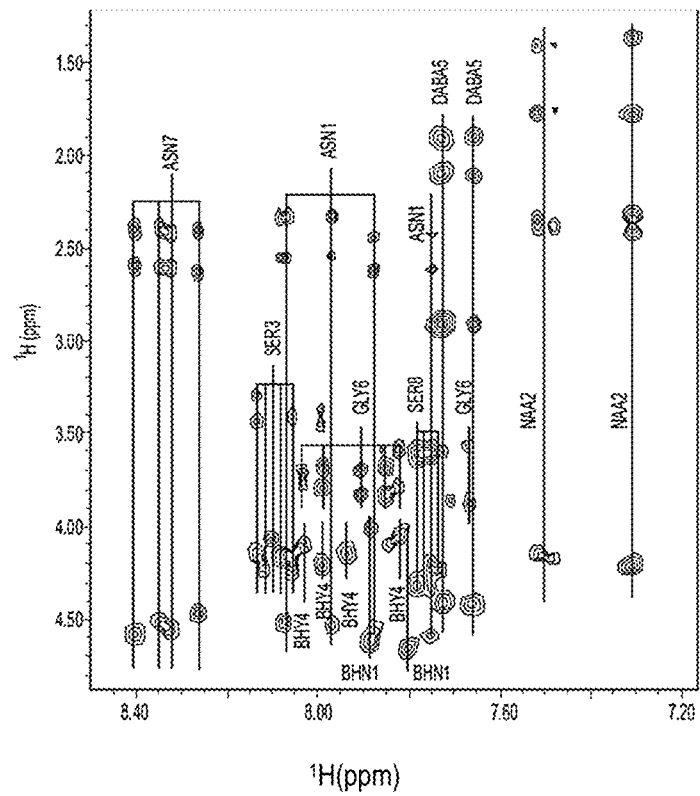
Figure 5B:
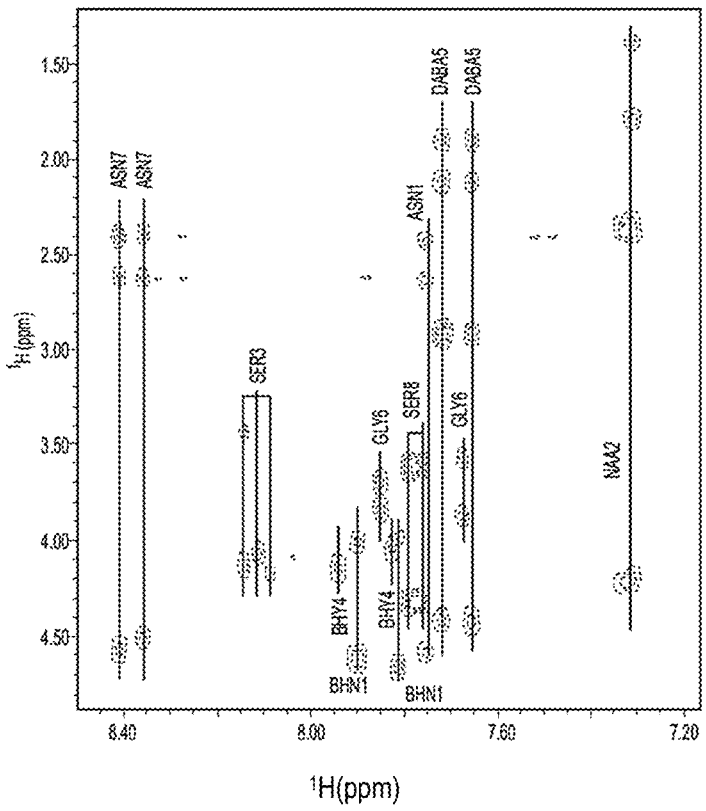
Figure 5C:
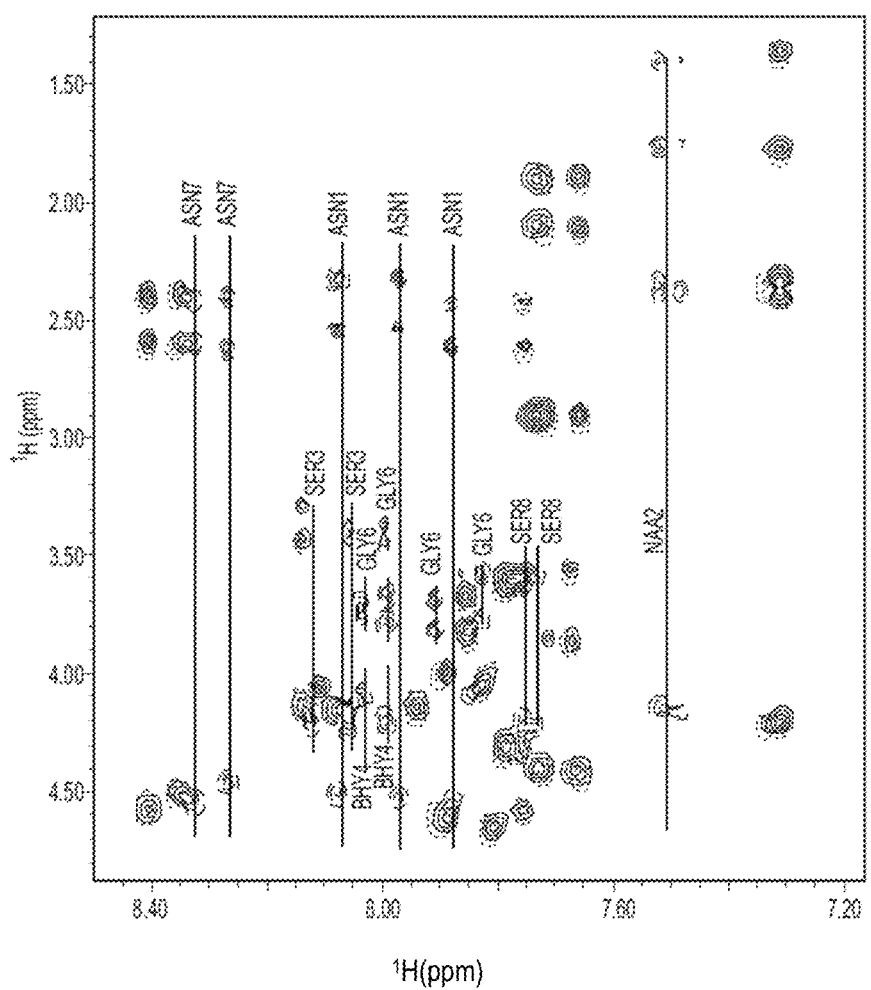

As discussed above, one aspect of the invention provides compositions enriched for occidiofungin diastereomers/conformers, in particular the occidiofungin diastereomers/conformers corresponding to the diastereomers/conformers having the TOCSY fingerprint identified in FIG. 5C (the grey NH correlations). Thus, the invention provides compositions enriched for such antifungal diastereomers/conformers for treating fungal infection. In certain embodiments of this aspect of the invention, pharmaceutical and agricultural compositions that contain a composition enriched for diastereomers/conformers having the TOCSY fingerprint identified in FIG. 5C (the grey NH correlations) are provided. Compositions enriched for a particular occidiofungin diastereomer/conformer can also be produced by the genetically modified microorganisms discussed below (e.g., microorganisms in which the function of ocfD and/or ocfN has been altered in order to favor the production of a particular diastereomer/conformer).

Novel antifungals are needed because of the importance of fungal infections in immunocompromised patients, and the limitations of currently-available antifungal agents regarding their spectra of activity and toxicities. In addition, new antifungals are crucial for food preservation and production of a sufficient and affordable food supply. In this context, this application relates to the disclosure of a composition enriched for occidiofungin diastereomers/conformers having increased antifungal activity as compared to occidiofungin compositions produced by *Burkholderia contaminans* MS14 (disclosed in U.S. Patent Application Publication 2011/0136729, the disclosure of which is hereby incorporated by reference in its entirety). Diastereomers/conformers have been characterized by a number of techniques, including COSY, TOCSY, NOESY, ROESY, and HSQC 2D NMR spectroscopy experiments.

The antifungal activity of the disclosed occidiofungin diastereomers/conformers (diastereomers/conformers having the TOCSY fingerprint identified in FIG. 5C (the grey NH correlations)) provides for compositions having greater antifungal activity as compared to as compared to occidiofungin compositions produced by *Burkholderia contaminans* MS14 when cultured under the same conditions.

The phrase "enriched for the disclosed occidiofungin diastereomers/conformers" is intended to convey that the a composition contains the disclosed occidiofungin diastereomers/conformers (diastereomers/conformers having the TOCSY fingerprint identified in FIG. 5C (the grey NH correlations)) in an amount higher/greater than that produced by *Burkholderia contaminans* MS14 as disclosed in the examples provided herein (in which approximately 36% of total amount of occidiofungin corresponds to occidiofungin diastereomers/conformers having the TOCSY fingerprint identified in FIG. 5C (the grey NH correlations). Thus, the phrase indicates that at least 37% of the total amount of occidiofungin diastereomers/conformers present within an enriched composition are the disclosed diastereomers/conformers having the TOCSY fingerprint identified in FIG. 5C (the grey NH correlations)). In various embodiments, compositions "enriched for the disclosed occidiofungin diastereomers/conformers" contain at least 40%, 41%, 42%, 43%, 44%, 45%, 46%, 47%, 48%, 49%, 50%, 51, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the disclosed diastereomers/conformers in relation to the total amount of occidiofungin diastereomers/conformers in the composition.

The phrase "enriched for a particular occidiofungin diastereomers/conformer" is intended to convey that a composition contains the an occidiofungin diastereomer/conformer that is produced by a microorganism in which the activity of the ocfD and/or ocfN thioesterase has been altered such that the production of a particular conformer is favored.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1. Covalent structure of occidiofungin. R1 and R2 represent the locations where a hydroxyl or chlorine is added, respectively (R1, —H or —OH; R2, —H or —Cl).

FIGS. 2A-2C. RP-HPLC Chromatograms. FIG. 2A. Chromatogram of the final purification step of the wild-type occidiofungin fraction at 220 nm using a 4.6×250 mm C18 column. FIG. 2B. Chromatogram of the final purification step of ocfN mutant occidiofungin fraction at 220 nm using a 4.6×250 mm C18 column. FIG. 2C. Overlay of the wild-type (black) and the mutant (grey) fractions of occidiofungin.

FIGS. 3A-3B. TOCSY (left panel, FIG. 3A) and HSQC (right panel, FIG. 3B) spectra of BHY4 in the wild-type sample. The proportions of Asn1 and BHN1 variants were determined by the measurement of the $^{13}$C-HSQC Ha-Ca cross peak intensities of BHY4 in the HSQC spectra. These values are listed next to their corresponding peaks in the right panel. The peaks in red and green represent the BHY4 peaks associated with BHN1 and Asn1 variants, respectively. Based on the calculation of their relative proportions, i.e. (34.81+87.97 for the BHY4 peaks found in the BHN1 conformational variants) and (32.79+37.61 for the BHY4 peaks found in the Asn1 conformational variants), the approximate proportion of the Asn1 variants could be calculated as (32.79+37.61)/(34.81+87.97)+(32.79+37.61).

FIGS. 4A-4B. ESI mass spectrometry. FIG. 4A. ESI mass spectrometry data of purified wild-type occidiofungin fraction. FIG. 4B. ESI mass spectrometry data of purified ocfN mutant occidiofungin fraction.

FIGS. 5A-5C. TOCSY fingerprint region (NH correlations). FIG. 5A. NH correlations in the wild-type sample. The two BHN1 and four Asn1 spin systems present in the wild-type sample are shown. FIG. 5B. NH correlations in the ocfN mutant sample. FIG. 5C. Overlay of the NH correlations found in the wild-type and ocfN mutant samples. NH correlations that are not present in the ocfN mutant sample are shown grey.

FIG. 6. Schematic of occidiofungin ring closure. The completely synthesized eight amino acid linear peptide is bound by a 4-phosphopantetheine cofactor (ppan) linker to the thiolation (T) domain. The peptide varies by the presence or absence of a hydroxyl group on the beta carbon of Asn1. The TE domain of OcfD is capable of forming the cyclic peptide of both variants in the absence of a functional OcfN cyclase thioesterase. However, it is not as efficient at producing the Asn1 cyclic peptide variant as OcfN. In the presence of a functional OcfN cyclase thioesterase, a novel diastereomers of occidiofungin is formed by the selective ring closure of the Asn1 cyclic peptide. R1 and R2 are BHN1 and Asn1, respectively.

FIGS. 7A-7B. Comparison of the bioactivity from the wild-type and ocfN mutant occidiofungin fractions. FIG. 7A. MICs of wild-type and ocfN mutant fraction determined by CLSI M27-A3 method in RPMI 1640. FIG. 7B. Comparison of the CFUs in the MIC wells of wild-type fraction to the corresponding well having the same concentration of the ocfN mutant occidiofungin fraction. Asterisks represent no detectable colonies in the MIC wells of the wild-type occidiofungin fraction. Black and grey bars are ocfN mutant and wild-type fractions, respectively. Standard deviations for the CFU measurements are presented.

FIGS. 8A-8C. Potato dextrose agar plates were inoculated with each of the strains and incubated for 3 days at 28° C. The plates were oversprayed with the indicator fungus *Geotrichum candidum* and incubated overnight. FIG. 8A:

Figures 8A, 8B, 8C:
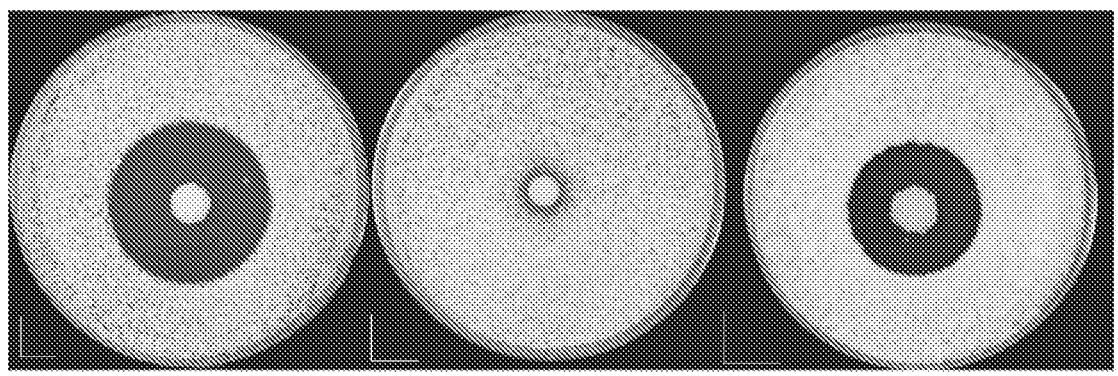

The wild-type strain MS14; FIG. 8B: Negative control MS14GG78 (ocfJ::nptII); FIG. 8C: MS14GG88 (ocfN::nptII).

Figure 9A:
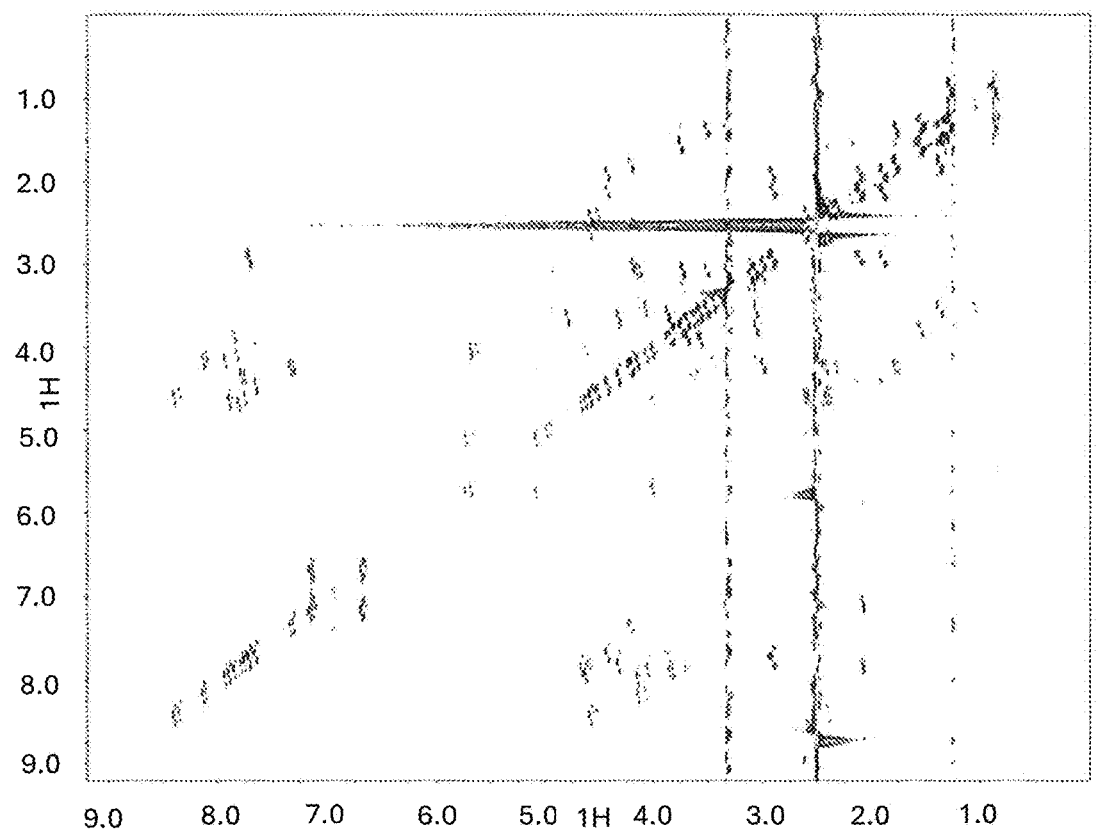
Figure 9B:
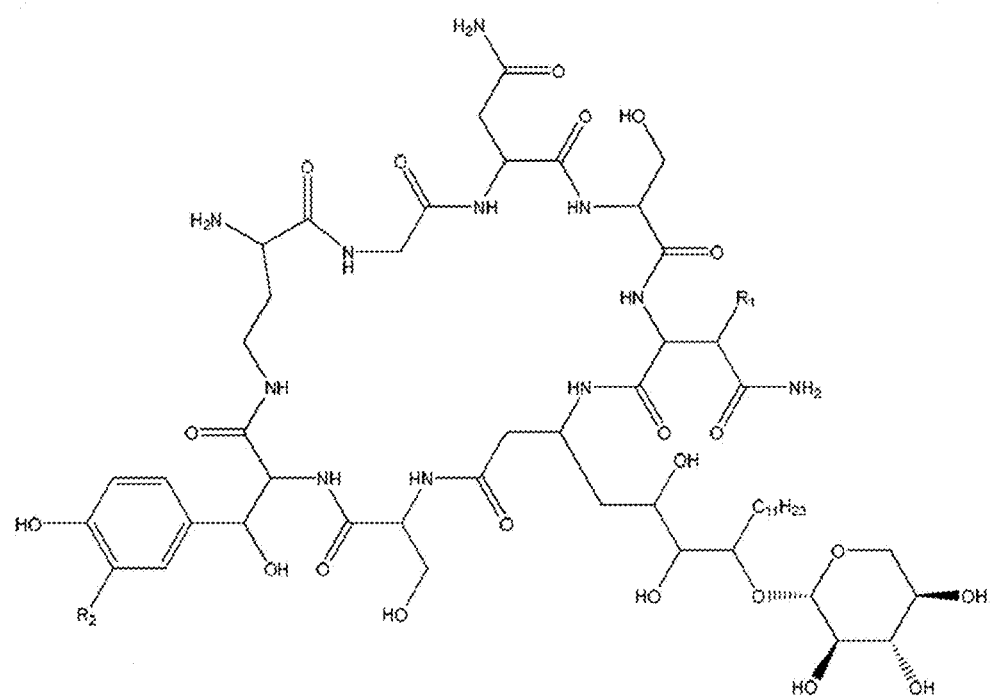

FIGS. 9A-9B. COSY60 NMR Spectrum of Occidiofungin from ocfN mutant MS14GG88 recorded at 600 MHz in DMSO-d6.

Figure 10A:
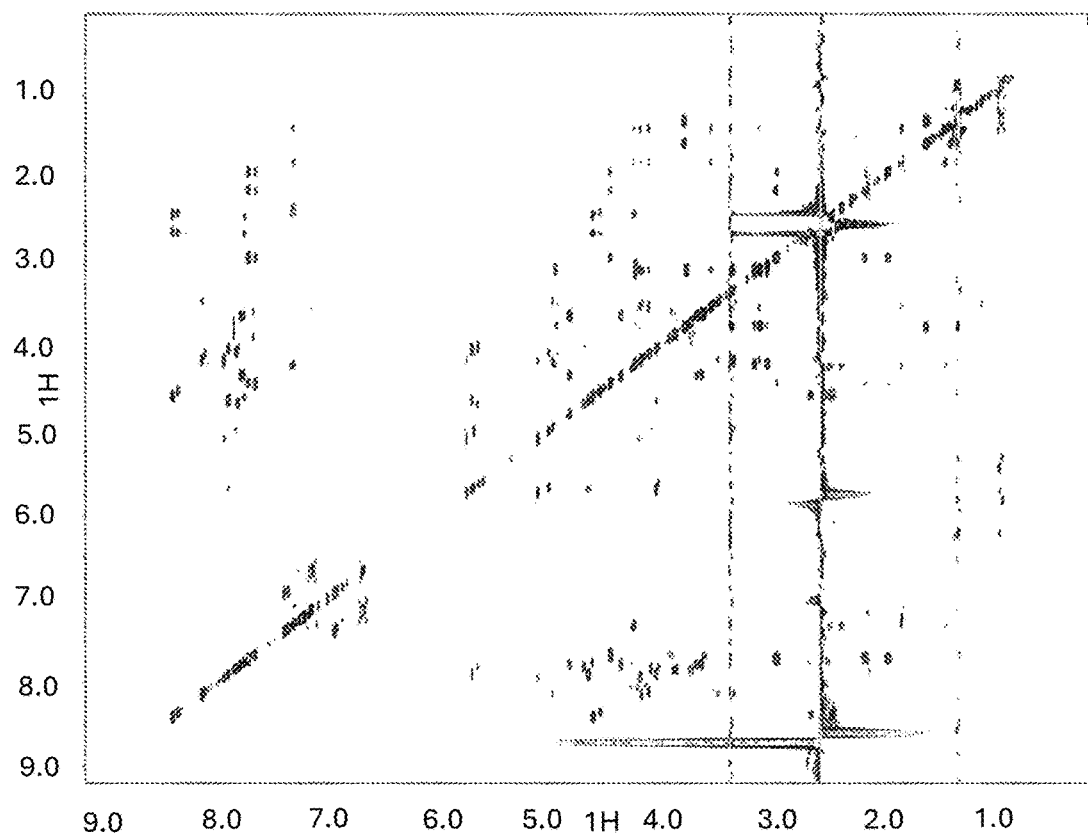
Figure 10B:
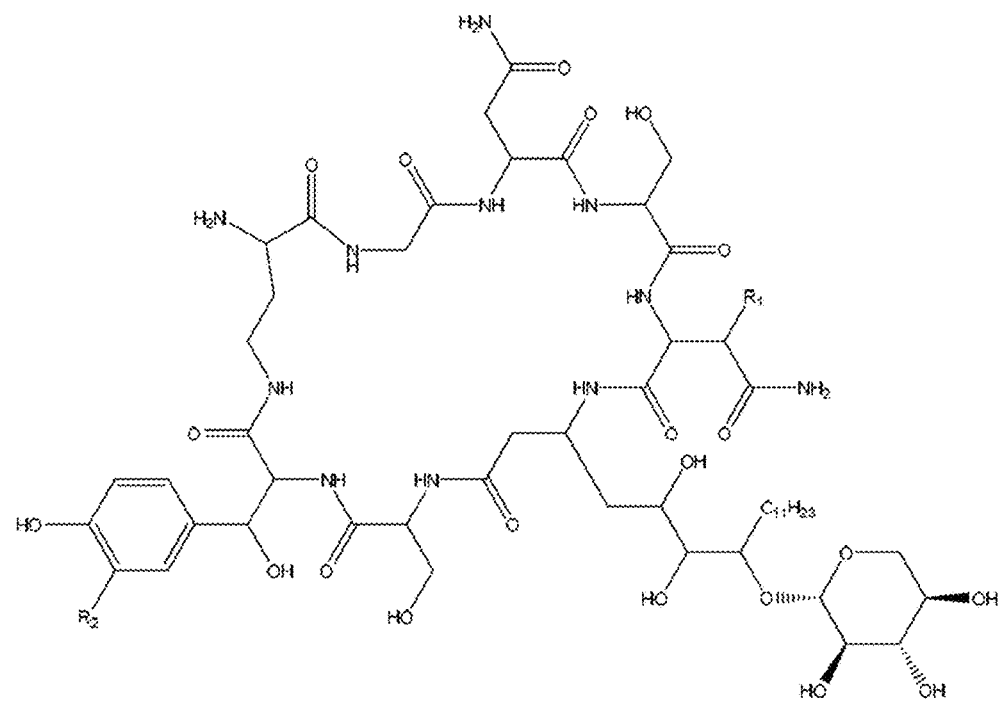

FIGS. 10A-10B. TOCSY60 NMR Spectrum of Occidiofungin from ocfN mutant MS14GG88 recorded at 600 MHz in DMSO-d6.

Figure 11A:
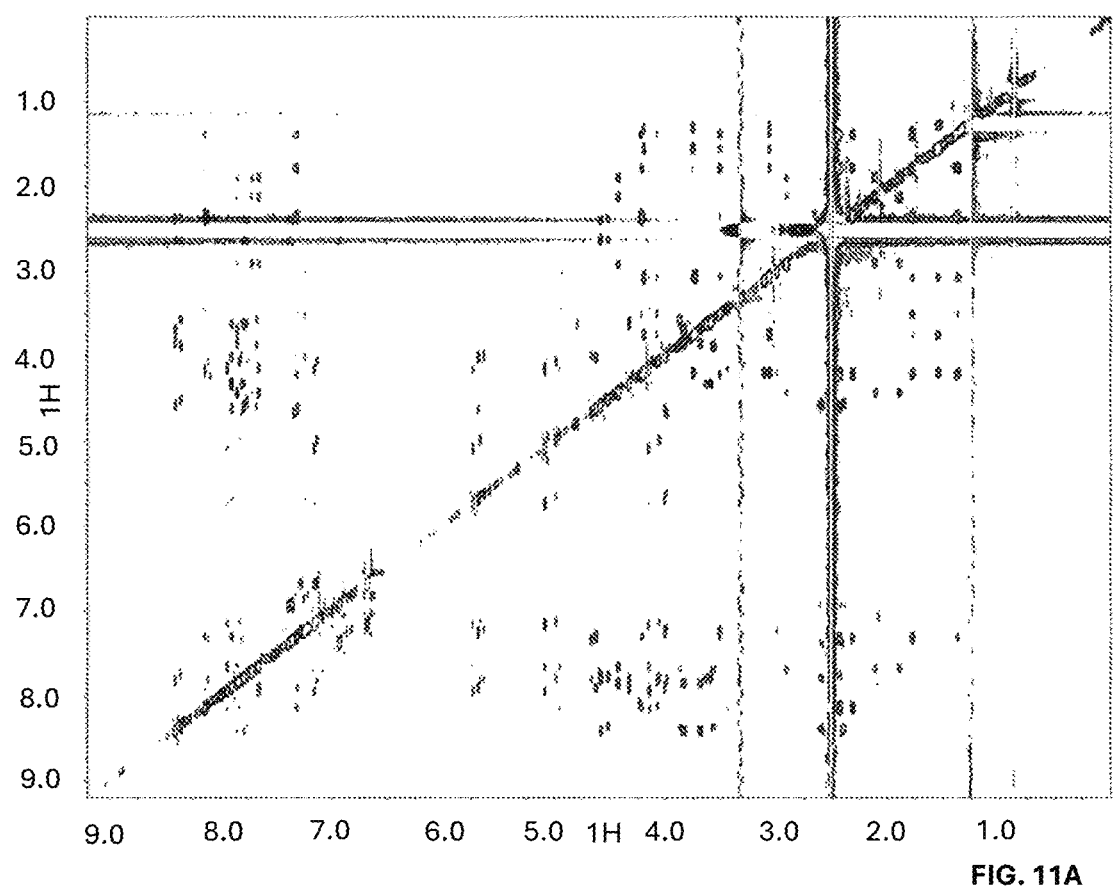
Figure 11B:
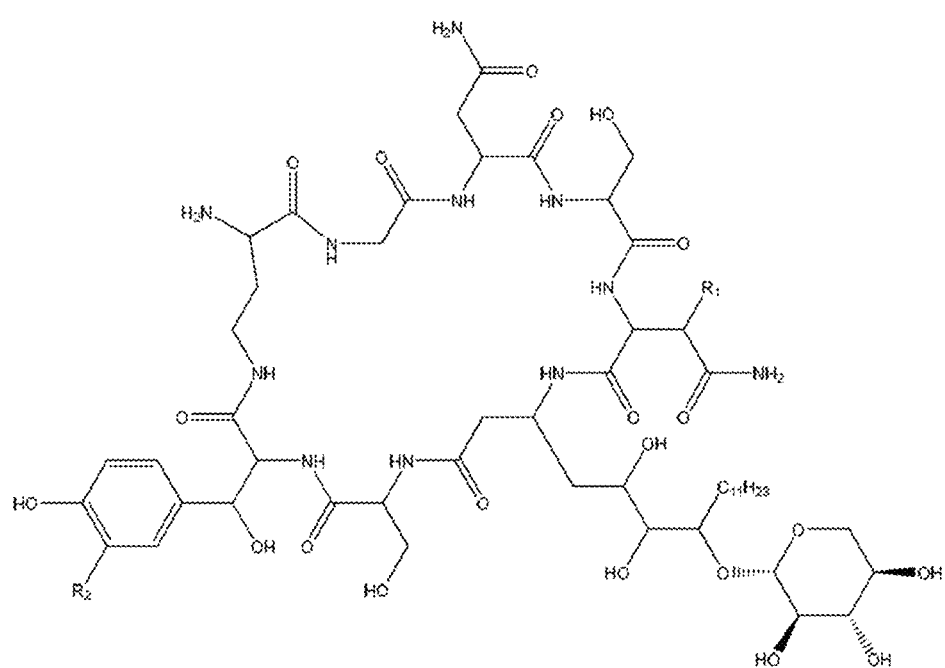

FIGS. 11A-11B. NOESY400 NMR Spectrum of Occidiofungin from ocfN mutant MS14GG88 recorded at 600 MHz in DMSO-d6.

Figure 12A:
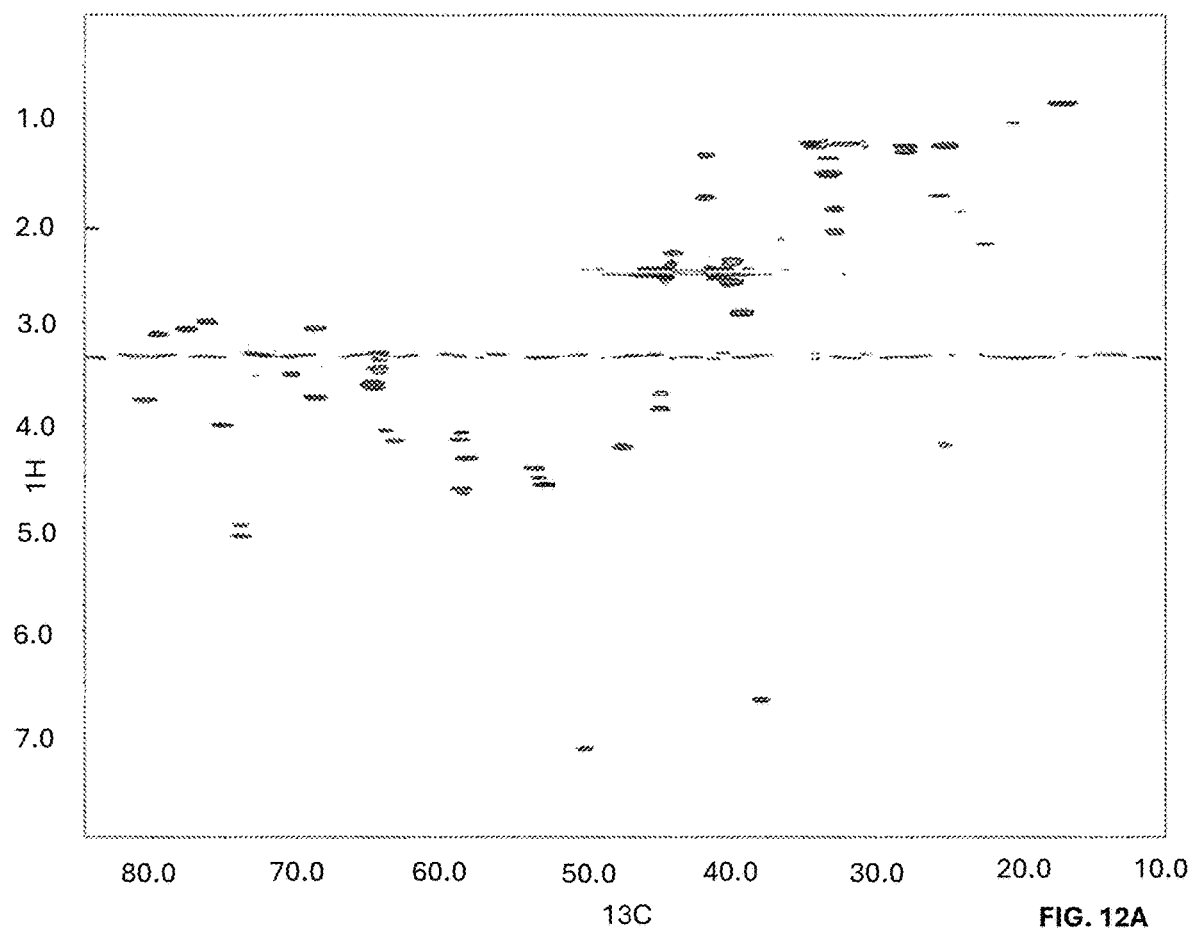
Figure 12B:
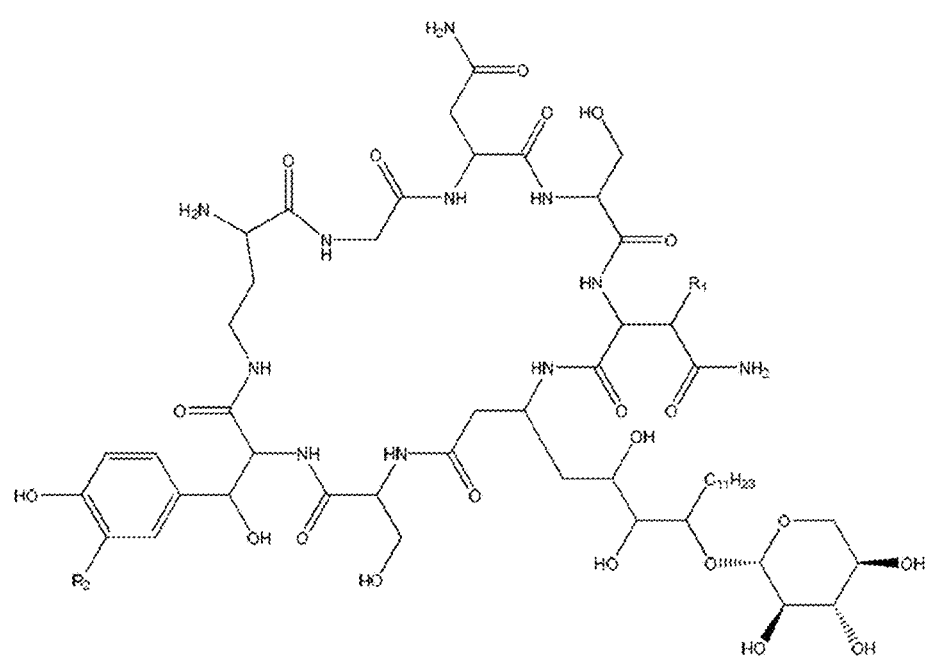

FIGS. 12A-12B. $^{13}$C-HSQC NMR Spectrum of Occidiofungin from ocfN mutant MS14GG88 recorded at 600 MHz in DMSO-d6.

Figures 13A, 13B:
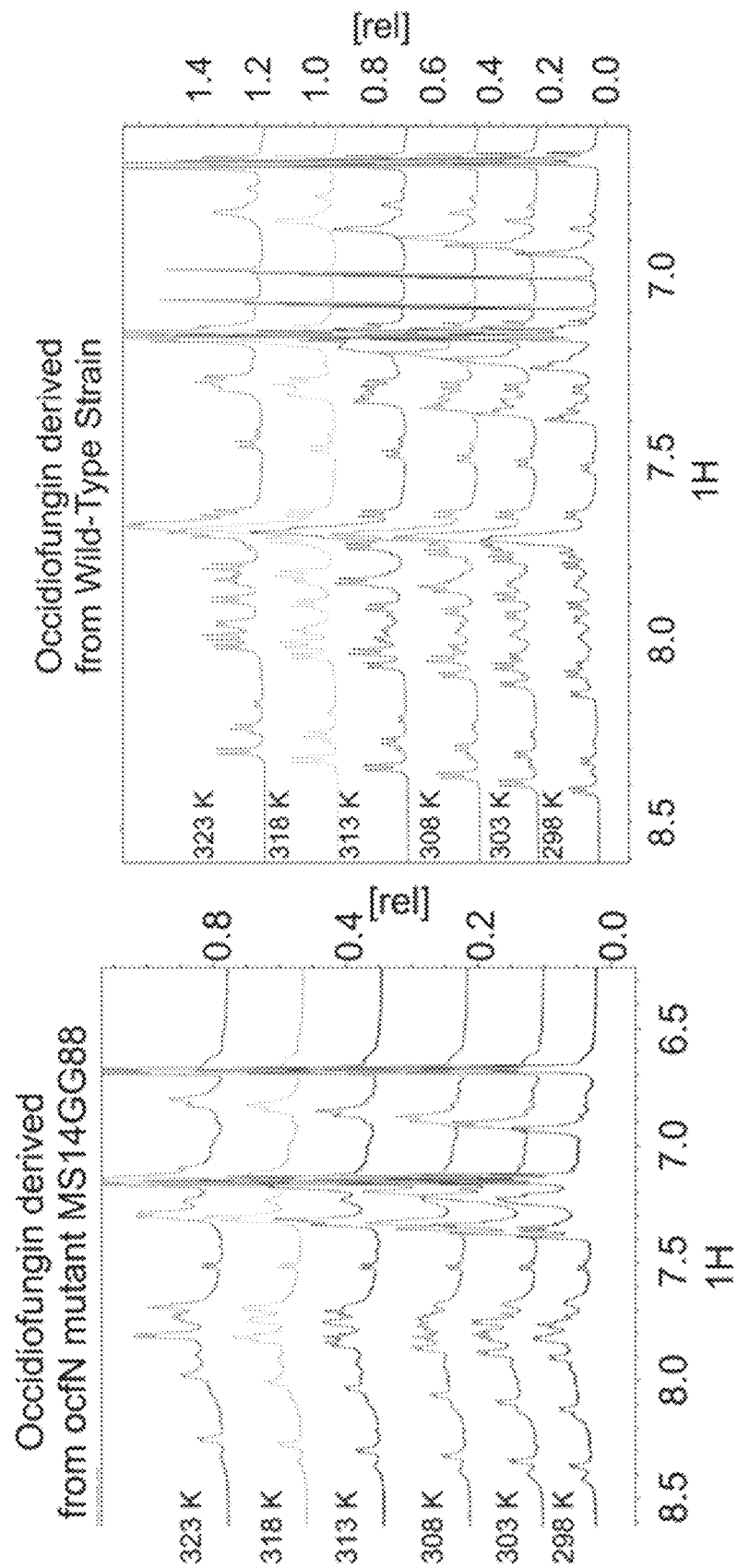

FIGS. 13A-13B. One-dimensional NMR temperature titration curves for occidiofungin derived from ocfN mutant MS14GG88 (FIG. 13A) and wild-type strain MS14 (FIG. 13B).

Figures 14A, 14B:
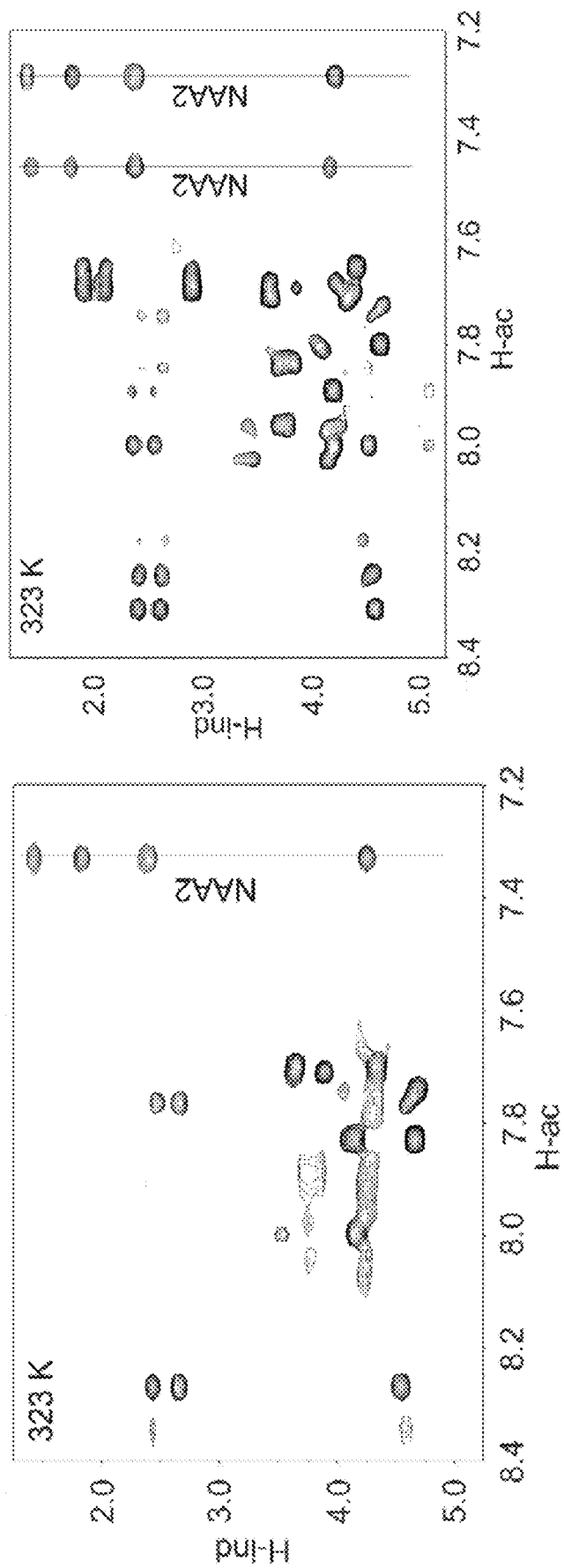

FIGS. 14A-14B. TOCSY fingerprint region (NH correlations) for occidiofungin derived from ocfN mutant MS14GG88 (FIG. 14A) and wild-type strain MS14 (FIG. 14B) at 50° C.

Figure 15:
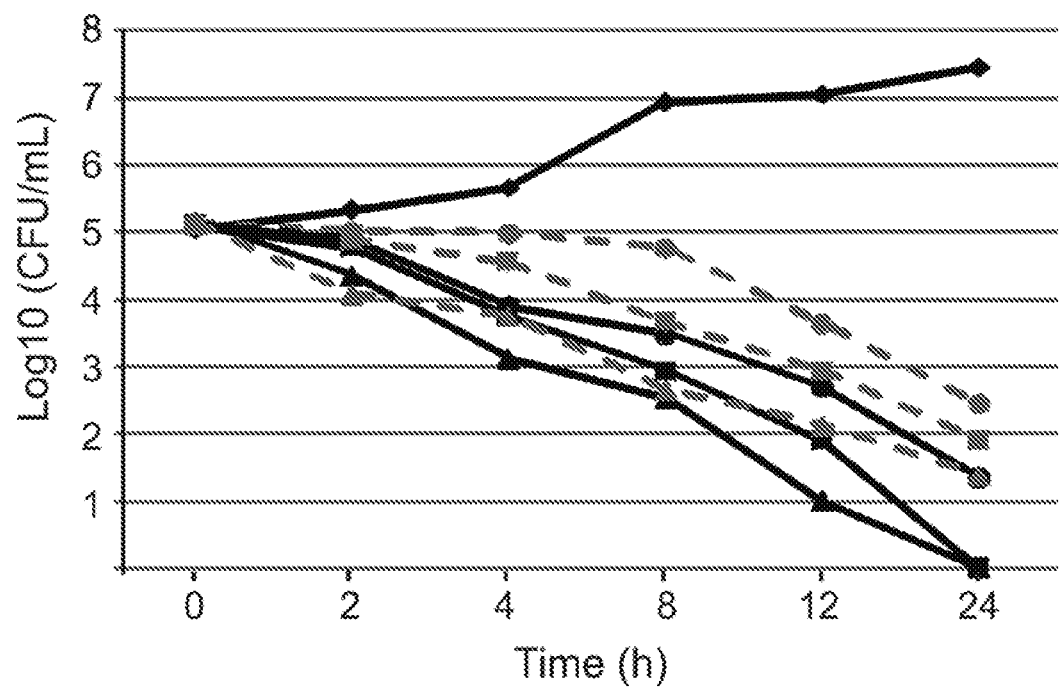

FIG. 15. Time-kill experiments performed against *Candida glabrata* ATCC66032. Solid black lines and dashed grey lines correspond to samples treated with occidiofungin derived from wild-type strain MS14 and ocfN mutant MS14GG88, respectively. Circles, squares, and triangles represent samples treated with 0.5, 1.0, and 2.0 μg/mL of occidiofungin, respectively. The diamond represents the sample treated with the blank control.

BRIEF DESCRIPTION OF THE SEQUENCES

SEQ ID NOs: 1-2: PCR primer sequences

```
SEQ ID NO: 3: amino acid sequence for OcfN (thioesterase; thioesterase motif of-
G-X-S-X-G- underlined (X is any amino acid))
MRLICFPYAGGSAAVYRTLQASLPGIEVCRHELAGRGSRLSEPAVRDMATLV

DTLLCDLDDCFDRPFALLGHSMGAAIAAELALRLPAHARPNLRHLEVSARAAPGKERHDR

RMQALDDRAFIDALREMGGTPKAVLDNSELMALLMPALRADFTMIENHRPVPGPRLAVDI

TAFAGRADKEIPVDAVAGWGAATTGREDFHVIEGDHFFLRNEMRTMAGIIAARMRRPEHA

ASSALQA

SEQ ID NO: 4: amino acid sequence for OcfD (thioesterase motif of-G-X-S-X-G-
underlined (X is any amino acid))
MQDNNVLVTD RESLSRVAGV YGIAAYAPSQ QPGRPLTRSV RLTPASLDLL RRIGDGELAE

FAVAAAGIAF LLWKYFRIPV TVLGTPGLAG HPSARAAIVP LIIEVRPDER IEDYLSRVAG

IVEDSYAEPR FPLETLVRNE KDMALAQLTK VALADDRVHH APTGRDDDLQ LHLRLARGEI

ELRYSGAIEP FIIDGFAGSL AAVLEAFEHL DGAVGDIEAA PPEQGPLLAA FNETATAGPS

HPTVVAMFEA QVARTPTAPA LVTDSSLMTY ADLNARANSL AHHLREHHGV GPESLVGIML

DRSEWMIVAI LGILKAGAAF VPLDPAYPAE RINHILGDTG LSLLVTQSSQ LAQWYEFSGV

TLLLDQELPG WQPLPDNPPH RAEPAHLAYV LYTSGSTGKP KGCLLEHRNL AHYIAWAAGY

YFPESTTGSF GLYSSLCFDF TLTNIFCPLV RGKTLRIYPQ SESIDTILAR MFQPGSGVDT

LKLTPTHIHL LEYMNLARSG VRKVIVGGEE LTPQHIATLR KIDPAIEIYN EYGPTEATVG

CIVERVEDAP PTVLIGRPIA DTRVYMLDDA LRPVPLGVPG EICLAGAGLA RGYHQRPDVT

AAKFVEHPFP GEARIYRTGD IGRWLPDGRI QCYGRVDHQV KIRGHRVELG EIEAAIAAHE

DVVGAAVMLR ESAHGVRKLA AYVKGAASLS VPNLRAYLAG KLPDYMVPSD IIPIAEFPLN

ANGKLDRPAL LALEPAAAPE EAPLDATPIQ RELVRIWRDV LDNPAVDLAG RFFDYGGDSL

QAMQLVSRIW SSFSVEIGID AIFELQTISA VSDLIEASSP HPGSTAGAIP PRSRANDLPL

SFPQQRLWFL AQLEGPSATY NISSALRFEG ELDVARLRFA VSEISRRHEI LRTTFPAVDG

RGVQRIAPPA PVALDVVDVA SESDTLALLA EEADRPFDLA AGPLYRVVLY RVHERLHVFG

IVMHHIVSDA WSSGILIGEL AALYAGESLP ELAVQYADYA VWQHERLASA DTHRELALLS

AALADAPDLI ELPTDRPRPA VQQFRGAVLP FQLSAERADG LRAIARASGT STFMVVLAAY

ALLLSRYSNQ QDLVIGSPIA NRRSSMTEPL IGFFANMLAL RVDLSGNPTF GDLLARVKRV

ALDGYSRQEI PFEQVVDSLE LERNLGRTPV FQVVFAYEKA QPRAVSFPGL VATPVAVETH

TAKFDLTLHV QDADDGLAGS LEYNLDLFDA ATIDRMAEHF RTLVDAVIAD PDRPLGALSL

SNDAERNLLT VEWNRTDTDF GEDAAQPLHR LFEQQVERTP DAVAIVFDDT ALTYAELNLR
```

```
ANRLAHHLVA LGVGPDSLVG VAMERSLDMS VALLAILKAG GAYVPVDPDY PAERVRFMID

HAQLRWLLTQ QHLHDALPDT DAHVIVVDRD SLDLDAAATS NPAPALNGDN LAYMIYTSGS

TGRPKGALNT HRAITNRILW MQHAYALDAD DAVLQKTPFS FDVSVWELFW PLVTGARLVF

ARPGGQRETD YLVELIERER ITTIHFVPSM LRAFLDHPDL DAHCASLRRV VCSGEALPHD

LQQRCLERLD VKLYNLYGPT EAAVDVTAWE CRRDDPHRIV PIGRPIANTR LYIVDAQMQP

TPIGVAGELL IGGTPVGRGY HGEPELSAEK FIADPFSADP LARLYRTGDL ARYRPDGNIE

FLGRIDHQIK LRGLRIEPGE IEAALRAHPS VDDCVVIAKT EGARTFLIAY VATAAPDIAD

LRGYLGGKLA DYMVPSQFFA LESLPMLPNG KINRKALPLP ADRGDAAQPH APAVTPREIL

LASICIDVLQ LPSVGIHDNF FELGGDSILS IQVIARANQA GLRVTAKQLF QYQTIAQLAA

APEERAACAP TLSPLGDAPL TPVQHWFFEQ EIDAPSHYNQ TVLIQVPADI DASRLADAFR

QVYEHHDALR LRFSHDAGRW TQQVVAGGEM PALFAKQVIA DDAGERLAAM RAAAADAERG

IDITHGPLLA ARLFCLADEP LARLFVSIHH LAVDGVSWRV LLEDLHAAYH GQPLPGKTTS

FREWALHLQQ LARSPAIGDE ARLWQALLAQ PVEPMPVDYP GTGAANNAVD DASSVSFELG

EADTTALLRR LPRAYDTRIN DVLLVALAQA CSMVTGNTRT RIDLESHGRH VSDAPLDLTR

TVGWFTSIYP VVLDADAMHA PEQALRAARQ QLRRIPADGL GYSLLRYQSP DAAVRDSLAA

LPKADILFNY HGQLDTVLRQ SDGWRPAAED LGSLRAGRSQ RTHAFEIVAA VADGKLQVDW

RYGERLHRRQ TVENLAAHFR DRLLDFAASV PDTAADDIED SYPLSSLQQG ILFHSLYDLD

PAAYFQQFSF VVSGPLQVPA LRQAWANALA RHAVLRTAFA WADRDHPVQT VRHTVDLPWT

FLDWRHRDAS RRAQDFDAFL ADDRRRGFDL QRAPLFRCTL IQETDTRHRF CWSAHHIILD

GWSTATLMKE VFDDYLSLAR TGMPAVAASA PGYRAYIDWL ARHPRSADET WWRAELAGFK

AATPVAASPA RQATGDAPRQ DKRRTQQFLL DEALAARLQT LTRTHRVTLN VLIRAVWALV

LRRHAGTDDV VFGVTVSGRP PMLDGVESIV GLFINTLPLR LRIAPERPFI EWLAEVHAAQ

TAMEPHSYSS LVDIQSWSEL PAGDSLFDSL LVFENFPVAA APDLGPDDIE ILDTRAFAES

NYPLTLTVHP NERIGFHISH DAHRIAPEVV RQMLDTLRTL LERFAENPGQ LTGQLADPPA

ADGRPSAPRS GAGPAIEAAA GAAAAARAVA HAADESTLLE IWRRIFKRDD IAVSDNYFDL

GGHSIIAIQL MAHVEKAFDR RLPISCLFEN PTIEKLAAAL AAKEPSAPAG GLVPIRDGGP

AAPLFLLPGA GGNVVYFRPL ANHLSGAHAI HGLEALGLDG ACEPLTRVED IAARHIERIW

PLVGAGPYYL AGHSFGAHVA LEMSRQLVAK GADVKLLAIF DASAPIDSSA ATYWQDWDDT

EWLVAIAHEI GTFLGTDLQV TRADLVHLDP DGQAGLILER IGDRGSWFAD AGSDRLRAYL

RVYQANFKSH YAPHATPLPV PIALFRSTER DPGDYAPSSE IAQLRLDATW GWSRFSAHPV

AVTDVPGDHL TMLLDPHAGV LAAHVNSFLE KTPS
```

SEQ ID NOs: 5-23: polynucleotide and polypeptides associated with GenBank Accession No. EU938698.5.

DETAILED DESCRIPTION OF THE INVENTION

This invention relates to antifungal compounds and their therapeutic use in the prevention or treatment of fungal infections and diseases. Particularly, various aspects of the invention provide compositions enriched for occidiofungin diastereomers/conformers that have higher activity against fungal infections or diseases. Thus, the invention relates to methods of making such occidiofungin diastereomers/conformers, compositions enriched for such diastereomers/conformers and methods of using compositions comprising occidiofungin diastereomers/conformers disclosed herein as fungicides for animals and plants. The invention further relates to the microorganisms that produce compositions enriched for occidiofungin enriched for occidiofungin diastereomers/conformers corresponding to diastereomers/conformers having the TOCSY fingerprint identified in FIG. 5C (the grey NH correlations). Methods of increasing the production of occidiofungin diastereomers/conformers corresponding to diastereomers/conformers having the TOCSY fingerprint identified in FIG. 5C (the grey NH correlations) in microorganisms and productions systems are also provided.

As discussed above, one aspect of the invention provides compositions enriched for occidiofungin diastereomers/conformers, in particular the occidiofungin diastereomers/conformers corresponding to the diastereomers/conformers having the TOCSY fingerprint identified in FIG. 5C (the grey NH correlations observed under the following conditions: 2 mM samples of occidiofungin diastereomers in dimethylsulfoxide (DMSO-d6, Cambridge Isotopes) subjected to 2-D TOCSY, spectra collected at 323 K with a mixing time of 60 milliseconds and data processing using NMRPipe with 45 degree sinebell squared shifts in both dimensions). Thus, the invention provides compositions enriched for such antifungal diastereomers/conformers for treating fungal infection. In certain embodiments of this aspect of the invention, pharmaceutical and agricultural compositions that contain a composition enriched for diastereomers/conformers having the TOCSY fingerprint identified in FIG. 5C (the grey NH correlations) are provided.

Another aspect of the invention provides for compositions that are enriched for a particular occidiofungin diastereomer/conformer. In this aspect of the invention, the activity of the ocfD and/or ocfN thioesterases is altered such that the activity of one of the thioesterases is decreased (or eliminated) and the activity of the second thioesterase remains functional or is increased. Thus, microorganisms can be genetically manipulated such that OcfD thioesterase activity is decreased or eliminated and the thioesterase activity of OcfN is increased or maintained at unaltered (e.g., levels of activity as observed in Burkholderia contaminans MS14 or microorganisms engineered with the biosynthetic pathway for the production of occidiofungin). Alternatively, microorganisms can be genetically manipulated such that OcfN activity is decreased or eliminated and the thioesterase activity of OcfD is increased or unaltered.

Compositions comprising occidiofungin diastereomers/conformers as disclosed herein may be formulated prior to administration in an agriculturally acceptable carrier, for example in an aqueous carrier, medium or suitable diluent, such as saline or other buffer. The formulated compositions may also be in the form of a dust or granular material, or a suspension in oil (vegetable or mineral), water or oil/water emulsions, a wettable powder, or in combination with any other carrier material suitable for agricultural application. Suitable agricultural carriers can be solid or liquid and are well known in the art. The term "agriculturally-acceptable carrier" covers all adjuvants, e.g. inert components, dispersants, surfactants, tackifiers, binders, etc. that are ordinarily used in the formulation of agricultural compositions; these are well known to those skilled in formulation of agricultural compositions.

A pharmaceutical composition contains a desired amount of an occidiofungin diastereomers/conformers as disclosed herein. Thus, the pharmaceutical composition can comprise occidiofungin diastereomers/conformers having the total correlation spectroscopy (TOCSY) fingerprint identified in FIG. 5C as the grey NH correlations or the pharmaceutical composition can comprise a particular occidiofungin diastereomer/conformer. Either of these pharmaceutical compositions can be in the form of, for example, a tablet, a caplet, a pill, a hard or soft capsule, a lozenge, a cachet, a dispensable powder, granules, a suspension, an elixir, a dispersion, a liquid, or any other form reasonably adapted for administration. If intended for parenteral administration, it can be in the form, for example, of a suspension or transdermal patch. Presently preferred are oral dosage forms that are discrete dose units each containing a predetermined amount of the disclosed occidiofungin diastereomers/conformers.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, ophthalmically, by nasal aerosol or inhalation.

Such compositions are prepared according to techniques well-known in the art of pharmaceutical formulation.

Compositions disclosed herein can be used to treat fungal infections in immunocompromised patients or patients having fungal infections. Thus, another aspect of the invention provides for administering compositions enriched for occidiofungin diastereomers/conformers (e.g., those corresponding to the diastereomers/conformers having the TOCSY fingerprint identified in FIG. 5C (the grey NH correlations) having increased antifungal activity as compared to occidiofungin compositions produced by *Burkholderia contaminans* MS14 (disclosed in U.S. Patent Application Publication 2011/0136729, the disclosure of which is hereby incorporated by reference in its entirety). These diastereomers/conformers have been characterized by a number of techniques, including COSY, TOCSY, NOESY, ROESY, and HSQC 2D NMR spectroscopy experiments.

The antifungal activity of the disclosed occidiofungin diastereomers/conformers (diastereomers/conformers having the TOCSY fingerprint identified in FIG. 5C (the grey NH correlations)) provides for compositions having greater antifungal activity as compared to as compared to occidiofungin compositions produced by *Burkholderia contaminans* MS14 when cultured under the same conditions. The phrase "enriched for the disclosed occidiofungin diastereomers/conformers" is intended to convey that the composition contains disclosed occidiofungin diastereomers/conformers (diastereomers/conformers having the TOCSY fingerprint identified in FIG. 5C (the grey NH correlations)) in amounts higher than that produced by a reference strain (e.g., *Burkholderia contaminans* MS14 as disclosed in the examples provided herein). Thus, the phrase indicates that at least 37% of the total amount of occidiofungin diastereomers/conformers present within an enriched composition are the disclosed diastereomers/conformers having the TOCSY fingerprint identified in FIG. 5C (the grey NH correlations)). In various embodiments, compositions "enriched for the disclosed occidiofungin diastereomers/conformers" contain at least 40%, 41%, 42%, 43%, 44%, 45%, 46%, 47%, 48%, 49%, 50%, 51, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the disclosed diastereomers/conformers in relation to the total amount of occidiofungin diastereomers/conformers in a composition.

As discussed above, one aspect of the invention provides microorganisms capable of producing compositions enriched for occidiofungin diastereomers/conformers corresponding to the diastereomers/conformers having the TOCSY fingerprint identified in FIG. 5C (the grey NH correlations). In this aspect of the invention, microorganisms are transformed with the genes associated with the biosynthesis of occidiofungin. These genes and open reading frames (ORFs) are disclosed in disclosed in U.S. Patent Application Publication 2011/0136729, the disclosure of which is hereby incorporated by reference in its entirety; Gu et al., Appl. Environ. Microbiol., 2011, 77:(17):6189-6198 which is also incorporated by reference in its entirety and GenBank Accession No. EU938698.5, which is also hereby incorporated by reference in its entirety and is also provided on pages 29-72 (SEQ ID NOs: 5-23). These transformed microorganisms are further manipulated genetically such that the microorganisms exhibit an increase in the level of OcfN thioesterase (SEQ ID NO: 3) activity. An increase in the level of OcfN thioesterase activity can be achieved by means of expressing the ocfN gene in a multicopy plasmid with a native promoter or any other promoter sequence. Another way to increase the expression of the ocfN gene within the cell is to chromosomally integrate additional copies of the ocfN gene using transposons. Yet a further means to increase ocfN thioesterase activity is to substitute the native promoter associated with the ocfN gene with a promoter that increases expression of the gene (relative to the native promoter). In certain embodiments of this aspect of the invention, the thioesterase activity of OcfD can be decreased or eliminated by a point mutation of the catalytic serine at position 2954 of SEQ ID NO: 4, insertional mutation or point mutation of amino acids within the thioesterase motif (in addition to the substitution of the serine residue) found in ocfD to reduce or eliminate its activity, deletion of the catalytic serine or other portions of SEQ ID NO: 4 (e.g., portions or the entirety of the thioesterase motif in SEQ ID NO: 4) or truncation SEQ ID NO: 4 such that thioesterase activity is reduced or eliminated (in addition to increasing the level of OcfN thioesterase activity) within the genetically modified microorganisms.

Another aspect of the invention provides for compositions enriched for a particular occidiofungin diastereomer/conformer. In this aspect of the invention, transformed microorganisms are manipulated genetically such that the microorganisms exhibit an increase in the level of OcfD thioesterase (SEQ ID NO: 4) activity. An increase in the level of OcfD thioesterase activity can be achieved by means of expressing the ocfD gene in a multicopy plasmid with a native promoter or any other promoter sequence. Another way to increase the expression of the ocfD gene within the cell is to chromosomally integrate additional copies of the ocfD gene using transposons. Yet a further means to increase ocfN thioesterase activity is to substitute the native promoter associated with the ocfD gene with a promoter that increases expression of the gene (relative to the native promoter). In certain embodiments of this aspect of the invention, the thioesterase activity of OcfN can be decreased or eliminated by a point mutation of the catalytic serine at position 73 of SEQ ID NO: 3, insertional mutation or point mutations of other amino acids within the thioesterase motif (in addition to the substitution of the serine residue) of the thioesterase to reduce or eliminate its activity, deletion of the catalytic serine or other portions of SEQ ID NO: 3 (e.g., portions or the entirety of the thioesterase motif in SEQ ID NO: 3), truncation SEQ ID NO: 3 such that thioesterase activity is reduced or eliminated or deletion of ocfN in its entirety (in addition to increasing the level of OcfD thioesterase activity) within the genetically modified microorganisms. Where the biosynthetic pathway for occidiofungin biosynthesis is engineered into a microorganisms, once can, of course, omit ocfN to achieve the same effect as the mutation or deletion of ocfN as discussed above.

Thus, microorganisms such as bacterial cells, fungal cells and yeast can be transformed with genes encoding the occidiofungin biosynthetic pathway and genetically manipulated, as discussed above, such that the cells have increased OcfN activity and/or decreased OcfD activity as compared to reference bacterial, fungal or yeast cells. Alternatively, microorganisms such as bacterial cells, fungal cells and yeast can be transformed with genes encoding the occidiofungin biosynthetic pathway and genetically manipulated, as discussed above, such that the cells have increased OcfD activity and/or decreased OcfN activity as compared to reference bacterial, fungal or yeast cells. Such cells can then be used to produce compositions enriched for occidiofungin diastereomers/conformers corresponding to the diastereomers/conformers having the TOCSY fingerprint identified in FIG. 5C (the grey NH correlations) or to produce compositions enriched for a particular occidiofungin diastereomer/conformer. The phrase "reference bacterial, fungal or yeast cells" refers to bacterial, fungal or yeast cells containing the genes associated with the biosynthetic pathway for the production of occidiofungin and where the function/activity of OcfN and/or OcfD has not been altered as disclosed herein. Thus, the phrase "reference bacterial, fungal or yeast cells" refers to cells containing, for example, polynucleotide (SEQ ID NO: 23 encoding the open reading frames (ORFs; SEQ ID NOs: 5-22)) disclosed in GenBank Accession No. EU938698.5. For the comparison of compositions comprising particular occidiofungin conformers (or compositions enriched for occidiofungin diastereomers/conformers corresponding to the diastereomers/conformers having the TOCSY fingerprint identified in FIG. 5C (the grey NH correlations)), compositions containing the diastereomers/conformers are obtained from cells genetically manipulated to have increased ocfN activity and/or decreased OcfD activity (or increased OcfD activity and/or decreased ocfN activity) and compared to compositions containing occidiofungin produced by reference bacterial, fungal or yeast cells cultured under similar or the same conditions (e.g., the same temperature and medium).

Bacterial cells can be selected Gram negative bacteria or Gram positive bacteria. In this aspect of the invention, the Gram-negative bacterial cell can be selected from the group consisting of *Escherichia, Zymomonas, Acinetobacter, Gluconobacter, Geobacter, Shewanella, Salmonella, Enterobacter* and *Klebsiella*. Gram-positive bacteria can be selected from the group consisting of *Bacillus, Clostridium, Corynebacterial, Lactobacillus, Lactococcus, Oenococcus, Streptococcus* and Eubacterial cells. Various thermophilic bacterial cells, such as Thermoanaerobes (e.g., *Thermoanaerobacterium saccharolyticum*), *Bacillus* spp., e.g., *Bacillus coagulans* strains, *Bacillus licheniformis* strains, *Bacillus subtilis* strains, *Bacillus amyloliquifaciens* strains, *Bacillus megaterium* strains, *Bacillus macerans* strains, *Paenibacillus* spp. strains or *Geobacillus* spp. such as *Geobacillus stearothermophilus*.

Yeast cells suitable for use in this aspect of the invention may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell. In this aspect of the invention, the yeast cell must be resistant to the effects of occidiofungin to be a viable production system for compositions enriched for occidiofungin diastereomers/conformers corresponding to the diastereomers/conformers having the TOCSY fingerprint identified in FIG. 5C (the grey NH correlations).

In other embodiments of this aspect of the invention, fungal cells can be manipulated to produce compositions enriched for occidiofungin diastereomers/conformers corresponding to the diastereomers/conformers having the TOCSY fingerprint identified in FIG. 5C (the grey NH correlations). "Fungi" as used herein includes the phyla Ascomycota, Basidiomycota, Chytridiomycota, and Zygomycota, Oomycota and all mitosporic fungi. A fungal cell may be a yeast cell. "Yeast" as used herein includes ascosporogenous yeast (Endomycetales), basidiosporogenous yeast, and yeast belonging to the Fungi Imperfecti (Blastomycetes). The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inhops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

In another embodiment of the present invention, the native promoter of the ocfN gene within *Burkholderia contaminans* MS14 can be replaced by promoter elements known to enhance the level of gene expression, thereby increasing OcfN thioesterase activity within *Burkholderia contaminans* MS14. *Burkholderia contaminans* MS14 can also be genetically modified by other techniques to produce compositions enriched for occidiofungin diastereomers/conformers corresponding to the diastereomers/conformers having the TOCSY fingerprint identified in FIG. 5C (the grey NH correlations). Genetic modifications that ocfN thioesterase activity include the introduction of multicopy plasmids comprising a native promoter or any other promoter sequence operably liked to an ocfN gene into *Burkholderia contaminans* MS14, integration of additional copies of the ocfN gene operably linked to a promoter into the chromosome of *Burkholderia contaminans* MS14 using transposon mutagenesis or by replacement of the native ocfN promoter in *Burkholderia contaminans* MS14 with a promoter that increases the expression of ocfN transcripts relative to the native promoter sequence.

Another aspect of the invention provides for the introduction of a point mutation into the nucleotide sequence encoding OcfD, the truncation of ocfD (or introduction of a frameshift mutation) such that the thioesterase activity is reduced or eliminated or the deletion of the segment of the ocfD gene encoding the catalytic serine in order to increase the amounts of occidiofungin diastereomers/conformers corresponding to the diastereomers/conformers having the TOCSY fingerprint identified in FIG. 5C (the grey NH correlations) produced by *Burkholderia contaminans* MS14 or by microorganisms genetically modified to produce occidiofungin (e.g., microorganisms into which the biosynthetic pathway for occidiofungin production have been introduced). In this aspect of the invention, a point mutation is introduced into the catalytic serine in the thioesterase domain of ocfD in order to reduce its activity. This amino acid is found at position 2954 of SEQ ID NO: 4. For example, the serine can be mutated into an alanine, glycine or proline residue (with glycine or alanine being preferred in this context). Certain embodiments of this aspect of the invention also provide for genetic modification of the microorganisms such that ocfN activity is increased as well (e.g., the level of OcfN thioesterase activity can be increased by means of expressing the ocfN gene in a multicopy plasmid with a native promoter or any other promoter sequence, chromosomal integration of additional copies of the ocfN gene using transposons or other means or substitution of the native promoter associated with the ocfN gene with a promoter that increases expression of the gene (relative to the native promoter)).

Another aspect of the invention provides for the introduction of a point mutation into the nucleotide sequence encoding OcfN, the truncation of ocfN (or introduction of a frameshift mutation) such that the thioesterase activity is reduced or eliminated, the deletion of the segment of the ocfN gene encoding the catalytic serine or chromosomal deletion of ocfN within a microorganism (e.g., *Burkholderia contaminans* MS14) in order to increase the amounts a particular occidiofungin diastereomer/conformer produced by a microorganism. As would be apparent to one skilled in the art, a similar effect can be obtained by transforming a microorganism with the genes encoding the occidiofungin biosynthetic pathway, with the exception of ocfN gene. In this aspect of the invention, a point mutation is introduced into the catalytic serine in the thioesterase domain of OcfN in order to reduce its activity. This amino acid is found at position 73 of SEQ ID NO: 3. For example, the serine can be mutated into an alanine, glycine or proline residue (with glycine or alanine being preferred in this context). Certain embodiments of this aspect of the invention also provide for genetic modification of the microorganisms such that OcfD activity is increased as well (e.g., the level of OcfD thioesterase activity can be increased by means of expressing the ocfD gene in a multicopy plasmid with a native promoter or any other promoter sequence, chromosomal integration of additional copies of the ocfD gene using transposons or other means or substitution of the native promoter associated with the ocfD gene with a promoter that increases expression of the gene (relative to the native promoter)).

Materials and Methods

Figure 2A:
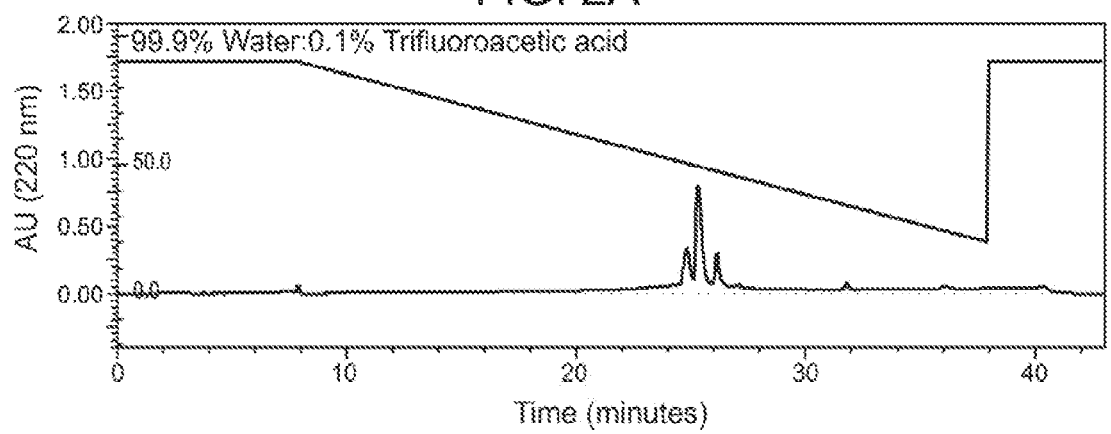
Figure 2B:
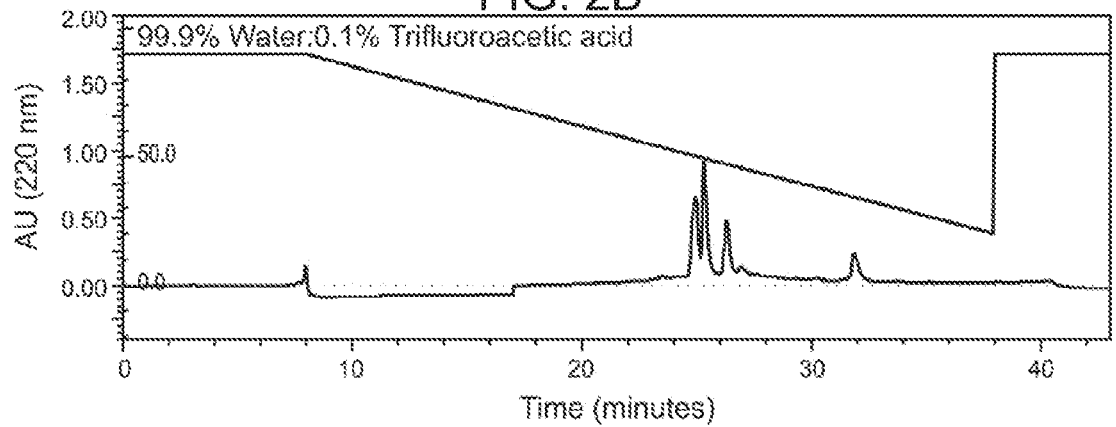
Figure 2C:
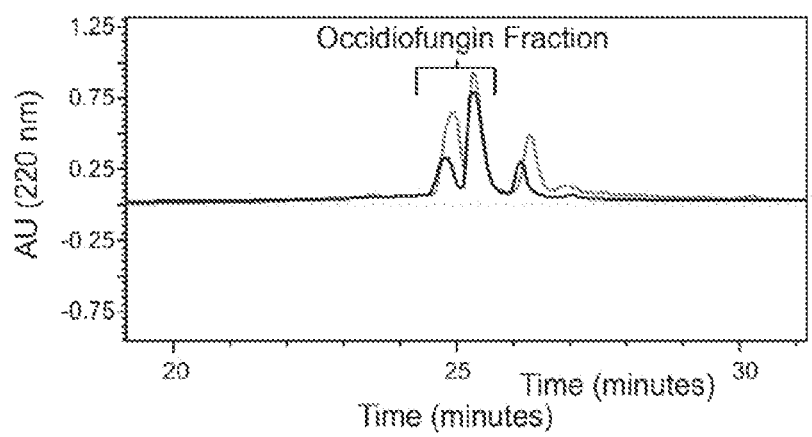

Proportion of Occidiofungin Variants in the Sample. The C-terminal TE domain of OcfD and the OcfN cyclase thioesterase in the occidiofungin biosynthetic gene cluster are both predicted to be involved in the termination of synthesis and formation of the cyclic peptide. Given that the N-terminal end of the linear peptide is an Asn or BHN, we hypothesized that each thioesterase was required for cyclization of the Asn1 and BHN1 variants. The Asn1 and BHN1 variants of occidiofungin are not separable by RP-HPLC (reverse phase high performance liquid phase chromatography), thus, both variants are present in the purified fraction (FIGS. 2A-2C). The final RP-HPLC step in the purification process reveals the presence of three peaks. Occidiofungin samples elute as a doublet peak before the third peak. Both the wild type strain MS14 and the ocfN mutant MS14GG88 have the same chromatographic profile as observed in the last purification step. Occidiofungin peaks were confirmed by MALDI-TOF and bioassays. It is important to note that the presence of the doublet peak is not associated with the presence of Asn1 or BHN1. Each peak of the doublet contains both the Asn1 and BHN1 variants.

Figure 3:
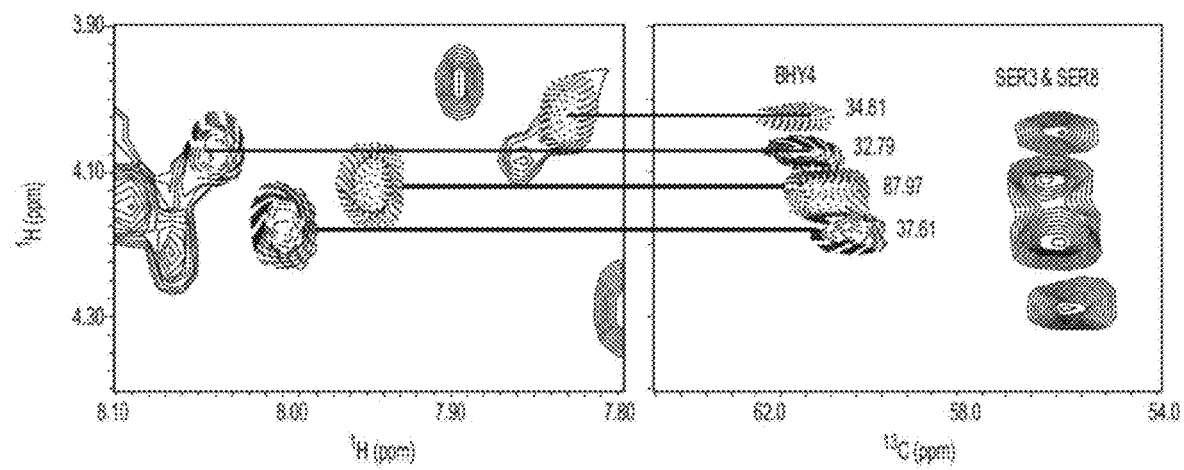
Figure 4:
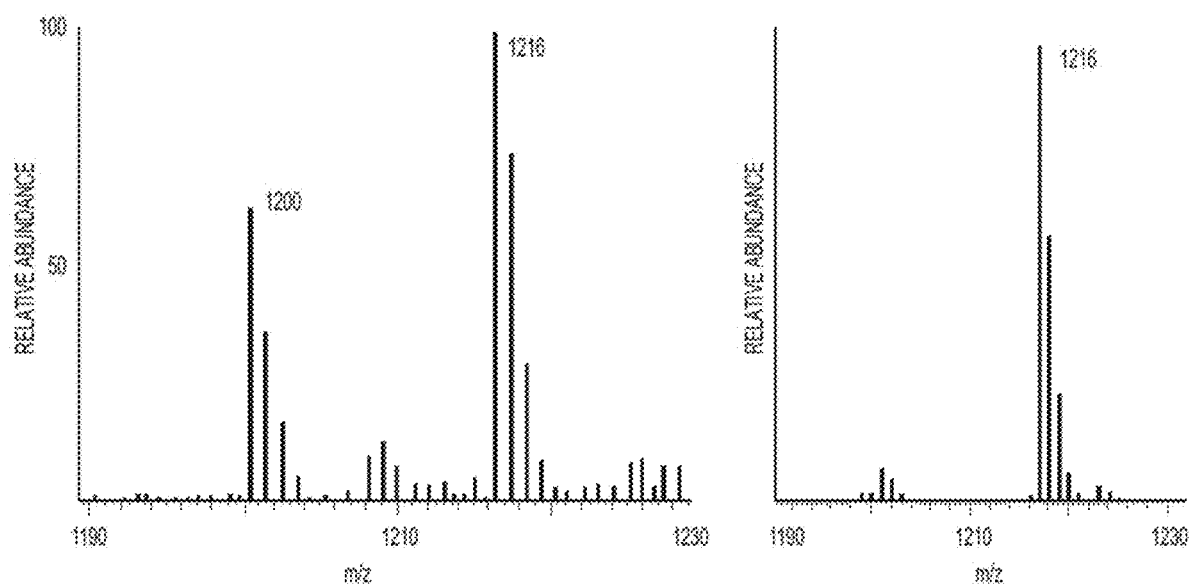

The relative proportion of the Asn1 and BHN1 variants could not be directly compared, because direct measurement of the Asn1 peak intensities could not be done due to the peaks overlapping with Asn7. The relative proportion of the Asn1 and BHN1 variants in the wild-type fraction was determined by measuring the $^{13}$C-HSQC Ha-Ca cross peak intensities of each BHY4 peak in the data set,[27, 28] given that each of the BHY4 peaks could be attributed to either the Asn1 or BHN1 variant. Based on the Ha-Ca cross peak intensities for BHY4 in HSQC spectrum, the Asn1 and BHN1 variants was determined by measuring the $^{13}$C-HSQC Ha-Ca cross peak intensities of each BHY4 peak in the data set[27, 28], and was determined to be approximately 36% and 64% of the total amount of occidiofungin, respectively (FIGS. 3A-3B). The peaks in red and green represent the BHY4 peaks associated with BHN1 and Asn1 variants, respectively. A similar ratio was also observed in the relative abundance of each peak in the ESI-MS spectrum (FIG. 4A). Furthermore, the $^{13}$C-HSQC Ha-Ca cross peak intensities for the BHN1 peaks in the spectra were determined to be 90.50 and 38.65, which support the intensities measured for BHY4 peaks corresponding to the BHN1 conformational variants.

Mutagenesis of the ocfN gene was conducted via a marker exchange procedure as described previously[22], to generate the mutant MS14GG88. The percentage of Asn1 to BHN1 variants in the ocfN mutant MS14GG88 fraction could be determined by measuring the proportion of each BHN1 variant using the HSQC data set and by the integration of the HN of Asn1 and BHN1 in the $^1$H NMR spectra. Asn1 and BHN1 variants are approximately 20% and 80% of the total amount of occidiofungin, respectively. The ESI-MS spectrum also shows a lower relative abundance for the Asn1 variant (1200.39 Da) compared to the BHN1 variant (1216.41 Da) (FIG. 4B).

Comparison of Wild-type and ocfN Mutant NMR Spectra. Occidiofungin has a complex spectrum for a peptide of only eight amino acids (FIG. 5A and Table 1). The NMR spectrum represents an average of the conformers on the NMR time scale. Conformers in slow exchange on the NMR time scale may result in multiple spin systems for each amino acid. In some situations, multiple conformers are known to arise for cyclic peptides due to slow interconverting conformational families.[29,30] Despite the conformation restrictions brought about by the ring closure, occidiofungin still has a significant amount of conformational freedom. Both Asn1 and BHN1 variants are visibly present in the wild-type fraction, which are colored red in FIG. 5A. The TOCSY fingerprint region (Ni correlations) is not as complex for the OcfN thioesterase MS14GG88 mutant spectra (FIG. 5B). A significant number of spin systems found in the wild-type spectra are absent in the ocfN thioesterase mutant spectra. Our experiments show that the TE domain on the C-terminal region of OcfD is able to perform the peptide macrocyclization of both the Asn1 and BHN1 variants. Although, there is only one amide spin system for Asn1 produced by OcfD. Whereas, the loss of OcfN results in the disappearance of the other three Asn1 amide spin systems.

An overlay of the wild-type and ocfN mutant NMR spectra shows the amino acid spin systems in grey that are absent in the mutant spectra (FIG. 5C). These spin systems are for Asn7, Ser8, Asn1, Novel Amino Acid 2 (NAA2), Ser3, BHY4, and Gly6. The loss of these spin systems suggests that the complex spin system observed for the wild-type occidiofungin fraction is not only due to interconverting conformational families, but is the result of distinct diastereomers formed by the regiospecific activity of the OcfN cyclase and OcfD TE domain. Dramatic chemical shifts observed, such as the 2 ppm shift for HN of the NAA2, support the formation of a structurally unique conformer of occidiofungin. A unique conformer is further supported by the subsequent loss of a NAA2 spin system in the ocfN mutant NMR spectra. Furthermore, the presence of both Asn1 and BHN1 spin systems in the mutant spectra along with the absence of the amide spin systems shown in grey indicate that the additional spin systems are not due to the presence of the O-hydroxyl on Asn1. The additional spin systems are due to the formation of unique diastereomer produced by OcfN cyclase thioesterase. To further test for the formation of a configurational isomer versus an interchangeable conformational isomer, one dimensional NMR temperature titrations were performed. Amide and aromatic regions revealed little change in the complexity of peaks present with the occidiofungin derived from ocfN mutant MS14GG88 or wild-type strain MS14 (FIGS. 13A-13B). Given that NAA2 spin systems are a good indicator for the presence of both diastereomers in the wild-type spectrum, we collected TOCSY spectra for occidiofungin derived from ocfN mutant MS14GG88 or wild-type strain at 50° C. (FIGS. 14A-14B). There was no loss or addition of a spin system for NAA2 in the mutant spectrum. Furthermore, both spin systems for NAA2 remained in the wild-type spectrum. This data supports that the stereoisomers are non-interchangeable isomers, supporting their classification as a diastereomers (configurational isomers) rather than a conformational isomer.

Figure 6:
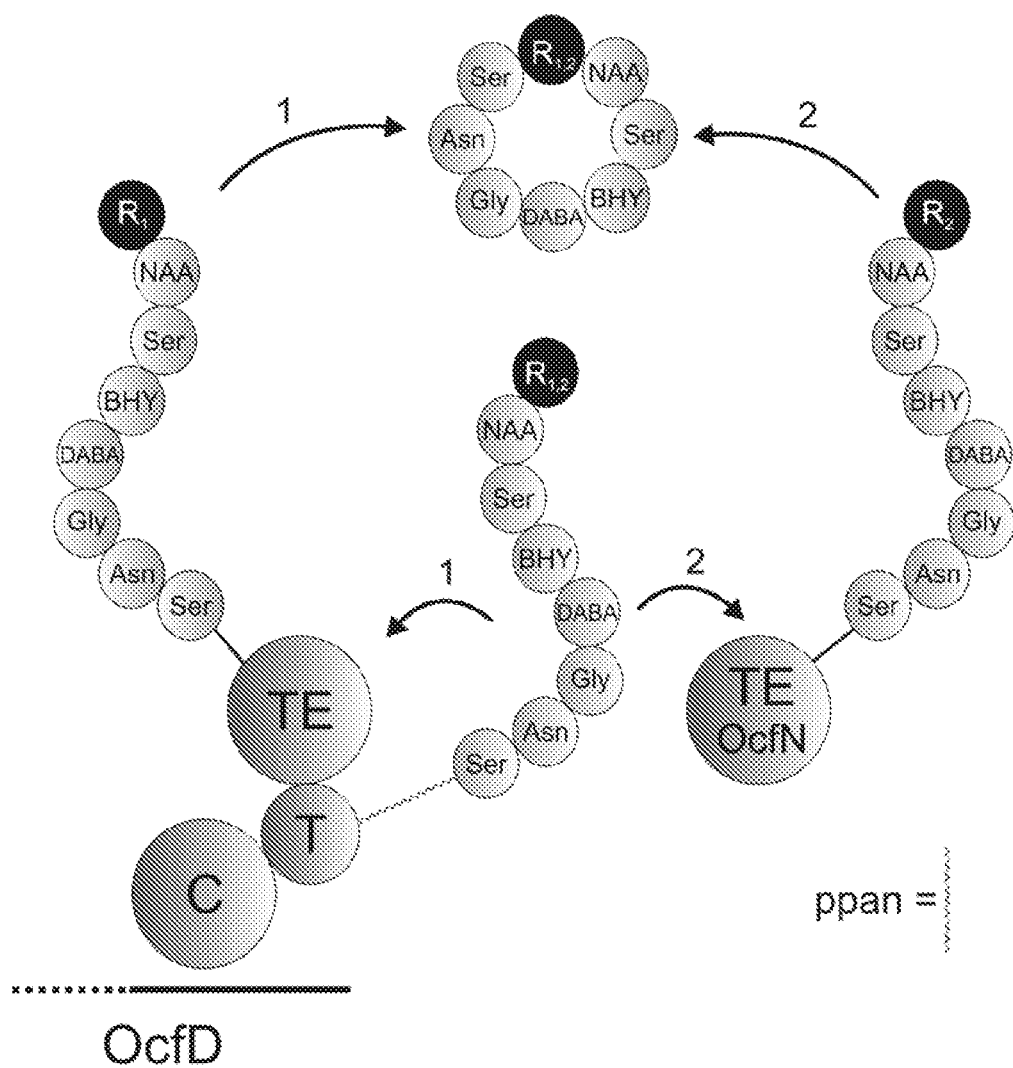

Model for the Coordinated Function of Two Cyclase Thioesterases. There was no loss of an amide spin system for a BHN1 in the ocfN mutant NMR spectra. This suggests that OcfN thioesterase has a substrate requirement for the peptide containing Asn1, since there is no concomitant loss of a BHN1 spin system with the observed loss of the Asn1 spin systems. The C-terminal TE domain of OcfD has a preference for the peptide containing the BHN1, but is capable, albeit at a lower efficiency of cyclizing the Asn1 variant. This provides an interesting scenario for the activity of the two thioesterases (FIG. 6). Both thioesterases contain the GXSXG motif, which is important for the catalytic transfer of the peptide from the T domain to the cyclase. This suggests that substrate recognition occurs prior to the catalytic transfer of the peptide to the cyclase. Presumably, OcfN cyclase has a higher affinity or better access for the Asn1 peptide product given that the proportion of the Asn1 cyclic peptide product produced by OcfD compared to the BHN1 product is reduced in the wild-type fraction. Therefore the biosynthesis of occidiofungin utilizes the structural differences between Asn and BHN to increase the conformational biodiversity of occidiofungin. The increase in conformational diversity is accomplished by the regiospecific activity of each cyclase, presumably by differences in their binding clefts that helps orientate the peptide before cyclization.

Figures 7A, 7B:
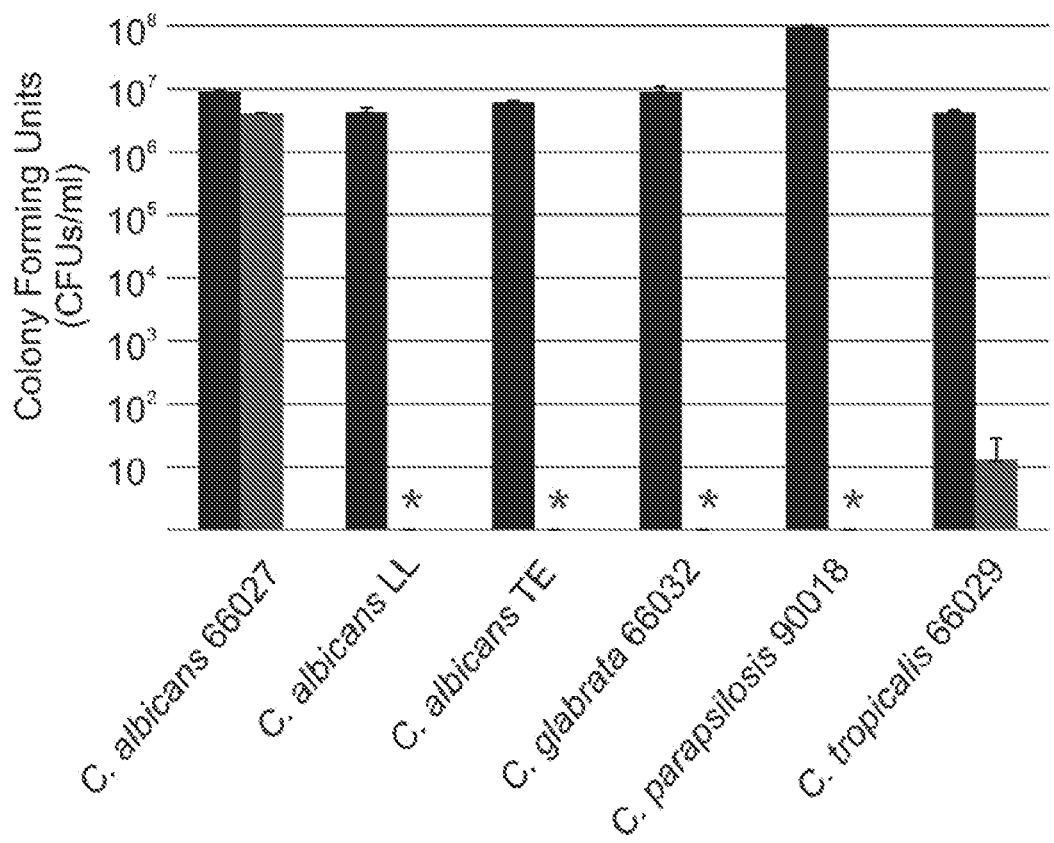

Comparison of the Bioactivity of the Wild-type and ocfN Mutant Product. To determine whether the increase in conformational diversity is important for bioactivity, minimum inhibitory concentrations were determined against medically relevant *Candida* species (FIG. 7A). There was a 2-fold decrease in the minimum inhibitory concentration (MIC) with the purified ocfN mutant product with respect to the wild-type product against *Candida albicans* LL, *Candida albicans* IL, *Candida glabrata* ATCC66032, *Candida parapsilosis* ATCC90018, and *Candida tropicalis* ATCC66029. There was no difference in the MIC for *Candida albicans* ATCC66027. Colony forming units (CFUs/mL) were determined for the MIC wells of wild-type product for each *Candida* species and compared to the corresponding well containing the same concentration of the ocfN mutant product (FIG. 7B). Following exposure to the same concentration of wild-type and ocfN mutant products, these results show a 5 to 7-log decrease in cell density of the *Candida* species treated with wild-type product. The differences in activity are also visualized by the rate of cell death. Time-kill experiments were performed against *Candida glabrata* ATCC66032. There was a ten-fold difference in yeast present at 4 and 8 hours when cells were treated with 0.5 µg/mL of occidiofungin derived from ocfN mutant MS14GG88 or wild-type strain (FIG. 15). Furthermore, a slower rate of cell death was also observed for yeast treated with occidiofungin derived from ocfN mutant MS14GG88 at 1.0 and 2.0 µg/mL. Given that the cyclic occidiofungin variants produced by OcfN constitute less than half of the total structural variants, a 2-fold loss in activity suggests that the configurational isomer made by OcfN are 4-fold more active than the stereoisomer produced by OcfD against five of the *Candida* species tested. Another possible explanation for the observed differences in activity could be attributed to possible synergism between the configurational isomers produced by each cyclase thioesterase. Furthermore, the antifungal activity of the ocfN mutant (MS14GG88: 8.79±0.38 mm) was also significantly reduced (P<0.05) compared to wild-type activity (inhibitory zone radius±SEM: 13.00±0.58 mm) in an overlay assay against *Geotrichum candidum* (FIGS. 8A-8C).

General Discussion. The findings from this study include experiments showing the following: the relative proportion of the Asn1 and BHN1 variants in the purified fraction; distinct differences in spin systems for the wild-type and ocfN mutant products; proposed model for the coordinated function of two cyclase thioesterases; and demonstrated differences in biological activity of wild-type and ocfN mutant products against therapeutically relevant *Candida* species. Expanding the conformational repertoire of cyclic peptide natural products can be beneficial to microorganisms. These data suggest that the bacterium *Burkholderia contaminans* MS14 is benefited by maintaining two distinct cyclase thioesterases that improves the spectrum of activity of occidiofungin.

Our data support the observation that cyclase thioesterase substrate recognition occurs prior to the catalytic transfer of the peptide. The presence or absence of a hydroxyl group on the beta carbon of the N-terminal amino acid (Asn1) appears to be important for the substrate recognition by the two cyclase thioesterases. It has also been shown that the N-terminal amino acid is important for substrate recognition for other thioesterases.[4, 8] It is possible that the presence of the hydroxyl group promotes a hydrogen bond with the ocfD cyclase thioesterase domain or more likely promotes an interaction within the T domain of the NRPS. Different bound orientations of the peptide to the T domain would establish a basis for the coordinated function of two cyclase thioesterases. It is also possible that the enzymatic conversion of one of the residues between L- and D-isomers is not completed by one of the epimerization domains. A combination of differences in the N-terminal amino acid and a possible difference in amino acid configuration (L or D), may contribute to the selective differences by the cyclase thioesterases that result in the formation of the observed configurational isomers.

The presence of the hydroxyl group on the beta carbon and the bound orientation of the peptide to the T domain may prevent the interaction of the OcfN cyclase, while enabling the continued substrate recognition by OcfD TE domain. There is evidence for the need of a bound orientation of the peptide to the T domain for the successful function of the cyclase thioesterase. Conformational diversity of the T domain has been shown to be important for the directed movement of the peptide substrate bound to the ppan cofactor and its interaction with externally acting enzymes.[3] More specifically, the active site serine of the cyclase thioesterase needs to attack the linear peptide attached by a thioester linkage to the ppan forming an acyl-O-TE intermediate. The position of the peptide bound to the ppan in the T domain will be important for bringing the peptide substrate in proximity of the appropriate cyclase thioesterase.

Furthermore, some cyclase thioesterases are capable of transacylation of the peptide to the active site serine, when the peptide is bound to a biomimetic prosthetic group.[4, 16] However, there are several cyclase thioesterases that will not function when the product is bound to a biomimetic group. These data suggest that the interaction of the peptide with the T domain is important for the enzymatic activity of some thioesterases and this interaction cannot be mimicked using a prosthetic group. It is conceivable that the coordinated function of the two cyclase thioesterases, involved in the synthesis of occidiofungin, utilize differences in the interaction of the ppan bound peptide within the T domain.

Presumably, ocfN was integrated into the occidiofungin biosynthetic gene cluster to improve its spectrum of activity against fungi. Given the broad spectrum of antifungal activity associated with occidiofungin, the molecular target is likely to be highly conserved. However, there must be some variation among fungal species to account for the differences in biological activity. Increasing the conformational repertoire must be a selective advantage to the bacterium for it to maintain the two functional cyclase thioesterases. The microbial environment is considerably different than how we intend to apply the natural products produced by microorganisms. For instance, the bacterium *Streptomyces roseosporus* is a soil saprotroph responsible for the production of daptomycin.[31, 32] The microbial community that this bacterium encounters is far more diverse than the group of bacteria that cause human infection. Thus, evolutionary pressures that selected for the current conformers of daptomycin may not necessarily be the best conformers for treating a *Staphylococcus aureus* infection. It is very likely that the therapeutic application of daptomycin or other cyclic peptide drugs could be improved by engineering novel conformational or configurational isomers.

Creating novel diastereomers of other cyclic peptide drugs using new or engineered cyclase thioesterases may lead to improvements in their therapeutic activity against clinically relevant pathogens. This is true for occidiofungin produced by the bacterium *Burkholderia contaminans* MS14, which accomplishes this goal by the evolutionary integration of an additional cyclase thioesterase into the occidiofungin biosynthetic gene cluster.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Experimental Section

Materials. Occidiofungin produced by both the wild type strain MS14 and the ocfN mutant MS14GG88 were purified as previously described for the wild-type sample.[23] Chemicals were purchased from Sigma-Aldrich (St. Louis, Missouri) and were the highest grade, unless otherwise stated. Media were purchased from Fisher Scientific, enzymes were purchased from New England BioLabs, and primers were purchased from Integrated DNA Technologies (IDT) unless otherwise stated. *Candida* strains used were purchased from the ATCC biological resource center and were a gift from Thomas Edlind (Drexel University College of Medicine).

Site Directed Mutagenesis. A nonpolar mutation was constructed in the open reading frame of wild-type ocfN by the insertion of a kanamycin resistance gene, nptII.[33] To mutate ocfN, a 1-kb fragment containing ocfN was obtained by PCR using primers MocfNF (5'-CGCCACCCGT-TACGAGGATTC, SEQ ID NO: 1) and MocfNR (5'-ACGCGTCCCCTCTTCCTACG, SEQ ID NO: 2). The 1-kb PCR product was cloned into the pGEM-T Easy Vector System I (Promega Corporation, Madison, WI) resulting in plasmid pGG30. The nptII gene was inserted into the cloned ocfN at SmaI, generating plasmid pGG31. The kb EcoRI fragment of pGG31 harboring the ocfN gene disrupted by insertion of nptII was cloned into pBR325[34] at the EcoRI site to generate pGG32. Mutagenesis of the ocfN gene was conducted via a marker exchange procedure as described previously[35], to generate the mutant MS14GG88. PCR analysis and sequencing were used to verify the double crossover mutants. Production and purification of the antifungal were done as previously described.[23]

NMR spectroscopy. A 2 mM sample of ocfN thioesterase mutant fraction of occidiofungin was prepared in dimethyl sulfoxide (DMSO-d6, Cambridge Isotopes) and data were collected as previously described for the wild-type fraction.[22] The NMR data were collected on a Bruker Advance DRX spectrometer, equipped with a CryoProbe, operating at a proton frequency of 600 MHz. The $^1$H resonances were assigned according to standard methods[36] using COSY (correlation spectroscopy), TOCSY (total correlation spectroscopy), NOESY (nuclear overhauser effect spectroscopy) and $^{13}$C-HSQC (heteronuclear single quantum coherence) experiments. NMR experiments were collected at 25° C. The carrier frequency was centered on the residual water resonance (3.333 ppm), which was suppressed minimally using standard presaturation methods. A 2.0 s relaxation delay was used between scans. The TOCSY experiment was acquired with a 60 ms mixing time using the Bruker DIPSI-2 spinlock sequence. The NOESY experiment was acquired with 400 ms mixing time. The parameters for collecting the HSQC spectrum were optimized to observe aliphatic and aromatic CH groups. The spectral sweep width for the TOCSY and NOESY was 11.35 ppm in both dimensions. The spectral sweep widths for HSQC were 11.35 ppm in the proton dimensions and 0 and 85 ppm for the carbon dimension. All 2D data were collected with 2048 complex points in the acquisition dimension and 256 complex points for the indirect dimensions, except for the HSQC which was collected with 2048 and 128 complex points in the direct and indirect dimension, respectively. Phase sensitive indirect detection for NOESY, TOCSY, and COSY experiments was achieved using the standard Bruker pulse sequences. $_1$H chemical shifts were referenced to the residual water peak (3.33 ppm). Data were processed with nmrPipe[37] by first removing the residual water signal by deconvolution, multiplying the data in both dimensions by a squared sinebell function with 45 or 60 degree shifts (for the $^1$H dimension of HSQC), zerofilling once, Fourier transformation, and baseline correction. Data were analyzed with the interactive computer program NMRView.[38] One-dimensional NMR temperature titrations were collected on the wild type and mutant peptides, using a Bruker AVANCE III HD 600 MHz spectrometer equipped with a cryoprobe. Eight scans were collected in each 1-D experiment, using 32K points, at a temperature of 298 K. The experiments were repeated using higher temperatures for both samples in 5 degrees K increments, up to a temperature of 323 K. 2-D TOCSY spectra were collected at a temperature of 323 K, using a mixing time of 60 milliseconds. Eight scans and 256 indirect points were used for both the wild type and mutant peptides. The 2-D spectra were processed using NMRPipe, with 45 degree sinebell squared shifts in both dimensions.

Mass Spectrometry. The wild-type occidiofungin and the ocfN mutant sample (10 μg) were evaporated to dryness in a Speed Vac Concentrator (ThermoScientific, San Jose, CA) and the residue was taken up in 50 μl methanol and analyzed by direct infusion at 3 μl/minutes into an LCQ DecaXP (ThermoScientific, San Jose, CA). Data were acquired over a mass range of m/z 200 to 2000.

In Vitro Susceptibility Testing. Microdilution broth susceptibility testing was performed in triplicate according to the CLSI M27-A3 method in RPMI (Roswell Park Memorial Institute) 1640 [buffered to a pH of 7.0 with MOPS (morpholinepropanesulfonic acid)] growth medium. 100× stock solutions of occidiofungin were prepared in dimethyl sulfoxide (DMSO). MIC endpoints for occidiofungin were determined by visual inspection and were based on the wells that had no visible growth (an optically clear well) after 24 hours of incubation. DMSO containing no antifungal agent was used as a negative control. Colony forming units (CFUs) were determined in triplicate by plating 100 μl from the MIC wells onto a Yeast Peptone Dextrose (YPD) plate as well as plating 100 μl from 10-fold serial dilutions of the cell suspension in Yeast Peptone Dextrose (YPD) Broth. Colony counts were performed and reported as CFUs/ml. Time-kill experiments were performed as previously reported.[19] *Candida glabrata* (ATCC 66032) colonies on 24-h-old YPD plates were suspended in 9 ml of sterile water. The density was adjusted to a 0.5 McFarland standard and was diluted 10-fold with RPMI 1640 medium to a final volume of 10 ml containing a final concentration of 2, 1, 0.5 and 0 μg/ml of occidiofungin from wild type strain MS14 and the ocfN mutant MS14GG88. The cultures were incubated at 35° C. with agitation. Samples were drawn, serially diluted, and plated on YPD medium for colony counts.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

Chemical Shift Values for Occidiofungin derived from

| Unit | No. | $\delta_C$ | $\delta_H$ |
|---|---|---|---|
| Asn1 | 2 | 52.71, CH | 4.59 |
| | 2-NH | | 7.75 |
| | 3 | 39.91, CH2 | 2.62, 2.41 |
| | 4 | — | |
| | 4-NH2 | | 7.39, 6.93 |
| BHN1 | 2 | 58.47, CH | 4.66, 4.61 |
| | 2-NH | | 7.81, 7.9 |
| | 3 | 75.01, C | 3.98, 4.02 |
| | 3-OH | | 4.66 |
| | 4 | — | |
| | 4-NH2 | | 7.24 |
| NAA2 | 2 | 43.88, CH2 | 2.34, 2.36 |
| | 3 | 47.25, CH | 4.23 |
| | 3-NH | | 7.31, 7.34 |
| | 4 | 41.57, CH2 | 1.39, 1.76 |
| | 5 | 66.36, CH | 3.50 |
| | 6 | 76.07, CH | 3.08 |
| | 7 | 79.61, CH | 3.72 |
| | 8 | 33.19, CH2 | 1.54 |
| | 9-17 | 25.14-28.02, CH2 | 1.27 |
| | 18 | 16.94, CH3 | 0.86 |
| Ser3 | 2 | 58.59, CH | 4.07, 4.15 |
| | 2-NH | | 8.11, 8.14 |
| | 3 | 70.23, 64.29 | 3.49, 3.45 |
| | 3-OH | | 4.95 |
| BHY4 | 2 | 58.71, CH | 4.06, 4.15 |
| | 2-NH | | 7.83, 7.94 |
| | 3 | 73.75, CH | 4.98, 5.08 |
| | 3-OH | | 5.66, 5.73 |
| | 4 | — | |
| | 5, 6 | — | 7.15 |
| | 8, 9 | — | 6.67 |
| DABA5 | 2 | 53.49, CH | 4.43 |
| | 2-NH2 | | 7.66 |
| | 3 | 32.68, CH2 | 1.88, 2.11 |
| | 4 | 39.17, CH2 | 2.92 |
| | 4, NH | | 7.71 |
| Gly6 | 2 | 44.76, CH2 | 3.87, 3.58, 3.84, 3.70 |
| | 2-NH | | 7.68, 7.85 |
| Asn7 | 2 | 53.25, CH | 4.51, 4.58 |
| | 2-NH | | 8.35, 8.41 |
| | 3 | 40.03, CH2 | 2.61, 2.38 |
| | 4 | — | |
| | 4-NH2 | | 7.39, 6.93 |
| Ser8 | 2 | 58.11, CH | 4.33, 4.32 |
| | 2-NH | | 7.76, 7.78 |
| | 3 | 64.59 | 3.61, 3.62 |
| | 3-OH | | 4.79 |

[a] Proton chemical shift values are from a TOCSY and NOESY experiments. Chemical shifts in brackets are $^{13}$C values from the HSQC experiment.

```
GenBank: EU938698.5
LOCUS       EU938698               58101 bp    DNA     linear   BCT 13-DEC-2010
DEFINITION  Burkholderia contaminans strain MS14 putative FAD linked
            oxidase domain protein gene, partial cds; and putative
            LuxR-type regulator (ambR1), putative LuxR-type regulator
            (ambR2), putative cyclic peptide transporter, hypothetical
            protein, putative glycosyl transferase, putative
            nonribosomal peptide synthetases, putative beta-lactamase
            domain protein, putative beta-ketoacyl synthase
            nonribosomal peptide synthetase, putative short chain
            dehydrogenase/reductase SDR, putative beta-ketoacyl
            synthetase, putative taurine catabolism dioxygenase,
            putative transaminase, putative epemerase/dehydratase,
            putative thioesterase, and hypothetical protein genes,
            complete cds.
ACCESSION   EU938698
VERSION     EU938698.5  GI:314950578
KEYWORDS    .
SOURCE      Burkholderia contaminans
  ORGANISM  Burkholderia contaminans
            Bacteria; Proteobacteria; Betaproteobacteria;
            Burkholderiales; Burkholderiaceae; Burkholderia;
            Burkholderia cepacia complex.
REFERENCE   1  (bases 1 to 58101)
  AUTHORS   Gu,G., Smith,L., Wang,N., Wang,H. and Lu,S.E.
  TITLE     Biosynthesis of an antifungal oligopeptide in Burkholderia
            contaminans strain M14
  JOURNAL   Biochem. Biophys. Res. Commun. 380 (2), 328-332 (2009)
  PUBMED    19167363
REFERENCE   2  (bases 1 to 58101)
  AUTHORS   Gu,G., Wang,N., Chaney,N., Smith,L. and Lu,S.E.
  TITLE     AmbR1 is a key transcriptional regulator for production of
            antifungal activity of Burkholderia contaminans strain MS14
  JOURNAL   FEMS Microbiol. Lett. 297 (1), 54-60 (2009)
  PUBMED    19500142
REFERENCE   3  (bases 1 to 58101)
  AUTHORS   Gu,G., Smith,L., Wang,N., Wang,H. and Lu,S.
  TITLE     Direct Submission
  JOURNAL   Submitted (01-AUG-2008) Entomology and Plant Pathology,
            Mississippi State University, 32 Creelman St., Mississippi
            State, MS 39762, USA
REFERENCE   4  (bases 1 to 58101)
  AUTHORS   Gu,G., Smith,L., Wang,N., Wang,H. and Lu,S.
  TITLE     Direct Submission
  JOURNAL   Submitted (12-NOV-2008) Entomology and Plant Pathology,
            Mississippi State University, 32 Creelman St., Mississippi
            State, MS 39762, USA
  REMARK    Sequence update by submitter
REFERENCE   5  (bases 1 to 58101)
  AUTHORS   Gu,G., Smith,L., Wang,N., Wang,H. and Lu,S.
  TITLE     Direct Submission
  JOURNAL   Submitted (15-JAN-2009) Entomology and Plant Pathology,
            Mississippi State University, 32 Creelman St., Mississippi
```

|           |                                              |
|-----------|----------------------------------------------|
|           | State, MS 39762, USA                         |
| REMARK    | Sequence update by submitter                 |
| REFERENCE | 6 (bases 1 to 58101)                         |
| AUTHORS   | Gu,G., Smith,L., Wang,N., Wang,H. and Lu,S.  |
| TITLE     | Direct Submission                            |
| JOURNAL   | Submitted (24-FEB-2009) Entomology and Plant Pathology, Mississippi State University, 32 Creelman St., Mississippi State, MS 39762, USA |
| REMARK    | Sequence update by submitter                 |
| REFERENCE | 7 (bases 1 to 58101)                         |
| AUTHORS   | Gu,G., Smith,L., Wang,N., Wang,H. and Lu,S.  |
| TITLE     | Direct Submission                            |
| JOURNAL   | Submitted (13-DEC-2010) Entomology and Plant Pathology, Mississippi State University, 32 Creelman St., Mississippi State, MS 39762, USA |
| REMARK    | Sequence update by submitter                 |
| COMMENT   | On Dec 13, 2010 this sequence version replaced gi:224016442. |
| FEATURES  | Location/Qualifiers                          |
| source    | 1..58101<br>/organism = "*Burkholderia* contaminans"<br>/mol_type = "genomic DNA"/strain = "MS14"<br>/db_xref = "taxon:488447" |
| CDS       | complement(<1..1175)<br>/note = "ORF1"<br>/codon_start = 1<br>/transl_table = 11<br>/product = "putative FAD linked oxidase domain protein"<br>/protein_id = "ACN32485.1"<br>/db_xref = "GI:224016443" |

/translation = "MSHDFRDEPAPRRAFLADMAKLAAAGIVTGWTPLYQVAAHARTA
GETPPGFPADIQLYKQAFLNWSGEIAVQDVWTAAPRSADDVVATVNWARANGYRIRPR
GYTHNWSPLTLDPGAGAANLVLLDTTKSLTAVSVDTSARPARVTAQTGVSLESLLATL
EQVGLGVIAAPAPGDITLGGALAIDAHGTAVPAAGETLQPGHTYGSLSNLVVALTAVV
FDPARQQYVLRRFERSDPEIGAFLAHIGRALVVEVTLTAGPNQRLRCQSYVDIPASEL
FAAPGTTGRTIASFLDGSGRVEAIWFPFTTKPWLKVWTPTPSKPFLSRAVTQPYNYPF
SDSISQSISDLVKRIVIGGEGALTPLFGQTQLAITTAGLALTLSGDIWGWSRTVLQE" (SEQ ID NO:
5)

|      |                                              |
|------|----------------------------------------------|
| gene | 2480..3301<br>/gene = "ambR1"                |
| CDS  | 2480..3301<br>/gene = "ambR1"<br>/note = "AmbR1"<br>/codon_start = 1<br>/transl_table = 11<br>/product = "putative LuxR-type regulator"<br>/protein_id = "ACN32486.1"<br>/db_xref = "GI:224016444" |

/translation = "MFAKLGKVISSAGSERFASDMHALLVESIPLTITRMTEWTLDEP
AGEVVRVQSLGADGAPGDDGRGAPAAHGEREPAAHPPLNRILAACDRQLIHINPLMRR
GNGGEVAPSRGPGGGFQCHLVSGKANRRYVISLHRTASHRDFSLREMSFLKNFADTLL
PLVEWHASTCRHGEREGATAPGATAGMPGVEALRHEFESRLARARVVLSARENEVCLG
LLAGKMLREMAGELGVKESTIETYIKRAAVKLGISGRHGLTKWMIDDSVPCASAA" (SEQ ID NO:
6)

|      |                                              |
|------|----------------------------------------------|
| gene | complement(3372..4262)<br>/gene = "ambR2"    |
| CDS  | complement(3372..4262)<br>/gene = "ambR2"    |

```
                    /note = "AmbR2"
                    /codon_start = 1
                    /transl_table = 11
                    /product = "putative LuxR-type regulator"
                    /protein_id = "ACI01437.2"
                    /db_xref = "GI:212381179"

/translation = "MEFSRLFAHVGEAISSSGSRRFPRMMYNLIAAAVPVDEIRISEL
AIDDVPDGPPEVRSLGAVGAALAKTGAAAVCCGPQMPPRPGTSPLHVDDTLAGHGPIH
AQLDRFILMQAAIVSPRYAQFHLVTRKRGHCYVISLYRTCTFDDFSPQERTFLKELSH
VLFPIVESHVAALDSAPPAARVTTAAPPATQSGRERVARRFADRLQQAGVKLSTREIE
ACTALLAGDTVPAIAMRFALRESTVETYLKRAAVKLGFSGRHGLTRWMLDETAGAATE
AAGGDMRSMRRDYASPRLGT" (SEQ ID NO: 7)

CDS             complement(4466..6169)
                    /note = "ORF2"
                    /codon_start = 1
                    /transl_table = 11
                    /product = "putative cyclic peptide transporter"
                    /protein_id = "ACJ24909.2"
                    /db_xref = "GI:220898663"

/translation = "MDSAQSKSPPWHSAATLMWRSHPWLTLGTVVTGLVSGIASIAGV
GLISTVLHDQDDRQTLLLLFIAVNVVAVVCRSCAAVMPSYACMKVMTRLRVNLCKRIL
ATPLDEIDRRGAPNVLTMLTQDIPQLSQTLLTIPTIIVQSVVLICSIAYLAYLSWIVF
ASTIILTLVGLVLYLFFYRKAVNFTERVRDEFVQFNEYTHGLVFGIKELKLNRARRRW
FTRAAIELSSKRVAGFNYIERFWFMSGDSIGQITVAVLLGCLLFGVPSLGVVDPSVLT
ASILAVLYMMGPLTMLINVLPVVAEGKTALARLAEFGFLIDDTQASHEEPRPAGNVET
LSAKSWKVIELKDVTMNYRDNEASVDFVLGPIDMTIHAGELVYVIGGNGSGKSTLGKV
LSGLYAPTGGTISLDGKVVDDAARERYRNLFSAVFTDFHLFNRIIGPDRGNESIELAR
KYLATLKLADKIEISGRTYSTTRALSTGQRKRLALLCAYIEDRPIYILDEWAADQDPV
FKRFSYEVLVPDLKSRGKCVVIITHDDQYFKLADRVIRLDSGRIFSDTAMCAVRAEAAG" (SEQ ID
NO: 8)

CDS             complement(6186..6668)
                    /note = "ORF3"
                    /codon_start = 1
                    /transl_table = 11
                    /product = "hypothetical protein"
                    /protein_id = "ACL81525.1"
                    /db_xref = "GI:220898664"

/translation = "MQLTTVDLEAAFVKAALDALHRDCKLGDAISLAYGKCESTAGVI
DLIFPLITKKLRIDYILMYSIESNPRTLLQFLRQIESGLARSEDWTAASVEAALRSVA
DSPDGVGWERAQRLLKCCILFSDSPLGIVESITFLGKHETSSRLRSAASNVELSHLIN" (SEQ ID
NO: 9)

CDS             complement(6722..7378)
                    /note = "ORF4"
                    /codon_start = 1
                    /transl_table = 11
                    /product = "putative glycosyl transferase"
                    /protein_id = "ACL81526.1"
                    /db_xref = "GI:220898665"

/translation = "MKSTPTIDNTFARKVCINLDRRPDRWEAMQRKFAEQNILTVERL
PAVDARLVSVPESLSHMRAQDYGCTMSHLAAVKQAKAAGAREVLIFEDDAFFDADFAA
RFPEFIAQVPDDWHMLFLGAYHFTPPIPVAPNIVKAVETLTAHAYVVRNSLYDAFIAI
NENPPAINDRNNLVLQQTFNCYCFEPNLVGQESGYSDIMDEVMPEKPLTYSMPIPDGW" (SEQ ID
NO: 10)

CDS             complement(7375..16869)
                    /note = "ORF5"
                    /codon_start = 1
                    /transl_table = 11
                    /product = "putative nonribosomal peptide synthetase"
                    /protein_id = "ACL81527.1"
                    /db_xref = "GI:220898666"

/translation = "MQDNNVLVTDHRYAATARFWRESLSRVAGVYGIAAYAPSQQPGR
PLTRSVRLTPASLDLLRRIGDGELAEFAVAAAGIAFLLWKYFRIPVTVLGTPGLAGHP
SARAAIVPLIIEVRPDERIEDYLSRVAGIVEDSYAEPRFPLETLVRNEKDMALAQLTK
VALADDRVHHAPTGRDDDLQLHLRLARGEIELRYSGAIEPFIIDGFAGSLAAVLEAFE
HLDGAVGDIEAAPPEQGPLLAAFNETATAGPSHPTVVAMFEAQVARTPTAPALVTDSS
LMTYADLNARANSLAHHLREHHGVGPESLVGIMLDRSEWMIVAILGILKAGAAFVPLD
PAYPAERINHILGDTGLSLLVTQSSQLAQWYEFSGVTLLLDQELPGWQPLPDNPPHRA
EPAHLAYVLYTSGSTGKPKGCLLEHRNLAHYIAWAAGYYFPESTTGSFGLYSSLCFDF
TLTNIFCPLVRGKTLRIYPQSESIDTILARMFQPGSGVDTLKLTPTHIHLLEYMNLAR
SGVRKVIVGGEELTPQHIATLRKIDPAIEIYNEYGPTEATVGCIVERVEDAPPTVLIG
```

-continued

```
RPIADTRVYMLDDALRPVPLGVPGEICLAGAGLARGYHQRPDVTAAKFVEHPFPGEAR
IYRTGDIGRWLPDGRIQCYGRVDHQVKIRGHRVELGEIEAAIAAHEDVVGAAVMLRES
AHGVRKLAAYVKGAASLSVPNLRAYLAGKLPDYMVPSDIIPIAEFPLNANGKLDRPAL
LALEPAAAPEEAPLDATPIQRELVRIWRDVLDNPAVDLAGRFFDYGGDSLQAMQLVSR
IWSSFSVEIGIDAIFELQTISAVSDLIEASSPHPGSTAGAIPPRSRANDLPLSFPQQR
LWFLAQLEGPSATYNISSALRFEGELDVARLRFAVSEISRRHEILRTTFPAVDGRGVQ
RIAPPAPVALDVVDVASESDTLALLAEEADRPFDLAAGPLYRVVLYRVHERLHVFGIV
MHHIVSDAWSSGILIGELAALYAGESLPELAVQYADYAVWQHERLASADTHRELALLS
AALADAPDLIELPTDRPRPAVQQFRGAVLPFQLSAERADGLRAIARASGTSTFMVVLA
AYALLLSRYSNQQDLVIGSPIANRRSSMTEPLIGFFANMLALRVDLSGNPTFGDLLAR
VKRVALDGYSRQEIPFEQVVDSLELERNLGRTPVFQVVFAYEKAQPRAVSFPGLVATP
VAVETHTAKFDLTLHVQDADDGLAGSLEYNLDLFDAATIDRMAEHFRTLVDAVIADPD
RPLGALSLSNDAERNLLTVEWNRTDTDFGEDAAQPLHRLFEQQVERTPDAVAIVFDDT
ALTYAELNLRANRLAHHLVALGVGPDSLVGVAMERSLDMSVALLAILKAGGAYVPVDP
DYPAERVRFMIDHAQLRWLLTQQHLHDALPDTDAHVIVVDRDSLDLDAAATSNPAPAL
NGDNLAYMIYTSGSTGRPKGALNTHRAITNRILWMQHAYALDADDAVLQKTPFSFDVS
VWELFWPLVTGARLVFARPGGQRETDYLVELIERERITTIHFVPSMLRAFLDHPDLDA
HCASLRRVVCSGEALPHDLQQRCLERLDVKLYNLYGPTEAAVDVTAWECRRDDPHRIV
PIGRPIANTRLYIVDAQMQPTPIGVAGELLIGGTPVGRGYHGEPELSAEKFIADPFSA
DPLARLYRTGDLARYRPDGNIEFLGRIDHQIKLRGLRIEPGEIEAALRAHPSVDDCVV
IAKTEGARTFLIAYVATAAPDIADLRGYLGGKLADYMVPSQFFALESLPMLPNGKINR
KALPLPADRGDAAQPHAPAVTPREILLASICIDVLQLPSVGIHDNFFELGGDSILSIQ
VIARANQAGLRVTAKQLFQYQTIAQLAAAPEERAACAPTLSPLGDAPLTPVQHWFFEQ
EIDAPSHYNQTVLIQVPADIDASRLADAFRQVYEHHDALRLRFSHDAGRWTQQVVAGG
EMPALFAKQVIADDAGERLAAMRAAAADAERGIDITHGPLLAARLFCLADEPLARLFV
SIHHLAVDGVSWRVLLEDLHAAYHGQPLPGKTTSFREWALHLQQLARSPAIGDEARLW
QALLAQPVEPMPVDYPGTGAANNAVDDASSVSFELGEADTTALLRRLPRAYDTRINDV
LLVALAQACSMVTGNTRTRIDLESHGRHVSDAPLDLTRTVGWFTSIYPVVLDADAMHA
PEQALRAARQQLRRIPADGLGYSLLRYQSPDAAVRDSLAALPKADILFNYHGQLDTVL
RQSDGWRPAAEDLGSLRAGRSQRTHAFEIVAAVADGKLQVDWRYGERLHRRQTVENLA
AHFRDRLLDFAASVPDTAADDIEDSYPLSSLQQGILFHSLYDLDPAAYFQQFSFVVSG
PLQVPALRQAWANALARHAVLRTAFAWADRDHPVQTVRHTVDLPWTFLDWRHRDASRR
AQDFDAFLADDRRRGFDLQRAPLFRCTLIQETDTRHRFCWSAHHIILDGWSTATLMKE
VFDDYLSLARTGMPAVAASAPGYRAYIDWLARHPRSADETWWRAELAGFKAATPVAAS
PARQATGDAPRQDKRRTQQFLLDEALAARLQTLTRTHRVTLNVLIRAVWALVLRRHAG
TDDVVFGVTVSGRPPMLDGVESIVGLFINTLPLRLRIAPERPFIEWLAEVHAAQTAME
PHSYSSLVDIQSWSELPAGDSLFDSLLVFENFPVAAAPDLGPDDIEILDTRAFAESNY
PLTLTVHPNERIGFHISHDAHRIAPEVVRQMLDTLRTLLERFAENPGQLTGQLADPPA
ADGRPSAPRSGAPPAIEAAAGAAAAARAVAHAADESTLLEIWRRIFKRDDIAVSDNYF
DLGGHSIIAIQLMAHVEKAFDRRLPISCLFENPTIEKLAAALAAKEPSAPAGGLVPIR
DGGPAAPLFLLPGAGGNVVYFRPLANHLSGAHAIHGLEALGLDGACEPLTRVEDIAAR
HIERIWPLVGAGPYYLAGHSFGAHVALEMSRQLVAKGADVKLLAIFDASAPIDSSAAT
YWQDWDDTEWLVAIAHEIGTFLGTDLQVTRADLVHLDPDGQAGLILERIGDRGSWFAD
AGSDRLRAYLRVYQANFKSHYAPHATPLPVPIALFRSTERDPGDYAPSSEIAQLRLDA
TWGWSRFSAHPVAVTDVPGDHLTMLLDPHAGVLAAHVNSFLEKTPS" (SEQ ID NO: 11)
```

```
CDS             complement(16957..26022)
                /note = "ORF6"
                /codon_start = 1
                /transl_table = 11
                /product = "putative nonribosomal peptide synthetase"
                /protein_id = "ACL81528.1"
                /db_xref = "GI:220898667"
```

```
/translation = "MQEGMLFHAVHEPGSRSSFNQLSCRITGSLDPALFHAAWQQLID
RHPVMRTSFHWEEFDKPMQVVHARATLPWVQDDWLDLPEHEQRSRWRAHLDNDLAEGF
ALDRAPLVRCRLVRVAADAYLFSWSHHHILADGWCLSLVIEEIFEVYGALARGVSPAL
PPVRPYRDYIQWLQQHEPQAAQQYWTRYLEGFRTPTPLPTAARAGADERFGQGLAQVQ
ADLSADLSARLRQFAARHHVTLNTLAQAAWALVLSRYSGETDVVFGAVVSGRGANLPG
IETMLGLFINTVPVRVRVDPRQPLVPWLKMIQARVAARAPFEHTPLPDIQRCSDVPPT
APLFESNITFMNYPLDASLTHGAHGLAVDEVQLYNRADIPLEFVVTARDDWKMELSFD
PRRRFDEDTMQRMLGHVAATLDAFAADPNRLLGRVPILPDAERRQLLETFNDTAVPFDA
ALTVVHRLEQAAADHPERPAVEYRDGVLSAGELNARANRIAHRLLAAADLGPDALVAI
CMHRSAQLMEAILAVWKCGAAYIPVDPNYPVARIRTILEDSGAALVITCDGLLPPELA
GIALVVSLDAATDAVDDSNPGRPVSPDSLAYVIYTSGSTGKPKGAMVEHAGMLNHMLA
EIDEFSISASSVIAQTAPHCFDISVWQFFTAPLVGGKTVIVDDDCIRDPARFVAYLET
TRISILELVPSYLSAVLDRASERPALMRHLRHLLVTGEMVSPALVKQWFDVFPAIPLV
NAYGPAEASDDVAQHRMTGAPSTPYVPVGKPIRNVRLYVVDPQMNLCPIGIPGELCVS
GVAVGRGYLNNEAATQDAFVEDPFHPQRGVRLYRTRDIGCYLPDGTIVLHGRKDHQLK
IRGYRIELGEIDQRRLADHSRKLRQAAALDYRDEAGRAALCAYVAFRDGASLSDAGIA
AALSATLPDYMVPGIYVVLDALPLSGNGKIDRNALPPLDRARLAATAHAPTPPRTPTE
TLLCRIWGEALGIPSPGIHDNLFALGGDSILSMRIVSLAAKAGLKLTTRLIFQHPTVA
ELAAVATRGTVGAAAFVASSGPLPLTPIQKRFFAQGKHDPDQYNQAVLLDVPADLDPV
LLRQALRHAVKWHDALRLRFREGESGWTQEVVDDPEIPVVVSDIARDQLAQYVAQSHA
SLNLADGPVVRADLFRVDEGRSLRLLLVAHHLVVDGVSWGALLETVYDAYTRLRNGKA
PEFAGGSATWTAWTRAISTWAGSGAADADLAHWQALARAALPGLPLDRDAPADANTVS
SADTIVVELGEAATTALLGAAPRAYDAQVNDVLLAALARAVSEWSGCADVLLDLEAHG
REELIDALDISRTVGWFTSVFPVLLTVDAGSHDPASLVASVRTRLRAVPNAGITYGLL
LDRLDGPLPQPRLQFNYLGQTDQLFTAARDWKQAAEPSGDGRNANQLREHLLDINAYV
```

```
TGNRLHVAWEFSRACHDTATILRVAQAYIAALETLVAGHAVPSASTRPATALPQAPAP
ASVSPDEIADVYPLTPTQQGMLFHSLYEPASDAYFSSLNFRIDGALDVERFRRAWETV
AHRHDILRTSFHWEDIESPVQVVHRRIDLPWHDEDLRAASAAEAEQRWEAYVAQDRAR
GFDFTRAPLMRLALFRVGEHAWRFHWSHHHILLDGWSSARLLSDVAAAYQAPPAEGAP
QRDAPPAFAGYVRWLARQDAAAAQRFWKTKLADFPATTPLVLGRPELDGTAAPGAVYE
EPLLLSESDTQRLVAFAQSRRLTLNTLAQGAWAQLLSRYSGESDVVFGTIVSGRPASL
PASDEMVGLFINTLPVRVRIDARPTSAWLAQLQMDLAQQEDYAHYPLADIQKFAGLPP
GVPLFESLLIFQNYPVEEALADALPGLRIGAFEVSDPNNYPLTLVVTPGKRLSLQVLY
DDGRFDRDTIVRLLRHVETLLTGLAGAEDRPNRSVPLLAAAERDAILLGWNDTFAPVP
SDRTLPELIEAVAAAHPERVAVRCGTEVRTYRDLVEGANRIAAHLLQTAPLQPDDRIA
VWMPRSPLMLETILAIWKCGAAYVPVDPAYPAQRVETILTLARPAVIVTTDCVPPPAL
ASIPLVDPARLPDRRGAEAPAPVTPRCRPADLAYVIFTSGSTGQPKGAMVEHRGMLNH
VLAMARRVGLGAQSAVAQTASHCSDISVWQCFAALASGGTTVIYPDAVILEPARLIDS
LHRDRITAMQFVPSYLATFLGELERHAAPAFPHLDTLLTIGETLQPATAQAWFRLNPA
VRLINAYGPTEASDSVAHYCLTRAPDGPAIPIGRPIENLRLYVVDADMNPCPAGVKGE
ICIGGVGVGRGYLFDEARTRAVFRDDPFSPEPGARLYRTGDIGCFGADGNLHFFGRRD
FQVKIRGYRIELGEIEAALTSLAGISHAVVVARETSDAEMTLCGYASGTGWTPQRVRD
ALRDTLPAHMVPDTVMLLPALPVMPNGKINRAALPLPDAASVPDGVRAEPRTPVEAAL
LRLFAEVLGRRPNGVDDDFFEHGGQSLKAIQMVSRIPRAALNVAVADIFHAPTPRALA
QRLAAMPVDGAADDDAIIPALAAQPSYAVSRAQKRIWLASRGADPSTYNMAGALQLDG
AVDTARLVRAFDTLVDRHESLRTVFAMIEGELRQRVLSREASGFRVEQRDLADDAGPQ
AIDALIRAECEQPFDLASGPLFRVKLVRLSQEKHLLLLNMHHVISDAWSIRVLTDDLH
ALYAGRDLPPLSIQYRDYAAWHNASLAGPRAAAHRAYWLEQLAPPLPRLQLASDFPRP
ERLGHAGQTLEVELPQPHAAELATLARAHHTSLHAVLLASFCVLMHRYTGREDIVIGS
VSAGRDSEQLESQVGVYLNTVVLRVPVRKSATVAEVIDGVAKASAQALEHASYPFDVL
LEDLKIRTPANHFPIFDIQVNHVSMPAPQPGLRITDISPADTTAKFDLSFQVVESEGR
HLIQFIYNTHLFRPSTIAAMRDRLLAIHDVFRRDPATPVDRIPLSDEAPAAGPRVRVG
LRLKRAPAVTADDALEEKT" (SEQ ID NO: 12)

CDS             complement(26061..29981)
                /note = "ORF7"
                /codon_start = 1
                /transl_table = 11
                /product = "putative nonribosomal peptide synthetase"
                /protein_id = "ACN32487.1"
                /db_xref = "GI:224016445"

/translation = "MSELNLNALSTSGQYQEHVAFWNDALGRIDEDFRLQQAWQAYAL
PLGPEPALTFALDGDAAQVLERLAAGNELGAFVVLLAALFRVLGRYNGAAGLFVASPQ
LIVEPASGCAEPVPLLDAGEPGPTVRAYLNQLRDSVQRSYSYQDFPIAALAHKLHGER
RATNVGVRFDGLHEAWAAADYDLSIEIRHRERYEIVLTGRPTVFTLHYLQHVARHLRN
VVAGFGALDAPLDTVSLLDDEERARLRSHAAPVAVQGTFLEQFAQRVAAAPDSVAVVT
ADASLTYAELDDQASRLASFLLAEYAIERGDVVGVVADRSERWIVGMLGALKAGAVYL
PLDPEFPRERLRFMIEDAKVKALLTHSEHLPLLADFWAIPMFALDFQLDTLAPASASA
QVEVRPDDAAYIIYTSGSTGVPKGVVLEHAGLLNMAQYHVDAFGFDSADRFVQFYSPG
FDGSIMEIFVTLLAGARLVLAKTAVIRDVPRFVDYIAQQGVTTVNATPAYLAALDWHA
LGAVKRVISAGDSARVADLRELARTRTCHNSYGPTEATVCIADYVVDPAITYGARLPV
GRPIHNTHLYLLDEHGALAPEGCAGEICVSGIALARGYVGRDDLTAAAFVAHPFEAGE
RLYRTGDLGVWLPDGNLEVTGRRDTQVKIRGYRIEMGEIEAALRQHAGVADAIVFVRE
DTPQHKQLVACVATATASVASLREHLKERLPEFMVPASIVTLERLPLTPNGKPDRKAL
AALELAPAPSETAYVAPANDVEARLGRIMCDVLGREPIGVHDNFFELGGDSILIIQVM
SLAQQVGLKFTADQFFAHPTIAELAQVATEAPSIRIAQEPVVGPAPLTPIQHWFFAQD
VADPHHYNQSTMIEVPASLRPDTIERALAAVATHHDALRLSFACVAGVWQQSHAAPPL
AIPLGVTSLADAAPAARQAAMLATATGMQESFTLSAPPLLRAHLFQFGPDAPQRLLAV
AHHLVIDGVSWRILFEDLYTACRQLEAGDAVQLPARTTAWRDWSTRLSGLGATALDGL
GLDYWLQGNAGEPACFDDMPAGTVAEAGSTIVEFDAQQTLALLQDVPRAFNTQINEVL
LTALLLAFGDWTGNASLVVDLEGHGREDIFDGVDTSRTIGWFTTHYPVCLNAGDATVA
VDALRHVKEQLRAVPMRGLGYGIARYLGHDAGIAAALERQPPAPVRFNYLGQVDRVLP
DDTGWKPVLDFQSPEHSPRARRGHLFEIDGMVFDGRLRLTWHYNREACAPGVIEQLTQ
CYRSRLLSIVAAGGDGPRALSPSDFPAARISQEALDALVSRIKS" (SEQ ID NO: 13)

CDS             complement(29969..31585)
                /note = "ORF8"
                /codon_start = 1
                /transl_table = 11
                /product = "putative beta-lactamase domain protein"
                /protein_id = "ACN32488.1"
                /db_xref = "GI:224016446"

/translation = "MTISSSAQVYLRQNIQFEPLINSWYAWYHTLPPLTAALNVAERF
LPLLKSYAASPMMHAAACKDPAMRGGPFLDLGGQRVDEIRTLIEQTTQRATRQLELAK
AYKAFSTLLLERATGMASDPLYPEIPEVLKGYVEIYYDLNHNPSFRVFESLLYASPFY
ARDAQSIALSAIEEHTPRPFILSTPRLRDERTVFSNMAFDDRALDTLFRMRDTPGSYA
KIVDLMRVEEKDEPLFRSFFVEEAPAPKPDRSFDGDDIRIRYYGHACVLIQSRGVSIL
IDPVISYGYDTALPRYTFADLPDQIDYVLITHSHHDHIVLETLLQLRHKVKTVVVGRN
LDGFPQDPSMELALRKLGFDDVLEVRDAQEIKVPGGAITAIPFMGEHNDLAIHSKQSF
MIRFGSRSVLCIADSCNLDPRLYEHVFRLAGKPDTLFVGMETEGAPPSWVYGPLFPKA
LPRDIDQSRRARGCQFGEAAALVDDFAFNAAYVYAMGQEPWLNHLLDNTFDENSPSHI
QSTQFVAHCKAKGIASEILYATREIVLCQN" (SEQ ID NO: 14)
```

```
CDS             complement(31596..45005)
                /note = "ORF9"
                /codon_start = 1
                /transl_table = 11
                /product = "putative beta-ketoacyl synthase nonribosomal
                peptide synthetase"
                /protein_id = "ACN32489.1"
                /db_xref = "GI:224016447"
```

/translation = "MNAKATHALKAALDELRLRRAEIAALRSDRNEPIAVIGMACRFP
GRSDTPDAFWQLLDGAHDAVTEVPGERWDIDRYYDPDPSTPGKMATRHGAFLERVDQF
DAAFFGIAPREATYLDPQQRLLLEVAWEALENAHLAPERFRQSATGVYVGITCFDHAI
QVSNASMPSSSYAGTGSALNMAAGRLSFVLGLTGPSMAIDTACSSSLVCLHLACESLR
SRESNMALAGGVNLMLSPEVMVSFSQARMLSPDGRCKTFDAAADGYVRGEGCGMVVLK
RLADALADGDRVLGIVRGTAVDQGGAGGGLTVPSRDSQERVIRRALNQAGLAPGDVSY
VEAHGTGTSLGDPIEVEALAGVYGPGRAANEPLVIGSVKTNIGHLESASGIAGLIKVL
LSFEHDRIPAHLHFTQPNPHTPWQDIPIRVAADPVAWRRGERRRIAGVSAFGFSGTNA
HAIVEEPPVAPAHAAQRALLLLSARSEAALAALVPRYERAIAGATPQELAAICRAAAT
GRSHYPFRAAYVSGARVASAAAPRTGKALRMGEGEGVPDTGVAHALHASEPLFRDAFA
RCSVPLDALETDAGRFAIQFAWAELWKGWGLRPAVVSGHGIGEYVAACVAGVVSVADA
LRLVAARSDAEALRAVLRDMPLARPSVRLISGYLGTDVTDEVTHPQYWLQLAGASDQA
DASHPPEGLADGWLPPPCAGDALERALAALYVQGAQFDWRALFPAPAQPATTLPNYPF
ERQRFSLEKIPSPIVGMDAGSIDAALRHLKSSGKYPEDMLNAFPDLLRTAFAAAETVA
SNAHPLYHVVWEQQAAMPAAPAAADASPWLIFADASGVGERLAALLRARGASCSLVRP
GIDYVTGAEAGWQVAPERPDDFVRLLNETAASGQRIVFLWALDEAVGETRMSAALLHL
VHALVGSEREWTPSTRPRISVVTRDAVEAGEAPHVSGLAQAALSGLARGAMIEHPEWF
GTAIDLDPAAPENETQALLQEMLGESREEQVALRHGARHVARLSPLAPAETAALPVDP
DAAYLITGGFGALGLHTARWLAARGAGTLILVGRQGAASDESQRAIAELRERNVTLRC
ERLDIADPAAVAAFFAALRRDGVPLKGIVHAAGIVGYKPIMQVERDELDAVLQPKVAG
AWLLHQQSEHFPLDFFLLLFSSIASAWGSREQAHYSAANRFLDALAHHRRGQGLPALSV
NWGPWAEGGMTFPEAEALLRRVGIRSLAADRALDVLNRLPAVPQVAVVDIDLALFQGS
YEARGPKPFLDHVRVAKSAPSAPAMPALSDASPRERKRLLADSIDRAVAQVLGYDAGT
LDRDLGFFEMGMDSLMALDVRTHLENALGIPLSVALLFDHPTVNALADFLAEQASGTA
QAQTVPPQQQPRPIAPAIEARDAGTPEPIAIVGMSCRFPGAAHDLDAYWNLLNDGVDA
ISEVPRERWDVDAYYDPDPEAPGRMYSREGGELDDVDQFDPAFFRITPREAAAMDPQQ
RLLLEVSHEALEHAGIPVDSLKGSRTGVFVGITTNDYANLQLRNGGGSGIDGYFFTGN
PLNTAAGRISYGLGVQGPSMAIDTACSSSLTAIHTASQNLRSGECDLAIAGGVNLILS
PDNSIAVSRTRALAPDGRCKTFDAAADGFVRSEGCGALVLKRLSDALAAGDRVLAVLR
GSAVNHDGASSGETAPNGRAQEAVIRQALGGLPAASIDYVEAHGTGTPLGDPVELQAL
ATVFGAGRDAGRRLRVGSVKTNIGHTESAAGIAGVIKVVLSLNHDRLPAHLHFRQPSP
LVQWDAMPVEICAEASAWPRGERPRRAGVSAFGASGTNAHLVLEEAPAPARQATPSRH
KVHPLVLSAKTPAALRELAGRYQRRLEAEPGLDIAAVAFSAATGRSHFAHRLAWPVTS
LDDAIDKLRAFHAKEPAGAAQPAPRVKMAFLFTGQGSQYAGMGRRLYDAYPVERDAID
RCRAVADPLLDKPLLEVLSAQGEDIHQTGYSQPALFSLQYALTTLLASFGVVPDAVMG
HSVGEYAAACAAGVFSPEDGLRLIAERGRLMQALPRDGEMAAIFTDLATVERAIDAWP
HEVAVAAVNGPASIVISGKRERIAMLVDAFAARDIRSVPLNTSHAFHSPLLEPMLDSF
QLAAKTVPVARPAIPFYSNLTGAVMDEAPTDTYWRRHCREPVQFASSVERLAEAGFNV
LVEIGPKPVLVNLARACCAPDAGIQFLALQRPQVEQQALIETLSSLYARGVDVDWAPT
ETPAPARIALPSYPFQRSRTWFQKADTSMTQTSASPIAAAPTHNRSGEILEWLRGKIG
ELIQADPATINIELPFLEMGADSIVLIEAIRHIEAEYGVKLAMRRFFEDLATVQALAE
YVADNLPAAAAPSGAEAVAVAVAAAEPSTPAVAVTPSAAGLAPLAAAPAEWVAAEGGS
TVERVLREQNQLLSHVMSQQMELLRTSLTGQPGVRPATAAVQAVASTASVAPKAASAA
PAAAPAAKPAPAAAAAPAADNPPPKPMMPWGSPVQQRARGLSAAQQEHLEALIVRYTT
RTRKSKDSVQASRPVLADSRATVGFRFSTKEMLYPIVGDRAAGSRLWDIDGNEYIDFT
MGFGVHLFGHTPDFIQQQVTREWQRPLELGARSSLVGEVAARFARVTGLDRVAFSNTG
TEAVMTAMRLARAVTGRDKIVMFTHSYHGHADGTLAAANAEGVTETIAPGVPFGSVEN
MILLDYGSDAALEAIRGMASTLAAVMVEPVQSRNPSLQPVAFLKELRRITEEAGVALI
FDEMITGFRVHPGGSQAMFGIRADLATYGKIIGGGLPLGVIAGTSRFMDAIDGGMWTY
GDHSFPAADRTAFGGTFCQYPLAMAAALAVLEKIEQEGPALQAALNERTAQIAGTLNA
FFAEAEAPIKVTWFGSMFRFEFTENLDLFFYHMLEKGIYIWEWRTCFLSTAHTDADID
RFIRAVKDSVADLRRGGFIRPHSKHGTVAALSEAQRQLWVLSEIDPEGSLAYNVNTTL
ELNGRLDEAAMRAAVQSLVDRHEALRTTVMADGSGQIVHPSLTLEIPLIDTDPNAWRE
QESRQPFDLVNGPLFRAALVRLGSERHLLVMTAHHIICDGSTFGVLLEDLARAYAGAA
PADAPLQFRAYLKQLDGQRHSPETKANREYWLAQCARQAAPLNLPVDYPRPAVKTFHG
ERVSLHLDAATAATLRTAARQNGCTLYMVLLAGFNLFLHRVAGQQEIVTGIPVTGRSV
AGSDRLAGYCTHLLPLHSTLPEQATVASFLAGTRQNLLDALEHQDYPFAELVREIGAQ
RDLNAAPLVSAVFNLEPVSALPELPGLTVGLVAPLIRHTAFDLNVNVLDAGQALLIDC
DYNTDLFDASTVQRFLDIYRTLLTHLADDASAAVARLPLSSDAERNLLTVEWNRTDTD
FGEDAAQPLHRLFEQQVERTPDAVAIVFDDTALTYAELNLRANRLAHHLVALGVGPDS
LVGVAMERSLDMSVALLAILKAGGAYVPVDPDYPAERVRFMIDHAQLRWLLTQQHLHD
ALPDTDAHVIVVDRDSLDLDAAATSNPAPALNGDNLAYMIYTSGSTGRPKGALNTHRA
ITNRILWMQHAYALGADDAVLQKTPFSFDVSVWELFWPLVTGARLVFARPGGQRETDY
LVELIERERITTIHFVPSMLRAFLDHPDLDAHCASLRRVVCSGEALPHDLQQRCLERL
DVELYNLYGPTEAAVDVTAWECRRDDPHRIVPIGRPIANTRLYIVDAQMQPTPIGVAG
ELLIGGTPVGRGYHGEPELSAEKFIADPFSADPLARLYRTGDLARYRPDGNIEFLGRI
DHQIKLRGLRIEPGEIEAALTSHPLVDAAVVALRGVDDGARLVGWLCSSHPEAELIEA
VRGHLRQRLPDYMVPSAFVVVSAFEHLPNGKLDRTRLPEPGDGLDHVAPVNALEAQLA
AIWQEVLGQARISTTGNFFDLGGNSLLATKVVARIRRDLHVKLEIRSLFALPTISSLA

```
KRIADTQPIDYAPVTPLPAQASYALSPAQTRLWVQDRLHAAQAEGPLPTSLLFEGVLD
VDALVRAFRALSERHEILRTRFVLEGNQPVQHVLPPGEAAFPVEIVDLQDAEDRDAQA
AAIQASERLVPMDLATGPLFRVKLLRLSEVRHVCLCTMHHIVSDGWSTEVLLDDLSAL
YDAFVQRRDDPLPALPIQYKDYAGWLNRLLAGPDGARMKDYWLTKLGGGLRALELPGD
VEQPAAPSWKSWRFDLPAAETAALESLGKRHGATLFIALLSAIKALFYRRSGQEDIVV
GTPVAGRELPELESQVGPYLNVLALRDRVAGDDRFDTLLTRVRDTTLEAFSHPLYPLD
RLLDELHIKRVAGRNPLFDIGLTLQNQRHGPVDRYAGQVHIAELPDHDPQRADTEAAT
DFWFLAEPHAEGLAIRVVYHAGRFSEALVQGLANELTSVIGEVLANPGVRIRNLTLGQ
RALHAEARQPTVELSAF" (SEQ ID NO: 15)
```

```
CDS             complement(45002..48325)
                /note = "ORF10"
                /codon_start = 1
                /transl_table = 11
                /product = "putative short chain dehydrogenase/reductase
                SDR"
                /protein_id = "ADT64845.1"
                /db_xref = "GI:314954101"
```

```
/translation = "MKFGLMFFASSEEALSGNKYQLVMESARFADANGFSSVWVPERH
FTEFGSLYPNPAVLHAALAAATQRVKLVAGSVVAALHNPIRIAEEWSMVDNLSNGRVG
VSFASGWNPDDFVFAPDKYATRQDDMLTTMRAVQHLWRGGTLDATNGVGKPVRLRVYP
TPVQPELPVWVTAASNPQTFVRAGEAGANLLTHVLDQDRDQLAHKIALYREARAKHGF
DPAAGTVSVMLHTFVGDDAAQAREQARVPFCNYIRSNIGLLNGLAQSRGQSVDVRAMG
ARELDEFVEFLYERFAQSRGLIGTPETCVELVRDLESIGVDEVACLLDFGPPVERILG
NLPQLRRLREMCAPRRSAAPTRFDAAEVQARCTETTSGADFNGEIRQHGVQIDGVFDA
IRQIWRTTGEALGKISLPADALASSPYQVHPAFLDACSRVLAAAIDPDALESGDLYLP
SSIGAVRVHQPPASTEAWSHATLRTPIGQGALEGDIRVHDLAGRLLIEIDALRLQQVR
AARAVERHDFAALLYQRVWRPSNVDAATGGSAHGEWLILADRGGVGAQLSALLEAHGD
TCTLRFADATPELPAADRPLKGVIHLWSLDLAPSDIAARRRASASVLHLVRALASRAP
SARQARLWLVTSGAMNVLDGESIAVAQAPLWGLGRAIAVEHAALWGGLVDLDPEQPSA
ADIMQAVQAGGREDMIAFRRDQRYVARIARDNREYVSHRPIRFHGDATYLVTGGLGGL
GLRLASWLADNGAGKIVLLGRGEPSAAAGKILRTLDARFIRADLSRREDVGQALGEIA
HSMPPLKGIFHLAGALDDALLTRQDDDFFHRAGSGKADGAWYLHELTAGLPLDHFVLF
SSMAALITMPGQGNYAAANSFLDALAQHRRAQGKPGLSVNWGPWAEIGHAATDYGRRA
HEQLGALGVGTLPPELAIATLERLMASGVAQSGVARIDWPTLFRVDAPAAGSALFSEL
TQPAAQPAQQETALLRQLHACAPRERVERITDTLAAMLAETLRLSGPDAIAPEQSLLD
LGLDSLVALELTDRLTKVFGRPFRATLFFSYPNLQTLAQYVLNELSPSLPAPVVDEAS
DDLDEDDLSELIAQEIGAQ" (SEQ ID NO: 16)
```

```
CDS             complement(48322..52749)
                /note = "ORF11"
                /codon_start = 1
                /transl_table = 11
                /product = "putative beta-ketoacyl synthetase"
                /protein_id = "ADT64846.1"
                /db_xref = "GI:314954102"
```

```
/translation = "MLPDTKFRTVTEILLFRGKVEPEKTAFIFLENGEAELTRLTFGD
LDKRARGIAARLQAIAQPGDRVLLVYPPGLEFICAWVGCLYAGLIGVPAYPPRRHRPA
DRLKAIVADATPVVALTDAATLDGIAHHADGYSDTLELKILATDQRFDAPAEQWRAPD
ITPQTLALLQYTSGSTGTPKGVMISHANILSNMAVIAEASDADASTVFVSWLPVFHDM
GFFGKVLLPIYLGVLSVLMAPAAFVQKPVRWLQAITKYRGTHCAAPDFAYDLCARKIA
DEARAQLDLSSWRVAFNGAEPVRAESVARFSRAFAACGFHAHTMRPVYGMAEATLFIS
GQPARSLPRVADYDADALAQGVATRNDSGKRHALVSCGRTWAEHRVRIVNPDTGERCA
PGRIGEIWLTGPSVGVGYWNRIDETERTFRAKLDGDDARYLRTGDLGFVDGEDLFVTG
RLKDLIIVAGRNHYPQDLEQSAEGSHPALAPNASAAFSIHVDNVERVVVACEVRREAL
NTLDAEAVAAEIRHTLAEVHDVDLYAAVLLKPATILRTSSGKIQRSRIRQAFLDEQGL
AIAGEWRRAFSAPPAPPQTAEPRDTQALVQWCIERVSRLSGIASGKIDPDAPFSVHGL
DSKDAIMLSGELQDWLGRPVSPTVVYDFPSISLLARHLSGTGSAMPDQAPGSAEARAD
IAIVGMGCRFPGAGNPDAFWQLLLEGRDAVGAATQRAADLPLAGLLDQVDQFDAAFFG
ISAREAESMDPQQRLLLEVAWETLEHAGIAPRSLAGGRTAVIVGISNSDYIRLAQDEV
ADVGPYVATGNALSVAANRISYALDLRGPSWAVDTACSSSLVAVHQACRALQRGESDA
ALAGGVNLILAPQLSASFTQAGMLSPDGRCKAFDAAANGYVRGEGVGMVLLKRLDDAL
ENGDTVFAVIRGSAVNQDGRSNGLTAPNGPAQQAVIHGALRDAGVRAQDIGFVETHGT
GTPLGDPIELNSLAAVLNESRRPDDLCWIGSVKTNIGHLESAAGIASLIKTALALHHR
AIPPNLHFRSINPQIALDGTPFRIPRQVTPWHSEHGPRLAGVSSFGFGGTNAHLILSE
APGLPEIEAEPVAPAARVVTLSARTPDALQALAASYAAYLDAHPEAGVRDVAFTANTG
RTHFTQRAAIVAPSRDSLRAQLDSVSSGEPAETPPAVTFHFCADDGASADAVRQLRAA
SPAFDALMQRQSDASGAPALAPDEAGFTRFQRALAQLWMSFGIAPDAVSSTGDGQRAA
AAWAGVPQAPDSGAAGHPGIVIDIGAHTAAWDAILHTLAALYVRGASIDWDAVEQGAP
HRRLALPTYPFERRGFWIRPHARRHPLLGRLMEQHAHAPATWIWQSRLDAPATNFLDG
HRVKGSPVLPYSAFVEMALSATSEIGAAGHTTLKDLALHPLPLHPHESHTVQTVLSR
RSWGPFSFAVYHRIDDTRAAATWQMCASAEIHESDRSHA" (SEQ ID NO: 17)
```

```
CDS             complement(52936..53922)
                /note = "ORF12"
                /codon_start = 1
                /transl_table = 11
```

```
                /product = "putative taurine catabolism dioxygenase"
                /protein_id = "ADT64847.1"
                /db_xref = "GI:314954103"

/translation = "MLGMTERKLLAEGSTPWLLEPVSNGRDLAQAVNDNRAALESRLL
EHGVLLFRGFDVSSVGGFEAFARAISAHQSDYVYRSTPRTSIGNGIFTATEYPPSETI
ALHCENAYQRSWPLRVAFCCLTPAATGGETPIADMREVSRRIGPRILDHFEARQVRYV
RHYRRHVDIPWETVFQTSDRNQVAAFCADNGIALEWLDDDTLRTAQINQGVAYHPVTG
ERVFFNQAHLFHISNLEASLASSIVSLFGEDRIPRNACHGDGSPFDLADLEQIRHAFR
ECAITFPWQRGDVLLVDNMRFAHGRNPFEGERKVVVSLLDPYTPDIEGIADR" (SEQ ID NO: 18)

CDS             complement(53999..55369)
                /note = "ORF13"
                /codon_start = 1
                /transl_table = 11
                /product = "putative transaminase"
                /protein_id = "ADT64848.1"
                /db_xref = "GI:314954104"

/translation = "MKRFSCASVHQSALQAGSARMEKLEYLKQVESNARTYATSFPRL
FTHAKGIRVRDADGQEYIDCLSNAGTLALGHNHPEVNEAVMRFLSSDQMQQALDLATP
AKHAFVEQLFSLLPGKIAESGKIQFCSPSGADGVEAAIKLTRHYTGRPTIMAFHGAYH
GMTSGALAASGNLTPKSAGGNGRDVHFLPYPYAFRCPFGTDGSATDQLSINYIRTVLS
DPESGITKPAAIIVEVVQGEGGCIPAPDTWLIELRELTLRHEIPLIVDEVQTGLGRTG
ALFAIEHSGIRPDVLVLSKAFGGGYPLSVVVYDERLDTWPPGAHAGTFRGNQIAMVAG
LSTMRIVEREDLSAHADRVGKLLVAGLEELAERFPCLGQIRGRGLMIGAEVVVPGTHG
RAGPPHTERARAIKQNCLRNGLIVETGGRNGAVLRFLPPLIVSEADIHDILNRFEHAV
ETACRA" (SEQ ID NO: 19)

CDS             complement(55516..56466)
                /note = "ORF14"
                /codon_start = 1
                /transl_table = 11
                /product = "putative epemerase/dehydratase"
                /protein_id = "ADT64849.1"
                /db_xref = "GI:314954105"

/translation = "MQRNRKRILVTGGAGFLGSHLCERLVELGHDVLCVDNYFTGTKQ
NVATLLGNPSFEALRHDVTFPLYVEVDEIYNLACPASPIHYQFDPVQTTKTSVMGAIN
MLGLAKRTHARVLQTSTSEVYGDPDVHPQPESYRGNVNPLGPRACYDEGKRCAETLFF
DYHRQQNVRIKVVRIFNTYGPRMHPNDGRVVSNFIVQALRGEDITLYGDSQTRAFCY
VDDMVDGLIRMMATPAELTGPINLGNPHEIAVSELAQIILRLTGSKSRLVFRPLPKDD
PTQRCPDISLARTHLDWEPTIGLEAGLQRTIDYFCSTLAA" (SEQ ID NO: 20)

CDS             complement(56622..57341)
                /note = "ORF15"
                /codon_start = 1
                /transl_table = 11
                /product = "putative thioesterase"
                /protein_id = "ADT64850.1"
                /db_xref = "GI:314954106"

/translation = "MRLICFPYAGGSAAVYRTLQASLPGIEVCRHELAGRGSRLSEPA
VRDMATLVDTLLCDLDDCFDRPFALLGHSMGAAIAAELALRLPAHARPNLRHLFVSAR
AAPGKERHDRRMQALDDRAFIDALREMGGTPKAVLDNSELMALLMPALRADFTMIENH
RPVPGPRLAVDITAFAGRADKEIPVDAVAGWGAATTGRFDFHVIEGDHFFLRNEMRTM
AGIIAARMRRPEHAASSALQA" (SEQ ID NO: 21)

CDS             57710..57997
                /note = "ORF16"
                /codon_start = 1
                /transl_table = 11
                /product = "hypothetical protein"
                /protein_id = "ADT64851.1"
                /db_xref = "GI:314954107"

/translation = "MQHRQKAVPTQQVANERVIVTEWRFAPGAETGWHVHRHDYVVVP
QTDGQLLLETAQGNRESQLHAGRSYAGLKGVEHNVVNATDHEVVFVEVEIL" (SEQ ID NO: 22)

ORIGIN
        1   aattcctgca gcacggtgcg cgaccagccc cagatgtccc cgctgagcgt gagtgcgaga
       61   ccggccgtcg tgatggccag ctgcgtctgg ccgaacagcg gcgtcaatgc gccttcgccg
      121   ccgatcacga tccgcttgac gagatccgag atggactgcg agatcgaatc ggagaacgga
      181   tagttgtacg gctgcgtgac ggcgcgcgac aggaacggct tgctgggcgt cggcgtccag
```

```
 241  accttgagcc acggcttggt cgtgaacggg aaccagatgg cttccacccg gcccgagccg
 301  tcgagaaacg atgcgatcgt gcggcccgtc gtgccgggcg cggcgaacag ttcggaggcc
 361  ggaatatcga cgtagctctg cagcgtagc  cgctggttcg gccctgccgt Cagcgtgact
 421  tcgacgacga gcgctcgccc gatgtgcgcg aggaacgcgc cgatctcggg atcgctgcgc
 481  tcgaaccggc gcagcacgta ttgctgccgg gccggatcga acacgaccgc cgtgagcgcg
 541  accacgagat tgctcagcga gccgtaggta tggcccggtt gcaaggtttc accgccgcg
 601  ggcacggcgg tgccgtgtgc atcgatcgcg agcgcgccgc cgagcgtgat gtcgcccggt
 661  gccggcgcgg caatcacgcc gaggccaacc tgctcgagcg tcgcgagcag cgactccagc
 721  gagacgcccg tttggcggt  gacgcgcgcc ggacgcgccg acgtgtcgac ggagacggcc
 781  gtcagcgact tcgtcgtatc gagcagcacg aggttcgcgg cgccgcgcc  cgggtccagc
 841  gtcagcggcg accagttgtg cgtgtagccg cgcgggcgta tccgatagcc gtttgcgcgc
 901  gcccagttga cggttgcgac gacgtcgtcg gcggagcgcg gcgcggcggt ccatacgtcc
 961  tgcacggcga tctcgccgct ccagttcagg aacgcctgct tgtaaagctg gatgtcggcc
1021  gggaagccgg gcggtgtctc gccggccgtt cgcgcgtgcg ccgcaacctg gtagagcggt
1081  gtccagccgg tgacgatgcc ggccgccgcg agcttcgcca tgtcggccag gaaggcgcga
1141  cgcggcgcag gttcgtctct gaagtcgtga ctcatggtgt gctccaattt ttcggaattg
1201  ttttgcagat tggaaagacg acaaatgacg cgttgagact cgtgtggcaa ttcgagcagg
1261  tgcgacgcgc gggaagtgtt gcgcgtgggt gggccaggat tgaaaaaaga cggtgcgttc
1321  ggcaatgcgc ggccgcacat catcacggac gtctaatagg aaatcggaaa accgcctggc
1381  gattgcttta attggccgtc ggccggttct gtcggcaagc agatagggag attcgacgga
1441  atcgcgcgcg gcgaagcgct agccgtggcg atcgataaaa gatgatttca cgtgaatatt
1501  aatcttcatg tttcgatttt taaataaacc cggccgcagt tcaaggttga ttgacgatgc
1561  gtcatgcatt tcggtcgaaa gcgtagcaat ttatctatcg ggtgacaagc ggcggagttg
1621  acgaattccg agtcatttaa tatggaaatt ttatgacggg aaatggcttc gtccgttgtg
1681  ggtattttgc aacgcggctg ccggtgtcgc gccacgtggg cttggagcgc aaattatgct
1741  ttgccgtcgc gtatattgaa tcgattgttg agcgaatcga ataacgtcc  ggaagacaat
1801  agctgaagcc gggtcgatga gcgggaggta gggtgaaatc cgataattcc tctctcgaat
1861  aacgctcctg gatgaaaatt cgtggtatgc gtcgcccggg tgattattac aaaagttcgt
1921  ggtaaacgga tgtcgattta tcggtgtatt cataataatg ccaatgagcg gctcgcgaat
1981  tgattgattt ccggttcgtg aaagatgtgt tttaaaaaaa tagatgtcgg gctgactgca
2041  aatgtctgaa tcgtcgctat catacgcggc tgggatatac atggatcaaa ttcaatggaa
2101  agaatcgttt cgcttttga  tcgcgatttt tctttgaatt cgccgggaac gcgcccgctt
2161  cgagccggcg ccgggttttc cgattcaggt ttcaggcacg tccggcggcg gcgcgttttc
2221  atccggcaac gcgaatcggc cgaaatggac gtttcagcct tttgcggctt cgcgagtcgc
2281  ccgcatcggg ctgaactggg aacggcacgc cgtcgtctcg catgagccgg acgcatcggc
2341  gcgcgctggg ggcggcgcgt tgcccgcctg aaaaggcgc  gcgacgcagc gcgacccgac
2401  gcgcgccgcg caaaccgtgc cggttcgccg gcgcttgcgt tgtgccaggt cctcaagcac
2461  gcacaacaag gagagtcaga tgttcgcgaa gctcgggaag gtgatttcga gcgcaggcag
3781  acgtgcgaga gttccttgag gaaggtccgc tcctgcggcg agaaatcgtc gaacgtacag
3841  gtgcgataca acgagatcac gtaacagtgg ccccgcttgc gggtcacgag gtggaattgc
```

```
-continued 3901  gcgtagcgcg gcgacacgat cgccgcctgc atgaggatga agcggtcgag ctgcgcgtgg
3961  atcgggccgt ggccggcgag cgtgtcgtcg acgtgcaggg ggctcgtgcc cgggcgcggc
4021  ggcatctgcg gcccgcaaca gacagcggcc gcgccggtct tcgcgagcgc cgcgccgacc
4081  gcgccgaggc tgcgcacctc gggagggccg tccggcacgt cgtcgatcgc aagctccgaa
4141  atgcggatct cgtcgacggg gaccgccgcg gcgatcaggt tgtacatcat ccggggaaaa
4201  cgtcggctcc cgctgctcga gatcgcttcg ccgacgtgtg cgaacaatct gctgaactcc
4261  atgaagggat tcctgatgag acgttgaagc tgcgcttgtg cgcatgaatg ccgacatgat
4321  ttaaacaccc ggttgcgaac gcgtctgtaa cggattgccg ggacagacgc aacattgccg
4381  gccgtcgaag ccggtacggc gcacggcgac cgttgcgccc gtctgcgacg gatggcgcgc
4441  accttgtccg agtccggatc gctgctcatc cggctgcctc ggcccggacg gcacacatgg
4501  ccgtatcgga gaagatgcgg ccgctatcca ggcgaatgac ccgatccgcc agcttgaagt
4561  actgatcgtc gtgggtgatg atgacaacgc atttcccgcg tgatttcaga tcggaaccag
4621  gcacttcata ggaaaatcgc ttgaacaccg gatcctgatc ggcggcccat tcgtccagga
4681  tataaatcgg acgatcctcg atgtacgcgc aaagcagcgc caagcgcttg cgttgccctg
4741  tcgataacgc gcgggtggtc gagtaggtcc ggccggaaat ctcgatcttg tccgccagtt
4801  tcagggtggc gaggtatttc cgggcaagct cgatgctttc attgccccga tccggtccga
4861  tgatgcgatt gaacaaatgg aaatcggtga agacggcgga aaacaggttt cggtagcgtt
4921  ccctcgcagc gtcgtcaacg acttttccgt cgagggaaat cgtgccgccg gtaggcgcat
4981  agaggccgct gaggaccttg ccaagcgtgc tcttgccgct gccgtttccg ccgatcacgt
5041  agacgagttc tccggcatga atcgtcatgt cgatggggcc gagcacgaag tcgaccgatg
5101  cttcattgtc acggtagttc atcgtcacgt ctttcaactc gatgaccttc catgacttgg
5161  ccgacagggt ttccacgttg cccgcagggc gcggttcctc gtgtgaggcc tgcgtgtcgt
5221  cgatcagaaa gccgaattcc gccagccggg cgagcgcggt cttgccttcg gccaccaccg
5281  gcagaacatt gatcagcatg gtcaagggcc ccatcatgta gagcacggcc agaatgctcg
5341  ccgtgagtac ggagggatcc acgacgccca gagaaggtac gccgaacagc aggcatccga
5401  gcaggaccgc tacggtgatc tggccgatgc tgtcgccgct catgaaccag aagcgttcta
5461  tgtaattgaa tcccgccacg cgcttcgacg acaattcgat cgcggcgcgg gtaaaccagc
5521  gtcgcctggc ccggttgagc ttgagctcct tgatgccgaa cacgaggcca tgtgtgtatt
5581  cgttgaactg gacgaattca tcgcgaaccc gctccgtaaa attgaccgcc ttccgataga
5641  aaaacagata aagcaccagg ccgacgaggg tcaggatgat cgtcgacgcg aacacgatcc
5701  acgagagata ggcgagatag gcgatgctgc agatcaggac gactgattga cgatgatcg
5761  tcgggatggt cagcagggtc tggctcagtt gcggaatgtc ctgtgtcagc atggtcagca
5821  cattgggggc gccgcgtctg tcgatttcat ccagcgggt tgccaggatc cgtttgcaca
5881  ggttgacgcg caacctcgtc atgactttca tgcaggcata ggagggcatc acggcggcgc
5941  agctcctgca gaccaccgcg acgacattca ccgcgatgaa cagcagcaac agcgtctggc
6001  gatcatcctg gtcgtgcagc acggtgctga tcaacccgac gcccgcgatc gacgcgatgc
6061  cgctgacgag gcccgtcacg accgtgccca gcgtcagcca gggatgactg cgccacatca
6121  gggtggcgg ggaatgccat ggcggcgatt tgctttgagc ggaatccatg agtggccaat
6181  aggtctcagt tgatcaggtg gctgagttcg acattgcttg ccgctgatct caacctcgac
```

```
6241  gaggtttcgt gcttgcccag gaacgtgatg ctttccacga ttcccagcgg cgaatcggaa
6301  aacaggatgc agcacttcag caggcgctgc gcacgctccc agccgacgcc gtccggtgaa
6361  tcggccacgc ttcgcaacgc ggcctcgacc gaggcggccg tccagtcttc gctccgtgcc
6421  agccccgact cgatctgccg aagaaattgc aggagcgtgc ggggattgct ttcgatgctg
6481  tacatgagga tgtaatcgat ccgcagtttc ttcgtgatca gcggaaaaat caggtcgatc
6541  acgccgcgg tcgattcgca tttcccatat gccagtgaaa tcgcgtcgcc gagcttgcag
6601  tcccggtgaa gcgcatccag cgcggccttg acgaacgccg cttcgaggtc aacggtggtg
6661  agttgcatga tgttcagtgg cctgtcgagt gttggatcgc ggcgagcacg ggcggcaggc
6721  gttaccagcc gtccggaatg ggcatggaat aggtcagcgg cttctccggc atcacttcgt
6781  ccatgatgtc ggagtagccg gactcctgtc cgaccagatt cggctcgaag cagtagcaat
6841  tgaacgtctg ctgcaggacg aggttgttgc ggtcgttgat cgccgcggg ttttcgttga
6901  tcgcgatgaa tgcgtcgtaa agcgagttcc tgacgacgta cgcgtgcgcg gtgagcgtct
6961  ccacggcctt gacgatgttc ggcgcgacgg gaatcggcgg cgtgaagtga tacgcgccca
7021  ggaacagcat gtgccagtcg tccggcactt gcgcgatgaa ctcgggaaag cgcgcggcga
7081  aatcggcgtc gaagaacgcg tcgtcctcga agatcaggac ttctctcgca ccggcggcct
7141  tcgcctgttt caccgcggcg agatggctca tcgtgcagcc gtagtcctgc gcacgcatat
7201  ggctcaacga ttccggcacg ctcaccagcc ttgcatcgac ggcaggcagc cgttccaccg
7261  tgaggatgtt ctgctctgcg aattttcgtt gcatcgcttc ccagcggtcg gggcgccggt
7321  ccaggttgat gcagaccttg cgggcaaaag tattgtcgat cgtcggcgtt gatttcatga
7381  gggcgttttt tccagaaacg aattgacatg ggcggcgagg acaccggcat gcggatcgag
7441  cagcatggtc aggtggtcgc cggggacgtc cgtcaccgcg acggggtgcg ccgagaagcg
7501  agaccatccc caggtcgcgt ccaggcgaag ctgcgcgatc tcggacgacg gcgcgtagtc
7561  gccgggatcg cgctcggtgc tgcggaacaa cgcgatcggc acgggcagcg gggtggcgtg
7621  cggcgcgtag tgcgacttga agttggcctg atagacgcgc aggtaggcgc gcaggcggtc
7681  ggacccggcg tccgcgaacc agctgccgcg gtcgccgatc cgttcgagga tcaggccggc
7741  ctggccgtcg ggatcgagat ggacgaggtc cgctcgcgtc acctgaaggt cggtcccgag
7801  gaaggtgcca atttcgtggg cgatcgcgac cagccattcg gtgtcgtccc agtcctgcca
7861  gtaagtggcg gccgagctgt cgatgggcgc ggacgcgtcg aagatcgcca gcaatttcac
7921  gtcgcgccc ttggcgacca gttgcctgct catttcgagc gccacgtgcg cgccgaacga
7981  gtggcccgcc aggtagtacg gacccgcgcc caccagcggc cagatgcgtt cgatatgacg
8041  ggccgcgatg tcttccacgc gggtgagcgg ctcgcacgcg ccgtcgaggc cgagcgcttc
8101  cagcccgtga atcgcgtgag cgccgctcag gtggttcgcg agcgggcgga agtagaccac
8161  gttcccgccg cgcgccggca gcaggaagag cggcgcggcg gggccgccgt cgcgaatcgg
8221  cacgagcccc ccggcgggcg cggacggttc tttcgcggcc agcgccgccg ccagtttctc
8281  gatcgtcgga ttctcgaaga cacaggaaat cggcagcctg cgatcgaacg ccttctcgac
8341  atgggccatc agctggatcg cgatgatcga gtggccgccc aggtcgaaat agttgtcgct
8401  gaccgcgatg tcgtctcttt tgaagatccg ccgccagatc tccagcaacg tgctttcgtc
8461  cgccgcatgc gcgacggcgc gcgccgccgc ggccgcaccg gcagcggctt cgatggccgg
8521  cccgccccg ctgcgcggcg cgctcggccg gcgtcggcg gccggcggat cggcgagctg
8581  gccggtcaac tggcccgggt tctcggcgaa tcgctcgagc aacgtgcgga gggtatcgag
```

```
8641   catctgccgc acgacctccg gcgcgatgcg gtgggcatcg tgcgaaatat ggaagccgat
8701   gcgctcgttc gggtgcacgg tcaggtcag  cgggtagttc gattccgcga acgcgcgggt
8761   gtcgaggatc tcgatgtcgt ccggcccgag atcggggcg  gcggcaaccg ggaagttctc
8821   gaagaccagc aggctgtcga acagactgtc gccggcgggc agttcgctcc acgactggat
8881   atcgaccagc gagctgtacg aatgcggctc catcgccgtc tgggctgcgt ggacctctgc
8941   cagccattcg atgaacgggc gctcgggcgc gatccgcagg cgcagcggca gcgtgttgat
9001   gaacagcccc acgatcgact cgacgccgtc gagcatcggc gggcgaccgg acacggtgac
9061   gccgaagacg acgtcgtccg ttccggcgtg gcgccgcagc accaacgccc agaccgcgcg
9121   gatcagcacg ttgagggtga cgcgatgcgt gcgcgtgagc gtttgcagcc gcgcggccag
9181   cgcctcgtcc agcaggaatt gctgggtccg gcgcttgtcc tgccgcgggg catcgccggt
9241   cgcctgccgg gccggactgg ccgcgaccgg cgtggcggcc ttgaagccgg ccagttcggc
9301   gcgccaccac gtttcgtcgg ccgagcgagg atgacgcgcg agccagtcga tgtacgcgcg
9361   gtatcccggc gccgacgccg cgaccgcggg catgccggtg cgggcgagcg acaggtagtc
9421   gtcgaacacc tccttcatca gggtcgcggt gctccagccg tcgaggatga tgtggtgcgc
9481   gctccagcag aagcgatggc gcgtgtccgt ttcctggatc agcgtgcagc ggaacaacgg
9541   cgcgcgctgc agatcgaagc cgcgccgccg gtcgtcggcg aggaacgcat cgaaatcctg
9601   cgcgcggcgg gacgcatcgc ggtgccgcca gtcaaggaac gtccatggca ggtcgaccgt
9661   gtgccgtacg gtctggacgg gatggtgcgc atcggcccac gcgaacgcgg tgcgcagcac
9721   ggcatggcgc gcgagcgcat tggcccacgc ctgccggagc gccggcacct ggagcgggcc
9781   gctgacgaca aagctgaact gctggaagta ggcggcagga tccaggtcgt acagcgaatg
9841   gaacaggatg ccctgttgca gcgacgagag cggatagctg tcctcgatat cgtccgctgc
9901   ggtgtcgggg accgacgccg cgaagtcgag caaccggtcc ctgaagtgcg cggccaggtt
9961   ctcgaccgtc tgccgccggt ggagccgctc gccgtagcgc cagtccacct ggagcttgcc
10021  gtcggcaacg gccgcgacga tctcgaaggc atgcgtgcgc tgcgaccgcc cggcgcgcag
10081  cgaaccgagg tcttcggccg ccgggcgcca gccatcggat tgccgcaata cggtatcgag
10141  ctgcccgtga tagttgaaga ggatatcggc cttcggcaac gcggcgagac tgtcgcgcac
10201  ggcggcgtcg gggctctggt agcggagcag cgaataaccg agaccgtcgg ccggaatccg
10261  gcgcagctgc tgccgtgcgg cacgcagcgc ttgctccggc gcgtgcatcg cgtcggcgtc
10321  gagcacgacg gggtagatgg acgtgaacca gcccaccgtc cgggtgaggt cgagcggcgc
10381  atccgacacg tggcggccgt gactctcgag atcgatccgc gtgcgggtgt acccgtgac
10441  catgctgcag gcttgcgcga gcgcgacgag caggacgtcg ttgatgcggg tgtcgtaggc
10501  ccgcggcagc cggcgcagca acgcggtggt atcggcttcg cccagctcga atgaaacgga
10561  cgacgcgtcg tcgactgcgt tgttggccgc gcccgtgcct ggatagtcaa ccggcatcgg
10621  ctcgacgggc tgcgcgagga gggcttgcca cagccgtgct tcgtcgccga tggcgggcga
10681  ccgggccagt tgctgcagat gcaacgccca ttcgcggaac gaagtcgtct tcccgggcaa
10741  cggctggccg tggtaagcgg catgcaggtc ctcgagaagc acgcgccatg acacgccgtc
10801  caccgccagg tgatggatcg acacgaacag gcgggcgagc ggctcgtcgg ccaggcagaa
10861  gagccgggcc gccagcaacg ggccatgcgt gatgtcgatg ccgcgctccg cgtcagcggc
10921  ggcggcacgc atcgccgcca ggcgctcgcc tgcgtcgtcg gcgatcacct gtttcgcaaa
```

| | | | | | |
|---|---|---|---|---|---|
| 10981 | gagcgccggc | atctcgccgc | cggcgacgac | ctgctgggtc | cagcggcccg | catcgtgcga |
| 11041 | gaaacgcagt | cgcaacgcat | cgtgatgttc | gtagacctgc | cggaacgcgt | cggccagcct |
| 11101 | cgatgcgtcg | atatccgccg | gcacctggat | caggaccgtc | tggttgtagt | gcgacggcgc |
| 11161 | atcgatctcc | tgttcgaaga | accagtgctg | caccggcgta | agcggcgcat | cgcccagcgg |
| 11221 | gctcaaggtc | ggcgcgcagg | ctgcccgctc | ctcgggcgcg | gcggccagct | gcgcgatcgt |
| 11281 | ctgatactgg | aacagctgct | tcgccgtcac | gcgcagccct | gcctgattgg | cgcgcgcgat |
| 11341 | cacctggatg | ctcaggatcg | agtcgccgcc | gagttcgaag | aaattgtcgt | ggatgccgac |
| 11401 | ggaaggcaac | tgcagcacgt | ctatgcagat | cgacgccagc | aggatttccc | gcggcgtgac |
| 11461 | ggcaggtgca | tgcggctggg | ccgcgtcgcc | ccgatccgcc | ggaagcggca | gcgccttgcg |
| 11521 | gttgatcttg | ccgttgggca | gcatcggcaa | ggattcaagg | gcgaagaact | gcgacggcac |
| 11581 | catgtagtcg | gcgagcttgc | cgcccagata | gccgcgcaga | tcggcgatgt | ccggcgcggc |
| 11641 | ggtcgcgaca | taggcgatca | ggaacgttcg | ggctccttcg | gttttcgcga | tcacgacgca |
| 11701 | gtcgtcgacc | gacggatgcg | cgcgcagcgc | cgcctcgatt | tcaccgggtt | cgatgcgcag |
| 11761 | gccgcgcagc | ttgatctggt | gatcgatgcg | gccgaggaac | tcgatgttgc | cgtcgggccg |
| 11821 | gtagcgcgcg | aggtcgccgg | tgcggtagag | gcgcgcgagc | gggtcggccg | agaacggatc |
| 11881 | ggcgatgaac | ttttcggcgc | tcagttcggg | ttcgccgtgg | tagccgcgcc | cgaccggtgt |
| 11941 | gccgccgatc | agcaattcgc | cggccacgcc | gatcggcgtg | ggctgcatct | gcgcgtcgac |
| 12001 | gatgtagagg | cgggtgttgg | cgatgggccg | gccgatcggc | acgatgcggt | gcggatcgtc |
| 12061 | gcgccggcat | tcccacgcgg | tcacgtcgac | ggcggcctcg | gtggggccgt | agaggttgta |
| 12121 | gagcttgacg | tccaggcgct | cgaggcaacg | ctgctgcagg | tcatggggca | aggcctcgcc |
| 12181 | gctgcacacg | acgcggcgca | gcgacgcgca | gtgcgcgtcg | aggtccggat | gatcgaggaa |
| 12241 | cgcgcgcagc | atcgacggca | cgaaatggat | cgtggtgatg | cgttcgcgct | cgatgagctc |
| 12301 | gaccaggtag | tcggtctcgc | gctggccgcc | ggggcgggcg | aacacgaggc | gcgcgccggt |
| 12361 | gacgagcggc | cagaagagtt | cccagaccga | gacgtcgaag | ctgaacgggg | tcttctgcag |
| 12421 | cacggcatcg | tcggcgtcga | gcgcataggc | gtgctgcatc | cagaggatgc | ggttggtgat |
| 12481 | cgcgcgatgg | gtgttgagcg | cgcccttggg | gcggccggtc | gagccggacg | tgtagatcat |
| 12541 | gtaggcgagg | ttgtcgccgt | tcagcgcggg | tgcggggttg | gacgtcgccg | cggcgtcgag |
| 12601 | gtcgagcgag | tcgcgatcga | cgacgatcac | gtgcgcgtcg | gtgtcgggca | gcgcgtcgtg |
| 12661 | cagatgctgc | tgggtgagga | gccagcgcaa | ctgcgcgtgg | tcgatcatga | agcgcacgcg |
| 12721 | ctcggcgggg | tagtcggggt | cgacggggac | gtaggcgccg | ccggccttga | ggatcgcgag |
| 12781 | cagggcaacg | ctcatgtcga | gcgaacgctc | catggcgacg | ccgacgagcg | agtcggggcc |
| 12841 | gacgccgagc | gcgacgaggt | ggtgggcgag | gcggttggcg | cgcaggttga | gttcggcgta |
| 12901 | ggtgagcgcg | gtgtcatcga | agacgatcgc | gacggcatcg | ggcgtgcgct | cgacctgctg |
| 12961 | ctcgaacagg | cggtgcagcg | gttgcgcggc | gtcctcgccg | aaatccgtgt | cggtgcggtt |
| 13021 | ccactcgacg | gtcagcaggt | tccgctccgc | gtcattcgac | aacgacagcg | cgccgagcgg |
| 13081 | ccggtccgga | tcggcgatca | cggcatcgac | gagcgtgcgg | aagtgttccg | ccatgcgatc |
| 13141 | gatcgtggcg | gcgtcgaaca | gatccaggtt | gtattccagc | gagcccgcga | ggccgtcgtc |
| 13201 | ggcatcctga | acatgaagcg | tgaggtcgaa | cttcgcggtg | tgggtctcca | ccgccaccgg |
| 13261 | cgtggccacg | agaccgggga | agctcactgc | ccggggttgc | gctttctcgt | atgcgaacac |
| 13321 | gacctggaac | accggcgtgc | ggcccaggtt | gcgttcgagc | tcgagcgagt | ccaccacctg |

```
13381  ctcgaacgga atctcctggc ggctgtagcc gtccagcgcg acgcgcttca cgcgcgccag
13441  caggtcgccg aaggtcggat tgcccgacag gtccacgcgc agcgcgagca tgttcgcgaa
13501  gaagccgatc agcggctcgg tcatgctgga acgccgattg gcgatcgggg agccgatgac
13561  gaggtcctgc tggttgctgt atcgcgacag gagcagcgca tacgcggcga gcacgaccat
13621  gaacgtgctg gtgccggacg cacgggcaat cgcgcgcagg ccgtcggcgc gttcggcgct
13681  cagctggaac ggcaggaccg cgccgcgaaa ctgctggacg gcgggccggg ggcggtcggt
13741  gggcagttcg atcaggtccg gcgcgtccgc cagcgcggcg ctcaggagcg ccagctcccg
13801  atgcgtgtcg gcggacgcca ggcgctcgtg ctgccacacg gcgtagtccg cgtactgcac
13861  ggccagttcc ggcagcgact cgccggcata gagcgcggcc agttcgccga tgaggatgcc
13921  tgacgaccat gcatcggaaa cgatgtgatg catcacgatg ccgaagacgt gcaggcgctc
13981  atggacgcga tacagcacga cgcgatagag cggcccggcg gcgagatcga acgggcggtc
14041  ggcttcctcc gcgagcagcg cgagcgtgtc ggattcgctg gcgacgtcga cgacgtcgag
14101  cgcgaccggc gccggcggcg caatgcgttg aaccccgcgg ccgtcgacgg cgggaaacgt
14161  cgtgcgcagg atctcgtgac gccggctgat ctcggacacg gcaaaccgca ggcgcgcgac
14221  gtcgagttcg ccttcgaagc gcagcgcgct cgagatgttg taggtggccg acgggccttc
14281  cagttgcgcg aggaaccaca gccgctgctg cggaaaggac agcggcaggt cgttcgcgcg
14341  cgagcggggc gggatggcgc cggccgtcga gccggggtgg ggcgacgacg cttcgatcag
14401  gtcggacacc gcgctgatgg tctggagttc gaagatcgcg tcgatgccga tctcgacgga
14461  gaagctgctc cagatccgcg agaccagttg catggcttgc agcgaatcgc cgccgtagtc
14521  gaagaagcgg ccggcgagat cgacggccgg attgtcgagc acgtcgcgcc agatgcgcac
14581  cagttcgcgc tgaatcggcg tggcgtcgag aggggcttcc tcgggcgcgg cggcaggctc
14641  cagggccagg agcgccgggc gatccagctt gccgttggcg ttgagcggga attcggcgat
14701  cgggatgatg tcggacggga ccatgtagtc cggcagcttc ccggccaggt aggcccgcag
14761  gttcggcacg ctcaggctcg cggcgcccct gacgtaggcc gccagcttgc gcaccccgtg
14821  ggcggattcg cgcagcatga ccgccgcgcc gacgacgtcc tcgtgcgcgg cgatcgcggc
14881  ctcgatctcg ccgagttcga cacggtgccc gcggatcttg acctggtggt cgacgcgtcc
14941  gtagcactgg atacgtccgt cgggcagcca ccggccgatg tcgccggtgc gatagatgcg
15001  cgcttcgccg ggaaacggat gctcgacgaa tttcgcggcg gtgacgtcgg gccgctggtg
15061  gtagccgcgt gcaaggccgg cgccggcgag gcagatttcc ccgggcacgc cgagcggaac
15121  cggccgcagc gcgtcgtcga gcatgtacac ccgggtgtcg gcgatgggac ggccgatcag
15181  caccgtgggc ggcgcgtcct cgacgcgctc gacgatgcag ccgaccgtcg cctcggtggg
15241  accgtactcg ttgtagattt cgatcgcggg atcgatcttg cgcagcgtgg cgatgtgctg
15301  gggcgtcagt tcctcgccgc ccacgatcac cttgcgcacg ccggagcgtg ccaggttcat
15361  gtattccagc aggtgaatgt gggtgggcgt gagcttgagg gtgtcgacgc cgctgccggg
15421  ctggaacatc cgggccagga tggtgtcgat gctttccgac tgcggataga tgcgcagcgt
15481  cttgccgcgc accagcgggc agaagatgtt ggtgagcgtg aagtcgaagc agagcgagct
15541  gtacaggccg aaactgccgg tcgtgctttc cggaaagtaa tacccggcgg cccacgcgat
15601  gtagtgggcc aggttccggt gttcgagcag gcagcctttg ggtttcccgg tcgagcccga
15661  cgtgtagagc acgtaggcca ggtgcgccgg ttcggcacgg tgcggcgggt tgtccggcag
```

-continued

| | | | | | |
|---|---|---|---|---|---|
| 15721 | cggctgccag | ccggggagtt | cctggtccag | cagcagcgtc | acgccggaga | attcatacca |
| 15781 | ctgcgcgagc | tgactcgact | gggtcaccag | cagcgacagg | cccgtgtcgc | cgaggatgtg |
| 15841 | attgatccgc | tcggccggat | acgcggggtc | cagcggaacg | aacgccgccc | ccgccttcag |
| 15901 | gatgccgaga | atcgcgacga | tcatccattc | ggaacggtcg | agcatgatgc | cgaccagcga |
| 15961 | ttccggcccg | acgccgtggt | gttcgcgcaa | gtgatgcgcg | aggctgttgg | cccgcgcgtt |
| 16021 | caggtcggcg | taggtcatca | gcgaactgtc | ggtgaccagg | gccggcgccg | tcggcgtgcg |
| 16081 | tgcgacctgg | gcttcgaaca | tggcgacgac | cgtcgggtgg | ctggggccgg | ccgtcgcggt |
| 16141 | ttcgttgaac | gcggccagca | gcgggccctg | ttccggcggg | gccgcttcga | tgtcgccgac |
| 16201 | ggcgccgtcg | aggtgttcga | atgcctccag | caccgcggcg | aggctgccgg | cgaaaccgtc |
| 16261 | gatgatgaaa | ggctcgatgg | ccccgctgta | acgaagctcg | atttcgccgc | gcgcgagccg |
| 16321 | caggtgcaac | tgcagatcgt | cgtcccgacc | ggtcggtgcg | tggtgcacgc | ggtcgtccgc |
| 16381 | cagcgcgact | ttcgtgagct | gcgcgagcgc | catgtccttt | tcgttgcgca | cgagcgtttc |
| 16441 | cagcgggaat | cgaggctcgg | cgtagctgtc | ttccacgatc | ccggccacgc | gcgacaggta |
| 16501 | gtcctcgatg | cgctcgtcgg | ggcggacctc | gatgatcagc | ggaacgatgg | cggcccgggc |
| 16561 | cgacggatgc | ccgccagcc | ccggcgtgcc | gagcaccgtg | accggaatcc | ggaagtattt |
| 16621 | ccagagcagg | aacgcgatgc | ccgccgccgc | gacggcgaat | tcggcaagct | cgccgtcgcc |
| 16681 | gatgcgccgc | aacaggtcga | gcgacgcggg | cgtgagccgc | accgagcggg | tcagcgggcg |
| 16741 | acccggctgc | tggctcgggg | cgtacgccgc | gattccgtac | acgccggcga | cccgggaaag |
| 16801 | gctttcgcgc | cagaaacgcg | cggtggctgc | atagcgatgg | tcggtgacca | gcacgttatt |
| 16861 | gtcttgcaca | ggaaactcct | tgagacgttt | tgttcacctg | aaacaacctg | aagcagcacg |
| 16921 | cacggcgcgc | gccgctcgaa | ccccggcggg | cgcgcatcac | gtcttctcct | cgagcgcgtc |
| 16981 | gtcggccgtg | accgcgggcg | cgcgcttcag | gcgcaggccg | acccggactc | gcgggccggc |
| 17041 | ggcgggcgcc | tcgtcggaga | gcgggatgcg | atcgaccggc | gtggccggat | cgcgacggaa |
| 17101 | gacgtcgtgg | atcgcgagca | gtcgatcgcg | catcgcggcg | atggtcgacg | ggcggaacag |
| 17161 | gtgggtgttg | tagatgaact | ggatcaggtg | ccggccttcg | cttcacga | cctggaagga |
| 17221 | caggtcgaac | ttggccgtcg | tgtccgccgg | cgagatgtcc | gtgatgcgaa | ggcctggctg |
| 17281 | cggcgccggc | atcgacacgt | ggttcacctg | aatgtcgaag | atcgggaaat | ggttcgccgg |
| 17341 | cgtgcggatc | ttcaggtctt | ccagcaacac | gtcgaacgga | taggacgcat | gctccagcgc |
| 17401 | ttgcgcggag | gctttcgcca | ccccgtcgat | cacctccgcg | accgtcgcgg | atttccgcac |
| 17461 | cggcacgcgc | agcacgacgg | tgttgaggta | cacgccgacc | tgcgattcga | gctgctcgct |
| 17521 | gtcgcgcccg | gccgacacgc | tgccgatgac | gatgtcctca | cgcccgtgt | agcggtgcat |
| 17581 | cagcacgcag | aacgacgcca | gtagcaccgc | gtggagcgac | gtgtggtgag | cgcggggccag |
| 17641 | cgtcgcgagt | tccgccgcgt | gcggctgcgg | cagttcgact | tcgagcgtct | gcccggcatg |
| 17701 | accgagccgc | tcgggacgcg | ggaagtcgga | tgccagttgc | aggcggggca | gcggcggcgc |
| 17761 | cagttgctcg | agccagtacg | cgcgatgcgc | ggcggcgcgc | ggacccgcga | ggctcgcgtt |
| 17821 | gtgccacgcg | gcgtagtcgc | gatactggat | cgacagcggc | ggcaggtcgc | gccccgcata |
| 17881 | cagcgcatgc | aggtcgtcgg | tcagcacgcg | gatcgaccat | gcatccgaga | tcacgtggtg |
| 17941 | catgttcagc | agcaacagat | gcttctcctg | cgacagccgg | accagcttga | cgcgaaagag |
| 18001 | cgggcccgac | gcgagatcga | acggctgctc | gcattccgcg | cgaatcagcg | catcgatcgc |
| 18061 | ttgcggcccg | gcatcgtccg | cgagatcgcg | ctgctcgacc | cggaatccgg | acgcttcgcg |

```
18121  gctgaggacg cgttgccgca actcgccttc gatcatcgcg aacacggtgc gcaggctctc
18181  gtggcgatcg accagcgtgt cgaatgcacg gacgaggcgc gccgtatcga cggcgccgtc
18241  cagctgcagc gcgcccgcca tgttgtacgt ggacggatcc gcgccgcggc tggcgagcca
18301  gatccgcttc tgtgcacgag acaccgcgta ggacggttgc gcggccagcg ccgggatgat
18361  cgcgtcgtcg tcggcggcgc cgtcgacggg catggcagcc agcctttgtg cgagcgcgcg
18421  cggcgtcggc gcatggaaga tgtcggcgac cgcgacgttc agtgcagccc ggggatccg
18481  gctgaccatc tggatcgcct tgaggctttg gcctccgtgc tcgaagaaat cgtcgtcgac
18541  gccgttcggc cggcggccga gcacctcggc gaagaggcgc agcagcgccg cttcgaccgg
18601  cgtgcgcggt tcggcccgca cgccgtcggg cacggacgcg gcatccggca gcggcagcgc
18661  ggcgcggttg atcttgccgt tcggcatgac gggcagcgcc ggcagcagca tcacggtgtc
18721  gggcaccatg tgcgccggca gcgtgtcgcg cagtgcgtcg cgcacgcgct ggggcgtcca
18781  gccggttccc gacgcgtagc cgcacagggt catttcggca tccgacgttt ccgggcgac
18841  caccacggcg tgggaaatgc cggcaagact ggtcagcgcg gcttcgattt ccccgagctc
18901  gatgcggtag ccacggatct tgacctggaa gtcgcggcgg ccgaagaagt gcagattgcc
18961  gtccgcccg aagcagccga tgtcgccggt gcgatacagg cgcgcgcctg gttccggact
19021  gaacggatcg tcgcggaaca ccgcccgggt gcgggcttcg tcgaacaggt agccgcgccc
19081  gacgccgacg ccccgatgc agatctcgcc cttgacgccg gccgggcacg gattcatgtc
19141  ggcatccacg acgtagaggc gcaggttctc gatcggccgg ccgatcggaa tcgccggccc
19201  atccggcgcg cgcgtcaggc agtaatgcgc gacggagtcc gacgcttcgg tcggcccata
19261  ggcgttgatg agccggacgg ccggattcag gcggaaccac gcttgcgcgg tggcgggctg
19321  cagcgtttcg ccgatcgtca gcaacgtgtc gaggtgaggg aaggccggtg ccgcgtgccg
19381  ttccagttcg ccgagaaagg tcgcgagata ggacggtacg aattgcattg ccgtgatgcg
19441  gtcgcggtgc aggctgtcga tcaggcgcgc gggctcgagg atcacggcat cgggatagat
19501  caccgtcgtg ccgcccgacg ccagcgccgc gaagcattgc cagaccgaaa tatcggagca
19561  gtgcgaagcg gtctgggcga ccgcgctctg cgcgccgagc ccgacccggc gcgccatcgc
19621  gagcacgtga ttgagcatgc cgcgatgttc gaccatcgcg cccttcggct ggccggtcga
19681  acccgacgtg aagatcacgt aggcgaggtc cgcgggccgg cagcgcggcg tcaccggcgc
19741  cggcgcttcg gcgccgcgac ggtcgggcag gcgggccgga tcgaccagcg ggatcgacgc
19801  cagcgccggc ggcggcacgc agtccgtcgt gacgatgacg gccggccgcg ccagcgtcag
19861  gatggtctcg acccgctggg ccgggtaggc cggatcgacc ggaacgtacg ccgcgccgca
19921  cttccagatg gccaggatcg tttccagcat cagcggcgag cgcggcatcc agacggcgat
19981  ccggtcgtcc ggctgcagcg gcgccgtctg cagaagatgc gcggcgatcc ggttggcgcc
20041  ttcgacgagg tcacggtagg tgcgaacctc cgtgccgcag cgaaccgcca cgcgctcggg
20101  gtgcgctgcg gcgacggcct cgatcagttc gggcagcgtc cggtcggacg gaaccggcgc
20161  gaacgtgtcg ttccagccga gcaggatggc gtcccgctcg gcggcagcga gaagcggcac
20221  gctgcggttc gggcgatctt ccgcgccggc caggccggtg agcagggtct cgacatggcg
20281  cagcaggcgg acgatcgtgt cgcgatcgaa ccggccgtcg tcgtacagca cctgcagcga
20341  caggcgcttg cccggcgtca cgaccagcgt cagcgggtaa ttgttcggat cggacacctc
20401  gaatgcgccg atccgcaggc cgggcagcgc atcggccagc gcttcttcca ccggataatt
```

```
20461  ctggaagatg agcaggcttt cgaagagcgg cacgccgggt ggcaggccgg cgaatttctg
20521  gatgtcggcc agcggatagt gcgcatagtc ctcctgctgc gcgagatcca tctgcaattg
20581  cgccagccac gctgacgtcg ggcgtgcgtc gatgcgcacc cgcaccggca gcgtgttgat
20641  gaacagcccg accatttcgt cggatgccgg cagcgacgcc gggcggccgg aaacgatcgt
20701  gccgaacacg acgtccgatt cgccgctgta gcggctcagc aactgcgccc atgcgccctg
20761  cgcgagcgtg ttcagggtga ggcggcggga ttgcgcgaat gcgacgagcc gttgcgtgtc
20821  gctttcggag agcagcagcg gctcttccac gtaggcgccc ggcgcggccg tgccgtcgag
20881  ttcggggcgg cccagcacga gcggcgtcgt cgccgggaaa tccgccagct tcgtcttcca
20941  gaaacgttgc gcggcggcgg cgtcctggcg tgccagccag cgcacgtaac cggcgaaggc
21001  aggcggcgcg tcccgctgcg gcgcgccttc ggccggcggc gcctgatagg cggcggccac
21061  gtcgctcagc aaccgggcgg agctccaccc gtcgagcagg atgtggtgat ggctccaatg
21121  gaagcgccat gcgtgctcgc ccacgcgaaa cagcgcgagc cgcatcagcg gcgcgcgggt
21181  aaagtcgaag ccgcgcgccc ggtcttgcgc cacgtaggct tcccagcgct gttcggcctc
21241  cgcggcggac gccgcgcgca gatcctcgtc gtgccacggc aagtcgatcc ggcgatgcac
21301  gacctgcacg gggctttcga tgtcttccca gtgaaacgac gtacgcagga tgtcgtgccg
21361  gtgcgccacg gtctcccacg cgcggcggaa ccgttcgacg tcgagcgccc cgtcgatacg
21421  gaaattcagg ctgctgaagt acgcatccga cgcgggttcg tacaggctgt ggaacagcat
21481  gccctgctgg gtcggcgtca gcgggtagac gtcggcgatc tcgtccggac tcaccgacgc
21541  cggcgccggc gcctgcggca acgcagtcgc gggccgggtc gatgcggacg ggacagcgtg
21601  gccggcgacc agggtttcga gcgccgcgat gtaggcttgc gcgacgcgca ggatggtggc
21661  cgtgtcgtgg caggcccggc tgaattccca cgcaacgtgc aggcgattac cggtcacgta
21721  cgcgttgatg tcgagcaggt gctcgcgcaa ctggttcgcg ttgcggccgt ccccgctcgg
21781  ctccgcggcc tgtttccagt cgcgtgcggc ggtgaacagc tggtcggtct gccccaggta
21841  gttgaactgc agtcgcggct gcggaagcgg gccgtcgagc cggtctagca gcaggccgta
21901  ggtgatgccc gcgttcggca ccgcgcgcag ccgcgtcctg accgatgcga cgaggctggc
21961  cggatcgtgc gaaccggcat cgaccgtcag caagaccggg aaaaccgacg taaaccagcc
22021  caccgtgcgc gagatgtcga gcgcgtcgat cagttcctcg cgcccgtgcg cttcgagatc
22081  cagcagcacg tcggcgcatc cgctccattc gctgacggca cgcgcgagcg cggcgagcag
22141  cacgtcgttg acctgcgcgt cgtaggcgcg gggcgcggcg cccagcaagg ccgtcgtcgc
22201  ggcttcgccc aactcgacga cgatcgtgtc ggcggacgac acggtattgg cgtcggcagg
22261  cgcatcgcga tcgagcggca ggcccgggcag ggcggcacgc gcgagggcct gccaatgggc
22321  gaggtcggcg tcggcggcgc cggagccggc ccaggtcgag atcgcccggg tccatgcggt
22381  ccaggtcgcg ctgccgcctg cgaattcggg cgccttgccg ttgcgcagcc gggtataggc
22441  gtcgtacacg gtttcgagca gcgcgcccca cgacacgccg tcgacgacca gatgatgggc
22501  gaccagcagc aggcggagcg aacggccttc gtcgacgcgg aacaggtccg cgcgcacgac
22561  ggggccgtcc gcgagattca ggctcgcatg cgactgcgcg acgtactgcg cgagctgatc
22621  gcgcgcaatg tcggacacga cgacggggat ctccgggtcg tcgacgactt cctgggtcca
22681  gccgctctcg ccctcgcgaa agcgcagccg cagcgcgtca tgccatttga ccgcatgccg
22741  cagcgcctgc gcagcaagag ccggatcgag gtcggccggc acgtcgagca ggaccgcctg
22801  gttgtactgg tccgggtcgt gcttgccctg cgcgaagaaa cgcttctgga tgggcgtcag
```

```
22861  cggcagcggg ccggacgatg cgacgaacgc cgccgcgccg accgtgccgc gcgtcgccac
22921  ggcggcgagt tcggccaccg tcggatgctg gaagatgagc cgggtggtga gcttcaggcc
22981  cgccttcgcg gccagcgaca cgatgcgcat gctcagaatc gaatcgccgc ccagcgcgaa
23041  gaggttgtcg tggatgccgg gcgacggaat gcccagcgct tcgccccaga tgcggcacag
23101  cagcgtctcg gtaggcgtgc ggggcggcgt cggcgcgtgt gccgtggcgg cgagtcgcgc
23161  gcggtccagc ggcggcagcg cgttgcggtc gatcttgccg ttgccgctca ggggcagcgc
23221  gtcgagcacc acgtagatgc cgggcaccat gtagtccggc agcgtggcgg acagcgcggc
23281  ggcgatcccg gcgtcgctca gcgacgcgcc gtcgcggaac gcgacgtacg cgcacagcgc
23341  ggcgcggccg gcctcgtcgc gatagtcgag cgcggcggcc tggcggagtt ccgcgaatg
23401  gtcggccagt cgtcgttggt cgatctcccc gagctcgatg cggtagccgc ggatcttcag
23461  ctggtggtcc ttgcggccgt gcagcacgat cgttccgtcg ggcaggtagc agccgatgtc
23521  gcgggtgcgg tacaggcgga cgccgcgctg aggatggaac ggatcctcga cgaacgcgtc
23581  ctgcgtggcg gcttcattgt tcagatagcc gcgaccgacg gcgacgccgg acacgcacag
23641  ctcgccggga atcccgatcg ggcacaggtt catctgcggg tcgacgacgt agaggcgaac
23701  gttgcggatc ggcttgccga ccggtacgta aggcgtggac ggcgcgcccg tcatgcggtg
23761  ctgtgcgacg tcgtcggacg cttcggccgg gccgtacgcg ttcaccagcg ggatcgccgg
23821  gaacacgtcg aaccactgtt tcaccagcgc cgggctgacc atctcgccgg tgacgagcag
23881  gtgccgcaga tgccgcatca gcgccggccg ttccgacgcg cggtcgagca cggcggacag
23941  ataggacggc accagttcga ggatgctgat ccgggtggtt tccaggtacg cgacgaaacg
24001  cgcgggatcg cgaatgcagt cgtcgtcgac gatcacggtc ttgccgccga cgagcggcgc
24061  cgtgaaaaat tgccagaccg aaatatcgaa gcaatgcggc gcggtttgcg cgatcaccga
24121  cgacgccgag atcgagaact cgtcgatctc ggcgagcatg tggttcagca tgccggcgtg
24181  ctcgaccatc gcgcctttgg gcttgccggt ggagccggac gtgtagatca cgtaggcgag
24241  gctgtcgggc gacacggggc ggccgggatt ggagtcgtcg acggcgtcgg tggcggcgtc
24301  gagcgacacg accagcgcga tcccggccag ctccgggggg aggagcccgt cgcaggtgat
24361  cacgagggcg gcgccggaat cctcgaggat ggtgcggatg cgggccaccg gataattcgg
24421  gtcgaccgga atataggcgg cgccgcactt ccagaccgcg aggatcgcct ccatcagctg
24481  ggcggaccgg tgcatgcaga ttgcgaccag cgcgtccggg cccaggtcgg cggcggcgag
24541  caggcggtgc gcgatgcggt tggcgcgcgc gttcagttcg cccgcgctca ggacgccatc
24601  ccggtactcg accgcgggcc gctcggggtg gtccgcggcg gcctgctcca ggcgatgcac
24661  cacggtgagc gcggcgtcga acggcacggc ggtgtcgttg aaggtctcca gcaactgccg
24721  gcgttccgcg tcgggcaaga tcggcacgcg gccgagcagc cggttcggat cggccgcgaa
24781  cgcgtcgagc gtcgcggcca cgtggcccag catccgctgc atcgtgtctt catcgaagcg
24841  ccgcgggtcg aacgacagtt ccatcttcca gtcgtcgcgc gccgtcacca cgaattcgag
24901  cggaatgtcg gcgcggttgt agagctgcac ctcgtcgacc gccagcccgt gcgcgccatg
24961  cgtgagcgac gcgtcgagcg ggtaattcat gaacgtgatg ttgctctcga acagcggcgc
25021  cgtcggcggc acgtcgctgc agcgctgaat gtcgggcaac ggggtgtgct cgaacggcgc
25081  gcgggcggcc acgcgcgcct ggatcatctt cagccacggc accagcggct gcctcgggtc
25141  gacccgcacc cgcaccggca ccgtattgat gaacaggccg agcatggttt cgatccccgg
```

```
25201  caggttggcg ccccgcccgg acacgacggc gccgaacacc acgtcggttt ccccgctgta
25261  acgcgacagc acgagcgccc acgccgcttg cgcgagggta ttgagggtga cgtgatggcg
25321  ggccgcgaat tgccgcaggc gcgcgctcag gtcggccgac aggtcggcct gcacttgcgc
25381  gaggccctgg ccgaagcgtt cgtccgcgcc cgcgcgcgcg gccgtgggca gcggggtcgg
25441  tgtgcggaac ccttcgagat agcgcgtcca gtattgctgc gcggcttgcg gctcgtgctg
25501  ctgcagccac tggatatagt cgcgataggg gcgcaccggc gggagcgccg gcgacacgcc
25561  gcgcgcgagc gcgccataga cctcgaagat ctcctcgatg acgagcgaca ggcaccagcc
25621  atcggccagg atgtgatggt ggctccagct gaacaggtag gcgtcggcg cgacgcgcac
25681  caggcgacag cgcacgagcg gcgcgcgatc gagcgcgaag ccctcggcca ggtcgttgtc
25741  gagatgcgcg cgccaccgtg agcgctgttc gtgttccggc aggtcgagcc agtcgtcctg
25801  cacccacggc agcgtggcgc gcgcgtgcac gacctgcatc ggcttgtcga actcctccca
25861  atggaacgac gtgcgcatca ccggatgccg atcgatgagc tgctgccacg cggcatgaaa
25921  cagcgcggga tcgaggctgc cggtgatccg gcaactgagc tggttgaagc tgcttctcga
25981  gccgggctcg tgcacggcat gaaagagcat cccctcctgc atcggggaga gctcgtagat
26041  atcggcgatg tgggggatg tcacgatttg atccttgaga caagggcgtc cagcgcttcc
26101  tggctgatgc gcgcggccgg aaagtccgac gggctcagcg cgcgcgggcc gtcgccgccg
26161  gccgcgacga tcgacagcag gcggctgcgg tagcactgcg tcagctgttc gatgacgccg
26221  ggtgcgcagg cctcgcggtt gtagtgccag gtcaggcgca gacggccgtc gaacaccatc
26281  ccgtcgatct cgaacagatg gccgcgacgt gcgcgcgggc tgtgctcggg gctctggaag
26341  tcgagtaccg gcttccagcc cgtgtcgtcg ggcagcacgc gatcgacctg gccgagatag
26401  ttgaagcgca ccggcgccgg cggctgccgt tcgagcgccg ccgcgatgcc ggcgtcgtgg
26461  ccgaggtagc gggcgatgcc gtagccgagc ccgcgcatcg gaaccgcgcg cagctgctcc
26521  ttgacgtggc gcagcgcgtc gaccgccacg gtggcgtcgc cggcgttcag gcacaccgga
26581  tagtgggtgg tgaaccagcc gatcgtgcgc gacgtatcga cgccgtcgaa aatgtcctcg
26641  cggccgtggc cttcgagatc gacgaccagc gacgcgttgc cggtccagtc gccgaacgcg
26701  agcagcaggg ccgtcagcag gacttcgttg atctgcgtgt tgaacgcacg cggcacgtcc
26761  tgcaacagcg cgagtgtctg ctgcgcatcg aactcgacga tcgtcgagcc cgcttcggcg
26821  acggtgccgg ccggcatgtc gtcgaagcac gccggctcgc cggcgttgcc ctggagccag
26881  tagtccagcc ccaggccgtc gagcgcggtc gcgccgagtc cggacaggcg cgtcgaccag
26941  tcgcgccagg ccgtcgtcct ggccgggagc tgtaccgcgt cgcccgcttc gagctggcga
27001  catgcggtgt acaggtcttc gaacaggatg cgccacgaca cgccgtcgat caccaggtga
27061  tgcgcgaccg cgagcaggcg ctgcggcgcg tcgggaccga actggaacag gtgcgcgcgc
27121  agcagcggcg gcgccgacag cgtgaagctt tcctgcatgc cggtggcggt cgcgagcatc
27181  gcggcctgcc gtgcggcagg cgccgcgtcc gccagcgacg tgacgccgag cggaatggcc
27241  agcggcggcg cggcatgcga ttgctgccac acgccggcga cgcacgcgaa actcagccgc
27301  agcgcgtcgt gatgcgtcgc gacggccgcc agcgcgcgct cgatcgtgtc cggccgcagc
27361  gatgcgggca cctcgatcat cgtcgactgg ttgtagtggt gcggatcggc gacgtcttgc
27421  gcgaagaacc agtgctggat cggcgtcagc ggggcggggc cgaccaccgg ctcctgcgcg
27481  atccggatca acgcgcctc cgtcgcgacc tgggcgagct cggcgatggt cgggtgtgcg
27541  aagaactggt cggcggtgaa cttgagcccg acttgctggg ccagcgacat cacctggatg
```

```
27601  atcaggatcg agtcgccgcc cagttcgaag aaattgtcgt gcacgccgat cggctcgcgg 27661  cccagcacgt cgcaccagat cctgcccagg cgcgcctcga cgtcattggc cggtgcgacg 27721  taggcggttt cgctcggcgc gggcgccagt tccagcgcgg cgagcgcctt gcggtcgggc 27781  ttgccgttcg gcgtcagcgg caggcgttcg agcgtcacga tcgacgccgg caccatgaac 27841  tcgggcaggc gttccttcag gtgttcccgc aggctggcga cgctggccgt cgccgtcgcg 27901  acgcaggcca ccagctgctt gtgctgcggc gtgtcctcgc gcacgaacac gatcgcgtcg 27961  gcgacgccgg cgtgctgcct gagcgccgcc tcgatctcgc ccatttcgat ccggtagccg 28021  cgaatcttca cctgcgtgtc gcgccgcccg gtgacttcca ggttgccgtc cggcagccag 28081  acgccgaggt cgccggtgcg atagaggcgc tcgcccgcct cgaacgggtg ggcgacgaac 28141  gcggcggccg tcaggtcgtc gcggccgaca tagccgcgcg ccagcgcgat gccggacacg 28201  cagatctcgc ccgcgcaacc ctcggggggcc agcgccccgt gctcgtcgag caggtacagg 28261  tgcgtgttgt ggatcgggcg gcccaccgga gacgggcgc cgtaggtgat ggccgggtcg 28321  accacgtagt ccgcgatgca cacggttgcc tcggtcgggc cgtacgagtt gtggcacgtg 28381  cgggtccggg ccagctcgcg cagatccgcc acgcgggcgc tgtcgcccgc gctgatgacc 28441  cgtttcacgg cgccgagcgc atgccagtcg agcgcggcaa ggtaggccgg cgtcgcgttg 28501  acggtggtga cgccctgctg tgcgatgtag tcgacgaaac gcggcacgtc ccggatcacg 28561  gcggtctttg ccagcaccag gcgggcgccc gcgagcagcg tgacgaagat ttccatgatc 28621  gagccgtcga agcccgggga gtagaactgg acgaagcggt cggcggaatc gaaaccgaat 28681  gcgtccacgt ggtactgcgc catgttcagg agccctgcgt gttcgagcac gacgcccttg 28741  ggcacgcccg tggagccgga cgtgtagatg atgtatgccg cgtcgtccgg ccgcaccctcg 28801  acctgcgccg atgccgacgc gggtgccagc gtgtcgagct ggaagtcgag ggcgaacatc 28861  gggatcgccc agaaatcggc gagcaacggc aggtgttccg agtgcgtcag cagcgccttg 28921  accttcgcgt cctcgatcat gaagcgcagg cgctcccgcg gaaattccgg gtcgagcggc 28981  agatacaccg cgcccgcctt gagggcgccg agcatgccga cgatccagcg ctcggaacgg 29041  tcggccacca cgcccaccac gtcgccgcgt tcgatcgcgt attccgcgag caggaagctc 29101  gccagccggg acgcctggtc gtcgagttcg gcataggtca gcgatgcgtc ggcggtcacc 29161  accgcgacgc tgtccggcgc ggccgcgacc cgttgcgcga actgctccag gaaggtgccc 29221  tgtaccgcga cgggcgccgc atgcgaacgc aggcgcgcgc gctcttcgtc gtcgagcagc 29281  gagacggtgt cgagcggcgc atccagtgcg ccgaagccgg ccacgacgtt gcgcaggtgc 29341  cgtgcgacat gctggagata gtgcagcgtg aacaccgtcg gccggcccgt cagcacgatc 29401  tcgtagcgct cccgatgccg gatctcgatc gacaggtcgt agtcggccgc tgcccaggct 29461  tcgtgaaggc cgtcgaagcg cacgccgacg ttggtcgcgc gccgttcgcc atgcagcttg 29521  tgcgcgaggc cggcgatcgg gaaatcctgg tacgaatagc tgcgctgcac gctgtcgcgc 29581  agctggttca ggtacgcgcg aaccgtgggg ccgggctcgc cggcgtcgag cagcgggaca 29641  ggctcggcgc agccgctcgc gggttcgacg atcagctgcg gcgacgccac gaacaggccg 29701  gccgcgccgt tgtagcgccc cagcacgcgg aacagcgcgg ccagcagcac gacgaacgcg 29761  cccagctcgt tgccggcggc gagccgctcc agcacctgcg ccgcgtcgcc gtcgagcgcg 29821  aacgtcagtg ccggctcggg gccgagcggc agcgcatacg cctgccacgc ctgctgaagg 29881  cggaaatctt catcgatgcg accgagcgcg tcgttccaga acgccacgtg ttcctggtat
```

```
29941  tgcccgctgg tcgagagcgc gttgagattc agttctgaca aagcacgatc tccctcgtcg
30001  cgtacaggat ttcggaagcg atgcccttgg ccttgcagtg cgcgacgaac tgggtggact
30061  ggatgtggct gggcgagttt tcgtcgaagg tgttgtcgag gaggtggttc agccagggct
30121  cctgacccat cgcatagaca tacgccgcgt tgaacgcgaa atcgtccacc agcgcggcgg
30181  cctcgccgaa ctggcagccg cgcgcccggc gtgattgatc gatgtcgcgc ggcagcgcct
30241  tgggaaacag cgggccgtag acccatgacg gcggcgcgcc ctcggtttcc atcccgacga
30301  acagggtgtc cggcttgccg gcgaggcgga agacatgctc gtagaggcgc gggtccaggt
30361  tgcacgaatc ggcgatgcac agcaccgagc gcgagccgaa gcggatcatg aagctctgct
30421  tgctgtggat cgccaggtcg ttgtgttcgc ccatgaacgg aatggcggtg atggcgccgc
30481  cgggcacctt gatttcctgc gcatcccgaa cttccagcac gtcgtcgaag ccgagcttgc
30541  gcaacgccag ctccatcgac ggatcttgcg gaaagccgtc gagattcctg ccgaccacca
30601  cggtcttgac cttgtggcga agctgcagca gcgtttcgag gacgatgtga tcgtgatggc
30661  tgtgcgtgat cagcacgtag tcgatctggt ccggcaggtc ggcgaacgta tagcgcggca
30721  gcgcggtgtc gtagccgtag ctgatcaccg gatcgatcag gatgctcacg ccccggctct
30781  ggatcagcac cacgcgtgg ccgtagtagc ggatgcggat gtcgtcgccg tcgaacgaac
30841  gatccggttt cggcgccggc gcctcctcga cgaagaacga gcggaacagc ggctcgtcct
30901  tctcctccac gcgcatcagg tcgacgatct tcgcgtagct gccgggcgtg tcgcgcatgc
30961  ggaacagcgt gtcgagcgcg cggtcgtcga aggccatgtt gctgaacacc gtgcgctcgt
31021  cgcggagccg gggcgtgctg aggatgaacg gccgcggcgt gtgctcctcg atcgccgaca
31081  gcgcgatgct ctgcgcatcg cgcgcataga acgggctcgc gtacagcagg ctttcgaaca
31141  cccggaagga cgggttgtgg ttcaggtcgt agtagatctc gacatagccc ttcagcacct
31201  ccggaatctc ggggtagagc gggtccgacg ccatccccgt ggcccgttcc agcagcagcg
31261  tggagaacgc cttgtatgcc ttcgccagtt ccagttgccg ggtcgcgcgt tgggtggtct
31321  gctcgatcag cgtgcggatt tcgtcgacgc gctggccgcc caggtcgagg aacggcccgc
31381  cgcgcatcgc gggatccttg caggccgccg catgcatcat cggcgatgcg gcataggact
31441  tcagcagcgg caggaaccgc tccgccacgt tgagggcggc ggtcaacggc ggaagcgtgt
31501  gataccacgc gtaccagctg ttgatcagcg gttcgaactg gatgttttgg cgcaggtaga
31561  cctgcgcgct ggacgaaata gtcaacgaag gctccttaga atgcgctgag ttcgacggtg
31621  ggctggcggg cttcggcgtg cagcgcgcgt tgtcccaggg tcaggttccg gatgcgaacg
31681  cccggattgg cgagcacctc gccgatgacg gacgtcagct cgttggcgag gccttgcacc
31741  agggcttcgc tgaaccgccc cgcgtgatag acgacgcgga tcgcgagacc ctcggcgtgc
31801  ggctcggcca ggaaccagaa atcggttgcg gcttccgtgt ccgcgcgctg cgggtcgtgg
31861  tccggcagct cggcgatatg cacttgtccc gcgtagcgat cgacgggcc gtgtcgctgg
31921  ttctgcagcg tcaggccgat gtcgaagagc ggattgcgtc ccgccacgcg tttgatgtgc
31981  agctcgtcga gcaggcgatc cagcgggtac agcgggtgcg agaacgcttc gagcgtggtg
32041  tcccgcaccc gggtcagcag cgtgtcgaac cggtcgtcgc ccgcgacacg atcgcgcagc
32101  gccagcacgt tcaggtaggg gccgacctgc gactcgagtt cgggcagttc gcggcccgcg
32161  accggcgtgc cgacgacgat gtcctcctg ccggagcggc ggtagaacag cgccttgatg
32221  gcggacagca gcgcgatgaa caaggtcgcg ccgtggcgct tgccgagcga ttccagcgcg
32281  gccgtctcgg cggcgggcag gtcgaatcgc caggatttcc agctcggcgc ggccggctgc
```

```
32341  tcgacgtcgc ccggcagttc cagtgcgcgc aggccgccgc ccagtttggt cagccagtag
32401  tccttcatgc gcgcgccgtc cggcccggcg agcaggcggt tcagccagcc ggcgtaatcc
32461  ttgtactgga tcgggagggc gggcagcgga tcgtcgcgac gctggacgaa tgcgtcatag
32521  agcgcggaca ggtcgtcgag cagtacctcc gtggaccagc cgtcgctcac gatgtgatgc
32581  atcgtgcaga ggcagacgtg acggacttcg gagagcctca gcagcttgac gcggaacagc
32641  gggccggtcg cgagatccat cggcacgagc cgttcgctcg cctggatcgc cgctgcctgg
32701  gcatcgcggt cctcggcatc ctgcagatcc acgatctcga ccgggaacgc ggcttcgccg
32761  ggcggcagca cgtgctggac cggctggttg ccttccagca cgaaacgcgt gcgcaggatc
32821  tcgtgacgct cgctcaacgc gcggaacgcc cgcacgagcg catccacgtc cagcacgccc
32881  tcgaacagca gcgacgtggg cagcggcccc tcggcttgcg ccgcatggag acgatcctgg
32941  acccacagcc gcgtctgtgc gggagagagc gcgtagcttg cctgcgccgg cagcggcgtc
33001  accgcgcgcgt aatcgatcgg ctgcgtatcg gcgatgcgct tcgcgaggct cgagatggtt
33061  gggagtgcga acaggctgcg gatttccagc ttcacatgca gatcgcgccg gatgcgcgcg
33121  acgaccttcg tcgccagcag cgaattgccg cccagatcga agaaattgcc ggtcgtgctg
33181  atccgcgcct ggccgagcac ttcctgccag atggcagcca actgcgcttc gagtgcgttg
33241  acgggcgcaa cgtggtccag gccgtcgccg ggttcgggca gcctggtgcg atcgagcttg
33301  ccgttgggca gatgctcgaa cgcgctcacg acgacgaacg cggagggcac catgtaatcc
33361  ggcagccgct gccgcaggtg gccgcgcacc gcttcgatca gttctgcttc ggggtgcgac
33421  gagcacagcc atccgaccag tctcgcgccg tcgtccacgc cgcgcagcgc gacgacggcg
33481  gcatcgacca gcgggtgcga cgtcagcgcc gcctcgattt caccgggttc gatgcgcagg
33541  ccgcgcagct tgatctggtg atcgatgcgg ccgaggaact cgatgttgcc gtcgggccgg
33601  tagcgcgcga ggtcgccggt gcggtagagg cgcgcgagcg ggtcggccga gaacggatcg
33661  gcgatgaact tttcggcgct cagttcgggt tcgccgtggt agccgcgccc gaccggtgtg
33721  ccgccgatca gcaattcgcc ggccacgccg atcggcgtgg gctgcatctg cgcgtcgacg
33781  atgtagaggc gggtgttggc gatgggccgg ccgatcggca cgatgcggtg cggatcgtcg
33841  cgccggcatt cccacgcggt cacgtcgacg gcggcctcgg tggggccgta gaggttgtag
33901  agctcgacgt ccaggcgctc gaggcaacgc tgctgcaggt catggggcaa ggcctcgccg
33961  ctgcacacga cgcggcgcag cgacgcgcag tgcgcgtcga ggtccggatg atcgaggaac
34021  gcgcgcagca tcgacggcac gaaatggatc gtggtgatgc gttcgcgctc gatgagctcg
34081  accaggtagt cggtctcgcg ctggccgccg gggcgggcga acacgaggcg cgcgccggtg
34141  acgagcggcc agaagagttc ccagaccgag acgtcgaagc tgaacggggt cttctgcagc
34201  acggcatcgt cggcgccgag ggcgtaggcg tgctgcatcc agaggatgcg gttggtgatc
34261  gcgcgatggg tgttgagcgc gcccttgggg cggccggtcg agccgacgt gtagatcatg
34321  taggcgaggt tgtcgccgtt cagcgcgggt gcggggttgg acgtcgccgc ggcgtcgagg
34381  tcgagcgagt cgcgatcgac gacgatcacg tgcgcgtcgg tgtcgggcag cgcgtcgtgc
34441  agatgctgct gggtgaggag ccagcgcaac tgcgcgtggt cgatcatgaa gcgcacgcgc
34501  tcggcggggt agtcggggtc gacggggacg taggcgccgc cggccttgag gatcgcgagc
34561  agggcaacgc tcatgtcgag cgaacgctcc atgcgcgacg cgacgagcga gtcggggccg
34621  acgccgagcg cgacgaggtg gtgggcgagg cggttggcgc gcaggttgag ttcggcgtag
```

-continued

```
34681  gtgagcgcgg tgtcatcgaa gacgatcgcg acggcatcgg gcgtgcgctc gacctgctgc
34741  tcgaacaggc ggtgcagcgg ttgcgcggcg tcctcgccga aatccgtgtc ggtgcggttc
34801  cactcgacgg tcagcaggtt ccgctccgca tcgctcgaca acggcagacg ggcaacggcg
34861  gccgacgcat cgtccgcgag atgcgtcagt agggtccggt agatgtcgag gaaacgctgc
34921  accgtgctcg cgtcgaacag atcggtgttg tagtcgcaat cgatcaggag tgcttgcccc
34981  gcgtcgagca cgttgacgtt caggtcgaac gcggtatggc ggatcagcgg cgccacgagg
35041  ccgaccgtca ggccgggcag ttcgggcagc gccgacacgg gttcgaggtt gaagaccgcc
35101  gataccagcg gcgcggcgtt gagatcgcgc tgtgcgccga tttcgcggac cagttcggcg
35161  aacggataat cctggtgctc gagcgcgtcg agcaggttct gccgggtgcc ggccaggaaa
35221  ctggccacgg tggcctgctc cggcagcgtg gagtgcagcg gcagcagatg cgtgcagtag
35281  ccggcgaggc gatcgctgcc ggccaccgag cggccggtca ccggaatgcc ggtgacgatc
35341  tcctgctggc cggcgacgcg gtgcaggaac agattgaagc cggcgagcag caccatgtag
35401  agcgtgcagc cgttctgacg ggccgcgtg cgcagcgtcg cggccgtcgc cgcgtccaga
35461  tgcagggaca cgcgctcgcc gtgaaacgtc ttcaccgcgg gccgcgggta gtccaccgga
35521  agattcagcg gtgcggcctg acgcgcgcat tgcgccagcc agtactcgcg attcgccttc
35581  gtttccgggc tgtggcgctg gccgtcgagc tgcttcaggt acgcgcgaaa ctgcagcggc
35641  gcgtcggccg gcgccgcacc ggcatacgcg cgggccagat cctcgagcag cacgccgaac
35701  gtcgagccgt cacagatgat gtgatgggcc gtcatcacca gcaggtgacg ctcgctgccg
35761  aggcgcacga gcgcggcccg aaagagcggc ccgttcacca ggtcgaacgg ctggcggctt
35821  tcctgctccc gccacgcgtt cgggtccgtg tcgatcagcg gaatctcgag tgtcagcgac
35881  gggtgcacga tctggcccga cccgtccgcc atcaccgtgg tgcgcagtgc ctcgtgccga
35941  tcgacgaggc tctggacggc cgcgcgcatc gcggcttcgt cgagccggcc gttcagttcg
36001  agcgtggtgt tgacgttgta ggcgagcgat ccttcgggat cgatttccga caacacccac
36061  agctggcgtt gcgcttcgct cagcgcggcc accgtgccgt gtttcgagtg cggccggatg
36121  aagccgcccc ggcgcaggtc ggcgacgctg tccttcaccg cccggatgaa gcggtcgata
36181  tcggcatcgg tatgcgcggt ggacaggaag caggtgcgcc attcccagat gtagatgccc
36241  ttttcgagca tgtgatagaa gaacaggtcg aggttctcgg tgaattcgaa gcggaacatc
36301  gagccgaacc acgtgacctt gatcggcgcc tcggcctccg cgaagaatgc attcagcgtg
36361  ccggcgatct gcgcggtgcg ttcgttgagc gcggcctgca gcgccggccc ctcctgttcg
36421  atcttctcga gcacggccag cgccgccgcc atcgcgagcg gatactggca gaaggtgccg
36481  ccgaacgcgg tgcggtccgc cgcggggaac gagtggtcgc cgtaggtcca catgccgccg
36541  tcgatggcat ccatgaagcg gctggtgccg gcgatcacgc ccagcggcag gccgccgccg
36601  atgatcttgc cgtacgtcgc gagatcggcc ctgatgccga acatggcttg cgagccgccc
36661  ggatggacgc ggaaaccggt gatcatttcg tcgaagatca gtgcgacgcc ggcctcctcg
36721  gtgatgcgac gcagttcctt gaggaatgcg acgggctgca gggaagggtt gcggctctgc
36781  accggctcca ccatcacggc ggcgagggtc gacgccatcc cgcgaatggc ctcgagcgcg
36841  gcgtcgctgc cgtagtcgag caggatcatg ttctcgacgg agccgaacgg tacgcccggg
36901  gcgatggttt ccgtcacgcc ttccgcgttc gccgcggcga gcgtgccgtc ggcatggccg
36961  tgatacgaat gcgtgaacat cacgatcttg tcgcgcccgg tcacgcgcg cgcgagccgc
37021  atcgcggtca tgacggcctc ggtgccggtg ttcgagaacg ccacgcgatc gaggccggtc
```

```
37081  acgcgggcaa agcgcgcggc gacttcgccg acgaggctgg agcgcgcacc cagttcgagc
37141  gggcgctgcc attcccgcgt gacctgctgc tggatgaaat ccggcgtgtg gccgaacagg
37201  tgcacgccga agcccatcgt gaaatcgatg tactcgttgc cgtcgatgtc ccacagccgc
37261  gaaccggccg cgcgatcgcc gacgatcgga tacagcatct ccttggtcga aaagcggaag
37321  ccgaccgtgg cgcggctgtc ggccagcacc gggcgcgacg cctgcaccga gtccttcgat
37381  ttccgggtgc gcgtcgtgta gcgcacgatc agcgcctcga gatgctcctg ctgcgcggcg
37441  gacagcccgc gcgcccgctg ctggaccggg ctgcccacg gcatcatcgg cttgggcggc
37501  gggttgtcgg ccgcgggcgc ggcggcagct gcaggcgcgg gcttcgccgc gggtgcggcg
37561  gccggggccg cgctcgccgc tttgggtgcg acgctcgccg tgctcgcgac ggcttgcacg
37621  gcggccgtcg ccggccggac gccgggctgg ccggtcagcg acgtgcgcag cagttccatc
37681  tgctggctca tcacgtgcga cagcagctga ttctgctccc gcagcacgcg ctcgaccgtc
37741  gagccgcctt cggccgccac ccattccgcg ggggcggccg cgagcggcgc aagccccgcc
37801  gcggacggcg tgaccgcgac cgccggcgtg gacggttccg ccgcggccac ggctacggct
37861  acggcctcgg ccccggacgg tgcggcggct gccggcaggt tgtccgcgac atattcggcg
37921  agcgcctgca ccgtcgcgag gtcttcgaag aagcggcgca tggccagctt cacgccgtac
37981  tccgcctcga tgtgccggat ggcctcgatc agcacgatcg agtcggcgcc catctcgagg
38041  aagggcagtt cgatgttgat ggtggcggga tcggcctgga tcaattcgcc gatcttgccg
38101  cgaagccatt cgagaatctc gccgctgcga ttgtgcgtcg gtgctgcggc gatgggtgat
38161  gcgcttgtct gagtcatgga cgtgtccgct ttctggaacc aggtacggct gcgttggaag
38221  ggataggacg gcaatgcgat gcgcgcgggc gcggtgttt cggtcggggc ccagtcgaca
38281  tcgacgccgc gggcatacag gctcgacagc gtttcgatca gcgcttgctg ctcgacttgc
38341  ggccgctgca gggcaaggaa ctggatcccg cgtccggcg cacagcacgc gcgggccagg
38401  ttgacgagca ccggcttcgg gccgatttcg accagcacgt tgaaaccggc ttcggcgagg
38461  cgctcgacgc tgctcgcgaa ctgcactggc tcccggcagt ggcggcgcca gtacgtgtcg
38521  gtgggtgcct cgtccatcac ggcgcccgtg agattcgaat agaacgggat cgccgggcgt
38581  gcgacgggca cggttttcgc cgcgagctgg aagctgtcca gcatcggctc gagcagcggc
38641  gagtgaaacg cgtgcgacgt attgagcggc acggaccgga tgtcccgcgc ggcgaacgca
38701  tcgaccagca tcgcgatgcg ctcgcgcttg ccggaaatca cgatgctcgc cgggccgttg
38761  acggccgcca ccgcgacctc gtgcggccac gcgtcgatcg cgcgctcgac cgtggcgagg
38821  tcggtgaaaa tcgccgccat ctcgccgtcg cggggcaacg cctgcatcag ccggccgcgt
38881  tcggcgatca gccgcaggcc gtcttccggc gagaagacgc cggccgcgca agccgccgcg
38941  tactcgccga cgctgtggcc catcacggcg tcgggcacca cgccgaacga cgccagcaac
39001  gtggtgagcg cgtactgcag cgagaacagg gccggctggc tgtagccggt ctggtggatg
39061  tcctcgccct gggccgacag cacttcgagc aacggcttgt cgagcaacgg atcggccacc
39121  gcgcggcaac ggtcgatggc gtctcggaac accggatacg cgtcgtacag gcggcggccc
39181  atgccggcgt attgcgagcc ctggccggtg aacaggaagg ccatcttcac gcgggggggcg
39241  ggctgcgccg cgccggccgg ttccttcgcg tggaaggcgc gcagcttgtc gatggcgtcg
39301  tcgagcgacg tcaccggcca tgccagccga tgcgcgaaat gcgagcggcc ggtcgccgcc
39361  gaaaaggcca cggccgcgat gtcgagaccg ggttcggctt cgagccgccg ctgatagcgc
```

-continued

```
39421  ccggccagct cgcgcaacgc cgcggggtc ttggccgaca gcaccagcgg atgcaccttg
39481  tgtctcgacg gcgtcgcctg ccgcgccggc gccggcgctt cttccagcac caggtgggca
39541  ttggtgccgc tcgcgccgaa cgcgctgacg ccggctcgcc gtggccgttc gccacgcggc
39601  cacgcgctcg cctcggcgca gatctcgacg ggcattgcgt cccactgcac cagcgggctc
39661  ggctggcgga aatgcaggtg ggcgggcagg cggtcgtggt tcagcgacag cacgaccttg
39721  atgacgcccg cgatgccggc ggcggactcc gtgtggccga tgttggtttt caccgagccg
39781  acgcgcagcc gccggcccgc gtcgcggcct gcgccgaaca ccgtcgccag cgcctgcaac
39841  tcgacgggat cgcccagcgg ggtgccggtg ccgtgcgctt ccacgtaatc gatggacgcg
39901  gcgggcaacc cgcccagcgc ctggcggatc acggcttcct gcgcacgacc gttcggcgcg
39961  gtaaagccgc tcgacgcgcc gtcgtggttg accgccgaac cccgcagcac ggccagcacg
40021  cgatcgcccg cggcgagcgc atcggacagg cgcttgagca ccagcgcgcc gcagccttcg
40081  ctgcgtacga agccgtccgc cgccgcgtcg aaggtcttgc agcggccgtc cggcgccagc
40141  gcccgcgtgc gcgagacggc gatggagttg tccggcgaca ggatcaggtt gacgccgccc
40201  gcgatggcga gatcgcactc gccgctgcgc aggttctggc tggcggtatg gatcgccgtg
40261  agcgacgacg agcaggcggt gtcgatcgcc atgcttggcc cctgcacgcc gagtccgtag
40321  gagatgcggc cggccgccgt gttcagcggg ttgccggtga agaaatagcc gtcgatgccg
40381  ctgccgccgc cgttgcgaag ctgcaggttc gcgtaatcgt tggtggtgat gccgacgaac
40441  acgccggtgc ggctgcccctt gagactgtcg accggaatgc cggcatgctc cagcgcttcg
40501  tgactgacct cgagcaacag gcgctgctgc gggtccatcg cggccgcttc gcgcggcgtg
40561  atgcggaaga acgccggatc gaactggtcg acgtcgtcga gaaaaccgcc gaagcggctg
40621  tacatacgcc ccggcgcttc cggatcggga tcgtagtacg cgtcgacatc ccagcgctcg
40681  cgcggcactt cggagatcgc atccacgccg tcgttcagca ggttccagta ggcgtcgaga
40741  tcgtgcgcgg cgcccggaaa ccggcagctc atgccgacga tcgcgatcgg ctccggcgtg
40801  ccggcgtcgc gggcctcgat ggccggcgcg atcggccgcg gctgctgctg cggcggcacg
40861  gtctgcgcct gcgccgtgcc ggacgcctgc tccgccagga aatccgcgag ggcgttgacc
40921  gtcggatgat cgaacaacag cgcgaccgac agcgggatgc ccagcgcatt ttcgaggtgc
40981  gtgcgcacgt ccagtgccat cagcgaatcc atgcccatct cgaagaagcc gagatcgcga
41041  tccagcgtcc ccgcgtcgta gcccagcacc tgggccaccg cgcgatcgat gctgtccgcc
41101  agcagccgct ttcgctcgcg cggcgatgcg tcgctcagcg ccggcattgc cggcgcgctc
41161  ggcgcgcttt tggccacccg cacgtggtcg aggaacggct tgggtccgcg cgcctcgtag
41221  gagccctgga acagcgccag gtcgatatcg acgaccgcga cctggggcac ggcggggaga
41281  cgattcagca cgtcgagcgc gcgatccgcc gccagcgacc ggatgccgac acgccgcagc
41341  agcgcttccg cctcggggaa cgtcatgccg ccttccgccc agggccccca gttcacgctc
41401  agcgccggca ggccctggcc gcggcgatga tgcgcgagcg cgtcgaggaa acggttcgct
41461  gcactgtagt gcgcctgctc acgcgagccc cacgcggacg cgatcgacga aaacaggagg
41521  aagaaatcga gcgggaagtg ctcgctctgc tgatggagca gccacgcgcc ggcgaccttc
41581  ggttgcagga ccgcgtccag ttcgtcgcgc tcgacctgca tgatcggctt gtagccgacg
41641  atgccggccg cgtgcacgat gcctttcagc ggcacgccgt cgcccgcag cgcggcgaag
41701  aaagcggcga ccgctgcggg gtcggcgata tcgaggcgct cgcagcgcag cgtgacgttc
41761  cgctcacgca gctcggcgat cgcccgctgg ctctcgtcgc tcgcggcccc ttgccggccg
```

```
41821  accaggatca gcgtgcccgc accgcgcgcc gccagccatc gggcggtgtg cagcccgagc
41881  gcgccgaacc cgccggtgat caggtaggcc gcgtccgggt cgaccggcag cgcggccgtt
41941  tcggctggcg cgagcgggct caggcgcgcg acatggcgcg cgccgtgccg caacgccacc
42001  tgctcctcgc ggctctcgcc gagcatctcc tgaagcagtg cctgcgtctc gttctccggc
42061  gcggccggat cgagatcgat cgcggtgccg aaccattccg gatgctcgat cattgccccg
42121  cgtgcgaggc ccgacagcgc agcctgggcg agcccggata cgtgcggcgc ttcgccggct
42181  tccaccgcgt cgcgcgtgac caccgagatc ctgggccggg tcgaaggcgt ccactcgcgc
42241  tcgctgccga ccagcgcgtg cacgagatgc agcagggcgg cggacatgcg cgtttcgccg
42301  acggcttcgt ccagcgccca taaaaagacg atgcgctggc cggaagcggc ggtttcgttc
42361  agcaagcgga cgaaatcgtc cggccgctcg ggcgcgacct gccagcccgc ttccgcgccg
42421  gtgacatagt cgatgccggg gcggaccagc gagcaggatg cgccgcgcgc gcgcagcagc
42481  gctgcaagcc gctcgccgac accgctcgca tccgcgaaga tcagccacgg ggacgcgtcg
42541  gcggcggccg gtgccgccgg catcgcggcc tgctgctccc acaccacgtg atagagcggg
42601  tgtgcgttcg acgcgacggt ctcggcgcg gcgaatgcag tcctgagcag gtccggaaac
42661  gcgttcagca tgtcctccgg gtacttgccg gacgacttga ggtgccgcaa cgctgcgtcg
42721  atgctgccgg catccatgcc gacgatcggc gacggaatct tctccaggct gaagcgctgc
42781  cgctcgaacg ggtagttcgg cagggtcgtg gcgggctggg cgggcgccgg aaacagcgcg
42841  cgccagtcga actgcgcgcc ctgcacgtac agcgccgcga gtgcgcgctc cagtgcatcg
42901  cccgcgcagg gcggcggcag ccagccgtcg gcgagcccct ccggcgggtg cgatgcgtcg
42961  gcctgatccg acgcgccagc cagttgcaac cagtactgcg ggtgcgtcac ctcgtcggtc
43021  acgtcggtgc cgagatagcc cgaaatcagg cggaccgacg gccgtgcgag cggcatgtcc
43081  cgaagcacgg cgcgcaacgc ttcggcatcc gaacgggcgg ccacgaggcg cagcgcgtcg
43141  gccacgctca cgacgcccgc cacgcaggcc gcgacatatt cgccgatgcc atggcccgac
43201  acgacgccg gcggaggcc ccatcccttc cacagttccg cccacgcgaa ctggatcgcg
43261  aaccggcccg cgtcggtctc gagtgcgtcc agcggcaccg agcaacgcgc gaacgcgtcg
43321  cggaacagcg gttccgacgc gtggagcgcg tgcgcgacgc cggtgtccgg cacaccgaac
43381  ccgaagccca tgcgcaacgc cttgcccgtg cgcggcgcgg ccgccgacgc taccctcgcg
43441  cccgatacat aggcggcgcg aaacggatag tgactccgcc cggtggcggc ggcacggcag
43501  atcgcggcta gctcctgcgg cgtcgcgccg gcgatcgcgc gctcgtagcg tggcacgagc
43561  gccgccagcg ccgcttcgga ccttgccgac agcagcagca acgcgcgctg cgcggcgtgt
43621  gccggcgcga cgggcggttc ctcgacgatg cgtgggcat tggtgccgct gaatccgaac
43681  gcgctcaccc cggcgatgcg cctgcgttcc ccgcgccgcc acgcgaccgg atcggccgcg
43741  acgcggatcg ggatgtcctg ccacggcgta tgcggattgg gttgcgtgaa atgcaggtgc
43801  gccggaatcc ggtcgtgctc gaacgacagc agcaccttga tcaggccggc gatgccggag
43861  gccgactcca gatgcccgat attggtcttg accgaaccga tcacgagcgg ctcgttcgcc
43921  gcgcgcccgg ggccatagac gccggccagc gcttcgacct cgatcgggtc gccgagggac
43981  gtgccggtgc cgtgggcctc gacgtaggac acgtcgccgg gcgcgaggcc ggcctggttc
44041  agtgcgcggg ggatcacccg ttcctgcgaa tcgcggctcg gcacggtcag cccgccgccc
44101  gcgccgccct ggtcgaccgc cgtgccgcgc acgatgccga gcacccggtc gccgtcggcg
```

```
44161  agcgcgtcgg cgaggcgctt gagcaccacc atgccgcacc cttcgccgcg cacatagccg
44221  tccgccgccg cgtcgaaggt cttgcagcgt ccgtccggcg acagcatgcg cgcctgcgag
44281  aagctgacca tgacctcggg cgacagcatc aggttgacgc cgcccgcgag cgccatgttg
44341  ctttcgcgcg agcgcaggct ttcgcaggcg aggtgcaggc acaccagcga agacgagcag
44401  gcggtgtcga tcgccatgct cgggccggtg aggcccagca cgaacgacag ccggcccgcg
44461  gccatgttca gcgcgctgcc cgtgccggca tagctgctcg acggcatcga cgcattggac
44521  acctggatcg cgtggtcgaa gcaggtgatg ccgacgtaca cgcccgtggc ggactgccgg
44581  aagcgttcgg gcgcgagatg ggcgttctcg agcgcctccc acgccacttc gagcaggagc
44641  cgttgttgcg gatcgaggta ggtcgcttcg cgcggcgcga tcccgaagaa cgccgcgtcg
44701  aattgatcca cgcgttcgag aaaggcgccg tggcgggtcg ccatcttgcc gggcgtggac
44761  ggatcggggt cgtagtagcg atcgatgtcc cagcgttcgc cgggcacttc ggtgacggca
44821  tcgtgcgcgc cgtcgagcaa ttgccagaac gcgtccggcg tatcgctgcg tccggggaag
44881  cggcaagcca tgccgatgac ggcgatcggc tcgttgcggt cagaacgcag cgccgcgatt
44941  tccgcgcgcc gcaggcgcag ttcgtcgagc gcggctttca gtgcatgcgt ggccttggcg
45001  ttcattgggc gccgatctcc tgggcgatca gttcggaaag gtcgtcctcg tcgaggtcgt
45061  cggatgcttc gtcgacgacc ggcgcgggga cgacggcga cagttcgttg agcacgtact
45121  gggcgagcgt ctgcaggttc ggataggaaa agaacaacgt cgcgcgaaac ggtcttccga
45181  ataccttggt gaggcggtcc gtcagttcga gcgcgaccag cgaatccagg ccgagatcga
45241  gcagcgattg ctcgggcgcg atggcatcgg ggccggaaag gcgcaaggtt tcagccagca
45301  tcgccgcgag cgtgtcggtg atgcgctcga cccgttcgcg cggcgcgcac gcatgcagct
45361  ggcgcagcaa cgccgtctcc tgctgcgccg gctgcgcggc cggttgcgtc agctcggaaa
45421  acagcgcgga cccggcggcc ggcgcatcga cccggaacag ggtcggccag tcgatccgcg
45481  cgactccgga ctgggcgacg ccggacgcca tcagccgttc cagcgtcgcg atggccagtt
45541  cgggcggcag cgtgccgacg ccgagcgcgc cgagttgttc gtgcgcgcgc cgtccgtagt
45601  cggtggcggc gtggccgatc tccgcccacg gcccccaatt gacgctgagc cccggtttcc
45661  cctgcgcgcg ccgatgctgg gcgagcgcgt cgaggaagct gttcgccgcc gcgtagttgc
45721  cctggcccgg catggtgatc agcgcggcca tcgacgagaa caggacgaaa tggtccagcg
45781  gcaagccggc cgtcagctcg tgcagatacc acgcgccgtc ggccttgccg ctgccggcgc
45841  gatggaagaa gtcgtcgtcc tggcgtgtca gcagcgcatc gtcgagcgcg ccggcgaggt
45901  gaaagatccc tttgagcggc ggcatcgaat gcgcgatttc accgagcgcc tgcccgacgt
45961  cctcgcgacg cgacaagtcg gcgcgaatga accgtgcgtc gagcgtgcgc aggattttcc
46021  cggctgcggc ggaaggttcg ccgcgcccca gcagcacgat tttcccggcg ccgttgtcgg
46081  caagccagga cgcgagccgc aggccgagcc cgccgagccc gccggtcaca agataggtcg
46141  cgtcaccgtg aaccggatcg gccggtggc tgacgtattc gcgattgtcg cggcgatgc
46201  gcgcgacgta gcgctggtcg cggcgaaacg cgatcatgtc ttcacggccg ccagcctgta
46261  ccgcttgcat gatgtccgct gccgacggct gctcgggatc gaggtcgacg agcccgcccc
46321  acagcgccgc atgctccacc gcgatcgcgc ggcccaatcc ccacagcggc gcctgtgcca
46381  ccgcgatcga ttcgccatcc agaacattca tcgcacccga cgtcaccagc cacaggcgag
46441  cctgccgggc cgacgcgcg cgtgacgcaa gcgccctgac caggtgcagc acgctcgcgc
46501  tggcacgccg tctcgccgcg atgtcagagg gtgcgagatc gagactccac aggtggatga
```

```
46561  cgcccttcag cgggcggtcg gccgcgggca gttccggcgt cgcgtcggcg aagcgcagcg
46621  tgcacgtatc gccgtgggct tccagcagag ctgacagctg ggcgcccacg ccgccgcggt
46681  ccgcgagaat cagccactcg ccgtgcgccg aaccgccggt tgccgcgtcg acgttcgacg
46741  gtctccagac gcgttgataa agcagcgcgg cgaagtcgtg ccgctcgacg gcgcgcgccg
46801  cgcgaacctg ttgcaaccgc agtgcatcga tctcgatcag cagtcggcca gcaaggtcat
46861  ggacgcggat gtcgccctcc agcgcgccct gtccgatcgg cgtgcgcagc gtggcgtgac
46921  tccatgcctc ggtcgacgcc ggcggctgat ggacccgtac cgcgccgatc gagctgggca
46981  ggtacaggtc gcccgactcc agcgcgtccg gatcgatggc ggcggcgagc acgcggctgc
47041  atgcgtcgag aaaggcgggg tgtacctggt acggcgacga cgccagcgca tctgccggca
47101  ggctgatttt ccccagcgcc tcgccggtcg tgcgccagat ctgccggatc gcgtcgaaca
47161  cgccgtcgat ctgcacgccg tgctgccgaa tttcgccgtt gaagtccgcg cccgacgtcg
47221  tttcggtgca gcgggcctgc acctcggcgg catcgaatcg cgtcggcgcg gcggatcgcc
47281  gggggcaca catttcccgg agccggcgca gctgcggaag attgccgagg atccgctcga
47341  ccggcggacc gaaatcgagc aggcaggcca cttcatccac gccgatcgac tcgagatccc
47401  gcaccagttc gacgcaggtt tccggcgtgc cgatgagccc gcgcgattgc gcgaagcgtt
47461  catagagaaa ctcgacgaac tcgtccagct cgcgtgcgcc catcgcgcgc acgtcgaccg
47521  actggccgcg actctgcgcc agcccgttca atagcccgat attgctgcgg atgtagttgc
47581  agaacggcac acgcgcctgt tcgcgcgcct gcgccgcatc gtcgccgacg aacgtatgca
47641  gcatcacgga aacggtgccg gccgccggat cgaagccatg cttcgcacgc gcctcgcggt
47701  agagcgcgat cttgtgcgcg agctggtcac gatcctggtc gagcacgtgg gtcagcaggt
47761  tggcgccggc ttcgccggca cgcacgaatg tctgcggatt gctcgcggcg gtcacccaga
47821  cgggcagctc cggctgcacc ggcgtcggat agacacgcaa ccgcaccggc ttgccgacac
47881  cgttcgtcgc atccagcgtg ccgccgcgcc acagatgctg gacggcgcgc atcgtggtca
47941  gcatgtcgtc ctgccgggtc gcatatttgt ccggggcaaa cacgaagtcg tcaggattcc
48001  atccggaggc gaacgacacg cccacgcggc cgttcgacag gttgtccacc atcgaccatt
48061  cttccgcgat ccggatcggg ttgtgcagcg ccgcgaccac gctgcccgcg accagcttca
48121  cgcgctgggg ggccgcggcg agcgcggcgt gcaggacggc gggattcggg taaagcgagc
48181  cgaattcggt gaaatggcgc tccggcaccc agacgctgga gaaccgttc gcatcggcga
48241  aacgcgcgct ctccatcacg agctggtact tgttgccgga cagcgcctct tcactgctgg
48301  cgaagaacat cagtccgaat tcatgcgtg gctccgatcc gattcgtgaa tttcggcact
48361  cgcgcacatc tgccacgtcg cggcggcgcg ggtgtcgtcg atccggtgat agacggcaaa
48421  cgaaaacggt ccccaggacc ggcggctcag cacggtctgc acggtgtgcg attcgtgcgg
48481  atgcagcggc aacggcgcat gcagtgcgag gtccttcaac gtcgtatggc cggctgcgcc
48541  gatttccgac gttgccgaca gcgccatttc cacgaaggcg aatagggca ggacgggcga
48601  ccccttgacg cgatgaccgt cgagaaagtt ggttgccggc gcatcgagac gcgattgcca
48661  gatccacgtg gccggcgcat gcgcgtgctg ctccatgagg cgcccgagca acggatgccg
48721  acgcgcatgt ggcctgatcc agaagccgcg ccgctcgaac gggtaggtcg gcagggcgag
48781  ccggcggtgc ggtgcaccct gctccacggc atcccagtcg atggatgcgc gcgtacgta
48841  gagcgcggcg agcgtgtgca ggatcgcgtc ccacgcggcc gtgtgcgcgc cgatgtcgat
```

```
48901  cacgatgccg gggtgtcctg ccgcaccgct gtccggcgcc tgcggcacgc cggcccacgc
48961  ggctgcggcg cgctgcccgt cgccggtgct gctgaccgca tccggtgcga tgccgaagga
49021  catccacagt tgcgcgagcg cgcgctggaa tctcgtgaac ccggcttcgt cgggggcgag
49081  cgcgggcgcg ccggatgcgt cggactgccg ctgcatcagc gcgtcgaaag cggggctggc
49141  cgcgcgcaat tgccgaaccg cgtcggcgct ggcgccgtcg tcggcgcaaa agtggaacgt
49201  caccgcgggc ggtgtttcgg caggctcccc ggacgaaacg gaatcaagtt gcgcacgcaa
49261  cgaatcgcga ctcggtgcga cgatggccgc gcgctgcgtg aagtgggtgc gcccggtatt
49321  ggccgtgaac gcgacatccc gcacaccggc ctcgggatgg gcgtcgagat aggccgcata
49381  ggacgcagcg agcgcttgca acgcgtccgg cgtgcgcgcg gagagcgtca cgacgcgcgc
49441  cgcgggtgca accggttcgg cttcgatctc cgggagcccg ggtgcttctg acaggatcag
49501  gtgcgcgttg gtgccgccga agccgaacga gctcacccct gccaggcgcg gcccgtgttc
49561  cgaatgccag ggcgtgacct gccgaggaat ccggaagggc gtgccgtcga gcgcgatttg
49621  cggattgatc gaccggaaat ggaggttcgg cggaatcgcg cgatggtgta gtgcaagggc
49681  ggtcttgatc aggctggcga tgcccgcggc cgattccagg tggccgatgt tggtcttgac
49741  cgacccgatc agcagagat cgtccgggcg gcgggattcg ttcaggacgg ccgccagcga
49801  gttcaactcg atcgggtcgc cgagcggcgt gcccgtcccg tgcgtctcga cgaagccgat
49861  gtcctgcgcg cgtacaccgg catcgcgcag cgcgccgtga atcacggcct gctgggccgg
49921  gccattcggc gcggtcaggc cgttgctgcg cccatcctga ttcaccgcgg agccgcggat
49981  cacggcgaac acggtgtcgc cgttctcgag cgcatcgtcg agccgcttga gcagcaccat
50041  gcccacgcct tcgccgcgaa cataaccgtt cgctgccgcg tcgaacgcct tgcatcggcc
50101  gtccggcgac agcatgcccg cttgcgtgaa ggacgcgctc aattgcggcg ccagaatcag
50161  gttgaccccg ccggccagcg ccgcatcgga ctcgccgcgc tgcagcgcgc ggcacgcctg
50221  gtgaaccgcg acgagcgagg acgaacacgc ggtgtcgacc gcccagctcg ggccgcgcaa
50281  atcgagcgcg taggaaatgc ggttggcggc gacgctgagc gcattgcccg tcgcgacata
50341  agggccgacg tccgcgactt cgtcctgcgc cagacggatg tagtccgaat tgctgatgcc
50401  gacgatgacc gcggtgcgtc cgccggcgag gctgcggggt gcgatccccg catgctcgag
50461  cgtctcccag gccacctcca gcagcaggcg ctgttgcgga tccatcgatt cggcttcgcg
50521  ggcgctgatg ccgaagaaag ccgcatcgaa ttgatcgacc tgatccagca gtccggcgag
50581  cggaaggtcg gccgcgcgct gcgtcgccgc accgaccgcg tcccgccct ccagcagaag
50641  ctgccagaat gcgtcgggat tgccggcgcc ggggaagcgg catcccatcc cgacgatcgc
50701  gatatccgcg cgtgcttcgg ccgagcccgg cgcctggtcc ggcatggcac tcccggtgcc
50761  gctcaaatgg cgcgccagca gggaaatact cggaaaatca tagacgacgg tcggggaaac
50821  cggccgcccg agccagtcct gcagctcgcc cgagagcatg atggcgtcct tcgaatcgag
50881  cccgtggacg ctgaacggcg cgtcggggtc gatcttgccg gaagcgattc ccgacagacg
50941  cgagacacgc tcgatgcacc attgcaccag cgcttgcgtg tcgcgtggct cggcagtctg
51001  cgggggggct ggcggcgcgg agaacgcacg ccgccattcg cccgcgatcg cgagcccctg
51061  ttcatcgagg aatgcctgcc tgatccggct ccgctggatt tttccgctgg acgtgcgcag
51121  gatcgtggca ggtttcaaca ggactgccgc atacagatcg acgtcgtgca cttcggcgag
51181  cgtgtgccgg atctcggcgg ccacggcttc cgcgtccagc gtgttgagcg cttcccggcg
51241  cacttcacag gcgacgacga cccgctccac gttatcgacg tggatcgaga aagccgccga
```

```
51301  tgcgttcggc gccagcgcgg ggtggctgcc ctccgcggat tgctcgagat cctgcgggta
51361  gtgattgcgg ccggcgacga tgatgaggtc tttcaagcgg ccggtaacga agagatcctc
51421  gccatcgacg aagccgagat cgcccgtgcg caggtaacgc gcgtcatcgc cgtccagctt
51481  cgcgcggaag gtgcgctccg tttcgtcgat acggttccag tagccgacgc cgacactcgg
51541  gccggtcagc cagatttcgc cgatccggcc gggcgcgcag cgctcaccgg tatccggatt
51601  cacgatgcgc acgcggtgct cagcccaggt ccggccgcat gagaccagcg cgtggcgctt
51661  gccggagtcg tttctcgtcg ccacgccttg tgccagcgcg tcggcatcgt agtccgccac
51721  gcgcggcagc gagcgtgccg gctggccgga gatgaacaag gtcgcctcgg ccatcccgta
51781  gacggggcgc atggtgtgcg cgtggaagcc gcacgcggcg aatgcgcgcg aaaaacgcgc
51841  caccgactcc gcgcgcaccg gttccgcgcc gttgaatgca cccgccagc tgctcaggtc
51901  cagctgcgcg cgcgcttcat cggcgatttt gcgagcacac aggtcatacg cgaaatccgg
51961  cgcggcacaa tgcgtgccgc gatacttcgt gatggcctgc agccagcgca cgggtttctg
52021  cacgaatgcc gcgggcgcca tcagcaccga cagcacgccg agatagatcg gcagcaacac
52081  cttcccgaag aaacccatgt cgtgaaacac cgggagccag ctgacgaaca ccgtcgacgc
52141  atcggcatcg ctcgcctcgg cgatgaccgc catattgctc aggatgttcg cgtggctgat
52201  catcacgcct ttgggcgtac cggtggagcc tgacgtgtat tgcagaagcg ccagcgtctg
52261  cggcgtgatg tccggtgcgc gccattgttc ggccggggcg tcgaagcgct ggtccgtcgc
52321  caggatcttc agttccagcg tgtcggaata accgtccgcg tgatgcgcga tgccgtcgag
52381  cgtcgcggcg tccgtcagcg cgacgaccgg cgtggcgtcg gcgacgatgg ccttgagacg
52441  atcggcggga cgatgcctgc gcggtggata cgcgggtacg ccgatcaggc cggcgtacag
52501  gcatcccacc catgcgcaga tgaattccag cccgggcgga taaaccagaa ggacgcgatc
52561  gcccggttga gcgatggctt gcagcctggc ggcgatgccg cgagcccgct tgtccaggtc
52621  gccgaacgtg aggcgggtca gctccgcttc gccgttctcg agaaaaatga atgcggtctt
52681  ctccggttcg accttgccgc gaaacaacaa aatttctgta acagtcctga attttgtatc
52741  gggaagcatg ctcaaccttc gttgtcttct aaacgttgaa tatctcagga ccggttgtgg
52801  cgatcccgcc aagcgtgctt catcggacgg tatcgaaatt agagcattgc tctaatccgg
52861  cgtctgcccc gtaatccaag gacacggcgt ttcgcgcact ggatcaatac ggcttgtcat
52921  tgatgtgcac gctcgctaac gatcggcgat tccttcgatg tcgggcgtgt acgggtccag
52981  cagcgacacg acgaccttgc gctcgccttc gaacgggttg cggccatgcg cgaagcgcat
53041  gttgtcgacc agcaggacgt cgcctcgttg ccacggaaac gtgatcgcgc attcgcggaa
53101  cgcgtggcgg atctgctcga ggtcggcgag atcgaacgga ctcccgtcgc catggcaggc
53161  attgcgcgga atgcgatcct cgccgaacag gctgacgatc gaactggcga gcgatgcttc
53221  caggttcgag atatggaaca gatgggcctg attgaagaac accccgctcgc cggtgaccgg
53281  atggtaggcc acgccctggt tgatctgcgc ggtgcgcaac gtgtcgtcgt cgagccattc
53341  gagcgcgatg ccgttatccg cgcagaaggc tgcaacctgg ttgcggtcgc tggtctggaa
53401  cacggtctcc cacggaatgt cgacgtgccg ccggtagtgc ctgacatagc ggacctgtct
53461  cgcctcgaag tgatccagga tgcgcggtcc gatcctgcgg ctcacctccc gcatgtcggc
53521  aatcggcgtt tcgccgccgg tcgcggccgg cgtcaggcaa cagaaggcca ctcgcagcgg
53581  ccagcttcgt tgatacgcgt tttcgcaatg aagggcgatc gtctcgctcg gcggatactc
```

-continued

```
53641  ggttgcggtg aagatgccgt tgccgatcga ggtgcgcggc gtggaacggt aaacgtagtc
53701  ggactgatgg gccgaaatcg cgcgagcaaa cgcttcgaag ccgcccacgg atgaaacgtc
53761  gaagccacga aacaggagta cgccgtgttc cagaagccgg gattcgagtg ccgcccggtt
53821  gtcgttcacc gcctgcgcca gatcgcgtcc attcgataca ggctccagca gccacggcgt
53881  gcttccctcg gcaagcaact tgcgttccgt catgcccagc atcgtcaata gtcctttcct
53941  gtacgtggat cacggcgaag ccgaacgggt cggcccgcgt ggtcgcgccg cggtgcggct
54001  atgcgcggca ggccgtttcc acggcatgct cgaagcgatt gagaatgtcg tggatgtccg
54061  cttccgaaac gatcagcggc ggcaggaacc ggagcaccgc gccgttgcgg ccgccggttt
54121  cgacgatgag cccgtttcgc aggcagttct gcttgatggc tcttgcccgt tccgtgtggg
54181  gcgggccggc tcggccgtgg gtgccgggca cgacgacttc ggcgccgatc atcaggccgc
54241  ggccgcgtat ctggcccagg caggggaagc gttcggcaag ctcctcgagg ccggcaacca
54301  ggagtttgcc gaccctgtcc gcgtgcgccg acagatcttc tctctcgacg atgcgcatgg
54361  tcgacaagcc ggccaccatc gcaatctggt tgcctcgaaa ggtgccggca tgcgcgccgg
54421  gcggccaggt gtccaggcgc tcgtcataga ccaccaccga taacggatag ccgccgccga
54481  atgccttcga cagcaccagt acgtccgcc ggatgccgga atgttcgatc gcgaacaggg
54541  cgccggtgcg accgagtccg gtctgcactt catcgacgat caacgggatt tcatgccgca
54601  gcgtcagctc gcgcaactcg atcaaccagg tgtcgggagc ggggatgcag cctccttcgc
54661  cttgcacgac ttcgacgatg atggccgccg gcttcgtgat cccgctctcg ggatcggaca
54721  ggacggtccg gatgtagttg atgctgagtt gatcggtcgc cgagccgtcg gtgccgaacg
54781  ggcagcgaaa ggcgtaggga tagggcagga aatgaacgtc gcgtccgttg ccgccggccg
54841  acttgggcgt gaggtttccc gacgcggcga gtgcgccgga cgtcatgccg tggtaggcgc
54901  cgtggaacgc catgatcgtc ggccggccgg tatagtgccg ggtcagcttg atcgccgctt
54961  cgacgccatc cgcgccactg gggctgcaaa actggatctt gccggattcg gcgatcttcc
55021  cgggcagaag cgagaaaagc tgctcgacga atgcgtgctt ggccggcgtc gccagatcga
55081  gtgcctgttg catctgatcg gacgacagaa accgcatcac ggcttcattg acttccgggt
55141  gattgtgtcc gagcgcgagc gtgcccgcat tcgacaggca gtcgatgtat tcctgcccgt
55201  cggcgtcgcg tacgcgtatg cctttcgcat gggtaaacag ccgcgggaag gaggttgcgt
55261  aggttcgcgc gttcgattcg acctgcttca gatactcgag ttttccatg cgcgcagatc
55321  cggcttgcaa ggcggattga tgcggactgg cgcacgagaa tcgcttcatc ctggccaatg
55381  gtgtttaacg gtacgaccgg attggagcat ggtctccgta tcgcgtctgt cacgtaaaaa
55441  tgggacatcg gccatgcgac gtcaccacgt catgccgttg ccttccgatc atcgaagcgg
55501  tttccgggcg cgacgtcagg cagcgagggt cgagcagaaa taatcgatgg tccgttggag
55561  acccgcttcg agcccgatcg tcggctccca gtcgaggtgg gtgcgtgcga ggctgatgtc
55621  ggggcaacgt tgcgtcggat cgtccttcgg cagcggacgg aatacgagcc gcgacttcga
55681  gccggtcagg cgcaagatga tctgcgccag ttcgctgacc gcgatctcgt gcggattgcc
55741  gaggttgatc gggccggtga gctccgcggg cgtggccatc atccggatca aaccgtcgac
55801  catgtcgtcg acatagcaga atgcccgggt ctggctgccg tcgccataca gcgtgatgtc
55861  ctcgccccgc agcgcctgca cgatgaagtt ggacacgacg cggccgtcgt tgggatgcat
55921  gcgcggcccg tacgtgttga agatgcgtac caccttgatt cgtacgttct gctggcggtg
55981  atagtcgaag aacagggtct ccgcgcaacg cttgccttcg tcgtagcagg cgcgcggccc
```

```
56041  gagcgggttg acgttgcccc ggtaactctc cggttgcgga tgcacatcgg ggtcgccgta
56101  cacctcgctc gtcgacgttt gcagaacgcg tgcatgcgtg cgcttggcga gcccgagcat
56161  gttgatcgcg cccatcacac tggtcttggt ggtctgcacg ggatcgaatt gatagtggat
56221  gggcgaagcc gggcaggcga ggttgtagat ctcgtccacc tccacgtaca acggaaaagt
56281  gacgtcgtgg cgcagcgcct cgaagctcgg gttgccgagc agcgtagcca cgttctgctt
56341  cgtgccggtg aaatagttgt cgacgcacaa tacgtcgtga ccgagttcga cgagacgctc
56401  gcaaagatgc gaaccgagga aacccgcgcc acccgttacg aggattcgct ttcgattacg
56461  ttgcacaatt gcactccaag tatcgcgcgc tgggaagcga cgcggcctcc ccgcacgctt
56521  gaccggcccg cggcaccggc aggggagcgg atcaggcgcg cgggcgtttg cattcgacga
56581  tcacggcgcc ggccggcacg ccgatcgcga ggatcggccc gtcatgcctg cagtgcgctc
56641  gacgcggcgt gctccgggcg ccgcatgcgc gccgcgatga tgccggccat cgttcgcatt
56701  tcgtttctca aaaagaaatg atccccttcg atgacgtgaa aatcgaagcg cccggtcgtc
56761  gcggcgcccc agcctgcaac ggcatcgacg gggatctctt tatccgcccg gcccgcgaac
56821  gcggtgatgt ccaccgccag cctgggcccg gcacgggcc ggtggttttc gatcatcgtg
56881  aaatccgcac gcagcgccgg catcagcagc gccatcagtt cgctgttgtc cagcaccgcc
56941  ttcggtgtgc cgcccatttc gcgcagcgca tcgatgaagg cgcggtcgtc cagcgcctgc
57001  atcgccgat cgtggcgctc cttgcccggt gcggcacgcg cgctcacgaa cagatgccgc
57061  aggttcggtc gtgcgtgggc gggaagccgc agggccagtt cggccgcaat ggccgcgccc
57121  atgctgtgtc cgagcagtgc gaagggacga tcgaagcagt cgtccaggtc gcacagcaac
57181  gtgtcgacca gcgtcgccat gtctcggacg gcaggctcgg acaggcggct gcctcggcct
57241  gcaagttcat gacggcacac ttcgatgccc ggtaacgacg cttgcagcgt gcgatagacg
57301  gcggccgagc cgcccgcata gggaaaacag atcagacgca tgcgggcggg tactcgagcg
57361  gctcatctgc tgccggcgcg caggcgatgg cgctgtggaa attcatgtgt tcggcgtttt
57421  tcaccattca ggttccagat ccggttgggc gtgagttaaa cacgaggctg cgtggatgta
57481  tgtcgtagga agaggggacg cgttgtcggc catgtcgaag cggttcgtct ctgaatggat
57541  cccggcgcgg acacggtatc ggcgaaaaca gatgcgcggg aaatcgcgac gcatctgagt
57601  gtgtcgaacg atgcgcttcg tctttagaat gggcagcgag catggcgagc catcagaatt
57661  gcggcatccg atggtgccgc cgcgctaccc gataagttgg agacatacta tgcaacaccg
57721  tcagaaagcc gtcccgaccc agcaagtcgc gaacgagcgc gtgatcgtca ccgaatggcg
57781  attcgcgccc ggcgccgaga ccggctggca tgttcaccgg catgactatg tcgtggtgcc
57841  gcaaacggac ggtcagcttc tcctcgaaac cgcacaaggc aaccgcgagt cgcaattgca
57901  cgccgggcgc agctatgcgg ggctgaaggg cgtcgagcat aacgtcgtca acgcgacgga
57961  ccacgaagtg gtgttcgtcg aagtcgagat tctctaaggg gcgtcaggcc ccgcgagcaa
58021  ggccacgaca gggagcagca ggatgaaaat gaccgacatc ccgtttggca cgaccgactg
58081  gcgcaccgtt gaaccgaccg a (SEQ ID NO: 23)
```

REFERENCES (1) Fischbach, M. A.; Walsh, C. T. *Chem. Rev.* 2006, 106, 3468-3496.

(2) Koglin, A.; Löhr, F.; Bernhard, F.; Rogov, V. V.; Frueh, D. P.; Strieter, E. R.; Mofid, M. R.; Güntert, P.; Wagner, G.; Walsh, C. T.; Marahiel, M. A.; Dötsch, V. *Nature* 2008, 454, 907-911.

(3) Koglin, A.; Mofid, M. R.; Lohr, F.; Schafer, B.; Rogov, V. V.; Blum, M.-M.; Mittag, T.; Marahiel, M. A.; Bernhard, F.; Dotsch, V. *Science* 2006, 312, 273-276.
(4) Kohli, R. M.; Takagi, J.; Walsh, C. T. *PNAS* 2002, 99, 1247-1252.
(5) Lautru, S.; Challis, G. L. *Microbiology* 2004, 150, 1629-1636.
(6) Samel, S. A.; Wagner, B.; Marahiel, M. A.; Essen, L.-O. *J. Mol. Biol.* 2006, 359, 876-889.
(7) Walsh, C. T. *Science* 2004, 303, 1805-1810.
(8) White, C. J.; Yudin, A. K. *Nat. Chem.* 2011, 3, 509-524.
(9) Yeh, E.; Kohli, R. M.; Bruner, S. D.; Walsh, C. T. *Chembiochem* 2004, 5, 1290-1293.
(10) Boddy, C. N. *Chem. Biol.* 2004, 11, 1599-1600.
(11) Boguslaysky, V.; Hruby, V. J.; O'Brien, D. F.; Misicka, A.; Lipkowski, A. W. *J. Pept. Res.* 2003, 61, 287-297.
(12) Fernandez-Lopez, S.; Kim, H. S.; Choi, E. C.; Delgado, M.; Granja, J. R.; Khasanov, A.; Kraehenbuehl, K.; Long, G.; Weinberger, D. A.; Wilcoxen, K. M.; Ghadiri, M. R. *Nature* 2001, 412, 452-455.
(13) Fridkin, G.; Gilon, C. *J. Pept. Res.* 2002, 60, 104-111.
(14) Jelokhani-Niaraki, M.; Hodges, R. S.; Meissner, J. E.; Hassenstein, U. E.; Wheaton, L. *Biophys. J.* 2008, 95, 3306-3321.
(15) Jelokhani-Niaraki, M.; Prenner, E. J.; Kondejewski, L. H.; Kay, C. M.; McElhaney, R. N.; Hodges, R. S. *J. Pept. Res.* 2001, 58, 293-306.
(16) Kohli, R. M.; Walsh, C. T.; Burkart, M. D. *Nature* 2002, 418, 658-661.
(17) Rayan, A.; Senderowitz, H.; Goldblum, A. *J. Mol. Graph. Model.* 2004, 22, 319-333.
(18) Schwarzer, D.; Mootz, H. D.; Marahiel, M. A., *Chem. Biol.* 2001, 8, 997-1010.
(19) Ellis, D.; Gosai, J.; Emrick, C.; Heintz, R.; Romans, L.; Gordon, D.; Lu, S.-E.; Austin, F.; Smith, L. *Antimicrob. Agents Ch.* 2012, 56, 765-769.
(20) Sieber, S. A.; Marahiel, M. A. *J. Bacteriol.* 2003, 185, 7036-7043.
(21) Tseng, C. C.; Bruner, S. D.; Kohli, R. M.; Marahiel, M. A.; Walsh, C. T.; Sieber, S. A. *Biochemistry* 2002, 41, 13350-13359.
(22) Gu, G.; Smith, L.; Liu, A.; Lu, S.-E. *Appl. Environ. Microbiol.* 2011, 77, 6189-6198.
(23) Gu, G.; Smith, L.; Wang, N.; Wang, H.; Lu, S.-E. *Biochem. Bioph. Res. Co.* 2009, 380, 328-332.
(24) Gu, G.; Wang, N.; Chaney, N.; Smith, L.; Lu, S.-E. *FEMS Microbiol. Lett.* 2009, 297, 54-60.
(25) Lu, S.-E.; Novak, J.; Austin, F. W.; Gu, G.; Ellis, D.; Kirk, M.; Wilson-Stanford, S.; Tonelli, M.; Smith, L. *Biochemistry* 2009, 48, 8312-8321.
(26) Tan, W.; Cooley, J.; Austin, F.; Lu, S.-E.; Smith, L.; Pruett, S. *Int. J Toxicol.* 2012, 31, 326-336.
(27) Heikkinen, S.; Toikka, M. M.; Karhunen, P. T.; Kilpelainen, I. A. *JACS* 2003, 125, 4362-4367.
(28) Rai, R. K.; Tripathi, P.; Sinha, N. *Anal. Chem.* 2009, 81, 10232-10238.
(29) Baysal, C.; Meirovitch, H. *Biopolymers* 1999, 50, 329-344.
(30) Bonmatin, J.-M.; Laprévote, O.; Peypoux, F. *Com. Chem. High T Scr.* 2003, 6, 541-556.
(31) Liao, G.; Shi, T.; Xie, J. *J. Cell. Biochem.* 2012, 113, 735-741.
(32) Vilhena, C.; Bettencourt, A. *Mini Rev. Med. Chem.* 2012, 12, 202-209.
(33) Alexeyev, M. F. *Biotechniques* 1995, 18, 52.
(34) Prentki, P.; Karch, F.; Iida, S.; Meyer, J. *Gene* 1981, 14, 289-299.
(35) Lu, S.-E.; Scholz-Schroeder, B. K.; Gross, D. C. *MPMI* 2002, 15, 43-53.
(36) Wüthrich, K., *NMR of Proteins and Nucleic Acids*; Wiley, New York, 1986.
(37) Delaglio, F.; Grzesiek, S.; Vuister, G. W.; Zhu, G.; Pfeifer, J.; Bax, A. *J. Biomol. NMR* 1995, 6, 277-293.
(38) Johnson, B. A.; Blevins, R. A. *J. Biomol. NMR* 1994, 4, 603-614.

We claim:

1. A method for promoting OcfN thioesterase activity in a bacterial strain of *Burkholderia contaminans* MS14 comprising a step of:
   contacting the bacterial strain of *Burkholderia contaminans* MS14 with a peptide containing more asparagine 1 than beta-hydroxy asparagine 1 to promote the OcfN thioesterase activity of the bacterial strain of *Burkholderia contaminans* MS14, to produce occidiofungin; wherein the bacterial strain of *Burkholderia contaminans* MS14 comprises one of the following features:
   (A) the bacterial strain of *Burkholderia contaminans* MS14 comprises an ocfN gene encoding the amino acid sequence of SEQ ID NO: 3 and the activity of the ocfN gene in the bacterial strain of *Burkholderia contaminans* MS14 is promoted by expressing the ocfN gene in a multicopy plasmid, integrating additional copies of the ocfN gene into the chromosome, or substituting the native promoter of the ocf gene with a promoter that increases expression of the ocfN relative to the native promoter, such that the ocfN gene in the bacterial strain of *Burkholderia contaminans* MS14 produces an increased OcfN thioesterase activity in comparison with the ocfN gene in a wild-type bacterial strain of *Burkholderia contaminans* M514; or
   (B) the bacterial strain of *Burkholderia contaminans* MS14 comprises an ocfD gene encoding the amino acid sequence of SEQ ID NO: 4 and the activity of the ocfD gene of the bacterial strain of *Burkholderia contaminans* M514 is decreased by a point mutation of the catalytic serine at position 2954 of the amino acid sequence of SEQ ID NO: 4, deletion, insertion or point mutations within the thioesterase motif of the amino acid sequence of SEQ ID NO: 4, deletion of the catalytic serine of the amino acid sequence of SEQ ID NO: 4, truncation of the ocfD gene, or frameshift mutation of the ocfD gene, such that the ocfD gene in the bacterial strain of *Burkholderia contaminans* M514 has reduced OcfD thioesterase activity in comparison with the OcfD thioesterase activity in a wild-type bacterial strain of *Burkholderia contaminans* M514.

2. The method of claim 1, wherein the ocfN gene is expressed in a multicopy plasmid with a native promoter or any other promoter sequence.

3. The method of claim 1, wherein the ocfN gene is integrated into the chromosome with additional copies of the ocfN gene using transposons.

4. The method of claim 1, wherein the bacterial strain of *Burkholderia contaminans* MS14 has two or more copies of the ocfN gene.

5. The method of claim 1, wherein the native promoter of the ocfN gene in the bacterial strain of *Burkholderia contaminans* MS14 is substituted with a promoter that increases expression of the ocfN relative to the native promoter.

6. The method of claim 1, wherein the ocfD gene of the bacterial strain of *Burkholderia contaminans* MS14 is truncated.

7. The method of claim 1, wherein the thioesterase motif in the amino acid sequence of SEQ ID NO: 4 is deleted in the bacterial strain of *Burkholderia contaminans* MS14.

8. The method of claim 1, wherein the ocfD gene of the bacterial strain of *Burkholderia contaminans* MS14 has a frameshift.

* * * * *

SEQUENCE LISTING

<160> NUMBER OF SEQ ID NOS: 23

<210> SEQ ID NO 1
<211> LENGTH: 21
<212> TYPE: DNA
<213> ORGANISM: Artificial sequence
<220> FEATURE:
<223> OTHER INFORMATION: primer

<400> SEQUENCE: 1
cgccacccgt tacgaggatt c                                    21

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
acgcgtcccc tcttcctacg                                      20

<210> SEQ ID NO 3
<211> LENGTH: 239
<212> TYPE: PRT
<213> ORGANISM: Burkholderia contaminans MS14

<400> SEQUENCE: 3

Met Arg Leu Ile Cys Phe Pro Tyr Ala Gly Gly Ser Ala Ala Val Tyr
1 5 10 15

Arg Thr Leu Gln Ala Ser Leu Pro Gly Ile Glu Val Cys Arg His Glu
20 25 30

Leu Ala Gly Arg Gly Ser Arg Leu Ser Glu Pro Ala Val Arg Asp Met
35 40 45

Ala Thr Leu Val Asp Thr Leu Leu Cys Asp Leu Asp Asp Cys Phe Asp
50 55 60

Arg Pro Phe Ala Leu Leu Gly His Ser Met Gly Ala Ala Ile Ala Ala
65 70 75 80

Glu Leu Ala Leu Arg Leu Pro Ala His Ala Arg Pro Asn Leu Arg His
85 90 95

Leu Phe Val Ser Ala Arg Ala Ala Pro Gly Lys Glu Arg His Asp Arg
100 105 110

Arg Met Gln Ala Leu Asp Asp Arg Ala Phe Ile Asp Ala Leu Arg Glu
115 120 125

Met Gly Gly Thr Pro Lys Ala Val Leu Asp Asn Ser Glu Leu Met Ala
130 135 140

Leu Leu Met Pro Ala Leu Arg Ala Asp Phe Thr Met Ile Glu Asn His
145 150 155 160

Arg Pro Val Pro Gly Pro Arg Leu Ala Val Asp Ile Thr Ala Phe Ala
165 170 175

Gly Arg Ala Asp Lys Glu Ile Pro Val Asp Ala Val Ala Gly Trp Gly
180 185 190

Ala Ala Thr Thr Gly Arg Phe Asp Phe His Val Ile Glu Gly Asp His
195 200 205

Phe Phe Leu Arg Asn Glu Met Arg Thr Met Ala Gly Ile Ile Ala Ala
210 215 220

Arg Met Arg Arg Pro Glu His Ala Ala Ser Ser Ala Leu Gln Ala
225 230 235

<210> SEQ ID NO 4
<211> LENGTH: 3154
<212> TYPE: PRT
<213> ORGANISM: Burkholderia contaminans MS14

<400> SEQUENCE: 4

Met Gln Asp Asn Asn Val Leu Val Thr Asp Arg Glu Ser Leu Ser Arg
1 5 10 15

Val Ala Gly Val Tyr Gly Ile Ala Ala Tyr Ala Pro Ser Gln Gln Pro
20 25 30

Gly Arg Pro Leu Thr Arg Ser Val Arg Leu Thr Pro Ala Ser Leu Asp
35 40 45

Leu Leu Arg Arg Ile Gly Asp Gly Glu Leu Ala Glu Phe Ala Val Ala
50 55 60

Ala Ala Gly Ile Ala Phe Leu Leu Trp Lys Tyr Phe Arg Ile Pro Val
65 70 75 80

Thr Val Leu Gly Thr Pro Gly Leu Ala Gly His Pro Ser Ala Arg Ala
85 90 95

Ala Ile Val Pro Leu Ile Ile Glu Val Arg Pro Asp Glu Arg Ile Glu
100 105 110

Asp Tyr Leu Ser Arg Val Ala Gly Ile Val Glu Asp Ser Tyr Ala Glu
115 120 125

-continued

```
Pro Arg Phe Pro Leu Glu Thr Leu Val Arg Asn Glu Lys Asp Met Ala
    130                 135                 140
Leu Ala Gln Leu Thr Lys Val Ala Leu Ala Asp Asp Arg Val His His
145                 150                 155                 160
Ala Pro Thr Gly Arg Asp Asp Leu Gln Leu His Leu Arg Leu Ala
                165                 170                 175
Arg Gly Glu Ile Glu Leu Arg Tyr Ser Gly Ala Ile Glu Pro Phe Ile
                180                 185                 190
Ile Asp Gly Phe Ala Gly Ser Leu Ala Ala Val Leu Glu Ala Phe Glu
                195                 200                 205
His Leu Asp Gly Ala Val Gly Asp Ile Glu Ala Ala Pro Pro Glu Gln
    210                 215                 220
Gly Pro Leu Leu Ala Ala Phe Asn Glu Thr Ala Thr Ala Gly Pro Ser
225                 230                 235                 240
His Pro Thr Val Val Ala Met Phe Glu Ala Gln Val Ala Arg Thr Pro
                245                 250                 255
Thr Ala Pro Ala Leu Val Thr Asp Ser Ser Leu Met Thr Tyr Ala Asp
                260                 265                 270
Leu Asn Ala Arg Ala Asn Ser Leu Ala His His Leu Arg Glu His His
            275                 280                 285
Gly Val Gly Pro Glu Ser Leu Val Gly Ile Met Leu Asp Arg Ser Glu
    290                 295                 300
Trp Met Ile Val Ala Ile Leu Gly Ile Leu Lys Ala Gly Ala Ala Phe
305                 310                 315                 320
Val Pro Leu Asp Pro Ala Tyr Pro Ala Glu Arg Ile Asn His Ile Leu
                325                 330                 335
Gly Asp Thr Gly Leu Ser Leu Leu Val Thr Gln Ser Ser Gln Leu Ala
                340                 345                 350
Gln Trp Tyr Glu Phe Ser Gly Val Thr Leu Leu Leu Asp Gln Glu Leu
            355                 360                 365
Pro Gly Trp Gln Pro Leu Pro Asp Asn Pro His Arg Ala Glu Pro
    370                 375                 380
Ala His Leu Ala Tyr Val Leu Tyr Thr Ser Gly Ser Thr Gly Lys Pro
385                 390                 395                 400
Lys Gly Cys Leu Leu Glu His Arg Asn Leu Ala His Tyr Ile Ala Trp
                405                 410                 415
Ala Ala Gly Tyr Tyr Phe Pro Glu Ser Thr Gly Ser Phe Gly Leu
                420                 425                 430
Tyr Ser Ser Leu Cys Phe Asp Phe Thr Leu Thr Asn Ile Phe Cys Pro
            435                 440                 445
Leu Val Arg Gly Lys Thr Leu Arg Ile Tyr Pro Gln Ser Glu Ser Ile
    450                 455                 460
Asp Thr Ile Leu Ala Arg Met Phe Gln Pro Gly Ser Gly Val Asp Thr
465                 470                 475                 480
Leu Lys Leu Thr Pro Thr His Ile His Leu Leu Glu Tyr Met Asn Leu
                485                 490                 495
Ala Arg Ser Gly Val Arg Lys Val Ile Val Gly Gly Glu Glu Leu Thr
                500                 505                 510
Pro Gln His Ile Ala Thr Leu Arg Lys Ile Asp Pro Ala Ile Glu Ile
            515                 520                 525
Tyr Asn Glu Tyr Gly Pro Thr Glu Ala Thr Val Gly Cys Ile Val Glu
    530                 535                 540
```

-continued

Arg Val Glu Asp Ala Pro Pro Thr Val Leu Ile Gly Arg Pro Ile Ala
545                 550                 555                 560

Asp Thr Arg Val Tyr Met Leu Asp Asp Ala Leu Arg Pro Val Pro Leu
            565                 570                 575

Gly Val Pro Gly Glu Ile Cys Leu Ala Gly Ala Gly Leu Ala Arg Gly
            580                 585                 590

Tyr His Gln Arg Pro Asp Val Thr Ala Ala Lys Phe Val Glu His Pro
            595                 600                 605

Phe Pro Gly Glu Ala Arg Ile Tyr Arg Thr Gly Asp Ile Gly Arg Trp
            610                 615                 620

Leu Pro Asp Gly Arg Ile Gln Cys Tyr Gly Arg Val Asp His Gln Val
625                 630                 635                 640

Lys Ile Arg Gly His Arg Val Glu Leu Gly Glu Ile Glu Ala Ala Ile
                645                 650                 655

Ala Ala His Glu Asp Val Val Gly Ala Ala Val Met Leu Arg Glu Ser
                660                 665                 670

Ala His Gly Val Arg Lys Leu Ala Ala Tyr Val Lys Gly Ala Ala Ser
            675                 680                 685

Leu Ser Val Pro Asn Leu Arg Ala Tyr Leu Ala Gly Lys Leu Pro Asp
            690                 695                 700

Tyr Met Val Pro Ser Asp Ile Ile Pro Ile Ala Glu Phe Pro Leu Asn
705                 710                 715                 720

Ala Asn Gly Lys Leu Asp Arg Pro Ala Leu Ala Leu Glu Pro Ala
                725                 730                 735

Ala Ala Pro Glu Glu Ala Pro Leu Asp Ala Thr Pro Ile Gln Arg Glu
            740                 745                 750

Leu Val Arg Ile Trp Arg Asp Val Leu Asp Asn Pro Ala Val Asp Leu
            755                 760                 765

Ala Gly Arg Phe Phe Asp Tyr Gly Gly Asp Ser Leu Gln Ala Met Gln
            770                 775                 780

Leu Val Ser Arg Ile Trp Ser Ser Phe Ser Val Glu Ile Gly Ile Asp
785                 790                 795                 800

Ala Ile Phe Glu Leu Gln Thr Ile Ser Ala Val Ser Asp Leu Ile Glu
                805                 810                 815

Ala Ser Ser Pro His Pro Gly Ser Thr Ala Gly Ala Ile Pro Pro Arg
            820                 825                 830

Ser Arg Ala Asn Asp Leu Pro Leu Ser Phe Pro Gln Gln Arg Leu Trp
            835                 840                 845

Phe Leu Ala Gln Leu Glu Gly Pro Ser Ala Thr Tyr Asn Ile Ser Ser
850                 855                 860

Ala Leu Arg Phe Glu Gly Glu Leu Asp Val Ala Arg Leu Arg Phe Ala
865                 870                 875                 880

Val Ser Glu Ile Ser Arg Arg His Glu Ile Leu Arg Thr Thr Phe Pro
                885                 890                 895

Ala Val Asp Gly Arg Gly Val Gln Arg Ile Ala Pro Ala Pro Val
            900                 905                 910

Ala Leu Asp Val Val Asp Val Ala Ser Glu Ser Asp Thr Leu Ala Leu
            915                 920                 925

Leu Ala Glu Glu Ala Asp Arg Pro Phe Asp Leu Ala Ala Gly Pro Leu
            930                 935                 940

Tyr Arg Val Val Leu Tyr Arg Val His Glu Arg Leu His Val Phe Gly
945                 950                 955                 960

Ile Val Met His His Ile Val Ser Asp Ala Trp Ser Ser Gly Ile Leu

```
              965                 970                 975
Ile Gly Glu Leu Ala Ala Leu Tyr Ala Gly Glu Ser Leu Pro Glu Leu
                980                 985                 990

Ala Val Gln Tyr Ala Asp Tyr Ala  Val Trp Gln His Glu  Arg Leu Ala
        995                1000                1005

Ser Ala  Asp Thr His Arg Glu  Leu Ala Leu Leu Ser  Ala Ala Leu
   1010                1015                1020

Ala Asp  Ala Pro Asp Leu Ile  Glu Leu Pro Thr Asp  Arg Pro Arg
   1025                1030                1035

Pro Ala  Val Gln Gln Phe Arg  Gly Ala Val Leu Pro  Phe Gln Leu
   1040                1045                1050

Ser Ala  Glu Arg Ala Asp Gly  Leu Arg Ala Ile Ala  Arg Ala Ser
   1055                1060                1065

Gly Thr  Ser Thr Phe Met Val  Val Leu Ala Ala Tyr  Ala Leu Leu
   1070                1075                1080

Leu Ser  Arg Tyr Ser Asn Gln  Gln Asp Leu Val Ile  Gly Ser Pro
   1085                1090                1095

Ile Ala  Asn Arg Arg Ser Ser  Met Thr Glu Pro Leu  Ile Gly Phe
   1100                1105                1110

Phe Ala  Asn Met Leu Ala Leu  Arg Val Asp Leu Ser  Gly Asn Pro
   1115                1120                1125

Thr Phe  Gly Asp Leu Leu Ala  Arg Val Lys Arg Val  Ala Leu Asp
   1130                1135                1140

Gly Tyr  Ser Arg Gln Glu Ile  Pro Phe Glu Gln Val  Val Asp Ser
   1145                1150                1155

Leu Glu  Leu Glu Arg Asn Leu  Gly Arg Thr Pro Val  Phe Gln Val
   1160                1165                1170

Val Phe  Ala Tyr Glu Lys Ala  Gln Pro Arg Ala Val  Ser Phe Pro
   1175                1180                1185

Gly Leu  Val Ala Thr Pro Val  Ala Val Glu Thr His  Thr Ala Lys
   1190                1195                1200

Phe Asp  Leu Thr Leu His Val  Gln Asp Ala Asp Asp  Gly Leu Ala
   1205                1210                1215

Gly Ser  Leu Glu Tyr Asn Leu  Asp Leu Phe Asp Ala  Ala Thr Ile
   1220                1225                1230

Asp Arg  Met Ala Glu His Phe  Arg Thr Leu Val Asp  Ala Val Ile
   1235                1240                1245

Ala Asp  Pro Asp Arg Pro Leu  Gly Ala Leu Ser Leu  Ser Asn Asp
   1250                1255                1260

Ala Glu  Arg Asn Leu Leu Thr  Val Glu Trp Asn Arg  Thr Asp Thr
   1265                1270                1275

Asp Phe  Gly Glu Asp Ala Ala  Gln Pro Leu His Arg  Leu Phe Glu
   1280                1285                1290

Gln Gln  Val Glu Arg Thr Pro  Asp Ala Val Ala Ile  Val Phe Asp
   1295                1300                1305

Asp Thr  Ala Leu Thr Tyr Ala  Glu Leu Asn Leu Arg  Ala Asn Arg
   1310                1315                1320

Leu Ala  His His Leu Val Ala  Leu Gly Val Gly Pro  Asp Ser Leu
   1325                1330                1335

Val Gly  Val Ala Met Glu Arg  Ser Leu Asp Met Ser  Val Ala Leu
   1340                1345                1350

Leu Ala  Ile Leu Lys Ala Gly  Gly Ala Tyr Val Pro  Val Asp Pro
   1355                1360                1365
```

```
Asp Tyr Pro Ala Glu Arg Val Arg Phe Met Ile Asp His Ala Gln
    1370            1375            1380

Leu Arg Trp Leu Leu Thr Gln Gln His Leu His Asp Ala Leu Pro
    1385            1390            1395

Asp Thr Asp Ala His Val Ile Val Val Asp Arg Asp Ser Leu Asp
    1400            1405            1410

Leu Asp Ala Ala Ala Thr Ser Asn Pro Ala Pro Ala Leu Asn Gly
    1415            1420            1425

Asp Asn Leu Ala Tyr Met Ile Tyr Thr Ser Gly Ser Thr Gly Arg
    1430            1435            1440

Pro Lys Gly Ala Leu Asn Thr His Arg Ala Ile Thr Asn Arg Ile
    1445            1450            1455

Leu Trp Met Gln His Ala Tyr Ala Leu Asp Ala Asp Asp Ala Val
    1460            1465            1470

Leu Gln Lys Thr Pro Phe Ser Phe Asp Val Ser Val Trp Glu Leu
    1475            1480            1485

Phe Trp Pro Leu Val Thr Gly Ala Arg Leu Val Phe Ala Arg Pro
    1490            1495            1500

Gly Gly Gln Arg Glu Thr Asp Tyr Leu Val Glu Leu Ile Glu Arg
    1505            1510            1515

Glu Arg Ile Thr Thr Ile His Phe Val Pro Ser Met Leu Arg Ala
    1520            1525            1530

Phe Leu Asp His Pro Asp Leu Asp Ala His Cys Ala Ser Leu Arg
    1535            1540            1545

Arg Val Val Cys Ser Gly Glu Ala Leu Pro His Asp Leu Gln Gln
    1550            1555            1560

Arg Cys Leu Glu Arg Leu Asp Val Lys Leu Tyr Asn Leu Tyr Gly
    1565            1570            1575

Pro Thr Glu Ala Ala Val Asp Val Thr Ala Trp Glu Cys Arg Arg
    1580            1585            1590

Asp Asp Pro His Arg Ile Val Pro Ile Gly Arg Pro Ile Ala Asn
    1595            1600            1605

Thr Arg Leu Tyr Ile Val Asp Ala Gln Met Gln Pro Thr Pro Ile
    1610            1615            1620

Gly Val Ala Gly Glu Leu Leu Ile Gly Gly Thr Pro Val Gly Arg
    1625            1630            1635

Gly Tyr His Gly Glu Pro Glu Leu Ser Ala Glu Lys Phe Ile Ala
    1640            1645            1650

Asp Pro Phe Ser Ala Asp Pro Leu Ala Arg Leu Tyr Arg Thr Gly
    1655            1660            1665

Asp Leu Ala Arg Tyr Arg Pro Asp Gly Asn Ile Glu Phe Leu Gly
    1670            1675            1680

Arg Ile Asp His Gln Ile Lys Leu Arg Gly Leu Arg Ile Glu Pro
    1685            1690            1695

Gly Glu Ile Glu Ala Ala Leu Arg Ala His Pro Ser Val Asp Asp
    1700            1705            1710

Cys Val Val Ile Ala Lys Thr Glu Gly Ala Arg Thr Phe Leu Ile
    1715            1720            1725

Ala Tyr Val Ala Thr Ala Ala Pro Asp Ile Ala Asp Leu Arg Gly
    1730            1735            1740

Tyr Leu Gly Gly Lys Leu Ala Asp Tyr Met Val Pro Ser Gln Phe
    1745            1750            1755
```

```
Phe Ala Leu Glu Ser Leu Pro Met Leu Pro Asn Gly Lys Ile Asn
1760                1765                1770

Arg Lys Ala Leu Pro Leu Pro Ala Asp Arg Gly Asp Ala Ala Gln
1775                1780                1785

Pro His Ala Pro Ala Val Thr Pro Arg Glu Ile Leu Leu Ala Ser
1790                1795                1800

Ile Cys Ile Asp Val Leu Gln Leu Pro Ser Val Gly Ile His Asp
1805                1810                1815

Asn Phe Phe Glu Leu Gly Gly Asp Ser Ile Leu Ser Ile Gln Val
1820                1825                1830

Ile Ala Arg Ala Asn Gln Ala Gly Leu Arg Val Thr Ala Lys Gln
1835                1840                1845

Leu Phe Gln Tyr Gln Thr Ile Ala Gln Leu Ala Ala Ala Pro Glu
1850                1855                1860

Glu Arg Ala Ala Cys Ala Pro Thr Leu Ser Pro Leu Gly Asp Ala
1865                1870                1875

Pro Leu Thr Pro Val Gln His Trp Phe Phe Glu Gln Glu Ile Asp
1880                1885                1890

Ala Pro Ser His Tyr Asn Gln Thr Val Leu Ile Gln Val Pro Ala
1895                1900                1905

Asp Ile Asp Ala Ser Arg Leu Ala Asp Ala Phe Arg Gln Val Tyr
1910                1915                1920

Glu His His Asp Ala Leu Arg Leu Arg Phe Ser His Asp Ala Gly
1925                1930                1935

Arg Trp Thr Gln Gln Val Val Ala Gly Gly Glu Met Pro Ala Leu
1940                1945                1950

Phe Ala Lys Gln Val Ile Ala Asp Asp Ala Gly Glu Arg Leu Ala
1955                1960                1965

Ala Met Arg Ala Ala Ala Asp Ala Glu Arg Gly Ile Asp Ile
1970                1975                1980

Thr His Gly Pro Leu Leu Ala Ala Arg Leu Phe Cys Leu Ala Asp
1985                1990                1995

Glu Pro Leu Ala Arg Leu Phe Val Ser Ile His His Leu Ala Val
2000                2005                2010

Asp Gly Val Ser Trp Arg Val Leu Leu Glu Asp Leu His Ala Ala
2015                2020                2025

Tyr His Gly Gln Pro Leu Pro Gly Lys Thr Thr Ser Phe Arg Glu
2030                2035                2040

Trp Ala Leu His Leu Gln Gln Leu Ala Arg Ser Pro Ala Ile Gly
2045                2050                2055

Asp Glu Ala Arg Leu Trp Gln Ala Leu Leu Ala Gln Pro Val Glu
2060                2065                2070

Pro Met Pro Val Asp Tyr Pro Gly Thr Gly Ala Ala Asn Asn Ala
2075                2080                2085

Val Asp Asp Ala Ser Ser Val Ser Phe Glu Leu Gly Glu Ala Asp
2090                2095                2100

Thr Thr Ala Leu Leu Arg Arg Leu Pro Arg Ala Tyr Asp Thr Arg
2105                2110                2115

Ile Asn Asp Val Leu Leu Val Ala Leu Ala Gln Ala Cys Ser Met
2120                2125                2130

Val Thr Gly Asn Thr Arg Arg Ile Asp Leu Glu Ser His Gly
2135                2140                2145

Arg His Val Ser Asp Ala Pro Leu Asp Leu Thr Arg Thr Val Gly
```

```
                2150                2155                2160
Trp Phe Thr Ser Ile Tyr Pro Val Val Leu Asp Ala Asp Ala Met
    2165                2170                2175
His Ala Pro Glu Gln Ala Leu Arg Ala Ala Arg Gln Gln Leu Arg
    2180                2185                2190
Arg Ile Pro Ala Asp Gly Leu Gly Tyr Ser Leu Leu Arg Tyr Gln
    2195                2200                2205
Ser Pro Asp Ala Ala Val Arg Asp Ser Leu Ala Ala Leu Pro Lys
    2210                2215                2220
Ala Asp Ile Leu Phe Asn Tyr His Gly Gln Leu Asp Thr Val Leu
    2225                2230                2235
Arg Gln Ser Asp Gly Trp Arg Pro Ala Ala Glu Asp Leu Gly Ser
    2240                2245                2250
Leu Arg Ala Gly Arg Ser Gln Arg Thr His Ala Phe Glu Ile Val
    2255                2260                2265
Ala Ala Val Ala Asp Gly Lys Leu Gln Val Asp Trp Arg Tyr Gly
    2270                2275                2280
Glu Arg Leu His Arg Arg Gln Thr Val Glu Asn Leu Ala Ala His
    2285                2290                2295
Phe Arg Asp Arg Leu Leu Asp Phe Ala Ala Ser Val Pro Asp Thr
    2300                2305                2310
Ala Ala Asp Asp Ile Glu Asp Ser Tyr Pro Leu Ser Ser Leu Gln
    2315                2320                2325
Gln Gly Ile Leu Phe His Ser Leu Tyr Asp Leu Asp Pro Ala Ala
    2330                2335                2340
Tyr Phe Gln Gln Phe Ser Phe Val Val Ser Gly Pro Leu Gln Val
    2345                2350                2355
Pro Ala Leu Arg Gln Ala Trp Ala Asn Ala Leu Ala Arg His Ala
    2360                2365                2370
Val Leu Arg Thr Ala Phe Ala Trp Ala Asp Arg Asp His Pro Val
    2375                2380                2385
Gln Thr Val Arg His Thr Val Asp Leu Pro Trp Thr Phe Leu Asp
    2390                2395                2400
Trp Arg His Arg Asp Ala Ser Arg Arg Ala Gln Asp Phe Asp Ala
    2405                2410                2415
Phe Leu Ala Asp Asp Arg Arg Arg Gly Phe Asp Leu Gln Arg Ala
    2420                2425                2430
Pro Leu Phe Arg Cys Thr Leu Ile Gln Glu Thr Asp Thr Arg His
    2435                2440                2445
Arg Phe Cys Trp Ser Ala His His Ile Ile Leu Asp Gly Trp Ser
    2450                2455                2460
Thr Ala Thr Leu Met Lys Glu Val Phe Asp Asp Tyr Leu Ser Leu
    2465                2470                2475
Ala Arg Thr Gly Met Pro Ala Val Ala Ala Ser Ala Pro Gly Tyr
    2480                2485                2490
Arg Ala Tyr Ile Asp Trp Leu Ala Arg His Pro Arg Ser Ala Asp
    2495                2500                2505
Glu Thr Trp Trp Arg Ala Glu Leu Ala Gly Phe Lys Ala Ala Thr
    2510                2515                2520
Pro Val Ala Ala Ser Pro Ala Arg Gln Ala Thr Gly Asp Ala Pro
    2525                2530                2535
Arg Gln Asp Lys Arg Arg Thr Gln Gln Phe Leu Leu Asp Glu Ala
    2540                2545                2550
```

-continued

Leu Ala Ala Arg Leu Gln Thr Leu Thr Arg Thr His Arg Val Thr
2555                2560                2565

Leu Asn Val Leu Ile Arg Ala Val Trp Ala Leu Val Leu Arg Arg
2570                2575                2580

His Ala Gly Thr Asp Asp Val Val Phe Gly Val Thr Val Ser Gly
2585                2590                2595

Arg Pro Pro Met Leu Asp Gly Val Glu Ser Ile Val Gly Leu Phe
2600                2605                2610

Ile Asn Thr Leu Pro Leu Arg Leu Arg Ile Ala Pro Glu Arg Pro
2615                2620                2625

Phe Ile Glu Trp Leu Ala Glu Val His Ala Ala Gln Thr Ala Met
2630                2635                2640

Glu Pro His Ser Tyr Ser Ser Leu Val Asp Ile Gln Ser Trp Ser
2645                2650                2655

Glu Leu Pro Ala Gly Asp Ser Leu Phe Asp Ser Leu Leu Val Phe
2660                2665                2670

Glu Asn Phe Pro Val Ala Ala Ala Pro Asp Leu Gly Pro Asp Asp
2675                2680                2685

Ile Glu Ile Leu Asp Thr Arg Ala Phe Ala Glu Ser Asn Tyr Pro
2690                2695                2700

Leu Thr Leu Thr Val His Pro Asn Glu Arg Ile Gly Phe His Ile
2705                2710                2715

Ser His Asp Ala His Arg Ile Ala Pro Glu Val Val Arg Gln Met
2720                2725                2730

Leu Asp Thr Leu Arg Thr Leu Leu Glu Arg Phe Ala Glu Asn Pro
2735                2740                2745

Gly Gln Leu Thr Gly Gln Leu Ala Asp Pro Pro Ala Ala Asp Gly
2750                2755                2760

Arg Pro Ser Ala Pro Arg Ser Gly Ala Gly Pro Ala Ile Glu Ala
2765                2770                2775

Ala Ala Gly Ala Ala Ala Ala Arg Ala Val Ala His Ala Ala
2780                2785                2790

Asp Glu Ser Thr Leu Leu Glu Ile Trp Arg Arg Ile Phe Lys Arg
2795                2800                2805

Asp Asp Ile Ala Val Ser Asp Asn Tyr Phe Asp Leu Gly Gly His
2810                2815                2820

Ser Ile Ile Ala Ile Gln Leu Met Ala His Val Glu Lys Ala Phe
2825                2830                2835

Asp Arg Arg Leu Pro Ile Ser Cys Leu Phe Glu Asn Pro Thr Ile
2840                2845                2850

Glu Lys Leu Ala Ala Ala Leu Ala Ala Lys Glu Pro Ser Ala Pro
2855                2860                2865

Ala Gly Gly Leu Val Pro Ile Arg Asp Gly Gly Pro Ala Ala Pro
2870                2875                2880

Leu Phe Leu Leu Pro Gly Ala Gly Gly Asn Val Val Tyr Phe Arg
2885                2890                2895

Pro Leu Ala Asn His Leu Ser Gly Ala His Ala Ile His Gly Leu
2900                2905                2910

Glu Ala Leu Gly Leu Asp Gly Ala Cys Glu Pro Leu Thr Arg Val
2915                2920                2925

Glu Asp Ile Ala Ala Arg His Ile Glu Arg Ile Trp Pro Leu Val
2930                2935                2940

```
Gly Ala Gly Pro Tyr Tyr Leu Ala Gly His Ser Phe Gly Ala His
    2945                2950                2955

Val Ala Leu Glu Met Ser Arg Gln Leu Val Ala Lys Gly Ala Asp
    2960                2965                2970

Val Lys Leu Leu Ala Ile Phe Asp Ala Ser Ala Pro Ile Asp Ser
    2975                2980                2985

Ser Ala Ala Thr Tyr Trp Gln Asp Trp Asp Thr Glu Trp Leu
    2990                2995                3000

Val Ala Ile Ala His Glu Ile Gly Thr Phe Leu Gly Thr Asp Leu
    3005                3010                3015

Gln Val Thr Arg Ala Asp Leu Val His Leu Asp Pro Asp Gly Gln
    3020                3025                3030

Ala Gly Leu Ile Leu Glu Arg Ile Gly Asp Arg Gly Ser Trp Phe
    3035                3040                3045

Ala Asp Ala Gly Ser Asp Arg Leu Arg Ala Tyr Leu Arg Val Tyr
    3050                3055                3060

Gln Ala Asn Phe Lys Ser His Tyr Ala Pro His Ala Thr Pro Leu
    3065                3070                3075

Pro Val Pro Ile Ala Leu Phe Arg Ser Thr Glu Arg Asp Pro Gly
    3080                3085                3090

Asp Tyr Ala Pro Ser Ser Glu Ile Ala Gln Leu Arg Leu Asp Ala
    3095                3100                3105

Thr Trp Gly Trp Ser Arg Phe Ser Ala His Pro Val Ala Val Thr
    3110                3115                3120

Asp Val Pro Gly Asp His Leu Thr Met Leu Leu Asp Pro His Ala
    3125                3130                3135

Gly Val Leu Ala Ala His Val Asn Ser Phe Leu Glu Lys Thr Pro
    3140                3145                3150

Ser

<210> SEQ ID NO 5
<211> LENGTH: 391
<212> TYPE: PRT
<213> ORGANISM: Burkholderia contaminans
<220> FEATURE:
<221> NAME/KEY: MISC_FEATURE
<222> LOCATION: (1)..(391)
<223> OTHER INFORMATION: putative FAD linked oxidase domain protein

<400> SEQUENCE: 5

Met Ser His Asp Phe Arg Asp Glu Pro Ala Pro Arg Arg Ala Phe Leu
1               5                   10                  15

Ala Asp Met Ala Lys Leu Ala Ala Ala Gly Ile Val Thr Gly Trp Thr
                20                  25                  30

Pro Leu Tyr Gln Val Ala Ala His Ala Arg Thr Ala Gly Glu Thr Pro
            35                  40                  45

Pro Gly Phe Pro Ala Asp Ile Gln Leu Tyr Lys Gln Ala Phe Leu Asn
        50                  55                  60

Trp Ser Gly Glu Ile Ala Val Gln Asp Val Trp Thr Ala Ala Pro Arg
65                  70                  75                  80

Ser Ala Asp Asp Val Val Ala Thr Val Asn Trp Ala Arg Ala Asn Gly
                85                  90                  95

Tyr Arg Ile Arg Pro Arg Gly Tyr Thr His Asn Trp Ser Pro Leu Thr
            100                 105                 110

Leu Asp Pro Gly Ala Gly Ala Ala Asn Leu Val Leu Leu Asp Thr Thr
        115                 120                 125
```

```
Lys Ser Leu Thr Ala Val Ser Val Asp Thr Ser Ala Arg Pro Ala Arg
            130                 135                 140

Val Thr Ala Gln Thr Gly Val Ser Leu Glu Ser Leu Leu Ala Thr Leu
145                 150                 155                 160

Glu Gln Val Gly Leu Gly Val Ile Ala Ala Pro Ala Pro Gly Asp Ile
                165                 170                 175

Thr Leu Gly Gly Ala Leu Ala Ile Asp Ala His Gly Thr Ala Val Pro
            180                 185                 190

Ala Ala Gly Glu Thr Leu Gln Pro Gly His Thr Tyr Gly Ser Leu Ser
            195                 200                 205

Asn Leu Val Val Ala Leu Thr Ala Val Val Phe Asp Pro Ala Arg Gln
            210                 215                 220

Gln Tyr Val Leu Arg Arg Phe Glu Arg Ser Asp Pro Glu Ile Gly Ala
225                 230                 235                 240

Phe Leu Ala His Ile Gly Arg Ala Leu Val Val Glu Val Thr Leu Thr
                245                 250                 255

Ala Gly Pro Asn Gln Arg Leu Arg Cys Gln Ser Tyr Val Asp Ile Pro
            260                 265                 270

Ala Ser Glu Leu Phe Ala Ala Pro Gly Thr Thr Gly Arg Thr Ile Ala
            275                 280                 285

Ser Phe Leu Asp Gly Ser Gly Arg Val Glu Ala Ile Trp Phe Pro Phe
290                 295                 300

Thr Thr Lys Pro Trp Leu Lys Val Trp Thr Pro Thr Pro Ser Lys Pro
305                 310                 315                 320

Phe Leu Ser Arg Ala Val Thr Gln Pro Tyr Asn Tyr Pro Phe Ser Asp
                325                 330                 335

Ser Ile Ser Gln Ser Ile Ser Asp Leu Val Lys Arg Ile Val Ile Gly
            340                 345                 350

Gly Glu Gly Ala Leu Thr Pro Leu Phe Gly Gln Thr Gln Leu Ala Ile
            355                 360                 365

Thr Thr Ala Gly Leu Ala Leu Thr Leu Ser Gly Asp Ile Trp Gly Trp
370                 375                 380

Ser Arg Thr Val Leu Gln Glu
385                 390

<210> SEQ ID NO 6
<211> LENGTH: 273
<212> TYPE: PRT
<213> ORGANISM: Burkholderia contaminans
<220> FEATURE:
<221> NAME/KEY: MISC_FEATURE
<222> LOCATION: (1)..(273)
<223> OTHER INFORMATION: putative LuxR-type regulator

<400> SEQUENCE: 6

Met Phe Ala Lys Leu Gly Lys Val Ile Ser Ser Ala Gly Ser Glu Arg
1               5                   10                  15

Phe Ala Ser Asp Met His Ala Leu Leu Val Glu Ser Ile Pro Leu Thr
                20                  25                  30

Ile Thr Arg Met Thr Glu Trp Thr Leu Asp Glu Pro Ala Gly Glu Val
            35                  40                  45

Val Arg Val Gln Ser Leu Gly Ala Asp Gly Ala Pro Gly Asp Asp Gly
        50                  55                  60

Arg Gly Ala Pro Ala Ala His Gly Glu Arg Glu Pro Ala Ala His Pro
65                  70                  75                  80
```

Pro Leu Asn Arg Ile Leu Ala Ala Cys Asp Arg Gln Leu Ile His Ile
                85                  90                  95

Asn Pro Leu Met Arg Arg Gly Asn Gly Glu Val Ala Pro Ser Arg
            100                 105                 110

Gly Pro Gly Gly Gly Phe Gln Cys His Leu Val Ser Gly Lys Ala Asn
            115                 120                 125

Arg Arg Tyr Val Ile Ser Leu His Arg Thr Ala Ser His Arg Asp Phe
            130                 135                 140

Ser Leu Arg Glu Met Ser Phe Leu Lys Asn Phe Ala Asp Thr Leu Leu
145                 150                 155                 160

Pro Leu Val Glu Trp His Ala Ser Thr Cys Arg His Gly Glu Arg Glu
                165                 170                 175

Gly Ala Thr Ala Pro Gly Ala Thr Ala Gly Met Pro Gly Val Glu Ala
                180                 185                 190

Leu Arg His Glu Phe Glu Ser Arg Leu Ala Arg Ala Arg Val Val Leu
                195                 200                 205

Ser Ala Arg Glu Asn Glu Val Cys Leu Gly Leu Leu Ala Gly Lys Met
            210                 215                 220

Leu Arg Glu Met Ala Gly Glu Leu Gly Val Lys Glu Ser Thr Ile Glu
225                 230                 235                 240

Thr Tyr Ile Lys Arg Ala Ala Val Lys Leu Gly Ile Ser Gly Arg His
                245                 250                 255

Gly Leu Thr Lys Trp Met Ile Asp Asp Ser Val Pro Cys Ala Ser Ala
            260                 265                 270

Ala

<210> SEQ ID NO 7
<211> LENGTH: 296
<212> TYPE: PRT
<213> ORGANISM: Burkholderia contaminans
<220> FEATURE:
<221> NAME/KEY: MISC_FEATURE
<222> LOCATION: (1)..(296)
<223> OTHER INFORMATION: putative LuxR-type regulator

<400> SEQUENCE: 7

Met Glu Phe Ser Arg Leu Phe Ala His Val Gly Glu Ala Ile Ser Ser
1               5                   10                  15

Ser Gly Ser Arg Arg Phe Pro Arg Met Met Tyr Asn Leu Ile Ala Ala
            20                  25                  30

Ala Val Pro Val Asp Glu Ile Arg Ile Ser Glu Leu Ala Ile Asp Asp
            35                  40                  45

Val Pro Asp Gly Pro Pro Glu Val Arg Ser Leu Gly Ala Val Gly Ala
50                  55                  60

Ala Leu Ala Lys Thr Gly Ala Ala Val Cys Cys Gly Pro Gln Met
65                  70                  75                  80

Pro Pro Arg Pro Gly Thr Ser Pro Leu His Val Asp Asp Thr Leu Ala
                85                  90                  95

Gly His Gly Pro Ile His Ala Gln Leu Asp Arg Phe Ile Leu Met Gln
            100                 105                 110

Ala Ala Ile Val Ser Pro Arg Tyr Ala Gln Phe His Leu Val Thr Arg
            115                 120                 125

Lys Arg Gly His Cys Tyr Val Ile Ser Leu Tyr Arg Thr Cys Thr Phe
            130                 135                 140

Asp Asp Phe Ser Pro Gln Glu Arg Thr Phe Leu Lys Glu Leu Ser His
145                 150                 155                 160

```
Val Leu Phe Pro Ile Val Glu Ser His Val Ala Ala Leu Asp Ser Ala
                165                 170                 175

Pro Pro Ala Ala Arg Val Thr Thr Ala Ala Pro Pro Ala Thr Gln Ser
            180                 185                 190

Gly Arg Glu Arg Val Ala Arg Arg Phe Ala Asp Arg Leu Gln Gln Ala
        195                 200                 205

Gly Val Lys Leu Ser Thr Arg Glu Ile Glu Ala Cys Thr Ala Leu Leu
    210                 215                 220

Ala Gly Asp Thr Val Pro Ala Ile Ala Met Arg Phe Ala Leu Arg Glu
225                 230                 235                 240

Ser Thr Val Glu Thr Tyr Leu Lys Arg Ala Ala Val Lys Leu Gly Phe
                245                 250                 255

Ser Gly Arg His Gly Leu Thr Arg Trp Met Leu Asp Glu Thr Ala Gly
                260                 265                 270

Ala Ala Thr Glu Ala Ala Gly Gly Asp Met Arg Ser Met Arg Arg Asp
            275                 280                 285

Tyr Ala Ser Pro Arg Leu Gly Thr
        290                 295

<210> SEQ ID NO 8
<211> LENGTH: 567
<212> TYPE: PRT
<213> ORGANISM: Burkholderia contaminans
<220> FEATURE:
<221> NAME/KEY: MISC_FEATURE
<222> LOCATION: (1)..(567)
<223> OTHER INFORMATION: putative cyclic peptide transporter

<400> SEQUENCE: 8

Met Asp Ser Ala Gln Ser Lys Ser Pro Pro Trp His Ser Ala Ala Thr
1               5                   10                  15

Leu Met Trp Arg Ser His Pro Trp Leu Thr Leu Gly Thr Val Val Thr
                20                  25                  30

Gly Leu Val Ser Gly Ile Ala Ser Ile Ala Gly Val Gly Leu Ile Ser
            35                  40                  45

Thr Val Leu His Asp Gln Asp Asp Arg Gln Thr Leu Leu Leu Leu Phe
        50                  55                  60

Ile Ala Val Asn Val Val Ala Val Val Cys Arg Ser Cys Ala Ala Val
65                  70                  75                  80

Met Pro Ser Tyr Ala Cys Met Lys Val Met Thr Arg Leu Arg Val Asn
                85                  90                  95

Leu Cys Lys Arg Ile Leu Ala Thr Pro Leu Asp Glu Ile Asp Arg Arg
                100                 105                 110

Gly Ala Pro Asn Val Leu Thr Met Leu Thr Gln Asp Ile Pro Gln Leu
            115                 120                 125

Ser Gln Thr Leu Leu Thr Ile Pro Thr Ile Ile Val Gln Ser Val Val
        130                 135                 140

Leu Ile Cys Ser Ile Ala Tyr Leu Ala Tyr Leu Ser Trp Ile Val Phe
145                 150                 155                 160

Ala Ser Thr Ile Ile Leu Thr Leu Val Gly Leu Val Leu Tyr Leu Phe
                165                 170                 175

Phe Tyr Arg Lys Ala Val Asn Phe Thr Glu Arg Val Arg Asp Glu Phe
            180                 185                 190

Val Gln Phe Asn Glu Tyr Thr His Gly Leu Val Phe Gly Ile Lys Glu
        195                 200                 205
```

```
Leu Lys Leu Asn Arg Ala Arg Arg Trp Phe Thr Arg Ala Ala Ile
    210                 215                 220

Glu Leu Ser Ser Lys Arg Val Ala Gly Phe Asn Tyr Ile Glu Arg Phe
225                 230                 235                 240

Trp Phe Met Ser Gly Asp Ser Ile Gly Gln Ile Thr Val Ala Val Leu
                245                 250                 255

Leu Gly Cys Leu Leu Phe Gly Val Pro Ser Leu Gly Val Val Asp Pro
            260                 265                 270

Ser Val Leu Thr Ala Ser Ile Leu Ala Val Leu Tyr Met Met Gly Pro
            275                 280                 285

Leu Thr Met Leu Ile Asn Val Leu Pro Val Val Ala Glu Gly Lys Thr
290                 295                 300

Ala Leu Ala Arg Leu Ala Glu Phe Gly Phe Leu Ile Asp Asp Thr Gln
305                 310                 315                 320

Ala Ser His Glu Glu Pro Arg Pro Ala Gly Asn Val Glu Thr Leu Ser
                325                 330                 335

Ala Lys Ser Trp Lys Val Ile Glu Leu Lys Asp Val Thr Met Asn Tyr
            340                 345                 350

Arg Asp Asn Glu Ala Ser Val Asp Phe Val Leu Gly Pro Ile Asp Met
            355                 360                 365

Thr Ile His Ala Gly Glu Leu Val Tyr Val Ile Gly Gly Asn Gly Ser
    370                 375                 380

Gly Lys Ser Thr Leu Gly Lys Val Leu Ser Gly Leu Tyr Ala Pro Thr
385                 390                 395                 400

Gly Gly Thr Ile Ser Leu Asp Gly Lys Val Val Asp Asp Ala Ala Arg
                405                 410                 415

Glu Arg Tyr Arg Asn Leu Phe Ser Ala Val Phe Thr Asp Phe His Leu
            420                 425                 430

Phe Asn Arg Ile Ile Gly Pro Asp Arg Gly Asn Glu Ser Ile Glu Leu
            435                 440                 445

Ala Arg Lys Tyr Leu Ala Thr Leu Lys Leu Ala Asp Lys Ile Glu Ile
    450                 455                 460

Ser Gly Arg Thr Tyr Ser Thr Thr Arg Ala Leu Ser Thr Gly Gln Arg
465                 470                 475                 480

Lys Arg Leu Ala Leu Leu Cys Ala Tyr Ile Glu Asp Arg Pro Ile Tyr
                485                 490                 495

Ile Leu Asp Glu Trp Ala Ala Asp Gln Asp Pro Val Phe Lys Arg Phe
            500                 505                 510

Ser Tyr Glu Val Leu Val Pro Asp Leu Lys Ser Arg Gly Lys Cys Val
            515                 520                 525

Val Ile Ile Thr His Asp Asp Gln Tyr Phe Lys Leu Ala Asp Arg Val
    530                 535                 540

Ile Arg Leu Asp Ser Gly Arg Ile Phe Ser Asp Thr Ala Met Cys Ala
545                 550                 555                 560

Val Arg Ala Glu Ala Ala Gly
                565

<210> SEQ ID NO 9
<211> LENGTH: 160
<212> TYPE: PRT
<213> ORGANISM: Burkholderia contaminans
<220> FEATURE:
<221> NAME/KEY: MISC_FEATURE
<222> LOCATION: (1)..(160)
<223> OTHER INFORMATION: hypothetical protein
```

<400> SEQUENCE: 9

Met Gln Leu Thr Thr Val Asp Leu Glu Ala Ala Phe Val Lys Ala Ala
1               5                   10                  15

Leu Asp Ala Leu His Arg Asp Cys Lys Leu Gly Asp Ala Ile Ser Leu
            20                  25                  30

Ala Tyr Gly Lys Cys Glu Ser Thr Ala Gly Val Ile Asp Leu Ile Phe
        35                  40                  45

Pro Leu Ile Thr Lys Lys Leu Arg Ile Asp Tyr Ile Leu Met Tyr Ser
    50                  55                  60

Ile Glu Ser Asn Pro Arg Thr Leu Leu Gln Phe Leu Arg Gln Ile Glu
65                  70                  75                  80

Ser Gly Leu Ala Arg Ser Glu Asp Trp Thr Ala Ala Ser Val Glu Ala
                85                  90                  95

Ala Leu Arg Ser Val Ala Asp Ser Pro Asp Gly Val Gly Trp Glu Arg
            100                 105                 110

Ala Gln Arg Leu Leu Lys Cys Cys Ile Leu Phe Ser Asp Ser Pro Leu
        115                 120                 125

Gly Ile Val Glu Ser Ile Thr Phe Leu Gly Lys His Glu Thr Ser Ser
    130                 135                 140

Arg Leu Arg Ser Ala Ala Ser Asn Val Glu Leu Ser His Leu Ile Asn
145                 150                 155                 160

<210> SEQ ID NO 10
<211> LENGTH: 218
<212> TYPE: PRT
<213> ORGANISM: Burkholderia contaminans
<220> FEATURE:
<221> NAME/KEY: MISC_FEATURE
<222> LOCATION: (1)..(218)
<223> OTHER INFORMATION: putative glycosyl transferase

<400> SEQUENCE: 10

Met Lys Ser Thr Pro Thr Ile Asp Asn Thr Phe Ala Arg Lys Val Cys
1               5                   10                  15

Ile Asn Leu Asp Arg Arg Pro Asp Arg Trp Glu Ala Met Gln Arg Lys
            20                  25                  30

Phe Ala Glu Gln Asn Ile Leu Thr Val Glu Arg Leu Pro Ala Val Asp
        35                  40                  45

Ala Arg Leu Val Ser Val Pro Glu Ser Leu Ser His Met Arg Ala Gln
    50                  55                  60

Asp Tyr Gly Cys Thr Met Ser His Leu Ala Ala Val Lys Gln Ala Lys
65                  70                  75                  80

Ala Ala Gly Ala Arg Glu Val Leu Ile Phe Glu Asp Asp Ala Phe Phe
                85                  90                  95

Asp Ala Asp Phe Ala Ala Arg Phe Pro Glu Phe Ile Ala Gln Val Pro
            100                 105                 110

Asp Asp Trp His Met Leu Phe Leu Gly Ala Tyr His Phe Thr Pro Pro
        115                 120                 125

Ile Pro Val Ala Pro Asn Ile Val Lys Ala Val Glu Thr Leu Thr Ala
    130                 135                 140

His Ala Tyr Val Val Arg Asn Ser Leu Tyr Asp Ala Phe Ile Ala Ile
145                 150                 155                 160

Asn Glu Asn Pro Pro Ala Ile Asn Asp Arg Asn Asn Leu Val Leu Gln
                165                 170                 175

Gln Thr Phe Asn Cys Tyr Cys Phe Glu Pro Asn Leu Val Gly Gln Glu
            180                 185                 190

```
Ser Gly Tyr Ser Asp Ile Met Asp Glu Val Met Pro Glu Lys Pro Leu
        195                 200                 205

Thr Tyr Ser Met Pro Ile Pro Asp Gly Trp
        210                 215

<210> SEQ ID NO 11
<211> LENGTH: 3164
<212> TYPE: PRT
<213> ORGANISM: Burkholderia contaminans
<220> FEATURE:
<221> NAME/KEY: MISC_FEATURE
<222> LOCATION: (1)..(3164)
<223> OTHER INFORMATION: putative nonribosomal peptide synthetase

<400> SEQUENCE: 11

Met Gln Asp Asn Asn Val Leu Val Thr Asp His Arg Tyr Ala Ala Thr
1               5                   10                  15

Ala Arg Phe Trp Arg Glu Ser Leu Ser Arg Val Ala Gly Val Tyr Gly
            20                  25                  30

Ile Ala Ala Tyr Ala Pro Ser Gln Gln Pro Gly Arg Pro Leu Thr Arg
        35                  40                  45

Ser Val Arg Leu Thr Pro Ala Ser Leu Asp Leu Arg Arg Ile Gly
    50                  55                  60

Asp Gly Glu Leu Ala Glu Phe Ala Val Ala Ala Gly Ile Ala Phe
65                  70                  75                  80

Leu Leu Trp Lys Tyr Phe Arg Ile Pro Val Thr Val Leu Gly Thr Pro
                85                  90                  95

Gly Leu Ala Gly His Pro Ser Ala Arg Ala Ala Ile Val Pro Leu Ile
            100                 105                 110

Ile Glu Val Arg Pro Asp Glu Arg Ile Glu Asp Tyr Leu Ser Arg Val
        115                 120                 125

Ala Gly Ile Val Glu Asp Ser Tyr Ala Glu Pro Arg Phe Pro Leu Glu
    130                 135                 140

Thr Leu Val Arg Asn Glu Lys Asp Met Ala Leu Ala Gln Leu Thr Lys
145                 150                 155                 160

Val Ala Leu Ala Asp Asp Arg Val His His Ala Pro Thr Gly Arg Asp
                165                 170                 175

Asp Asp Leu Gln Leu His Leu Arg Leu Ala Arg Gly Glu Ile Glu Leu
            180                 185                 190

Arg Tyr Ser Gly Ala Ile Glu Pro Phe Ile Ile Asp Gly Phe Ala Gly
        195                 200                 205

Ser Leu Ala Ala Val Leu Glu Ala Phe Glu His Leu Asp Gly Ala Val
    210                 215                 220

Gly Asp Ile Glu Ala Ala Pro Pro Glu Gln Gly Pro Leu Leu Ala Ala
225                 230                 235                 240

Phe Asn Glu Thr Ala Thr Ala Gly Pro Ser His Pro Thr Val Ala
                245                 250                 255

Met Phe Glu Ala Gln Val Ala Arg Thr Pro Thr Ala Pro Ala Leu Val
            260                 265                 270

Thr Asp Ser Ser Leu Met Thr Tyr Ala Asp Leu Asn Ala Arg Ala Asn
        275                 280                 285

Ser Leu Ala His His Leu Arg Glu His His Gly Val Gly Pro Glu Ser
    290                 295                 300

Leu Val Gly Ile Met Leu Asp Arg Ser Glu Trp Met Ile Val Ala Ile
305                 310                 315                 320
```

```
Leu Gly Ile Leu Lys Ala Gly Ala Ala Phe Val Pro Leu Asp Pro Ala
            325                 330                 335

Tyr Pro Ala Glu Arg Ile Asn His Ile Leu Gly Asp Thr Gly Leu Ser
        340                 345                 350

Leu Leu Val Thr Gln Ser Ser Gln Leu Ala Gln Trp Tyr Glu Phe Ser
        355                 360                 365

Gly Val Thr Leu Leu Asp Gln Glu Leu Pro Gly Trp Gln Pro Leu
370                 375                 380

Pro Asp Asn Pro Pro His Arg Ala Glu Pro Ala His Leu Ala Tyr Val
385                 390                 395                 400

Leu Tyr Thr Ser Gly Ser Thr Gly Lys Pro Lys Gly Cys Leu Leu Glu
            405                 410                 415

His Arg Asn Leu Ala His Tyr Ile Ala Trp Ala Ala Gly Tyr Tyr Phe
            420                 425                 430

Pro Glu Ser Thr Thr Gly Ser Phe Gly Leu Tyr Ser Ser Leu Cys Phe
            435                 440                 445

Asp Phe Thr Leu Thr Asn Ile Phe Cys Pro Leu Val Arg Gly Lys Thr
            450                 455                 460

Leu Arg Ile Tyr Pro Gln Ser Glu Ser Ile Asp Thr Ile Leu Ala Arg
465                 470                 475                 480

Met Phe Gln Pro Gly Ser Gly Val Asp Thr Leu Lys Leu Thr Pro Thr
                485                 490                 495

His Ile His Leu Leu Glu Tyr Met Asn Leu Ala Arg Ser Gly Val Arg
            500                 505                 510

Lys Val Ile Val Gly Gly Glu Leu Thr Pro Gln His Ile Ala Thr
        515                 520                 525

Leu Arg Lys Ile Asp Pro Ala Ile Glu Ile Tyr Asn Glu Tyr Gly Pro
530                 535                 540

Thr Glu Ala Thr Val Gly Cys Ile Val Glu Arg Val Glu Asp Ala Pro
545                 550                 555                 560

Pro Thr Val Leu Ile Gly Arg Pro Ile Ala Asp Thr Arg Val Tyr Met
                565                 570                 575

Leu Asp Asp Ala Leu Arg Pro Val Pro Leu Gly Val Pro Gly Glu Ile
            580                 585                 590

Cys Leu Ala Gly Ala Gly Leu Ala Arg Gly Tyr His Gln Arg Pro Asp
            595                 600                 605

Val Thr Ala Ala Lys Phe Val Glu His Pro Phe Pro Gly Glu Ala Arg
            610                 615                 620

Ile Tyr Arg Thr Gly Asp Ile Gly Arg Trp Leu Pro Asp Gly Arg Ile
625                 630                 635                 640

Gln Cys Tyr Gly Arg Val Asp His Gln Val Lys Ile Arg Gly His Arg
                645                 650                 655

Val Glu Leu Gly Glu Ile Glu Ala Ala Ile Ala Ala His Glu Asp Val
            660                 665                 670

Val Gly Ala Ala Val Met Leu Arg Glu Ser Ala His Gly Val Arg Lys
            675                 680                 685

Leu Ala Ala Tyr Val Lys Gly Ala Ala Ser Leu Ser Val Pro Asn Leu
        690                 695                 700

Arg Ala Tyr Leu Ala Gly Lys Leu Pro Asp Tyr Met Val Pro Ser Asp
705                 710                 715                 720

Ile Ile Pro Ile Ala Glu Phe Pro Leu Asn Ala Asn Gly Lys Leu Asp
                725                 730                 735

Arg Pro Ala Leu Leu Ala Leu Glu Pro Ala Ala Ala Pro Glu Glu Ala
```

-continued

```
            740                 745                 750
Pro Leu Asp Ala Thr Pro Ile Gln Arg Glu Leu Val Arg Ile Trp Arg
                755                 760                 765
Asp Val Leu Asp Asn Pro Ala Val Asp Leu Ala Gly Arg Phe Phe Asp
                770                 775                 780
Tyr Gly Gly Asp Ser Leu Gln Ala Met Gln Leu Val Ser Arg Ile Trp
785                 790                 795                 800
Ser Ser Phe Ser Val Glu Ile Gly Ile Asp Ala Ile Phe Glu Leu Gln
                805                 810                 815
Thr Ile Ser Ala Val Ser Asp Leu Ile Glu Ala Ser Ser Pro His Pro
                820                 825                 830
Gly Ser Thr Ala Gly Ala Ile Pro Pro Arg Ser Arg Ala Asn Asp Leu
                835                 840                 845
Pro Leu Ser Phe Pro Gln Gln Arg Leu Trp Phe Leu Ala Gln Leu Glu
                850                 855                 860
Gly Pro Ser Ala Thr Tyr Asn Ile Ser Ser Ala Leu Arg Phe Glu Gly
865                 870                 875                 880
Glu Leu Asp Val Ala Arg Leu Arg Phe Ala Val Ser Glu Ile Ser Arg
                885                 890                 895
Arg His Glu Ile Leu Arg Thr Thr Phe Pro Ala Val Asp Gly Arg Gly
                900                 905                 910
Val Gln Arg Ile Ala Pro Pro Ala Pro Val Ala Leu Asp Val Val Asp
                915                 920                 925
Val Ala Ser Glu Ser Asp Thr Leu Ala Leu Leu Ala Glu Glu Ala Asp
                930                 935                 940
Arg Pro Phe Asp Leu Ala Ala Gly Pro Leu Tyr Arg Val Val Leu Tyr
945                 950                 955                 960
Arg Val His Glu Arg Leu His Val Phe Gly Ile Val Met His His Ile
                965                 970                 975
Val Ser Asp Ala Trp Ser Ser Gly Ile Leu Ile Gly Glu Leu Ala Ala
                980                 985                 990
Leu Tyr Ala Gly Glu Ser Leu Pro Glu Leu Ala Val Gln Tyr Ala Asp
                995                 1000                1005
Tyr Ala Val Trp Gln His Glu Arg Leu Ala Ser Ala Asp Thr His
                1010                1015                1020
Arg Glu Leu Ala Leu Leu Ser Ala Ala Leu Ala Asp Ala Pro Asp
                1025                1030                1035
Leu Ile Glu Leu Pro Thr Asp Arg Pro Arg Pro Ala Val Gln Gln
                1040                1045                1050
Phe Arg Gly Ala Val Leu Pro Phe Gln Leu Ser Ala Glu Arg Ala
                1055                1060                1065
Asp Gly Leu Arg Ala Ile Ala Arg Ala Ser Gly Thr Ser Thr Phe
                1070                1075                1080
Met Val Val Leu Ala Ala Tyr Ala Leu Leu Leu Ser Arg Tyr Ser
                1085                1090                1095
Asn Gln Gln Asp Leu Val Ile Gly Ser Pro Ile Ala Asn Arg Arg
                1100                1105                1110
Ser Ser Met Thr Glu Pro Leu Ile Gly Phe Phe Ala Asn Met Leu
                1115                1120                1125
Ala Leu Arg Val Asp Leu Ser Gly Asn Pro Thr Phe Gly Asp Leu
                1130                1135                1140
Leu Ala Arg Val Lys Arg Val Ala Leu Asp Gly Tyr Ser Arg Gln
                1145                1150                1155
```

-continued

```
Glu Ile Pro Phe Glu Gln Val Val Asp Ser Leu Glu Leu Glu Arg
    1160            1165                1170

Asn Leu Gly Arg Thr Pro Val Phe Gln Val Val Phe Ala Tyr Glu
    1175            1180                1185

Lys Ala Gln Pro Arg Ala Val Ser Phe Pro Gly Leu Val Ala Thr
    1190            1195                1200

Pro Val Ala Val Glu Thr His Thr Ala Lys Phe Asp Leu Thr Leu
    1205            1210                1215

His Val Gln Asp Ala Asp Asp Gly Leu Ala Gly Ser Leu Glu Tyr
    1220            1225                1230

Asn Leu Asp Leu Phe Asp Ala Ala Thr Ile Asp Arg Met Ala Glu
    1235            1240                1245

His Phe Arg Thr Leu Val Asp Ala Val Ile Ala Asp Pro Asp Arg
    1250            1255                1260

Pro Leu Gly Ala Leu Ser Leu Ser Asn Asp Ala Glu Arg Asn Leu
    1265            1270                1275

Leu Thr Val Glu Trp Asn Arg Thr Asp Thr Asp Phe Gly Glu Asp
    1280            1285                1290

Ala Ala Gln Pro Leu His Arg Leu Phe Glu Gln Gln Val Glu Arg
    1295            1300                1305

Thr Pro Asp Ala Val Ala Ile Val Phe Asp Asp Thr Ala Leu Thr
    1310            1315                1320

Tyr Ala Glu Leu Asn Leu Arg Ala Asn Arg Leu Ala His His Leu
    1325            1330                1335

Val Ala Leu Gly Val Gly Pro Asp Ser Leu Val Gly Val Ala Met
    1340            1345                1350

Glu Arg Ser Leu Asp Met Ser Val Ala Leu Leu Ala Ile Leu Lys
    1355            1360                1365

Ala Gly Gly Ala Tyr Val Pro Val Asp Pro Asp Tyr Pro Ala Glu
    1370            1375                1380

Arg Val Arg Phe Met Ile Asp His Ala Gln Leu Arg Trp Leu Leu
    1385            1390                1395

Thr Gln Gln His Leu His Asp Ala Leu Pro Asp Thr Asp Ala His
    1400            1405                1410

Val Ile Val Val Asp Arg Asp Ser Leu Asp Leu Asp Ala Ala Ala
    1415            1420                1425

Thr Ser Asn Pro Ala Pro Ala Leu Asn Gly Asp Asn Leu Ala Tyr
    1430            1435                1440

Met Ile Tyr Thr Ser Gly Ser Thr Gly Arg Pro Lys Gly Ala Leu
    1445            1450                1455

Asn Thr His Arg Ala Ile Thr Asn Arg Ile Leu Trp Met Gln His
    1460            1465                1470

Ala Tyr Ala Leu Asp Ala Asp Ala Val Leu Gln Lys Thr Pro
    1475            1480                1485

Phe Ser Phe Asp Val Ser Val Trp Glu Leu Phe Trp Pro Leu Val
    1490            1495                1500

Thr Gly Ala Arg Leu Val Phe Ala Arg Pro Gly Gly Gln Arg Glu
    1505            1510                1515

Thr Asp Tyr Leu Val Glu Leu Ile Glu Arg Glu Arg Ile Thr Thr
    1520            1525                1530

Ile His Phe Val Pro Ser Met Leu Arg Ala Phe Leu Asp His Pro
    1535            1540                1545
```

-continued

Asp Leu Asp Ala His Cys Ala Ser Leu Arg Arg Val Val Cys Ser
1550                1555                1560

Gly Glu Ala Leu Pro His Asp Leu Gln Gln Arg Cys Leu Glu Arg
1565                1570                1575

Leu Asp Val Lys Leu Tyr Asn Leu Tyr Gly Pro Thr Glu Ala Ala
1580                1585                1590

Val Asp Val Thr Ala Trp Glu Cys Arg Arg Asp Asp Pro His Arg
1595                1600                1605

Ile Val Pro Ile Gly Arg Pro Ile Ala Asn Thr Arg Leu Tyr Ile
1610                1615                1620

Val Asp Ala Gln Met Gln Pro Thr Pro Ile Gly Val Ala Gly Glu
1625                1630                1635

Leu Leu Ile Gly Gly Thr Pro Val Gly Arg Gly Tyr His Gly Glu
1640                1645                1650

Pro Glu Leu Ser Ala Glu Lys Phe Ile Ala Asp Pro Phe Ser Ala
1655                1660                1665

Asp Pro Leu Ala Arg Leu Tyr Arg Thr Gly Asp Leu Ala Arg Tyr
1670                1675                1680

Arg Pro Asp Gly Asn Ile Glu Phe Leu Gly Arg Ile Asp His Gln
1685                1690                1695

Ile Lys Leu Arg Gly Leu Arg Ile Glu Pro Gly Glu Ile Glu Ala
1700                1705                1710

Ala Leu Arg Ala His Pro Ser Val Asp Asp Cys Val Val Ile Ala
1715                1720                1725

Lys Thr Glu Gly Ala Arg Thr Phe Leu Ile Ala Tyr Val Ala Thr
1730                1735                1740

Ala Ala Pro Asp Ile Ala Asp Leu Arg Gly Tyr Leu Gly Gly Lys
1745                1750                1755

Leu Ala Asp Tyr Met Val Pro Ser Gln Phe Phe Ala Leu Glu Ser
1760                1765                1770

Leu Pro Met Leu Pro Asn Gly Lys Ile Asn Arg Lys Ala Leu Pro
1775                1780                1785

Leu Pro Ala Asp Arg Gly Asp Ala Ala Gln Pro His Ala Pro Ala
1790                1795                1800

Val Thr Pro Arg Glu Ile Leu Leu Ala Ser Ile Cys Ile Asp Val
1805                1810                1815

Leu Gln Leu Pro Ser Val Gly Ile His Asp Asn Phe Phe Glu Leu
1820                1825                1830

Gly Gly Asp Ser Ile Leu Ser Ile Gln Val Ile Ala Arg Ala Asn
1835                1840                1845

Gln Ala Gly Leu Arg Val Thr Ala Lys Gln Leu Phe Gln Tyr Gln
1850                1855                1860

Thr Ile Ala Gln Leu Ala Ala Ala Pro Glu Glu Arg Ala Ala Cys
1865                1870                1875

Ala Pro Thr Leu Ser Pro Leu Gly Asp Ala Pro Leu Thr Pro Val
1880                1885                1890

Gln His Trp Phe Phe Glu Gln Glu Ile Asp Ala Pro Ser His Tyr
1895                1900                1905

Asn Gln Thr Val Leu Ile Gln Val Pro Ala Asp Ile Asp Ala Ser
1910                1915                1920

Arg Leu Ala Asp Ala Phe Arg Gln Val Tyr Glu His His Asp Ala
1925                1930                1935

Leu Arg Leu Arg Phe Ser His Asp Ala Gly Arg Trp Thr Gln Gln

```
                    1940                1945                1950
Val Val Ala Gly Gly Glu Met Pro Ala Leu Phe Ala Lys Gln Val
        1955                1960                1965
Ile Ala Asp Asp Ala Gly Glu Arg Leu Ala Ala Met Arg Ala Ala
        1970                1975                1980
Ala Ala Asp Ala Glu Arg Gly Ile Asp Ile Thr His Gly Pro Leu
        1985                1990                1995
Leu Ala Ala Arg Leu Phe Cys Leu Ala Asp Glu Pro Leu Ala Arg
        2000                2005                2010
Leu Phe Val Ser Ile His His Leu Ala Val Asp Gly Val Ser Trp
        2015                2020                2025
Arg Val Leu Leu Glu Asp Leu His Ala Ala Tyr His Gly Gln Pro
        2030                2035                2040
Leu Pro Gly Lys Thr Thr Ser Phe Arg Glu Trp Ala Leu His Leu
        2045                2050                2055
Gln Gln Leu Ala Arg Ser Pro Ala Ile Gly Asp Glu Ala Arg Leu
        2060                2065                2070
Trp Gln Ala Leu Leu Ala Gln Pro Val Glu Pro Met Pro Val Asp
        2075                2080                2085
Tyr Pro Gly Thr Gly Ala Ala Asn Asn Ala Val Asp Asp Ala Ser
        2090                2095                2100
Ser Val Ser Phe Glu Leu Gly Glu Ala Asp Thr Thr Ala Leu Leu
        2105                2110                2115
Arg Arg Leu Pro Arg Ala Tyr Asp Thr Arg Ile Asn Asp Val Leu
        2120                2125                2130
Leu Val Ala Leu Ala Gln Ala Cys Ser Met Val Thr Gly Asn Thr
        2135                2140                2145
Arg Thr Arg Ile Asp Leu Glu Ser His Gly Arg His Val Ser Asp
        2150                2155                2160
Ala Pro Leu Asp Leu Thr Arg Thr Val Gly Trp Phe Thr Ser Ile
        2165                2170                2175
Tyr Pro Val Val Leu Asp Ala Asp Ala Met His Ala Pro Glu Gln
        2180                2185                2190
Ala Leu Arg Ala Ala Arg Gln Gln Leu Arg Arg Ile Pro Ala Asp
        2195                2200                2205
Gly Leu Gly Tyr Ser Leu Leu Arg Tyr Gln Ser Pro Asp Ala Ala
        2210                2215                2220
Val Arg Asp Ser Leu Ala Ala Leu Pro Lys Ala Asp Ile Leu Phe
        2225                2230                2235
Asn Tyr His Gly Gln Leu Asp Thr Val Leu Arg Gln Ser Asp Gly
        2240                2245                2250
Trp Arg Pro Ala Ala Glu Asp Leu Gly Ser Leu Arg Ala Gly Arg
        2255                2260                2265
Ser Gln Arg Thr His Ala Phe Glu Ile Val Ala Ala Val Ala Asp
        2270                2275                2280
Gly Lys Leu Gln Val Asp Trp Arg Tyr Gly Glu Arg Leu His Arg
        2285                2290                2295
Arg Gln Thr Val Glu Asn Leu Ala Ala His Phe Arg Asp Arg Leu
        2300                2305                2310
Leu Asp Phe Ala Ala Ser Val Pro Asp Thr Ala Ala Asp Asp Ile
        2315                2320                2325
Glu Asp Ser Tyr Pro Leu Ser Ser Leu Gln Gln Gly Ile Leu Phe
        2330                2335                2340
```

```
His Ser Leu Tyr Asp Leu Asp Pro Ala Ala Tyr Phe Gln Gln Phe
    2345                2350                2355

Ser Phe Val Val Ser Gly Pro Leu Gln Val Pro Ala Leu Arg Gln
    2360                2365                2370

Ala Trp Ala Asn Ala Leu Ala Arg His Ala Val Leu Arg Thr Ala
    2375                2380                2385

Phe Ala Trp Ala Asp Arg Asp His Pro Val Gln Thr Val Arg His
    2390                2395                2400

Thr Val Asp Leu Pro Trp Thr Phe Leu Asp Trp Arg His Arg Asp
    2405                2410                2415

Ala Ser Arg Arg Ala Gln Asp Phe Asp Ala Phe Leu Ala Asp Asp
    2420                2425                2430

Arg Arg Arg Gly Phe Asp Leu Gln Arg Ala Pro Leu Phe Arg Cys
    2435                2440                2445

Thr Leu Ile Gln Glu Thr Asp Thr Arg His Arg Phe Cys Trp Ser
    2450                2455                2460

Ala His His Ile Ile Leu Asp Gly Trp Ser Thr Ala Thr Leu Met
    2465                2470                2475

Lys Glu Val Phe Asp Asp Tyr Leu Ser Leu Ala Arg Thr Gly Met
    2480                2485                2490

Pro Ala Val Ala Ala Ser Ala Pro Gly Tyr Arg Ala Tyr Ile Asp
    2495                2500                2505

Trp Leu Ala Arg His Pro Arg Ser Ala Asp Glu Thr Trp Trp Arg
    2510                2515                2520

Ala Glu Leu Ala Gly Phe Lys Ala Ala Thr Pro Val Ala Ala Ser
    2525                2530                2535

Pro Ala Arg Gln Ala Thr Gly Asp Ala Pro Arg Gln Asp Lys Arg
    2540                2545                2550

Arg Thr Gln Gln Phe Leu Leu Asp Glu Ala Leu Ala Ala Arg Leu
    2555                2560                2565

Gln Thr Leu Thr Arg Thr His Arg Val Thr Leu Asn Val Leu Ile
    2570                2575                2580

Arg Ala Val Trp Ala Leu Val Leu Arg Arg His Ala Gly Thr Asp
    2585                2590                2595

Asp Val Val Phe Gly Val Thr Val Ser Gly Arg Pro Pro Met Leu
    2600                2605                2610

Asp Gly Val Glu Ser Ile Val Gly Leu Phe Ile Asn Thr Leu Pro
    2615                2620                2625

Leu Arg Leu Arg Ile Ala Pro Glu Arg Pro Phe Ile Glu Trp Leu
    2630                2635                2640

Ala Glu Val His Ala Ala Gln Thr Ala Met Glu Pro His Ser Tyr
    2645                2650                2655

Ser Ser Leu Val Asp Ile Gln Ser Trp Ser Glu Leu Pro Ala Gly
    2660                2665                2670

Asp Ser Leu Phe Asp Ser Leu Leu Val Phe Glu Asn Phe Pro Val
    2675                2680                2685

Ala Ala Ala Pro Asp Leu Gly Pro Asp Asp Ile Glu Ile Leu Asp
    2690                2695                2700

Thr Arg Ala Phe Ala Glu Ser Asn Tyr Pro Leu Thr Leu Thr Val
    2705                2710                2715

His Pro Asn Glu Arg Ile Gly Phe His Ile Ser His Asp Ala His
    2720                2725                2730
```

```
Arg Ile Ala Pro Glu Val Val Arg Gln Met Leu Asp Thr Leu Arg
    2735                2740                2745

Thr Leu Leu Glu Arg Phe Ala Glu Asn Pro Gly Gln Leu Thr Gly
    2750                2755                2760

Gln Leu Ala Asp Pro Pro Ala Ala Asp Gly Arg Pro Ser Ala Pro
    2765                2770                2775

Arg Ser Gly Ala Gly Pro Ala Ile Glu Ala Ala Gly Ala Ala
    2780                2785                2790

Ala Ala Ala Arg Ala Val Ala His Ala Ala Asp Glu Ser Thr Leu
    2795                2800                2805

Leu Glu Ile Trp Arg Arg Ile Phe Lys Arg Asp Ile Ala Val
    2810                2815                2820

Ser Asp Asn Tyr Phe Asp Leu Gly Gly His Ser Ile Ile Ala Ile
    2825                2830                2835

Gln Leu Met Ala His Val Glu Lys Ala Phe Asp Arg Arg Leu Pro
    2840                2845                2850

Ile Ser Cys Leu Phe Glu Asn Pro Thr Ile Glu Lys Leu Ala Ala
    2855                2860                2865

Ala Leu Ala Ala Lys Glu Pro Ser Ala Pro Ala Gly Gly Leu Val
    2870                2875                2880

Pro Ile Arg Asp Gly Gly Pro Ala Ala Pro Leu Phe Leu Leu Pro
    2885                2890                2895

Gly Ala Gly Gly Asn Val Val Tyr Phe Arg Pro Leu Ala Asn His
    2900                2905                2910

Leu Ser Gly Ala His Ala Ile His Gly Leu Glu Ala Leu Gly Leu
    2915                2920                2925

Asp Gly Ala Cys Glu Pro Leu Thr Arg Val Glu Asp Ile Ala Ala
    2930                2935                2940

Arg His Ile Glu Arg Ile Trp Pro Leu Val Gly Ala Gly Pro Tyr
    2945                2950                2955

Tyr Leu Ala Gly His Ser Phe Gly Ala His Val Ala Leu Glu Met
    2960                2965                2970

Ser Arg Gln Leu Val Ala Lys Gly Ala Asp Val Lys Leu Leu Ala
    2975                2980                2985

Ile Phe Asp Ala Ser Ala Pro Ile Asp Ser Ser Ala Ala Thr Tyr
    2990                2995                3000

Trp Gln Asp Trp Asp Asp Thr Glu Trp Leu Val Ala Ile Ala His
    3005                3010                3015

Glu Ile Gly Thr Phe Leu Gly Thr Asp Leu Gln Val Thr Arg Ala
    3020                3025                3030

Asp Leu Val His Leu Asp Pro Asp Gly Gln Ala Gly Leu Ile Leu
    3035                3040                3045

Glu Arg Ile Gly Asp Arg Gly Ser Trp Phe Ala Asp Ala Gly Ser
    3050                3055                3060

Asp Arg Leu Arg Ala Tyr Leu Arg Val Tyr Gln Ala Asn Phe Lys
    3065                3070                3075

Ser His Tyr Ala Pro His Ala Thr Pro Leu Pro Val Pro Ile Ala
    3080                3085                3090

Leu Phe Arg Ser Thr Glu Arg Asp Pro Gly Asp Tyr Ala Pro Ser
    3095                3100                3105

Ser Glu Ile Ala Gln Leu Arg Leu Asp Ala Thr Trp Gly Trp Ser
    3110                3115                3120

Arg Phe Ser Ala His Pro Val Ala Val Thr Asp Val Pro Gly Asp
```

```
                3125                3130                3135

His Leu Thr Met Leu Leu Asp Pro His Ala Gly Val Leu Ala Ala
        3140                3145                3150

His Val Asn Ser Phe Leu Glu Lys Thr Pro Ser
        3155                3160

<210> SEQ ID NO 12
<211> LENGTH: 3021
<212> TYPE: PRT
<213> ORGANISM: Burkholderia contaminans
<220> FEATURE:
<221> NAME/KEY: MISC_FEATURE
<222> LOCATION: (1)..(3021)
<223> OTHER INFORMATION: putative nonribosomal peptide synthetase

<400> SEQUENCE: 12

Met Gln Glu Gly Met Leu Phe His Ala Val His Glu Pro Gly Ser Arg
1               5                   10                  15

Ser Ser Phe Asn Gln Leu Ser Cys Arg Ile Thr Gly Ser Leu Asp Pro
                20                  25                  30

Ala Leu Phe His Ala Ala Trp Gln Gln Leu Ile Asp Arg His Pro Val
            35                  40                  45

Met Arg Thr Ser Phe His Trp Glu Glu Phe Asp Lys Pro Met Gln Val
    50                  55                  60

Val His Ala Arg Ala Thr Leu Pro Trp Val Gln Asp Asp Trp Leu Asp
65                  70                  75                  80

Leu Pro Glu His Glu Gln Arg Ser Arg Trp Arg Ala His Leu Asp Asn
                85                  90                  95

Asp Leu Ala Glu Gly Phe Ala Leu Asp Arg Ala Pro Leu Val Arg Cys
            100                 105                 110

Arg Leu Val Arg Val Ala Ala Asp Ala Tyr Leu Phe Ser Trp Ser His
        115                 120                 125

His His Ile Leu Ala Asp Gly Trp Cys Leu Ser Leu Val Ile Glu Glu
    130                 135                 140

Ile Phe Glu Val Tyr Gly Ala Leu Ala Arg Gly Val Ser Pro Ala Leu
145                 150                 155                 160

Pro Pro Val Arg Pro Tyr Arg Asp Tyr Ile Gln Trp Leu Gln Gln His
                165                 170                 175

Glu Pro Gln Ala Ala Gln Gln Tyr Trp Thr Arg Tyr Leu Glu Gly Phe
            180                 185                 190

Arg Thr Pro Thr Pro Leu Pro Thr Ala Ala Arg Ala Gly Ala Asp Glu
        195                 200                 205

Arg Phe Gly Gln Gly Leu Ala Gln Val Gln Ala Asp Leu Ser Ala Asp
    210                 215                 220

Leu Ser Ala Arg Leu Arg Gln Phe Ala Ala Arg His His Val Thr Leu
225                 230                 235                 240

Asn Thr Leu Ala Gln Ala Ala Trp Ala Leu Val Leu Ser Arg Tyr Ser
                245                 250                 255

Gly Glu Thr Asp Val Val Phe Gly Ala Val Val Ser Gly Arg Gly Ala
            260                 265                 270

Asn Leu Pro Gly Ile Glu Thr Met Leu Gly Leu Phe Ile Asn Thr Val
        275                 280                 285

Pro Val Arg Val Arg Val Asp Pro Arg Gln Pro Leu Val Pro Trp Leu
    290                 295                 300

Lys Met Ile Gln Ala Arg Val Ala Ala Arg Ala Pro Phe Glu His Thr
305                 310                 315                 320
```

```
Pro Leu Pro Asp Ile Gln Arg Cys Ser Asp Val Pro Thr Ala Pro
            325                 330                 335

Leu Phe Glu Ser Asn Ile Thr Phe Met Asn Tyr Pro Leu Asp Ala Ser
            340                 345                 350

Leu Thr His Gly Ala His Gly Leu Ala Val Asp Glu Val Gln Leu Tyr
            355                 360                 365

Asn Arg Ala Asp Ile Pro Leu Glu Phe Val Val Thr Ala Arg Asp Asp
        370                 375                 380

Trp Lys Met Glu Leu Ser Phe Asp Pro Arg Arg Phe Asp Glu Asp Thr
385                 390                 395                 400

Met Gln Arg Met Leu Gly His Val Ala Ala Thr Leu Asp Ala Phe Ala
                405                 410                 415

Ala Asp Pro Asn Arg Leu Leu Gly Arg Val Pro Ile Leu Pro Asp Ala
                420                 425                 430

Glu Arg Arg Gln Leu Leu Glu Thr Phe Asn Asp Thr Ala Val Pro Phe
            435                 440                 445

Asp Ala Ala Leu Thr Val Val His Arg Leu Glu Gln Ala Ala Ala Asp
        450                 455                 460

His Pro Glu Arg Pro Ala Val Glu Tyr Arg Asp Gly Val Leu Ser Ala
465                 470                 475                 480

Gly Glu Leu Asn Ala Arg Ala Asn Arg Ile Ala His Arg Leu Leu Ala
                485                 490                 495

Ala Ala Asp Leu Gly Pro Asp Ala Leu Val Ala Ile Cys Met His Arg
                500                 505                 510

Ser Ala Gln Leu Met Glu Ala Ile Leu Ala Val Trp Lys Cys Gly Ala
            515                 520                 525

Ala Tyr Ile Pro Val Asp Pro Asn Tyr Pro Val Ala Arg Ile Arg Thr
        530                 535                 540

Ile Leu Glu Asp Ser Gly Ala Ala Leu Val Ile Thr Cys Asp Gly Leu
545                 550                 555                 560

Leu Pro Pro Glu Leu Ala Gly Ile Ala Leu Val Val Ser Leu Asp Ala
                565                 570                 575

Ala Thr Asp Ala Val Asp Ser Asn Pro Gly Arg Pro Val Ser Pro
                580                 585                 590

Asp Ser Leu Ala Tyr Val Ile Tyr Thr Ser Gly Ser Thr Gly Lys Pro
            595                 600                 605

Lys Gly Ala Met Val Glu His Ala Gly Met Leu Asn His Met Leu Ala
            610                 615                 620

Glu Ile Asp Glu Phe Ser Ile Ser Ala Ser Ser Val Ile Ala Gln Thr
625                 630                 635                 640

Ala Pro His Cys Phe Asp Ile Ser Val Trp Gln Phe Phe Thr Ala Pro
                645                 650                 655

Leu Val Gly Gly Lys Thr Val Ile Val Asp Asp Asp Cys Ile Arg Asp
                660                 665                 670

Pro Ala Arg Phe Val Ala Tyr Leu Glu Thr Thr Arg Ile Ser Ile Leu
        675                 680                 685

Glu Leu Val Pro Ser Tyr Leu Ser Ala Val Leu Asp Arg Ala Ser Glu
            690                 695                 700

Arg Pro Ala Leu Met Arg His Leu Arg His Leu Leu Val Thr Gly Glu
705                 710                 715                 720

Met Val Ser Pro Ala Leu Val Lys Gln Trp Phe Asp Val Phe Pro Ala
                725                 730                 735
```

```
Ile Pro Leu Val Asn Ala Tyr Gly Pro Ala Glu Ala Ser Asp Asp Val
            740                 745                 750

Ala Gln His Arg Met Thr Gly Ala Pro Ser Thr Pro Tyr Val Pro Val
    755                 760                 765

Gly Lys Pro Ile Arg Asn Val Arg Leu Tyr Val Val Asp Pro Gln Met
    770                 775                 780

Asn Leu Cys Pro Ile Gly Ile Pro Gly Glu Leu Cys Val Ser Gly Val
785                 790                 795                 800

Ala Val Gly Arg Gly Tyr Leu Asn Asn Glu Ala Ala Thr Gln Asp Ala
            805                 810                 815

Phe Val Glu Asp Pro Phe His Pro Gln Arg Gly Val Arg Leu Tyr Arg
            820                 825                 830

Thr Arg Asp Ile Gly Cys Tyr Leu Pro Asp Gly Thr Ile Val Leu His
            835                 840                 845

Gly Arg Lys Asp His Gln Leu Lys Ile Arg Gly Tyr Arg Ile Glu Leu
            850                 855                 860

Gly Glu Ile Asp Gln Arg Arg Leu Ala Asp His Ser Arg Lys Leu Arg
865                 870                 875                 880

Gln Ala Ala Ala Leu Asp Tyr Arg Asp Glu Ala Gly Arg Ala Ala Leu
            885                 890                 895

Cys Ala Tyr Val Ala Phe Arg Asp Gly Ala Ser Leu Ser Asp Ala Gly
            900                 905                 910

Ile Ala Ala Ala Leu Ser Ala Thr Leu Pro Asp Tyr Met Val Pro Gly
            915                 920                 925

Ile Tyr Val Val Leu Asp Ala Leu Pro Leu Ser Gly Asn Gly Lys Ile
            930                 935                 940

Asp Arg Asn Ala Leu Pro Pro Leu Asp Arg Ala Arg Leu Ala Ala Thr
945                 950                 955                 960

Ala His Ala Pro Thr Pro Pro Arg Thr Pro Thr Glu Thr Leu Leu Cys
            965                 970                 975

Arg Ile Trp Gly Glu Ala Leu Gly Ile Pro Ser Pro Gly Ile His Asp
            980                 985                 990

Asn Leu Phe Ala Leu Gly Gly Asp Ser Ile Leu Ser Met Arg Ile Val
            995                 1000                1005

Ser Leu Ala Ala Lys Ala Gly Leu Lys Leu Thr Thr Arg Leu Ile
            1010                1015                1020

Phe Gln His Pro Thr Val Ala Glu Leu Ala Ala Val Ala Thr Arg
            1025                1030                1035

Gly Thr Val Gly Ala Ala Ala Phe Val Ala Ser Ser Gly Pro Leu
            1040                1045                1050

Pro Leu Thr Pro Ile Gln Lys Arg Phe Phe Ala Gln Gly Lys His
            1055                1060                1065

Asp Pro Asp Gln Tyr Asn Gln Ala Val Leu Leu Asp Val Pro Ala
            1070                1075                1080

Asp Leu Asp Pro Val Leu Leu Arg Gln Ala Leu Arg His Ala Val
            1085                1090                1095

Lys Trp His Asp Ala Leu Arg Leu Arg Phe Arg Glu Gly Glu Ser
            1100                1105                1110

Gly Trp Thr Gln Glu Val Val Asp Asp Pro Glu Ile Pro Val Val
            1115                1120                1125

Val Ser Asp Ile Ala Arg Asp Gln Leu Ala Gln Tyr Val Ala Gln
            1130                1135                1140

Ser His Ala Ser Leu Asn Leu Ala Asp Gly Pro Val Val Arg Ala
```

```
             1145                1150                1155

Asp Leu Phe Arg Val Asp Glu Gly Arg Ser Leu Arg Leu Leu Leu
            1160                1165            1170

Val Ala His His Leu Val Val Asp Gly Val Ser Trp Gly Ala Leu
            1175                1180            1185

Leu Glu Thr Val Tyr Asp Ala Tyr Thr Arg Leu Arg Asn Gly Lys
            1190                1195            1200

Ala Pro Glu Phe Ala Gly Gly Ser Ala Thr Trp Thr Ala Trp Thr
            1205                1210            1215

Arg Ala Ile Ser Thr Trp Ala Gly Ser Gly Ala Ala Asp Ala Asp
            1220                1225            1230

Leu Ala His Trp Gln Ala Leu Ala Arg Ala Ala Leu Pro Gly Leu
            1235                1240            1245

Pro Leu Asp Arg Asp Ala Pro Ala Asp Ala Asn Thr Val Ser Ser
            1250                1255            1260

Ala Asp Thr Ile Val Val Glu Leu Gly Glu Ala Ala Thr Thr Ala
            1265                1270            1275

Leu Leu Gly Ala Ala Pro Arg Ala Tyr Asp Ala Gln Val Asn Asp
            1280                1285            1290

Val Leu Leu Ala Ala Leu Ala Arg Ala Val Ser Glu Trp Ser Gly
            1295                1300            1305

Cys Ala Asp Val Leu Leu Asp Leu Glu Ala His Gly Arg Glu Glu
            1310                1315            1320

Leu Ile Asp Ala Leu Asp Ile Ser Arg Thr Val Gly Trp Phe Thr
            1325                1330            1335

Ser Val Phe Pro Val Leu Leu Thr Val Asp Ala Gly Ser His Asp
            1340                1345            1350

Pro Ala Ser Leu Val Ala Ser Val Arg Thr Arg Leu Arg Ala Val
            1355                1360            1365

Pro Asn Ala Gly Ile Thr Tyr Gly Leu Leu Leu Asp Arg Leu Asp
            1370                1375            1380

Gly Pro Leu Pro Gln Pro Arg Leu Gln Phe Asn Tyr Leu Gly Gln
            1385                1390            1395

Thr Asp Gln Leu Phe Thr Ala Ala Arg Asp Trp Lys Gln Ala Ala
            1400                1405            1410

Glu Pro Ser Gly Asp Gly Arg Asn Ala Asn Gln Leu Arg Glu His
            1415                1420            1425

Leu Leu Asp Ile Asn Ala Tyr Val Thr Gly Asn Arg Leu His Val
            1430                1435            1440

Ala Trp Glu Phe Ser Arg Ala Cys His Asp Thr Ala Thr Ile Leu
            1445                1450            1455

Arg Val Ala Gln Ala Tyr Ile Ala Ala Leu Glu Thr Leu Val Ala
            1460                1465            1470

Gly His Ala Val Pro Ser Ala Ser Thr Arg Pro Ala Thr Ala Leu
            1475                1480            1485

Pro Gln Ala Pro Ala Pro Ala Ser Val Ser Pro Asp Glu Ile Ala
            1490                1495            1500

Asp Val Tyr Pro Leu Thr Pro Thr Gln Gln Gly Met Leu Phe His
            1505                1510            1515

Ser Leu Tyr Glu Pro Ala Ser Asp Ala Tyr Phe Ser Ser Leu Asn
            1520                1525            1530

Phe Arg Ile Asp Gly Ala Leu Asp Val Glu Arg Phe Arg Arg Ala
            1535                1540            1545
```

```
Trp Glu Thr Val Ala His Arg His Asp Ile Leu Arg Thr Ser Phe
    1550                1555                1560

His Trp Glu Asp Ile Glu Ser Pro Val Gln Val Val His Arg Arg
    1565                1570                1575

Ile Asp Leu Pro Trp His Asp Glu Asp Leu Arg Ala Ala Ser Ala
    1580                1585                1590

Ala Glu Ala Glu Gln Arg Trp Glu Ala Tyr Val Ala Gln Asp Arg
    1595                1600                1605

Ala Arg Gly Phe Asp Phe Thr Arg Ala Pro Leu Met Arg Leu Ala
    1610                1615                1620

Leu Phe Arg Val Gly Glu His Ala Trp Arg Phe His Trp Ser His
    1625                1630                1635

His His Ile Leu Leu Asp Gly Trp Ser Ser Ala Arg Leu Leu Ser
    1640                1645                1650

Asp Val Ala Ala Ala Tyr Gln Ala Pro Pro Ala Glu Gly Ala Pro
    1655                1660                1665

Gln Arg Asp Ala Pro Pro Ala Phe Ala Gly Tyr Val Arg Trp Leu
    1670                1675                1680

Ala Arg Gln Asp Ala Ala Ala Ala Gln Arg Phe Trp Lys Thr Lys
    1685                1690                1695

Leu Ala Asp Phe Pro Ala Thr Thr Pro Leu Val Leu Gly Arg Pro
    1700                1705                1710

Glu Leu Asp Gly Thr Ala Ala Pro Gly Ala Tyr Val Glu Glu Pro
    1715                1720                1725

Leu Leu Leu Ser Glu Ser Asp Thr Gln Arg Leu Val Ala Phe Ala
    1730                1735                1740

Gln Ser Arg Arg Leu Thr Leu Asn Thr Leu Ala Gln Gly Ala Trp
    1745                1750                1755

Ala Gln Leu Leu Ser Arg Tyr Ser Gly Glu Ser Asp Val Val Phe
    1760                1765                1770

Gly Thr Ile Val Ser Gly Arg Pro Ala Ser Leu Pro Ala Ser Asp
    1775                1780                1785

Glu Met Val Gly Leu Phe Ile Asn Thr Leu Pro Val Arg Val Arg
    1790                1795                1800

Ile Asp Ala Arg Pro Thr Ser Ala Trp Leu Ala Gln Leu Gln Met
    1805                1810                1815

Asp Leu Ala Gln Gln Glu Asp Tyr Ala His Tyr Pro Leu Ala Asp
    1820                1825                1830

Ile Gln Lys Phe Ala Gly Leu Pro Pro Gly Val Pro Leu Phe Glu
    1835                1840                1845

Ser Leu Leu Ile Phe Gln Asn Tyr Pro Val Glu Glu Ala Leu Ala
    1850                1855                1860

Asp Ala Leu Pro Gly Leu Arg Ile Gly Ala Phe Glu Val Ser Asp
    1865                1870                1875

Pro Asn Asn Tyr Pro Leu Thr Leu Val Val Thr Pro Gly Lys Arg
    1880                1885                1890

Leu Ser Leu Gln Val Leu Tyr Asp Asp Gly Arg Phe Asp Arg Asp
    1895                1900                1905

Thr Ile Val Arg Leu Leu Arg His Val Glu Thr Leu Leu Thr Gly
    1910                1915                1920

Leu Ala Gly Ala Glu Asp Arg Pro Asn Arg Ser Val Pro Leu Leu
    1925                1930                1935
```

```
Ala Ala Ala Glu Arg Asp Ala Ile Leu Leu Gly Trp Asn Asp Thr
1940                1945                1950

Phe Ala Pro Val Pro Ser Asp Arg Thr Leu Pro Glu Leu Ile Glu
1955                1960                1965

Ala Val Ala Ala Ala His Pro Glu Arg Val Ala Val Arg Cys Gly
1970                1975                1980

Thr Glu Val Arg Thr Tyr Arg Asp Leu Val Glu Gly Ala Asn Arg
1985                1990                1995

Ile Ala Ala His Leu Leu Gln Thr Ala Pro Leu Gln Pro Asp Asp
2000                2005                2010

Arg Ile Ala Val Trp Met Pro Arg Ser Pro Leu Met Leu Glu Thr
2015                2020                2025

Ile Leu Ala Ile Trp Lys Cys Gly Ala Ala Tyr Val Pro Val Asp
2030                2035                2040

Pro Ala Tyr Pro Ala Gln Arg Val Glu Thr Ile Leu Thr Leu Ala
2045                2050                2055

Arg Pro Ala Val Ile Val Thr Thr Asp Cys Val Pro Pro Ala
2060                2065                2070

Leu Ala Ser Ile Pro Leu Val Asp Pro Ala Arg Leu Pro Asp Arg
2075                2080                2085

Arg Gly Ala Glu Ala Pro Ala Pro Val Thr Pro Arg Cys Arg Pro
2090                2095                2100

Ala Asp Leu Ala Tyr Val Ile Phe Thr Ser Gly Ser Thr Gly Gln
2105                2110                2115

Pro Lys Gly Ala Met Val Glu His Arg Gly Met Leu Asn His Val
2120                2125                2130

Leu Ala Met Ala Arg Arg Val Gly Leu Gly Ala Gln Ser Ala Val
2135                2140                2145

Ala Gln Thr Ala Ser His Cys Ser Asp Ile Ser Val Trp Gln Cys
2150                2155                2160

Phe Ala Ala Leu Ala Ser Gly Gly Thr Thr Val Ile Tyr Pro Asp
2165                2170                2175

Ala Val Ile Leu Glu Pro Ala Arg Leu Ile Asp Ser Leu His Arg
2180                2185                2190

Asp Arg Ile Thr Ala Met Gln Phe Val Pro Ser Tyr Leu Ala Thr
2195                2200                2205

Phe Leu Gly Glu Leu Glu Arg His Ala Ala Pro Ala Phe Pro His
2210                2215                2220

Leu Asp Thr Leu Leu Thr Ile Gly Glu Thr Leu Gln Pro Ala Thr
2225                2230                2235

Ala Gln Ala Trp Phe Arg Leu Asn Pro Ala Val Arg Leu Ile Asn
2240                2245                2250

Ala Tyr Gly Pro Thr Glu Ala Ser Asp Ser Val Ala His Tyr Cys
2255                2260                2265

Leu Thr Arg Ala Pro Asp Gly Pro Ala Ile Pro Ile Gly Arg Pro
2270                2275                2280

Ile Glu Asn Leu Arg Leu Tyr Val Val Asp Ala Asp Met Asn Pro
2285                2290                2295

Cys Pro Ala Gly Val Lys Gly Glu Ile Cys Ile Gly Gly Val Gly
2300                2305                2310

Val Gly Arg Gly Tyr Leu Phe Asp Glu Ala Arg Thr Arg Ala Val
2315                2320                2325

Phe Arg Asp Asp Pro Phe Ser Pro Glu Pro Gly Ala Arg Leu Tyr
```

-continued

```
            2330                2335                2340
Arg Thr Gly Asp Ile Gly Cys Phe Gly Ala Asp Gly Asn Leu His
    2345                2350                2355

Phe Phe Gly Arg Arg Asp Phe Gln Val Lys Ile Arg Gly Tyr Arg
    2360                2365                2370

Ile Glu Leu Gly Glu Ile Glu Ala Ala Leu Thr Ser Leu Ala Gly
    2375                2380                2385

Ile Ser His Ala Val Val Ala Arg Glu Thr Ser Asp Ala Glu
    2390                2395                2400

Met Thr Leu Cys Gly Tyr Ala Ser Gly Thr Gly Trp Thr Pro Gln
    2405                2410                2415

Arg Val Arg Asp Ala Leu Arg Asp Thr Leu Pro Ala His Met Val
    2420                2425                2430

Pro Asp Thr Val Met Leu Leu Pro Ala Leu Pro Val Met Pro Asn
    2435                2440                2445

Gly Lys Ile Asn Arg Ala Ala Leu Pro Leu Pro Asp Ala Ala Ser
    2450                2455                2460

Val Pro Asp Gly Val Arg Ala Glu Pro Arg Thr Pro Val Glu Ala
    2465                2470                2475

Ala Leu Leu Arg Leu Phe Ala Glu Val Leu Gly Arg Arg Pro Asn
    2480                2485                2490

Gly Val Asp Asp Asp Phe Phe Glu His Gly Gly Gln Ser Leu Lys
    2495                2500                2505

Ala Ile Gln Met Val Ser Arg Ile Pro Arg Ala Ala Leu Asn Val
    2510                2515                2520

Ala Val Ala Asp Ile Phe His Ala Pro Thr Pro Arg Ala Leu Ala
    2525                2530                2535

Gln Arg Leu Ala Ala Met Pro Val Asp Gly Ala Ala Asp Asp Asp
    2540                2545                2550

Ala Ile Ile Pro Ala Leu Ala Ala Gln Pro Ser Tyr Ala Val Ser
    2555                2560                2565

Arg Ala Gln Lys Arg Ile Trp Leu Ala Ser Arg Gly Ala Asp Pro
    2570                2575                2580

Ser Thr Tyr Asn Met Ala Gly Ala Leu Gln Leu Asp Gly Ala Val
    2585                2590                2595

Asp Thr Ala Arg Leu Val Arg Ala Phe Asp Thr Leu Val Asp Arg
    2600                2605                2610

His Glu Ser Leu Arg Thr Val Phe Ala Met Ile Glu Gly Glu Leu
    2615                2620                2625

Arg Gln Arg Val Leu Ser Arg Glu Ala Ser Gly Phe Arg Val Glu
    2630                2635                2640

Gln Arg Asp Leu Ala Asp Asp Ala Gly Pro Gln Ala Ile Asp Ala
    2645                2650                2655

Leu Ile Arg Ala Glu Cys Glu Gln Pro Phe Asp Leu Ala Ser Gly
    2660                2665                2670

Pro Leu Phe Arg Val Lys Leu Val Arg Leu Ser Gln Glu Lys His
    2675                2680                2685

Leu Leu Leu Leu Asn Met His His Val Ile Ser Asp Ala Trp Ser
    2690                2695                2700

Ile Arg Val Leu Thr Asp Asp Leu His Ala Leu Tyr Ala Gly Arg
    2705                2710                2715

Asp Leu Pro Pro Leu Ser Ile Gln Tyr Arg Asp Tyr Ala Ala Trp
    2720                2725                2730
```

```
His Asn Ala Ser Leu Ala Gly Pro Arg Ala Ala His Arg Ala
2735                2740                2745

Tyr Trp Leu Glu Gln Leu Ala Pro Pro Leu Pro Arg Leu Gln Leu
    2750                2755                2760

Ala Ser Asp Phe Pro Arg Pro Glu Arg Leu Gly His Ala Gly Gln
2765                2770                2775

Thr Leu Glu Val Glu Leu Pro Gln Pro His Ala Ala Glu Leu Ala
    2780                2785                2790

Thr Leu Ala Arg Ala His His Thr Ser Leu His Ala Val Leu Leu
2795                2800                2805

Ala Ser Phe Cys Val Leu Met His Arg Tyr Thr Gly Arg Glu Asp
    2810                2815                2820

Ile Val Ile Gly Ser Val Ser Ala Gly Arg Asp Ser Glu Gln Leu
2825                2830                2835

Glu Ser Gln Val Gly Val Tyr Leu Asn Thr Val Val Leu Arg Val
    2840                2845                2850

Pro Val Arg Lys Ser Ala Thr Val Ala Glu Val Ile Asp Gly Val
2855                2860                2865

Ala Lys Ala Ser Ala Gln Ala Leu Glu His Ala Ser Tyr Pro Phe
    2870                2875                2880

Asp Val Leu Leu Glu Asp Leu Lys Ile Arg Thr Pro Ala Asn His
2885                2890                2895

Phe Pro Ile Phe Asp Ile Gln Val Asn His Val Ser Met Pro Ala
    2900                2905                2910

Pro Gln Pro Gly Leu Arg Ile Thr Asp Ile Ser Pro Ala Asp Thr
2915                2920                2925

Thr Ala Lys Phe Asp Leu Ser Phe Gln Val Val Glu Ser Glu Gly
    2930                2935                2940

Arg His Leu Ile Gln Phe Ile Tyr Asn Thr His Leu Phe Arg Pro
2945                2950                2955

Ser Thr Ile Ala Ala Met Arg Asp Arg Leu Leu Ala Ile His Asp
    2960                2965                2970

Val Phe Arg Arg Asp Pro Ala Thr Pro Val Asp Arg Ile Pro Leu
2975                2980                2985

Ser Asp Glu Ala Pro Ala Ala Gly Pro Arg Val Arg Val Gly Leu
    2990                2995                3000

Arg Leu Lys Arg Ala Pro Ala Val Thr Ala Asp Asp Ala Leu Glu
3005                3010                3015

Glu Lys Thr
    3020

<210> SEQ ID NO 13
<211> LENGTH: 1306
<212> TYPE: PRT
<213> ORGANISM: Burkholderia contaminans
<220> FEATURE:
<221> NAME/KEY: MISC_FEATURE
<222> LOCATION: (1)..(1306)
<223> OTHER INFORMATION: putative nonribosomal peptide synthetase

<400> SEQUENCE: 13

Met Ser Glu Leu Asn Leu Asn Ala Leu Ser Thr Ser Gly Gln Tyr Gln
1               5                   10                  15

Glu His Val Ala Phe Trp Asn Asp Ala Leu Gly Arg Ile Asp Glu Asp
            20                  25                  30
```

```
Phe Arg Leu Gln Gln Ala Trp Gln Ala Tyr Ala Leu Pro Leu Gly Pro
         35                  40                  45

Glu Pro Ala Leu Thr Phe Ala Leu Asp Gly Asp Ala Ala Gln Val Leu
 50                  55                  60

Glu Arg Leu Ala Ala Gly Asn Glu Leu Gly Ala Phe Val Val Leu Leu
 65                  70                  75                  80

Ala Ala Leu Phe Arg Val Leu Gly Arg Tyr Asn Gly Ala Ala Gly Leu
                 85                  90                  95

Phe Val Ala Ser Pro Gln Leu Ile Val Glu Pro Ala Ser Gly Cys Ala
            100                 105                 110

Glu Pro Val Pro Leu Leu Asp Ala Gly Glu Pro Gly Pro Thr Val Arg
            115                 120                 125

Ala Tyr Leu Asn Gln Leu Arg Asp Ser Val Gln Arg Ser Tyr Ser Tyr
            130                 135                 140

Gln Asp Phe Pro Ile Ala Ala Leu Ala His Lys Leu His Gly Glu Arg
145                 150                 155                 160

Arg Ala Thr Asn Val Gly Val Arg Phe Asp Gly Leu His Glu Ala Trp
                165                 170                 175

Ala Ala Ala Asp Tyr Asp Leu Ser Ile Glu Ile Arg His Arg Glu Arg
            180                 185                 190

Tyr Glu Ile Val Leu Thr Gly Arg Pro Thr Val Phe Thr Leu His Tyr
            195                 200                 205

Leu Gln His Val Ala Arg His Leu Arg Asn Val Val Ala Gly Phe Gly
            210                 215                 220

Ala Leu Asp Ala Pro Leu Asp Thr Val Ser Leu Leu Asp Asp Glu Glu
225                 230                 235                 240

Arg Ala Arg Leu Arg Ser His Ala Ala Pro Val Ala Val Gln Gly Thr
                245                 250                 255

Phe Leu Glu Gln Phe Ala Gln Arg Val Ala Ala Pro Asp Ser Val
            260                 265                 270

Ala Val Val Thr Ala Asp Ala Ser Leu Thr Tyr Ala Glu Leu Asp Asp
            275                 280                 285

Gln Ala Ser Arg Leu Ala Ser Phe Leu Leu Ala Glu Tyr Ala Ile Glu
            290                 295                 300

Arg Gly Asp Val Val Gly Val Ala Asp Arg Ser Glu Arg Trp Ile
305                 310                 315                 320

Val Gly Met Leu Gly Ala Leu Lys Ala Gly Ala Val Tyr Leu Pro Leu
                325                 330                 335

Asp Pro Glu Phe Pro Arg Glu Arg Leu Arg Phe Met Ile Glu Asp Ala
            340                 345                 350

Lys Val Lys Ala Leu Leu Thr His Ser Glu His Leu Pro Leu Leu Ala
            355                 360                 365

Asp Phe Trp Ala Ile Pro Met Phe Ala Leu Asp Phe Gln Leu Asp Thr
            370                 375                 380

Leu Ala Pro Ala Ser Ala Ser Ala Gln Val Glu Val Arg Pro Asp Asp
385                 390                 395                 400

Ala Ala Tyr Ile Ile Tyr Thr Ser Gly Ser Thr Gly Val Pro Lys Gly
                405                 410                 415

Val Val Leu Glu His Ala Gly Leu Leu Asn Met Ala Gln Tyr His Val
            420                 425                 430

Asp Ala Phe Gly Phe Asp Ser Ala Asp Arg Phe Val Gln Phe Tyr Ser
            435                 440                 445

Pro Gly Phe Asp Gly Ser Ile Met Glu Ile Phe Val Thr Leu Leu Ala
```

```
            450             455             460
Gly Ala Arg Leu Val Leu Ala Lys Thr Ala Val Ile Arg Asp Val Pro
465                 470                 475                 480

Arg Phe Val Asp Tyr Ile Ala Gln Gln Gly Val Thr Thr Val Asn Ala
                485                 490                 495

Thr Pro Ala Tyr Leu Ala Ala Leu Asp Trp His Ala Leu Gly Ala Val
                500                 505                 510

Lys Arg Val Ile Ser Ala Gly Asp Ser Ala Arg Val Ala Asp Leu Arg
                515                 520                 525

Glu Leu Ala Arg Thr Arg Thr Cys His Asn Ser Tyr Gly Pro Thr Glu
            530                 535                 540

Ala Thr Val Cys Ile Ala Asp Tyr Val Val Asp Pro Ala Ile Thr Tyr
545                 550                 555                 560

Gly Ala Arg Leu Pro Val Gly Arg Pro Ile His Asn Thr His Leu Tyr
                565                 570                 575

Leu Leu Asp Glu His Gly Ala Leu Ala Pro Glu Gly Cys Ala Gly Glu
            580                 585                 590

Ile Cys Val Ser Gly Ile Ala Leu Ala Arg Gly Tyr Val Gly Arg Asp
            595                 600                 605

Asp Leu Thr Ala Ala Ala Phe Val Ala His Pro Phe Glu Ala Gly Glu
            610                 615                 620

Arg Leu Tyr Arg Thr Gly Asp Leu Gly Val Trp Leu Pro Asp Gly Asn
625                 630                 635                 640

Leu Glu Val Thr Gly Arg Arg Asp Thr Gln Val Lys Ile Arg Gly Tyr
                645                 650                 655

Arg Ile Glu Met Gly Glu Ile Glu Ala Ala Leu Arg Gln His Ala Gly
                660                 665                 670

Val Ala Asp Ala Ile Val Phe Val Arg Glu Asp Thr Pro Gln His Lys
            675                 680                 685

Gln Leu Val Ala Cys Val Ala Thr Ala Thr Ala Ser Val Ala Ser Leu
            690                 695                 700

Arg Glu His Leu Lys Glu Arg Leu Pro Glu Phe Met Val Pro Ala Ser
705                 710                 715                 720

Ile Val Thr Leu Glu Arg Leu Pro Leu Thr Pro Asn Gly Lys Pro Asp
                725                 730                 735

Arg Lys Ala Leu Ala Ala Leu Glu Leu Ala Pro Ala Pro Ser Glu Thr
                740                 745                 750

Ala Tyr Val Ala Pro Ala Asn Asp Val Glu Ala Arg Leu Gly Arg Ile
                755                 760                 765

Trp Cys Asp Val Leu Gly Arg Glu Pro Ile Gly Val His Asp Asn Phe
770                 775                 780

Phe Glu Leu Gly Gly Asp Ser Ile Leu Ile Ile Gln Val Met Ser Leu
785                 790                 795                 800

Ala Gln Gln Val Gly Leu Lys Phe Thr Ala Asp Gln Phe Phe Ala His
                805                 810                 815

Pro Thr Ile Ala Glu Leu Ala Gln Val Ala Thr Glu Ala Pro Ser Ile
                820                 825                 830

Arg Ile Ala Gln Glu Pro Val Val Gly Pro Ala Pro Leu Thr Pro Ile
            835                 840                 845

Gln His Trp Phe Phe Ala Gln Asp Val Ala Asp Pro His His Tyr Asn
            850                 855                 860

Gln Ser Thr Met Ile Glu Val Pro Ala Ser Leu Arg Pro Asp Thr Ile
865                 870                 875                 880
```

-continued

```
Glu Arg Ala Leu Ala Ala Val Ala Thr His His Asp Ala Leu Arg Leu
            885                 890                 895

Ser Phe Ala Cys Val Ala Gly Val Trp Gln Gln Ser His Ala Ala Pro
            900                 905                 910

Pro Leu Ala Ile Pro Leu Gly Val Thr Ser Leu Ala Asp Ala Ala Pro
            915                 920                 925

Ala Ala Arg Gln Ala Ala Met Leu Ala Thr Ala Thr Gly Met Gln Glu
        930                 935                 940

Ser Phe Thr Leu Ser Ala Pro Pro Leu Leu Arg Ala His Leu Phe Gln
945                 950                 955                 960

Phe Gly Pro Asp Ala Pro Gln Arg Leu Leu Ala Val Ala His His Leu
            965                 970                 975

Val Ile Asp Gly Val Ser Trp Arg Ile Leu Phe Glu Asp Leu Tyr Thr
            980                 985                 990

Ala Cys Arg Gln Leu Glu Ala Gly Asp Ala Val Gln Leu Pro Ala Arg
            995                 1000                1005

Thr Thr Ala Trp Arg Asp Trp Ser Thr Arg Leu Ser Gly Leu Gly
            1010                1015                1020

Ala Thr Ala Leu Asp Gly Leu Gly Leu Asp Tyr Trp Leu Gln Gly
            1025                1030                1035

Asn Ala Gly Glu Pro Ala Cys Phe Asp Asp Met Pro Ala Gly Thr
            1040                1045                1050

Val Ala Glu Ala Gly Ser Thr Ile Val Glu Phe Asp Ala Gln Gln
            1055                1060                1065

Thr Leu Ala Leu Leu Gln Asp Val Pro Arg Ala Phe Asn Thr Gln
            1070                1075                1080

Ile Asn Glu Val Leu Leu Thr Ala Leu Leu Ala Phe Gly Asp
            1085                1090                1095

Trp Thr Gly Asn Ala Ser Leu Val Val Asp Leu Glu Gly His Gly
            1100                1105                1110

Arg Glu Asp Ile Phe Asp Gly Val Asp Thr Ser Arg Thr Ile Gly
            1115                1120                1125

Trp Phe Thr Thr His Tyr Pro Val Cys Leu Asn Ala Gly Asp Ala
            1130                1135                1140

Thr Val Ala Val Asp Ala Leu Arg His Val Lys Glu Gln Leu Arg
            1145                1150                1155

Ala Val Pro Met Arg Gly Leu Gly Tyr Gly Ile Ala Arg Tyr Leu
            1160                1165                1170

Gly His Asp Ala Gly Ile Ala Ala Ala Leu Glu Arg Gln Pro Pro
            1175                1180                1185

Ala Pro Val Arg Phe Asn Tyr Leu Gly Gln Val Asp Arg Val Leu
            1190                1195                1200

Pro Asp Asp Thr Gly Trp Lys Pro Val Leu Asp Phe Gln Ser Pro
            1205                1210                1215

Glu His Ser Pro Arg Ala Arg Gly His Leu Phe Glu Ile Asp
            1220                1225                1230

Gly Met Val Phe Asp Gly Arg Leu Arg Leu Thr Trp His Tyr Asn
            1235                1240                1245

Arg Glu Ala Cys Ala Pro Gly Val Ile Glu Gln Leu Thr Gln Cys
            1250                1255                1260

Tyr Arg Ser Arg Leu Leu Ser Ile Val Ala Ala Gly Gly Asp Gly
            1265                1270                1275
```

```
Pro Arg Ala Leu Ser Pro Ser Asp Phe Pro Ala Ala Arg Ile Ser
    1280                1285                1290

Gln Glu Ala Leu Asp Ala Leu Val Ser Arg Ile Lys Ser
    1295                1300                1305

<210> SEQ ID NO 14
<211> LENGTH: 538
<212> TYPE: PRT
<213> ORGANISM: Burkholderia contaminans
<220> FEATURE:
<221> NAME/KEY: MISC_FEATURE
<222> LOCATION: (1)..(538)
<223> OTHER INFORMATION: putative beta-lactamase domain protein

<400> SEQUENCE: 14

Met Thr Ile Ser Ser Ala Gln Val Tyr Leu Arg Gln Asn Ile Gln
1               5                   10                  15

Phe Glu Pro Leu Ile Asn Ser Trp Tyr Ala Trp Tyr His Thr Leu Pro
                20                  25                  30

Pro Leu Thr Ala Ala Leu Asn Val Ala Glu Arg Phe Leu Pro Leu Leu
            35                  40                      45

Lys Ser Tyr Ala Ala Ser Pro Met Met His Ala Ala Cys Lys Asp
50                      55                      60

Pro Ala Met Arg Gly Gly Pro Phe Leu Asp Leu Gly Gly Gln Arg Val
65                  70                  75                  80

Asp Glu Ile Arg Thr Leu Ile Glu Gln Thr Thr Gln Arg Ala Thr Arg
                85                  90                  95

Gln Leu Glu Leu Ala Lys Ala Tyr Lys Ala Phe Ser Thr Leu Leu Leu
            100                 105                 110

Glu Arg Ala Thr Gly Met Ala Ser Asp Pro Leu Tyr Pro Glu Ile Pro
        115                 120                 125

Glu Val Leu Lys Gly Tyr Val Glu Ile Tyr Tyr Asp Leu Asn His Asn
130                 135                 140

Pro Ser Phe Arg Val Phe Glu Ser Leu Leu Tyr Ala Ser Pro Phe Tyr
145                 150                 155                 160

Ala Arg Asp Ala Gln Ser Ile Ala Leu Ser Ala Ile Glu Glu His Thr
                165                 170                 175

Pro Arg Pro Phe Ile Leu Ser Thr Pro Arg Leu Arg Asp Glu Arg Thr
            180                 185                 190

Val Phe Ser Asn Met Ala Phe Asp Asp Arg Ala Leu Asp Thr Leu Phe
        195                 200                 205

Arg Met Arg Asp Thr Pro Gly Ser Tyr Ala Lys Ile Val Asp Leu Met
210                 215                 220

Arg Val Glu Glu Lys Asp Glu Pro Leu Phe Arg Ser Phe Phe Val Glu
225                 230                 235                 240

Glu Ala Pro Ala Pro Lys Pro Asp Arg Ser Phe Asp Gly Asp Ile
                245                 250                 255

Arg Ile Arg Tyr Tyr Gly His Ala Cys Val Leu Ile Gln Ser Arg Gly
            260                 265                 270

Val Ser Ile Leu Ile Asp Pro Val Ile Ser Tyr Gly Tyr Asp Thr Ala
        275                 280                 285

Leu Pro Arg Tyr Thr Phe Ala Asp Leu Pro Asp Gln Ile Asp Tyr Val
    290                 295                 300

Leu Ile Thr His Ser His His Asp His Ile Val Leu Glu Thr Leu Leu
305                 310                 315                 320

Gln Leu Arg His Lys Val Lys Thr Val Val Val Gly Arg Asn Leu Asp
```

```
                  325                 330                 335
Gly Phe Pro Gln Asp Pro Ser Met Glu Leu Ala Leu Arg Lys Leu Gly
            340                 345                 350
Phe Asp Asp Val Leu Glu Val Arg Asp Ala Gln Glu Ile Lys Val Pro
            355                 360                 365
Gly Gly Ala Ile Thr Ala Ile Pro Phe Met Gly Glu His Asn Asp Leu
        370                 375                 380
Ala Ile His Ser Lys Gln Ser Phe Met Ile Arg Phe Gly Ser Arg Ser
385                 390                 395                 400
Val Leu Cys Ile Ala Asp Ser Cys Asn Leu Asp Pro Arg Leu Tyr Glu
                405                 410                 415
His Val Phe Arg Leu Ala Gly Lys Pro Asp Thr Leu Phe Val Gly Met
                420                 425                 430
Glu Thr Glu Gly Ala Pro Pro Ser Trp Val Tyr Gly Pro Leu Phe Pro
            435                 440                 445
Lys Ala Leu Pro Arg Asp Ile Asp Gln Ser Arg Arg Ala Arg Gly Cys
        450                 455                 460
Gln Phe Gly Glu Ala Ala Ala Leu Val Asp Asp Phe Ala Phe Asn Ala
465                 470                 475                 480
Ala Tyr Val Tyr Ala Met Gly Gln Glu Pro Trp Leu Asn His Leu Leu
                485                 490                 495
Asp Asn Thr Phe Asp Glu Asn Ser Pro Ser His Ile Gln Ser Thr Gln
                500                 505                 510
Phe Val Ala His Cys Lys Ala Lys Gly Ile Ala Ser Glu Ile Leu Tyr
            515                 520                 525
Ala Thr Arg Glu Ile Val Leu Cys Gln Asn
        530                 535

<210> SEQ ID NO 15
<211> LENGTH: 4469
<212> TYPE: PRT
<213> ORGANISM: Burkholderia contaminans
<220> FEATURE:
<221> NAME/KEY: MISC_FEATURE
<222> LOCATION: (1)..(4469)
<223> OTHER INFORMATION: putative beta-ketoacyl synthase nonribosomal
      peptide synthetase

<400> SEQUENCE: 15

Met Asn Ala Lys Ala Thr His Ala Leu Lys Ala Ala Leu Asp Glu Leu
1               5                   10                  15
Arg Leu Arg Arg Ala Glu Ile Ala Ala Leu Arg Ser Asp Arg Asn Glu
            20                  25                  30
Pro Ile Ala Val Ile Gly Met Ala Cys Arg Phe Pro Gly Arg Ser Asp
        35                  40                  45
Thr Pro Asp Ala Phe Trp Gln Leu Leu Asp Gly Ala His Asp Ala Val
    50                  55                  60
Thr Glu Val Pro Gly Glu Arg Trp Asp Ile Asp Arg Tyr Tyr Asp Pro
65                  70                  75                  80
Asp Pro Ser Thr Pro Gly Lys Met Ala Thr Arg His Gly Ala Phe Leu
                85                  90                  95
Glu Arg Val Asp Gln Phe Asp Ala Ala Phe Phe Gly Ile Ala Pro Arg
            100                 105                 110
Glu Ala Thr Tyr Leu Asp Pro Gln Gln Arg Leu Leu Leu Glu Val Ala
        115                 120                 125
Trp Glu Ala Leu Glu Asn Ala His Leu Ala Pro Glu Arg Phe Arg Gln
```

-continued

```
            130                 135                 140
Ser Ala Thr Gly Val Tyr Val Gly Ile Thr Cys Phe Asp His Ala Ile
145                 150                 155                 160

Gln Val Ser Asn Ala Ser Met Pro Ser Ser Tyr Ala Gly Thr Gly
                165                 170                 175

Ser Ala Leu Asn Met Ala Ala Gly Arg Leu Ser Phe Val Leu Gly Leu
                180                 185                 190

Thr Gly Pro Ser Met Ala Ile Asp Thr Ala Cys Ser Ser Leu Val
                195                 200                 205

Cys Leu His Leu Ala Cys Glu Ser Leu Arg Ser Arg Glu Ser Asn Met
        210                 215                 220

Ala Leu Ala Gly Gly Val Asn Leu Met Leu Ser Pro Glu Val Met Val
225                 230                 235                 240

Ser Phe Ser Gln Ala Arg Met Leu Ser Pro Asp Gly Arg Cys Lys Thr
                245                 250                 255

Phe Asp Ala Ala Ala Asp Gly Tyr Val Arg Gly Glu Gly Cys Gly Met
                260                 265                 270

Val Val Leu Lys Arg Leu Ala Asp Ala Leu Ala Asp Gly Asp Arg Val
            275                 280                 285

Leu Gly Ile Val Arg Gly Thr Ala Val Asp Gln Gly Ala Gly Gly
        290                 295                 300

Gly Leu Thr Val Pro Ser Arg Asp Ser Gln Glu Arg Val Ile Arg Arg
305                 310                 315                 320

Ala Leu Asn Gln Ala Gly Leu Ala Pro Gly Asp Val Ser Tyr Val Glu
                325                 330                 335

Ala His Gly Thr Gly Thr Ser Leu Gly Asp Pro Ile Glu Val Glu Ala
                340                 345                 350

Leu Ala Gly Val Tyr Gly Pro Gly Arg Ala Ala Asn Glu Pro Leu Val
                355                 360                 365

Ile Gly Ser Val Lys Thr Asn Ile Gly His Leu Glu Ser Ala Ser Gly
            370                 375                 380

Ile Ala Gly Leu Ile Lys Val Leu Leu Ser Phe Glu His Asp Arg Ile
385                 390                 395                 400

Pro Ala His Leu His Phe Thr Gln Pro Asn Pro His Thr Pro Trp Gln
                405                 410                 415

Asp Ile Pro Ile Arg Val Ala Asp Pro Val Ala Trp Arg Arg Gly
            420                 425                 430

Glu Arg Arg Arg Ile Ala Gly Val Ser Ala Phe Gly Phe Ser Gly Thr
                435                 440                 445

Asn Ala His Ala Ile Val Glu Glu Pro Pro Val Ala Pro Ala His Ala
            450                 455                 460

Ala Gln Arg Ala Leu Leu Leu Ser Ala Arg Ser Glu Ala Ala Leu
465                 470                 475                 480

Ala Ala Leu Val Pro Arg Tyr Glu Arg Ala Ile Ala Gly Ala Thr Pro
                485                 490                 495

Gln Glu Leu Ala Ala Ile Cys Arg Ala Ala Thr Gly Arg Ser His
                500                 505                 510

Tyr Pro Phe Arg Ala Ala Tyr Val Ser Gly Ala Arg Val Ala Ser Ala
                515                 520                 525

Ala Ala Pro Arg Thr Gly Lys Ala Leu Arg Met Gly Phe Gly Phe Gly
            530                 535                 540

Val Pro Asp Thr Gly Val Ala His Ala Leu His Ala Ser Glu Pro Leu
545                 550                 555                 560
```

```
Phe Arg Asp Ala Phe Ala Arg Cys Ser Val Pro Leu Asp Ala Leu Glu
            565                 570                 575

Thr Asp Ala Gly Arg Phe Ala Ile Gln Phe Ala Trp Ala Glu Leu Trp
            580                 585                 590

Lys Gly Trp Gly Leu Arg Pro Ala Val Val Ser Gly His Gly Ile Gly
            595                 600                 605

Glu Tyr Val Ala Ala Cys Val Ala Gly Val Val Ser Val Ala Asp Ala
            610                 615                 620

Leu Arg Leu Val Ala Ala Arg Ser Asp Ala Glu Ala Leu Arg Ala Val
625                 630                 635                 640

Leu Arg Asp Met Pro Leu Ala Arg Pro Ser Val Arg Leu Ile Ser Gly
            645                 650                 655

Tyr Leu Gly Thr Asp Val Thr Asp Glu Val Thr His Pro Gln Tyr Trp
            660                 665                 670

Leu Gln Leu Ala Gly Ala Ser Asp Gln Ala Asp Ala Ser His Pro Pro
            675                 680                 685

Glu Gly Leu Ala Asp Gly Trp Leu Pro Pro Cys Ala Gly Asp Ala
            690                 695                 700

Leu Glu Arg Ala Leu Ala Ala Leu Tyr Val Gln Gly Ala Gln Phe Asp
705                 710                 715                 720

Trp Arg Ala Leu Phe Pro Ala Pro Ala Gln Pro Ala Thr Thr Leu Pro
            725                 730                 735

Asn Tyr Pro Phe Glu Arg Gln Arg Phe Ser Leu Glu Lys Ile Pro Ser
            740                 745                 750

Pro Ile Val Gly Met Asp Ala Gly Ser Ile Asp Ala Ala Leu Arg His
            755                 760                 765

Leu Lys Ser Ser Gly Lys Tyr Pro Glu Asp Met Leu Asn Ala Phe Pro
            770                 775                 780

Asp Leu Leu Arg Thr Ala Phe Ala Ala Ala Glu Thr Val Ala Ser Asn
785                 790                 795                 800

Ala His Pro Leu Tyr His Val Trp Glu Gln Gln Ala Ala Met Pro
            805                 810                 815

Ala Ala Pro Ala Ala Asp Ala Ser Pro Trp Leu Ile Phe Ala Asp
            820                 825                 830

Ala Ser Gly Val Gly Glu Arg Leu Ala Ala Leu Leu Arg Ala Arg Gly
            835                 840                 845

Ala Ser Cys Ser Leu Val Arg Pro Gly Ile Asp Tyr Val Thr Gly Ala
850                 855                 860

Glu Ala Gly Trp Gln Val Ala Pro Glu Arg Pro Asp Asp Phe Val Arg
865                 870                 875                 880

Leu Leu Asn Glu Thr Ala Ala Ser Gly Gln Arg Ile Val Phe Leu Trp
            885                 890                 895

Ala Leu Asp Glu Ala Val Gly Glu Thr Arg Met Ser Ala Ala Leu Leu
            900                 905                 910

His Leu Val His Ala Leu Val Gly Ser Glu Arg Glu Trp Thr Pro Ser
            915                 920                 925

Thr Arg Pro Arg Ile Ser Val Val Thr Arg Asp Ala Val Glu Ala Gly
            930                 935                 940

Glu Ala Pro His Val Ser Gly Leu Ala Gln Ala Ala Leu Ser Gly Leu
945                 950                 955                 960

Ala Arg Gly Ala Met Ile Glu His Pro Glu Trp Phe Gly Thr Ala Ile
            965                 970                 975
```

```
Asp Leu Asp Pro Ala Ala Pro Glu Asn Glu Thr Gln Ala Leu Leu Gln
            980                 985                 990

Glu Met Leu Gly Glu Ser Arg Glu Glu Gln Val Ala Leu Arg His Gly
            995                 1000                1005

Ala Arg His Val Ala Arg Leu Ser Pro Leu Ala Pro Ala Glu Thr
        1010                1015                1020

Ala Ala Leu Pro Val Asp Pro Asp Ala Ala Tyr Leu Ile Thr Gly
        1025                1030                1035

Gly Phe Gly Ala Leu Gly Leu His Thr Ala Arg Trp Leu Ala Ala
        1040                1045                1050

Arg Gly Ala Gly Thr Leu Ile Leu Val Gly Arg Gln Gly Ala Ala
        1055                1060                1065

Ser Asp Glu Ser Gln Arg Ala Ile Ala Glu Leu Arg Glu Arg Asn
        1070                1075                1080

Val Thr Leu Arg Cys Glu Arg Leu Asp Ile Ala Asp Pro Ala Ala
        1085                1090                1095

Val Ala Ala Phe Phe Ala Ala Leu Arg Arg Asp Gly Val Pro Leu
        1100                1105                1110

Lys Gly Ile Val His Ala Ala Gly Ile Val Gly Tyr Lys Pro Ile
        1115                1120                1125

Met Gln Val Glu Arg Asp Glu Leu Asp Ala Val Leu Gln Pro Lys
        1130                1135                1140

Val Ala Gly Ala Trp Leu Leu His Gln Gln Ser Glu His Phe Pro
        1145                1150                1155

Leu Asp Phe Phe Leu Leu Phe Ser Ser Ile Ala Ser Ala Trp Gly
        1160                1165                1170

Ser Arg Glu Gln Ala His Tyr Ser Ala Ala Asn Arg Phe Leu Asp
        1175                1180                1185

Ala Leu Ala His His Arg Arg Gly Gln Gly Leu Pro Ala Leu Ser
        1190                1195                1200

Val Asn Trp Gly Pro Trp Ala Glu Gly Gly Met Thr Phe Pro Glu
        1205                1210                1215

Ala Glu Ala Leu Leu Arg Arg Val Gly Ile Arg Ser Leu Ala Ala
        1220                1225                1230

Asp Arg Ala Leu Asp Val Leu Asn Arg Leu Pro Ala Val Pro Gln
        1235                1240                1245

Val Ala Val Val Asp Ile Asp Leu Ala Leu Phe Gln Gly Ser Tyr
        1250                1255                1260

Glu Ala Arg Gly Pro Lys Pro Phe Leu Asp His Val Arg Val Ala
        1265                1270                1275

Lys Ser Ala Pro Ser Ala Pro Ala Met Pro Ala Leu Ser Asp Ala
        1280                1285                1290

Ser Pro Arg Glu Arg Lys Arg Leu Leu Ala Asp Ser Ile Asp Arg
        1295                1300                1305

Ala Val Ala Gln Val Leu Gly Tyr Asp Ala Gly Thr Leu Asp Arg
        1310                1315                1320

Asp Leu Gly Phe Phe Glu Met Gly Met Asp Ser Leu Met Ala Leu
        1325                1330                1335

Asp Val Arg Thr His Leu Glu Asn Ala Leu Gly Ile Pro Leu Ser
        1340                1345                1350

Val Ala Leu Leu Phe Asp His Pro Thr Val Asn Ala Leu Ala Asp
        1355                1360                1365

Phe Leu Ala Glu Gln Ala Ser Gly Thr Ala Gln Ala Gln Thr Val
```

```
              1370                1375                1380
Pro Pro Gln Gln Gln Pro Arg Pro Ile Ala Pro Ala Ile Glu Ala
        1385                1390                1395
Arg Asp Ala Gly Thr Pro Glu Pro Ile Ala Ile Val Gly Met Ser
    1400                1405                1410
Cys Arg Phe Pro Gly Ala Ala His Asp Leu Asp Ala Tyr Trp Asn
    1415                1420                1425
Leu Leu Asn Asp Gly Val Asp Ala Ile Ser Glu Val Pro Arg Glu
    1430                1435                1440
Arg Trp Asp Val Asp Ala Tyr Tyr Asp Pro Asp Glu Ala Pro
    1445                1450                1455
Gly Arg Met Tyr Ser Arg Phe Gly Gly Phe Leu Asp Val Asp
    1460                1465                1470
Gln Phe Asp Pro Ala Phe Phe Arg Ile Thr Pro Arg Glu Ala Ala
    1475                1480                1485
Ala Met Asp Pro Gln Gln Arg Leu Leu Leu Glu Val Ser His Glu
    1490                1495                1500
Ala Leu Glu His Ala Gly Ile Pro Val Asp Ser Leu Lys Gly Ser
    1505                1510                1515
Arg Thr Gly Val Phe Val Gly Ile Thr Thr Asn Asp Tyr Ala Asn
    1520                1525                1530
Leu Gln Leu Arg Asn Gly Gly Ser Gly Ile Asp Gly Tyr Phe
    1535                1540                1545
Phe Thr Gly Asn Pro Leu Asn Thr Ala Ala Gly Arg Ile Ser Tyr
    1550                1555                1560
Gly Leu Gly Val Gln Gly Pro Ser Met Ala Ile Asp Thr Ala Cys
    1565                1570                1575
Ser Ser Ser Leu Thr Ala Ile His Thr Ala Ser Gln Asn Leu Arg
    1580                1585                1590
Ser Gly Glu Cys Asp Leu Ala Ile Ala Gly Gly Val Asn Leu Ile
    1595                1600                1605
Leu Ser Pro Asp Asn Ser Ile Ala Val Ser Arg Thr Arg Ala Leu
    1610                1615                1620
Ala Pro Asp Gly Arg Cys Lys Thr Phe Asp Ala Ala Ala Asp Gly
    1625                1630                1635
Phe Val Arg Ser Glu Gly Cys Gly Ala Leu Val Leu Lys Arg Leu
    1640                1645                1650
Ser Asp Ala Leu Ala Ala Gly Asp Arg Val Leu Ala Val Leu Arg
    1655                1660                1665
Gly Ser Ala Val Asn His Asp Gly Ala Ser Ser Gly Phe Thr Ala
    1670                1675                1680
Pro Asn Gly Arg Ala Gln Glu Ala Val Ile Arg Gln Ala Leu Gly
    1685                1690                1695
Gly Leu Pro Ala Ala Ser Ile Asp Tyr Val Glu Ala His Gly Thr
    1700                1705                1710
Gly Thr Pro Leu Gly Asp Pro Val Glu Leu Gln Ala Leu Ala Thr
    1715                1720                1725
Val Phe Gly Ala Gly Arg Asp Ala Gly Arg Arg Leu Arg Val Gly
    1730                1735                1740
Ser Val Lys Thr Asn Ile Gly His Thr Glu Ser Ala Ala Gly Ile
    1745                1750                1755
Ala Gly Val Ile Lys Val Val Leu Ser Leu Asn His Asp Arg Leu
    1760                1765                1770
```

```
Pro Ala His Leu His Phe Arg Gln Pro Ser Pro Leu Val Gln Trp
1775                 1780                1785

Asp Ala Met Pro Val Glu Ile Cys Ala Glu Ala Ser Ala Trp Pro
1790                 1795                1800

Arg Gly Glu Arg Pro Arg Arg Ala Gly Val Ser Ala Phe Gly Ala
1805                 1810                1815

Ser Gly Thr Asn Ala His Leu Val Leu Glu Glu Ala Pro Ala Pro
1820                 1825                1830

Ala Arg Gln Ala Thr Pro Ser Arg His Lys Val His Pro Leu Val
1835                 1840                1845

Leu Ser Ala Lys Thr Pro Ala Ala Leu Arg Glu Leu Ala Gly Arg
1850                 1855                1860

Tyr Gln Arg Arg Leu Glu Ala Glu Pro Gly Leu Asp Ile Ala Ala
1865                 1870                1875

Val Ala Phe Ser Ala Ala Thr Gly Arg Ser His Phe Ala His Arg
1880                 1885                1890

Leu Ala Trp Pro Val Thr Ser Leu Asp Asp Ala Ile Asp Lys Leu
1895                 1900                1905

Arg Ala Phe His Ala Lys Glu Pro Ala Gly Ala Ala Gln Pro Ala
1910                 1915                1920

Pro Arg Val Lys Met Ala Phe Leu Phe Thr Gly Gln Gly Ser Gln
1925                 1930                1935

Tyr Ala Gly Met Gly Arg Arg Leu Tyr Asp Ala Tyr Pro Val Phe
1940                 1945                1950

Arg Asp Ala Ile Asp Arg Cys Arg Ala Val Ala Asp Pro Leu Leu
1955                 1960                1965

Asp Lys Pro Leu Leu Glu Val Leu Ser Ala Gln Gly Glu Asp Ile
1970                 1975                1980

His Gln Thr Gly Tyr Ser Gln Pro Ala Leu Phe Ser Leu Gln Tyr
1985                 1990                1995

Ala Leu Thr Thr Leu Leu Ala Ser Phe Gly Val Val Pro Asp Ala
2000                 2005                2010

Val Met Gly His Ser Val Gly Glu Tyr Ala Ala Ala Cys Ala Ala
2015                 2020                2025

Gly Val Phe Ser Pro Glu Asp Gly Leu Arg Leu Ile Ala Glu Arg
2030                 2035                2040

Gly Arg Leu Met Gln Ala Leu Pro Arg Asp Gly Glu Met Ala Ala
2045                 2050                2055

Ile Phe Thr Asp Leu Ala Thr Val Glu Arg Ala Ile Asp Ala Trp
2060                 2065                2070

Pro His Glu Val Ala Val Ala Ala Val Asn Gly Pro Ala Ser Ile
2075                 2080                2085

Val Ile Ser Gly Lys Arg Glu Arg Ile Ala Met Leu Val Asp Ala
2090                 2095                2100

Phe Ala Ala Arg Asp Ile Arg Ser Val Pro Leu Asn Thr Ser His
2105                 2110                2115

Ala Phe His Ser Pro Leu Leu Glu Pro Met Leu Asp Ser Phe Gln
2120                 2125                2130

Leu Ala Ala Lys Thr Val Pro Val Ala Arg Pro Ala Ile Pro Phe
2135                 2140                2145

Tyr Ser Asn Leu Thr Gly Ala Val Met Asp Glu Ala Pro Thr Asp
2150                 2155                2160
```

```
Thr Tyr Trp Arg Arg His Cys Arg Glu Pro Val Gln Phe Ala Ser
    2165            2170            2175

Ser Val Glu Arg Leu Ala Glu Ala Gly Phe Asn Val Leu Val Glu
    2180            2185            2190

Ile Gly Pro Lys Pro Val Leu Val Asn Leu Ala Arg Ala Cys Cys
    2195            2200            2205

Ala Pro Asp Ala Gly Ile Gln Phe Leu Ala Leu Gln Arg Pro Gln
    2210            2215            2220

Val Glu Gln Gln Ala Leu Ile Glu Thr Leu Ser Ser Leu Tyr Ala
    2225            2230            2235

Arg Gly Val Asp Val Asp Trp Ala Pro Thr Glu Thr Pro Ala Pro
    2240            2245            2250

Ala Arg Ile Ala Leu Pro Ser Tyr Pro Phe Gln Arg Ser Arg Thr
    2255            2260            2265

Trp Phe Gln Lys Ala Asp Thr Ser Met Thr Gln Thr Ser Ala Ser
    2270            2275            2280

Pro Ile Ala Ala Ala Pro Thr His Asn Arg Ser Gly Glu Ile Leu
    2285            2290            2295

Glu Trp Leu Arg Gly Lys Ile Gly Glu Leu Ile Gln Ala Asp Pro
    2300            2305            2310

Ala Thr Ile Asn Ile Glu Leu Pro Phe Leu Glu Met Gly Ala Asp
    2315            2320            2325

Ser Ile Val Leu Ile Glu Ala Ile Arg His Ile Glu Ala Glu Tyr
    2330            2335            2340

Gly Val Lys Leu Ala Met Arg Arg Phe Phe Glu Asp Leu Ala Thr
    2345            2350            2355

Val Gln Ala Leu Ala Glu Tyr Val Ala Asp Asn Leu Pro Ala Ala
    2360            2365            2370

Ala Ala Pro Ser Gly Ala Glu Ala Val Ala Val Ala Val Ala Ala
    2375            2380            2385

Ala Glu Pro Ser Thr Pro Ala Val Ala Val Thr Pro Ser Ala Ala
    2390            2395            2400

Gly Leu Ala Pro Leu Ala Ala Ala Pro Ala Glu Trp Val Ala Ala
    2405            2410            2415

Glu Gly Gly Ser Thr Val Glu Arg Val Leu Arg Glu Gln Asn Gln
    2420            2425            2430

Leu Leu Ser His Val Met Ser Gln Gln Met Glu Leu Leu Arg Thr
    2435            2440            2445

Ser Leu Thr Gly Gln Pro Gly Val Arg Pro Ala Thr Ala Ala Val
    2450            2455            2460

Gln Ala Val Ala Ser Thr Ala Ser Val Ala Pro Lys Ala Ala Ser
    2465            2470            2475

Ala Ala Pro Ala Ala Ala Pro Ala Ala Lys Pro Ala Pro Ala Ala
    2480            2485            2490

Ala Ala Ala Pro Ala Ala Asp Asn Pro Pro Pro Lys Pro Met Met
    2495            2500            2505

Pro Trp Gly Ser Pro Val Gln Gln Arg Ala Arg Gly Leu Ser Ala
    2510            2515            2520

Ala Gln Gln Glu His Leu Glu Ala Leu Ile Val Arg Tyr Thr Thr
    2525            2530            2535

Arg Thr Arg Lys Ser Lys Asp Ser Val Gln Ala Ser Arg Pro Val
    2540            2545            2550

Leu Ala Asp Ser Arg Ala Thr Val Gly Phe Arg Phe Ser Thr Lys
```

```
            2555                2560                2565

Glu Met Leu Tyr Pro Ile Val Gly Asp Arg Ala Ala Gly Ser Arg
        2570                2575                2580

Leu Trp Asp Ile Asp Gly Asn Glu Tyr Ile Asp Phe Thr Met Gly
        2585                2590                2595

Phe Gly Val His Leu Phe Gly His Thr Pro Asp Phe Ile Gln Gln
        2600                2605                2610

Gln Val Thr Arg Glu Trp Gln Arg Pro Leu Glu Leu Gly Ala Arg
        2615                2620                2625

Ser Ser Leu Val Gly Glu Val Ala Ala Arg Phe Ala Arg Val Thr
        2630                2635                2640

Gly Leu Asp Arg Val Ala Phe Ser Asn Thr Gly Thr Glu Ala Val
        2645                2650                2655

Met Thr Ala Met Arg Leu Ala Arg Ala Val Thr Gly Arg Asp Lys
        2660                2665                2670

Ile Val Met Phe Thr His Ser Tyr His Gly His Ala Asp Gly Thr
        2675                2680                2685

Leu Ala Ala Ala Asn Ala Glu Gly Val Thr Glu Thr Ile Ala Pro
        2690                2695                2700

Gly Val Pro Phe Gly Ser Val Glu Asn Met Ile Leu Leu Asp Tyr
        2705                2710                2715

Gly Ser Asp Ala Ala Leu Glu Ala Ile Arg Gly Met Ala Ser Thr
        2720                2725                2730

Leu Ala Ala Val Met Val Glu Pro Val Gln Ser Arg Asn Pro Ser
        2735                2740                2745

Leu Gln Pro Val Ala Phe Leu Lys Glu Leu Arg Arg Ile Thr Glu
        2750                2755                2760

Glu Ala Gly Val Ala Leu Ile Phe Asp Glu Met Ile Thr Gly Phe
        2765                2770                2775

Arg Val His Pro Gly Gly Ser Gln Ala Met Phe Gly Ile Arg Ala
        2780                2785                2790

Asp Leu Ala Thr Tyr Gly Lys Ile Ile Gly Gly Gly Leu Pro Leu
        2795                2800                2805

Gly Val Ile Ala Gly Thr Ser Arg Phe Met Asp Ala Ile Asp Gly
        2810                2815                2820

Gly Met Trp Thr Tyr Gly Asp His Ser Phe Pro Ala Ala Asp Arg
        2825                2830                2835

Thr Ala Phe Gly Gly Thr Phe Cys Gln Tyr Pro Leu Ala Met Ala
        2840                2845                2850

Ala Ala Leu Ala Val Leu Glu Lys Ile Glu Gln Glu Gly Pro Ala
        2855                2860                2865

Leu Gln Ala Ala Leu Asn Glu Arg Thr Ala Gln Ile Ala Gly Thr
        2870                2875                2880

Leu Asn Ala Phe Phe Ala Glu Ala Glu Ala Pro Ile Lys Val Thr
        2885                2890                2895

Trp Phe Gly Ser Met Phe Arg Phe Glu Phe Thr Glu Asn Leu Asp
        2900                2905                2910

Leu Phe Phe Tyr His Met Leu Glu Lys Gly Ile Tyr Ile Trp Glu
        2915                2920                2925

Trp Arg Thr Cys Phe Leu Ser Thr Ala His Thr Asp Ala Asp Ile
        2930                2935                2940

Asp Arg Phe Ile Arg Ala Val Lys Asp Ser Val Ala Asp Leu Arg
        2945                2950                2955
```

-continued

```
Arg Gly Gly Phe Ile Arg Pro His Ser Lys His Gly Thr Val Ala
    2960             2965             2970

Ala Leu Ser Glu Ala Gln Arg Gln Leu Trp Val Leu Ser Glu Ile
    2975             2980             2985

Asp Pro Glu Gly Ser Leu Ala Tyr Asn Val Asn Thr Thr Leu Glu
    2990             2995             3000

Leu Asn Gly Arg Leu Asp Glu Ala Ala Met Arg Ala Ala Val Gln
    3005             3010             3015

Ser Leu Val Asp Arg His Glu Ala Leu Arg Thr Thr Val Met Ala
    3020             3025             3030

Asp Gly Ser Gly Gln Ile Val His Pro Ser Leu Thr Leu Glu Ile
    3035             3040             3045

Pro Leu Ile Asp Thr Asp Pro Asn Ala Trp Arg Glu Gln Glu Ser
    3050             3055             3060

Arg Gln Pro Phe Asp Leu Val Asn Gly Pro Leu Phe Arg Ala Ala
    3065             3070             3075

Leu Val Arg Leu Gly Ser Glu Arg His Leu Leu Val Met Thr Ala
    3080             3085             3090

His His Ile Ile Cys Asp Gly Ser Thr Phe Gly Val Leu Leu Glu
    3095             3100             3105

Asp Leu Ala Arg Ala Tyr Ala Gly Ala Ala Pro Ala Asp Ala Pro
    3110             3115             3120

Leu Gln Phe Arg Ala Tyr Leu Lys Gln Leu Asp Gly Gln Arg His
    3125             3130             3135

Ser Pro Glu Thr Lys Ala Asn Arg Glu Tyr Trp Leu Ala Gln Cys
    3140             3145             3150

Ala Arg Gln Ala Ala Pro Leu Asn Leu Pro Val Asp Tyr Pro Arg
    3155             3160             3165

Pro Ala Val Lys Thr Phe His Gly Glu Arg Val Ser Leu His Leu
    3170             3175             3180

Asp Ala Ala Thr Ala Ala Thr Leu Arg Thr Ala Ala Arg Gln Asn
    3185             3190             3195

Gly Cys Thr Leu Tyr Met Val Leu Leu Ala Gly Phe Asn Leu Phe
    3200             3205             3210

Leu His Arg Val Ala Gly Gln Gln Glu Ile Val Thr Gly Ile Pro
    3215             3220             3225

Val Thr Gly Arg Ser Val Ala Gly Ser Asp Arg Leu Ala Gly Tyr
    3230             3235             3240

Cys Thr His Leu Leu Pro Leu His Ser Thr Leu Pro Glu Gln Ala
    3245             3250             3255

Thr Val Ala Ser Phe Leu Ala Gly Thr Arg Gln Asn Leu Leu Asp
    3260             3265             3270

Ala Leu Glu His Gln Asp Tyr Pro Phe Ala Glu Leu Val Arg Glu
    3275             3280             3285

Ile Gly Ala Gln Arg Asp Leu Asn Ala Ala Pro Leu Val Ser Ala
    3290             3295             3300

Val Phe Asn Leu Glu Pro Val Ser Ala Leu Pro Glu Leu Pro Gly
    3305             3310             3315

Leu Thr Val Gly Leu Val Ala Pro Leu Ile Arg His Thr Ala Phe
    3320             3325             3330

Asp Leu Asn Val Asn Val Leu Asp Ala Gly Gln Ala Leu Leu Ile
    3335             3340             3345
```

```
Asp Cys Asp Tyr Asn Thr Asp Leu Phe Asp Ala Ser Thr Val Gln
3350                3355                3360

Arg Phe Leu Asp Ile Tyr Arg Thr Leu Leu Thr His Leu Ala Asp
3365                3370                3375

Asp Ala Ser Ala Ala Val Ala Arg Leu Pro Leu Ser Ser Asp Ala
3380                3385                3390

Glu Arg Asn Leu Leu Thr Val Glu Trp Asn Arg Thr Asp Thr Asp
3395                3400                3405

Phe Gly Glu Asp Ala Ala Gln Pro Leu His Arg Leu Phe Glu Gln
3410                3415                3420

Gln Val Glu Arg Thr Pro Asp Ala Val Ala Ile Val Phe Asp Asp
3425                3430                3435

Thr Ala Leu Thr Tyr Ala Glu Leu Asn Leu Arg Ala Asn Arg Leu
3440                3445                3450

Ala His His Leu Val Ala Leu Gly Val Gly Pro Asp Ser Leu Val
3455                3460                3465

Gly Val Ala Met Glu Arg Ser Leu Asp Met Ser Val Ala Leu Leu
3470                3475                3480

Ala Ile Leu Lys Ala Gly Gly Ala Tyr Val Pro Val Asp Pro Asp
3485                3490                3495

Tyr Pro Ala Glu Arg Val Arg Phe Met Ile Asp His Ala Gln Leu
3500                3505                3510

Arg Trp Leu Leu Thr Gln Gln His Leu His Asp Ala Leu Pro Asp
3515                3520                3525

Thr Asp Ala His Val Ile Val Val Asp Arg Asp Ser Leu Asp Leu
3530                3535                3540

Asp Ala Ala Thr Ser Asn Pro Ala Pro Ala Leu Asn Gly Asp
3545                3550                3555

Asn Leu Ala Tyr Met Ile Tyr Thr Ser Gly Ser Thr Gly Arg Pro
3560                3565                3570

Lys Gly Ala Leu Asn Thr His Arg Ala Ile Thr Asn Arg Ile Leu
3575                3580                3585

Trp Met Gln His Ala Tyr Ala Leu Gly Ala Asp Asp Ala Val Leu
3590                3595                3600

Gln Lys Thr Pro Phe Ser Phe Asp Val Ser Val Trp Glu Leu Phe
3605                3610                3615

Trp Pro Leu Val Thr Gly Ala Arg Leu Val Phe Ala Arg Pro Gly
3620                3625                3630

Gly Gln Arg Glu Thr Asp Tyr Leu Val Glu Leu Ile Glu Arg Glu
3635                3640                3645

Arg Ile Thr Thr Ile His Phe Val Pro Ser Met Leu Arg Ala Phe
3650                3655                3660

Leu Asp His Pro Asp Leu Asp Ala His Cys Ala Ser Leu Arg Arg
3665                3670                3675

Val Val Cys Ser Gly Glu Ala Leu Pro His Asp Leu Gln Gln Arg
3680                3685                3690

Cys Leu Glu Arg Leu Asp Val Glu Leu Tyr Asn Leu Tyr Gly Pro
3695                3700                3705

Thr Glu Ala Ala Val Asp Val Thr Ala Trp Glu Cys Arg Arg Asp
3710                3715                3720

Asp Pro His Arg Ile Val Pro Ile Gly Arg Pro Ile Ala Asn Thr
3725                3730                3735

Arg Leu Tyr Ile Val Asp Ala Gln Met Gln Pro Thr Pro Ile Gly
```

```
                3740                3745                3750
Val Ala Gly Glu Leu Leu Ile Gly Gly Thr Pro Val Gly Arg Gly
    3755                3760                3765

Tyr His Gly Glu Pro Glu Leu Ser Ala Glu Lys Phe Ile Ala Asp
    3770                3775                3780

Pro Phe Ser Ala Asp Pro Leu Ala Arg Leu Tyr Arg Thr Gly Asp
    3785                3790                3795

Leu Ala Arg Tyr Arg Pro Asp Gly Asn Ile Glu Phe Leu Gly Arg
    3800                3805                3810

Ile Asp His Gln Ile Lys Leu Arg Gly Leu Arg Ile Glu Pro Gly
    3815                3820                3825

Glu Ile Glu Ala Ala Leu Thr Ser His Pro Leu Val Asp Ala Ala
    3830                3835                3840

Val Val Ala Leu Arg Gly Val Asp Asp Gly Ala Arg Leu Val Gly
    3845                3850                3855

Trp Leu Cys Ser Ser His Pro Glu Ala Glu Leu Ile Glu Ala Val
    3860                3865                3870

Arg Gly His Leu Arg Gln Arg Leu Pro Asp Tyr Met Val Pro Ser
    3875                3880                3885

Ala Phe Val Val Val Ser Ala Phe Glu His Leu Pro Asn Gly Lys
    3890                3895                3900

Leu Asp Arg Thr Arg Leu Pro Glu Pro Gly Asp Gly Leu Asp His
    3905                3910                3915

Val Ala Pro Val Asn Ala Leu Glu Ala Gln Leu Ala Ala Ile Trp
    3920                3925                3930

Gln Glu Val Leu Gly Gln Ala Arg Ile Ser Thr Thr Gly Asn Phe
    3935                3940                3945

Phe Asp Leu Gly Gly Asn Ser Leu Leu Ala Thr Lys Val Val Ala
    3950                3955                3960

Arg Ile Arg Arg Asp Leu His Val Lys Leu Glu Ile Arg Ser Leu
    3965                3970                3975

Phe Ala Leu Pro Thr Ile Ser Ser Leu Ala Lys Arg Ile Ala Asp
    3980                3985                3990

Thr Gln Pro Ile Asp Tyr Ala Pro Val Thr Pro Leu Pro Ala Gln
    3995                4000                4005

Ala Ser Tyr Ala Leu Ser Pro Ala Gln Thr Arg Leu Trp Val Gln
    4010                4015                4020

Asp Arg Leu His Ala Ala Gln Ala Glu Gly Pro Leu Pro Thr Ser
    4025                4030                4035

Leu Leu Phe Glu Gly Val Leu Asp Val Asp Ala Leu Val Arg Ala
    4040                4045                4050

Phe Arg Ala Leu Ser Glu Arg His Glu Ile Leu Arg Thr Arg Phe
    4055                4060                4065

Val Leu Glu Gly Asn Gln Pro Val Gln His Val Leu Pro Pro Gly
    4070                4075                4080

Glu Ala Ala Phe Pro Val Glu Ile Val Asp Leu Gln Asp Ala Glu
    4085                4090                4095

Asp Arg Asp Ala Gln Ala Ala Ile Gln Ala Ser Glu Arg Leu
    4100                4105                4110

Val Pro Met Asp Leu Ala Thr Gly Pro Leu Phe Arg Val Lys Leu
    4115                4120                4125

Leu Arg Leu Ser Glu Val Arg His Val Cys Leu Cys Thr Met His
    4130                4135                4140
```

His Ile Val Ser Asp Gly Trp Ser Thr Glu Val Leu Leu Asp Asp
    4145                4150                4155

Leu Ser Ala Leu Tyr Asp Ala Phe Val Gln Arg Arg Asp Asp Pro
    4160                4165                4170

Leu Pro Ala Leu Pro Ile Gln Tyr Lys Asp Tyr Ala Gly Trp Leu
    4175                4180                4185

Asn Arg Leu Leu Ala Gly Pro Asp Gly Ala Arg Met Lys Asp Tyr
    4190                4195                4200

Trp Leu Thr Lys Leu Gly Gly Leu Arg Ala Leu Glu Leu Pro
    4205                4210                4215

Gly Asp Val Glu Gln Pro Ala Ala Pro Ser Trp Lys Ser Trp Arg
    4220                4225                4230

Phe Asp Leu Pro Ala Ala Glu Thr Ala Ala Leu Glu Ser Leu Gly
    4235                4240                4245

Lys Arg His Gly Ala Thr Leu Phe Ile Ala Leu Leu Ser Ala Ile
    4250                4255                4260

Lys Ala Leu Phe Tyr Arg Arg Ser Gly Gln Glu Asp Ile Val Val
    4265                4270                4275

Gly Thr Pro Val Ala Gly Arg Glu Leu Pro Glu Leu Glu Ser Gln
    4280                4285                4290

Val Gly Pro Tyr Leu Asn Val Leu Ala Leu Arg Asp Arg Val Ala
    4295                4300                4305

Gly Asp Asp Arg Phe Asp Thr Leu Leu Thr Arg Val Arg Asp Thr
    4310                4315                4320

Thr Leu Glu Ala Phe Ser His Pro Leu Tyr Pro Leu Asp Arg Leu
    4325                4330                4335

Leu Asp Glu Leu His Ile Lys Arg Val Ala Gly Arg Asn Pro Leu
    4340                4345                4350

Phe Asp Ile Gly Leu Thr Leu Gln Asn Gln Arg His Gly Pro Val
    4355                4360                4365

Asp Arg Tyr Ala Gly Gln Val His Ile Ala Glu Leu Pro Asp His
    4370                4375                4380

Asp Pro Gln Arg Ala Asp Thr Glu Ala Ala Thr Asp Phe Trp Phe
    4385                4390                4395

Leu Ala Glu Pro His Ala Glu Gly Leu Ala Ile Arg Val Val Tyr
    4400                4405                4410

His Ala Gly Arg Phe Ser Glu Ala Leu Val Gln Gly Leu Ala Asn
    4415                4420                4425

Glu Leu Thr Ser Val Ile Gly Glu Val Leu Ala Asn Pro Gly Val
    4430                4435                4440

Arg Ile Arg Asn Leu Thr Leu Gly Gln Arg Ala Leu His Ala Glu
    4445                4450                4455

Ala Arg Gln Pro Thr Val Glu Leu Ser Ala Phe
    4460                4465

<210> SEQ ID NO 16
<211> LENGTH: 1107
<212> TYPE: PRT
<213> ORGANISM: Burkholderia contaminans
<220> FEATURE:
<221> NAME/KEY: MISC_FEATURE
<222> LOCATION: (1)..(1107)
<223> OTHER INFORMATION: putative short chain dehydrogenase/reductase
      SDR

<400> SEQUENCE: 16

```
Met Lys Phe Gly Leu Met Phe Ala Ser Ser Glu Glu Ala Leu Ser
1               5                   10                  15

Gly Asn Lys Tyr Gln Leu Val Met Glu Ser Ala Arg Phe Ala Asp Ala
                20                  25                  30

Asn Gly Phe Ser Ser Val Trp Val Pro Glu Arg His Phe Thr Glu Phe
            35                  40                  45

Gly Ser Leu Tyr Pro Asn Pro Ala Val Leu His Ala Ala Leu Ala Ala
        50                  55                  60

Ala Thr Gln Arg Val Lys Leu Val Ala Gly Ser Val Val Ala Ala Leu
65                  70                  75                  80

His Asn Pro Ile Arg Ile Ala Glu Glu Trp Ser Met Val Asp Asn Leu
                85                  90                  95

Ser Asn Gly Arg Val Gly Val Ser Phe Ala Ser Gly Trp Asn Pro Asp
                100                 105                 110

Asp Phe Val Phe Ala Pro Asp Lys Tyr Ala Thr Arg Gln Asp Asp Met
            115                 120                 125

Leu Thr Thr Met Arg Ala Val Gln His Leu Trp Arg Gly Gly Thr Leu
    130                 135                 140

Asp Ala Thr Asn Gly Val Gly Lys Pro Val Arg Leu Arg Val Tyr Pro
145                 150                 155                 160

Thr Pro Val Gln Pro Glu Leu Pro Val Trp Val Thr Ala Ala Ser Asn
                165                 170                 175

Pro Gln Thr Phe Val Arg Ala Gly Glu Ala Gly Ala Asn Leu Leu Thr
                180                 185                 190

His Val Leu Asp Gln Asp Arg Asp Gln Leu Ala His Lys Ile Ala Leu
                195                 200                 205

Tyr Arg Glu Ala Arg Ala Lys His Gly Phe Asp Pro Ala Ala Gly Thr
210                 215                 220

Val Ser Val Met Leu His Thr Phe Val Gly Asp Asp Ala Ala Gln Ala
225                 230                 235                 240

Arg Glu Gln Ala Arg Val Pro Phe Cys Asn Tyr Ile Arg Ser Asn Ile
                245                 250                 255

Gly Leu Leu Asn Gly Leu Ala Gln Ser Arg Gly Gln Ser Val Asp Val
                260                 265                 270

Arg Ala Met Gly Ala Arg Glu Leu Asp Glu Phe Val Glu Phe Leu Tyr
                275                 280                 285

Glu Arg Phe Ala Gln Ser Arg Gly Leu Ile Gly Thr Pro Glu Thr Cys
                290                 295                 300

Val Glu Leu Val Arg Asp Leu Glu Ser Ile Gly Val Asp Glu Val Ala
305                 310                 315                 320

Cys Leu Leu Asp Phe Gly Pro Pro Val Glu Arg Ile Leu Gly Asn Leu
                325                 330                 335

Pro Gln Leu Arg Arg Leu Arg Glu Met Cys Ala Pro Arg Arg Ser Ala
                340                 345                 350

Ala Pro Thr Arg Phe Asp Ala Ala Glu Val Gln Ala Arg Cys Thr Glu
                355                 360                 365

Thr Thr Ser Gly Ala Asp Phe Asn Gly Glu Ile Arg Gln His Gly Val
                370                 375                 380

Gln Ile Asp Gly Val Phe Asp Ala Ile Arg Gln Ile Trp Arg Thr Thr
385                 390                 395                 400

Gly Glu Ala Leu Gly Lys Ile Ser Leu Pro Ala Asp Ala Leu Ala Ser
                405                 410                 415
```

Ser Pro Tyr Gln Val His Pro Ala Phe Leu Asp Ala Cys Ser Arg Val
            420                 425                 430

Leu Ala Ala Ile Asp Pro Asp Ala Leu Glu Ser Gly Asp Leu Tyr
        435                 440                 445

Leu Pro Ser Ser Ile Gly Ala Val Arg Val His Gln Pro Pro Ala Ser
        450                 455                 460

Thr Glu Ala Trp Ser His Ala Thr Leu Arg Thr Pro Ile Gly Gln Gly
465                 470                 475                 480

Ala Leu Glu Gly Asp Ile Arg Val His Asp Leu Ala Gly Arg Leu Leu
                485                 490                 495

Ile Glu Ile Asp Ala Leu Arg Leu Gln Gln Val Arg Ala Ala Arg Ala
            500                 505                 510

Val Glu Arg His Asp Phe Ala Ala Leu Leu Tyr Gln Arg Val Trp Arg
            515                 520                 525

Pro Ser Asn Val Asp Ala Ala Thr Gly Gly Ser Ala His Gly Glu Trp
        530                 535                 540

Leu Ile Leu Ala Asp Arg Gly Val Gly Ala Gln Leu Ser Ala Leu
545                 550                 555                 560

Leu Glu Ala His Gly Asp Thr Cys Thr Leu Arg Phe Ala Asp Ala Thr
                565                 570                 575

Pro Glu Leu Pro Ala Ala Asp Arg Pro Leu Lys Gly Val Ile His Leu
            580                 585                 590

Trp Ser Leu Asp Leu Ala Pro Ser Asp Ile Ala Ala Arg Arg Ala
        595                 600                 605

Ser Ala Ser Val Leu His Leu Val Arg Ala Leu Ala Ser Arg Ala Pro
610                 615                 620

Ser Ala Arg Gln Ala Arg Leu Trp Leu Val Thr Ser Gly Ala Met Asn
625                 630                 635                 640

Val Leu Asp Gly Glu Ser Ile Ala Val Ala Gln Ala Pro Leu Trp Gly
                645                 650                 655

Leu Gly Arg Ala Ile Ala Val Glu His Ala Ala Leu Trp Gly Gly Leu
                660                 665                 670

Val Asp Leu Asp Pro Glu Gln Pro Ser Ala Ala Asp Ile Met Gln Ala
        675                 680                 685

Val Gln Ala Gly Gly Arg Glu Asp Met Ile Ala Phe Arg Arg Asp Gln
        690                 695                 700

Arg Tyr Val Ala Arg Ile Ala Arg Asp Asn Arg Glu Tyr Val Ser His
705                 710                 715                 720

Arg Pro Ile Arg Phe His Gly Asp Ala Thr Tyr Leu Val Thr Gly Gly
                725                 730                 735

Leu Gly Gly Leu Gly Leu Arg Leu Ala Ser Trp Leu Ala Asp Asn Gly
            740                 745                 750

Ala Gly Lys Ile Val Leu Leu Gly Arg Gly Glu Pro Ser Ala Ala Ala
        755                 760                 765

Gly Lys Ile Leu Arg Thr Leu Asp Ala Arg Phe Ile Arg Ala Asp Leu
        770                 775                 780

Ser Arg Arg Glu Asp Val Gly Gln Ala Leu Gly Glu Ile Ala His Ser
785                 790                 795                 800

Met Pro Pro Leu Lys Gly Ile Phe His Leu Ala Gly Ala Leu Asp Asp
                805                 810                 815

Ala Leu Leu Thr Arg Gln Asp Asp Phe Phe His Arg Ala Gly Ser
        820                 825                 830

Gly Lys Ala Asp Gly Ala Trp Tyr Leu His Glu Leu Thr Ala Gly Leu

-continued

```
                835                 840                 845
Pro Leu Asp His Phe Val Leu Phe Ser Ser Met Ala Ala Leu Ile Thr
    850                 855                 860
Met Pro Gly Gln Gly Asn Tyr Ala Ala Ala Asn Ser Phe Leu Asp Ala
865                 870                 875                 880
Leu Ala Gln His Arg Arg Ala Gln Gly Lys Pro Gly Leu Ser Val Asn
                885                 890                 895
Trp Gly Pro Trp Ala Glu Ile Gly His Ala Ala Thr Asp Tyr Gly Arg
                900                 905                 910
Arg Ala His Glu Gln Leu Gly Ala Leu Gly Val Gly Thr Leu Pro Pro
                915                 920                 925
Glu Leu Ala Ile Ala Thr Leu Glu Arg Leu Met Ala Ser Gly Val Ala
                930                 935                 940
Gln Ser Gly Val Ala Arg Ile Asp Trp Pro Thr Leu Phe Arg Val Asp
945                 950                 955                 960
Ala Pro Ala Ala Gly Ser Ala Leu Phe Ser Glu Leu Thr Gln Pro Ala
                965                 970                 975
Ala Gln Pro Ala Gln Gln Glu Thr Ala Leu Leu Arg Gln Leu His Ala
                980                 985                 990
Cys Ala Pro Arg Glu Arg Val Glu Arg Ile Thr Asp Thr Leu Ala Ala
                995                 1000                1005
Met Leu Ala Glu Thr Leu Arg Leu Ser Gly Pro Asp Ala Ile Ala
    1010                1015                1020
Pro Glu Gln Ser Leu Leu Asp Leu Gly Leu Asp Ser Leu Val Ala
    1025                1030                1035
Leu Glu Leu Thr Asp Arg Leu Thr Lys Val Phe Gly Arg Pro Phe
    1040                1045                1050
Arg Ala Thr Leu Phe Phe Ser Tyr Pro Asn Leu Gln Thr Leu Ala
    1055                1060                1065
Gln Tyr Val Leu Asn Glu Leu Ser Pro Ser Leu Pro Ala Pro Val
    1070                1075                1080
Val Asp Glu Ala Ser Asp Asp Leu Asp Glu Asp Leu Ser Glu
    1085                1090                1095
Leu Ile Ala Gln Glu Ile Gly Ala Gln
    1100                1105
```

<210> SEQ ID NO 17
<211> LENGTH: 1475
<212> TYPE: PRT
<213> ORGANISM: Burkholderia contaminans
<220> FEATURE:
<221> NAME/KEY: MISC_FEATURE
<222> LOCATION: (1)..(1475)
<223> OTHER INFORMATION: putative beta-ketoacyl synthetase

<400> SEQUENCE: 17

```
Met Leu Pro Asp Thr Lys Phe Arg Thr Val Thr Glu Ile Leu Leu Phe
1               5                   10                  15
Arg Gly Lys Val Glu Pro Glu Lys Thr Ala Phe Ile Phe Leu Glu Asn
                20                  25                  30
Gly Glu Ala Glu Leu Thr Arg Leu Thr Phe Gly Asp Leu Asp Lys Arg
            35                  40                  45
Ala Arg Gly Ile Ala Ala Arg Leu Gln Ala Ile Ala Gln Pro Gly Asp
        50                  55                  60
Arg Val Leu Leu Val Tyr Pro Pro Gly Leu Glu Phe Ile Cys Ala Trp
65                  70                  75                  80
```

```
Val Gly Cys Leu Tyr Ala Gly Leu Ile Gly Val Pro Ala Tyr Pro Pro
                85                  90                  95

Arg Arg His Arg Pro Ala Asp Arg Leu Lys Ala Ile Val Ala Asp Ala
                100                 105                 110

Thr Pro Val Val Ala Leu Thr Asp Ala Ala Thr Leu Asp Gly Ile Ala
                115                 120                 125

His His Ala Asp Gly Tyr Ser Asp Thr Leu Glu Leu Lys Ile Leu Ala
        130                 135                 140

Thr Asp Gln Arg Phe Asp Ala Pro Ala Glu Gln Trp Arg Ala Pro Asp
145                 150                 155                 160

Ile Thr Pro Gln Thr Leu Ala Leu Leu Gln Tyr Thr Ser Gly Ser Thr
                165                 170                 175

Gly Thr Pro Lys Gly Val Met Ile Ser His Ala Asn Ile Leu Ser Asn
                180                 185                 190

Met Ala Val Ile Ala Glu Ala Ser Asp Ala Asp Ala Ser Thr Val Phe
                195                 200                 205

Val Ser Trp Leu Pro Val Phe His Asp Met Gly Phe Phe Gly Lys Val
        210                 215                 220

Leu Leu Pro Ile Tyr Leu Gly Val Leu Ser Val Leu Met Ala Pro Ala
225                 230                 235                 240

Ala Phe Val Gln Lys Pro Val Arg Trp Leu Gln Ala Ile Thr Lys Tyr
                245                 250                 255

Arg Gly Thr His Cys Ala Ala Pro Asp Phe Ala Tyr Asp Leu Cys Ala
                260                 265                 270

Arg Lys Ile Ala Asp Glu Ala Arg Ala Gln Leu Asp Leu Ser Ser Trp
        275                 280                 285

Arg Val Ala Phe Asn Gly Ala Glu Pro Val Arg Ala Glu Ser Val Ala
        290                 295                 300

Arg Phe Ser Arg Ala Phe Ala Ala Cys Gly Phe His Ala His Thr Met
305                 310                 315                 320

Arg Pro Val Tyr Gly Met Ala Glu Ala Thr Leu Phe Ile Ser Gly Gln
                325                 330                 335

Pro Ala Arg Ser Leu Pro Arg Val Ala Asp Tyr Asp Ala Asp Ala Leu
                340                 345                 350

Ala Gln Gly Val Ala Thr Arg Asn Asp Ser Gly Lys Arg His Ala Leu
        355                 360                 365

Val Ser Cys Gly Arg Thr Trp Ala Glu His Arg Val Arg Ile Val Asn
        370                 375                 380

Pro Asp Thr Gly Glu Arg Cys Ala Pro Gly Arg Ile Gly Glu Ile Trp
385                 390                 395                 400

Leu Thr Gly Pro Ser Val Gly Val Gly Tyr Trp Asn Arg Ile Asp Glu
                405                 410                 415

Thr Glu Arg Thr Phe Arg Ala Lys Leu Asp Gly Asp Ala Arg Tyr
                420                 425                 430

Leu Arg Thr Gly Asp Leu Gly Phe Val Asp Gly Glu Asp Leu Phe Val
        435                 440                 445

Thr Gly Arg Leu Lys Asp Leu Ile Ile Val Ala Gly Arg Asn His Tyr
        450                 455                 460

Pro Gln Asp Leu Glu Gln Ser Ala Glu Gly Ser His Pro Ala Leu Ala
465                 470                 475                 480

Pro Asn Ala Ser Ala Ala Phe Ser Ile His Val Asp Asn Val Glu Arg
                485                 490                 495
```

-continued

```
Val Val Val Ala Cys Glu Val Arg Arg Glu Ala Leu Asn Thr Leu Asp
            500                 505                 510
Ala Glu Ala Val Ala Ala Glu Ile Arg His Thr Leu Ala Glu Val His
        515                 520                 525
Asp Val Asp Leu Tyr Ala Ala Val Leu Leu Lys Pro Ala Thr Ile Leu
        530                 535                 540
Arg Thr Ser Ser Gly Lys Ile Gln Arg Ser Arg Ile Arg Gln Ala Phe
545                 550                 555                 560
Leu Asp Glu Gln Gly Leu Ala Ile Ala Gly Trp Arg Arg Ala Phe
                565                 570                 575
Ser Ala Pro Pro Ala Pro Pro Gln Thr Ala Glu Pro Arg Asp Thr Gln
            580                 585                 590
Ala Leu Val Gln Trp Cys Ile Glu Arg Val Ser Arg Leu Ser Gly Ile
        595                 600                 605
Ala Ser Gly Lys Ile Asp Pro Asp Ala Pro Phe Ser Val His Gly Leu
        610                 615                 620
Asp Ser Lys Asp Ala Ile Met Leu Ser Gly Leu Gln Asp Trp Leu
625                 630                 635                 640
Gly Arg Pro Val Ser Pro Thr Val Val Tyr Asp Phe Pro Ser Ile Ser
            645                 650                 655
Leu Leu Ala Arg His Leu Ser Gly Thr Gly Ser Ala Met Pro Asp Gln
            660                 665                 670
Ala Pro Gly Ser Ala Glu Ala Arg Ala Asp Ile Ala Ile Val Gly Met
        675                 680                 685
Gly Cys Arg Phe Pro Gly Ala Gly Asn Pro Asp Ala Phe Trp Gln Leu
        690                 695                 700
Leu Leu Glu Gly Arg Asp Ala Val Gly Ala Ala Thr Gln Arg Ala Ala
705                 710                 715                 720
Asp Leu Pro Leu Ala Gly Leu Leu Asp Gln Val Asp Gln Phe Asp Ala
            725                 730                 735
Ala Phe Phe Gly Ile Ser Ala Arg Glu Ala Glu Ser Met Asp Pro Gln
            740                 745                 750
Gln Arg Leu Leu Leu Glu Val Ala Trp Glu Thr Leu Glu His Ala Gly
        755                 760                 765
Ile Ala Pro Arg Ser Leu Ala Gly Gly Arg Thr Ala Val Ile Val Gly
        770                 775                 780
Ile Ser Asn Ser Asp Tyr Ile Arg Leu Ala Gln Asp Glu Val Ala Asp
785                 790                 795                 800
Val Gly Pro Tyr Val Ala Thr Gly Asn Ala Leu Ser Val Ala Ala Asn
            805                 810                 815
Arg Ile Ser Tyr Ala Leu Asp Leu Arg Gly Pro Ser Trp Ala Val Asp
            820                 825                 830
Thr Ala Cys Ser Ser Ser Leu Val Ala Val His Gln Ala Cys Arg Ala
        835                 840                 845
Leu Gln Arg Gly Glu Ser Asp Ala Ala Leu Ala Gly Gly Val Asn Leu
        850                 855                 860
Ile Leu Ala Pro Gln Leu Ser Ala Ser Phe Thr Gln Ala Gly Met Leu
865                 870                 875                 880
Ser Pro Asp Gly Arg Cys Lys Ala Phe Asp Ala Ala Ala Asn Gly Tyr
            885                 890                 895
Val Arg Gly Glu Gly Val Gly Met Val Leu Leu Lys Arg Leu Asp Asp
            900                 905                 910
Ala Leu Glu Asn Gly Asp Thr Val Phe Ala Val Ile Arg Gly Ser Ala
```

-continued

```
            915                 920                 925
Val Asn Gln Asp Gly Arg Ser Asn Gly Leu Thr Ala Pro Asn Gly Pro
            930                 935                 940

Ala Gln Gln Ala Val Ile His Gly Ala Leu Arg Asp Ala Gly Val Arg
945                 950                 955                 960

Ala Gln Asp Ile Gly Phe Val Glu Thr His Gly Thr Gly Thr Pro Leu
                965                 970                 975

Gly Asp Pro Ile Glu Leu Asn Ser Leu Ala Ala Val Leu Asn Glu Ser
            980                 985                 990

Arg Arg Pro Asp Asp Leu Cys Trp Ile Gly Ser Val Lys Thr Asn Ile
            995                 1000                1005

Gly His Leu Glu Ser Ala Ala Gly Ile Ala Ser Leu Ile Lys Thr
            1010                1015                1020

Ala Leu Ala Leu His His Arg Ala Ile Pro Pro Asn Leu His Phe
            1025                1030                1035

Arg Ser Ile Asn Pro Gln Ile Ala Leu Asp Gly Thr Pro Phe Arg
            1040                1045                1050

Ile Pro Arg Gln Val Thr Pro Trp His Ser Glu His Gly Pro Arg
            1055                1060                1065

Leu Ala Gly Val Ser Ser Phe Gly Phe Gly Gly Thr Asn Ala His
            1070                1075                1080

Leu Ile Leu Ser Glu Ala Pro Gly Leu Pro Glu Ile Glu Ala Glu
            1085                1090                1095

Pro Val Ala Pro Ala Ala Arg Val Val Thr Leu Ser Ala Arg Thr
            1100                1105                1110

Pro Asp Ala Leu Gln Ala Leu Ala Ala Ser Tyr Ala Ala Tyr Leu
            1115                1120                1125

Asp Ala His Pro Glu Ala Gly Val Arg Asp Val Ala Phe Thr Ala
            1130                1135                1140

Asn Thr Gly Arg Thr His Phe Thr Gln Arg Ala Ala Ile Val Ala
            1145                1150                1155

Pro Ser Arg Asp Ser Leu Arg Ala Gln Leu Asp Ser Val Ser Ser
            1160                1165                1170

Gly Glu Pro Ala Glu Thr Pro Pro Ala Val Thr Phe His Phe Cys
            1175                1180                1185

Ala Asp Asp Gly Ala Ser Ala Asp Ala Val Arg Gln Leu Arg Ala
            1190                1195                1200

Ala Ser Pro Ala Phe Asp Ala Leu Met Gln Arg Gln Ser Asp Ala
            1205                1210                1215

Ser Gly Ala Pro Ala Leu Ala Pro Asp Glu Ala Gly Phe Thr Arg
            1220                1225                1230

Phe Gln Arg Ala Leu Ala Gln Leu Trp Met Ser Phe Gly Ile Ala
            1235                1240                1245

Pro Asp Ala Val Ser Ser Thr Gly Asp Gly Gln Arg Ala Ala Ala
            1250                1255                1260

Ala Trp Ala Gly Val Pro Gln Ala Pro Asp Ser Gly Ala Ala Gly
            1265                1270                1275

His Pro Gly Ile Val Ile Asp Ile Gly Ala His Thr Ala Ala Trp
            1280                1285                1290

Asp Ala Ile Leu His Thr Leu Ala Ala Leu Tyr Val Arg Gly Ala
            1295                1300                1305

Ser Ile Asp Trp Asp Ala Val Glu Gln Gly Ala Pro His Arg Arg
            1310                1315                1320
```

```
Leu Ala Leu Pro Thr Tyr Pro Phe Glu Arg Arg Gly Phe Trp Ile
    1325                1330                1335

Arg Pro His Ala Arg Arg His Pro Leu Leu Gly Arg Leu Met Glu
    1340                1345                1350

Gln His Ala His Ala Pro Ala Thr Trp Ile Trp Gln Ser Arg Leu
    1355                1360                1365

Asp Ala Pro Ala Thr Asn Phe Leu Asp Gly His Arg Val Lys Gly
    1370                1375                1380

Ser Pro Val Leu Pro Tyr Ser Ala Phe Val Glu Met Ala Leu Ser
    1385                1390                1395

Ala Thr Ser Glu Ile Gly Ala Ala Gly His Thr Thr Leu Lys Asp
    1400                1405                1410

Leu Ala Leu His Ala Pro Leu Pro Leu His Pro His Glu Ser His
    1415                1420                1425

Thr Val Gln Thr Val Leu Ser Arg Arg Ser Trp Gly Pro Phe Ser
    1430                1435                1440

Phe Ala Val Tyr His Arg Ile Asp Asp Thr Arg Ala Ala Ala Thr
    1445                1450                1455

Trp Gln Met Cys Ala Ser Ala Glu Ile His Glu Ser Asp Arg Ser
    1460                1465                1470

His Ala
    1475

<210> SEQ ID NO 18
<211> LENGTH: 328
<212> TYPE: PRT
<213> ORGANISM: Burkholderia contaminans
<220> FEATURE:
<221> NAME/KEY: MISC_FEATURE
<222> LOCATION: (1)..(328)
<223> OTHER INFORMATION: putative taurine catabolism dioxygenase

<400> SEQUENCE: 18

Met Leu Gly Met Thr Glu Arg Lys Leu Leu Ala Glu Gly Ser Thr Pro
1               5                   10                  15

Trp Leu Leu Glu Pro Val Ser Asn Gly Arg Asp Leu Ala Gln Ala Val
                20                  25                  30

Asn Asp Asn Arg Ala Ala Leu Glu Ser Arg Leu Leu Glu His Gly Val
            35                  40                  45

Leu Leu Phe Arg Gly Phe Asp Val Ser Ser Val Gly Gly Phe Glu Ala
        50                  55                  60

Phe Ala Arg Ala Ile Ser Ala His Gln Ser Asp Tyr Val Tyr Arg Ser
65                  70                  75                  80

Thr Pro Arg Thr Ser Ile Gly Asn Gly Ile Phe Thr Ala Thr Glu Tyr
                85                  90                  95

Pro Pro Ser Glu Thr Ile Ala Leu His Cys Glu Asn Ala Tyr Gln Arg
            100                 105                 110

Ser Trp Pro Leu Arg Val Ala Phe Cys Cys Leu Thr Pro Ala Ala Thr
        115                 120                 125

Gly Gly Glu Thr Pro Ile Ala Asp Met Arg Gly Val Ser Arg Arg Ile
    130                 135                 140

Gly Pro Arg Ile Leu Asp His Phe Glu Ala Arg Gln Val Arg Tyr Val
145                 150                 155                 160

Arg His Tyr Arg Arg His Val Asp Ile Pro Trp Glu Thr Val Phe Gln
                165                 170                 175
```

```
Thr Ser Asp Arg Asn Gln Val Ala Ala Phe Cys Ala Asp Asn Gly Ile
            180                 185                 190

Ala Leu Glu Trp Leu Asp Asp Thr Leu Arg Thr Ala Gln Ile Asn
        195                 200                 205

Gln Gly Val Ala Tyr His Pro Val Thr Gly Glu Arg Val Phe Phe Asn
    210                 215                 220

Gln Ala His Leu Phe His Ile Ser Asn Leu Glu Ala Ser Leu Ala Ser
225                 230                 235                 240

Ser Ile Val Ser Leu Phe Gly Glu Asp Arg Ile Pro Arg Asn Ala Cys
                245                 250                 255

His Gly Asp Gly Ser Pro Phe Asp Leu Ala Asp Leu Glu Gln Ile Arg
            260                 265                 270

His Ala Phe Arg Glu Cys Ala Ile Thr Phe Pro Trp Gln Arg Gly Asp
        275                 280                 285

Val Leu Leu Val Asp Asn Met Arg Phe Ala His Gly Arg Asn Pro Phe
    290                 295                 300

Glu Gly Glu Arg Lys Val Val Ser Leu Leu Asp Pro Tyr Thr Pro
305                 310                 315                 320

Asp Ile Glu Gly Ile Ala Asp Arg
                325
```

<210> SEQ ID NO 19
<211> LENGTH: 456
<212> TYPE: PRT
<213> ORGANISM: Burkholderia contaminans
<220> FEATURE:
<221> NAME/KEY: MISC_FEATURE
<222> LOCATION: (1)..(456)
<223> OTHER INFORMATION: putative transaminase

<400> SEQUENCE: 19

```
Met Lys Arg Phe Ser Cys Ala Ser Val His Gln Ser Ala Leu Gln Ala
1               5                   10                  15

Gly Ser Ala Arg Met Glu Lys Leu Glu Tyr Leu Lys Gln Val Glu Ser
            20                  25                  30

Asn Ala Arg Thr Tyr Ala Thr Ser Phe Pro Arg Leu Phe Thr His Ala
        35                  40                  45

Lys Gly Ile Arg Val Arg Asp Ala Asp Gly Gln Glu Tyr Ile Asp Cys
    50                  55                  60

Leu Ser Asn Ala Gly Thr Leu Ala Leu Gly His Asn His Pro Glu Val
65                  70                  75                  80

Asn Glu Ala Val Met Arg Phe Leu Ser Ser Asp Gln Met Gln Gln Ala
                85                  90                  95

Leu Asp Leu Ala Thr Pro Ala Lys His Ala Phe Val Glu Gln Leu Phe
            100                 105                 110

Ser Leu Leu Pro Gly Lys Ile Ala Glu Ser Gly Lys Ile Gln Phe Cys
        115                 120                 125

Ser Pro Ser Gly Ala Asp Gly Val Glu Ala Ala Ile Lys Leu Thr Arg
    130                 135                 140

His Tyr Thr Gly Arg Pro Thr Ile Met Ala Phe His Gly Ala Tyr His
145                 150                 155                 160

Gly Met Thr Ser Gly Ala Leu Ala Ala Ser Gly Asn Leu Thr Pro Lys
                165                 170                 175

Ser Ala Gly Gly Asn Gly Arg Asp Val His Phe Leu Pro Tyr Pro Tyr
            180                 185                 190

Ala Phe Arg Cys Pro Phe Gly Thr Asp Gly Ser Ala Thr Asp Gln Leu
```

```
              195                 200                 205
Ser Ile Asn Tyr Ile Arg Thr Val Leu Ser Asp Pro Glu Ser Gly Ile
    210                 215                 220

Thr Lys Pro Ala Ala Ile Ile Val Glu Val Val Gln Gly Glu Gly Gly
225                 230                 235                 240

Cys Ile Pro Ala Pro Asp Thr Trp Leu Ile Glu Leu Arg Glu Leu Thr
                245                 250                 255

Leu Arg His Glu Ile Pro Leu Ile Val Asp Glu Val Gln Thr Gly Leu
            260                 265                 270

Gly Arg Thr Gly Ala Leu Phe Ala Ile Glu His Ser Gly Ile Arg Pro
        275                 280                 285

Asp Val Leu Val Leu Ser Lys Ala Phe Gly Gly Tyr Pro Leu Ser
    290                 295                 300

Val Val Val Tyr Asp Glu Arg Leu Asp Thr Trp Pro Pro Gly Ala His
305                 310                 315                 320

Ala Gly Thr Phe Arg Gly Asn Gln Ile Ala Met Val Ala Gly Leu Ser
                325                 330                 335

Thr Met Arg Ile Val Glu Arg Glu Asp Leu Ser Ala His Ala Asp Arg
            340                 345                 350

Val Gly Lys Leu Leu Val Ala Gly Leu Glu Leu Ala Glu Arg Phe
        355                 360                 365

Pro Cys Leu Gly Gln Ile Arg Gly Arg Gly Leu Met Ile Gly Ala Glu
    370                 375                 380

Val Val Val Pro Gly Thr His Gly Arg Ala Gly Pro Pro His Thr Glu
385                 390                 395                 400

Arg Ala Arg Ala Ile Lys Gln Asn Cys Leu Arg Asn Gly Leu Ile Val
                405                 410                 415

Glu Thr Gly Gly Arg Asn Gly Ala Val Leu Arg Phe Leu Pro Pro Leu
            420                 425                 430

Ile Val Ser Glu Ala Asp Ile His Asp Ile Leu Asn Arg Phe Glu His
        435                 440                 445

Ala Val Glu Thr Ala Cys Arg Ala
    450                 455

<210> SEQ ID NO 20
<211> LENGTH: 316
<212> TYPE: PRT
<213> ORGANISM: Burkholderia contaminans
<220> FEATURE:
<221> NAME/KEY: MISC_FEATURE
<222> LOCATION: (1)..(316)
<223> OTHER INFORMATION: putative epemerase/dehydratase

<400> SEQUENCE: 20

Met Gln Arg Asn Arg Lys Arg Ile Leu Val Thr Gly Gly Ala Gly Phe
1               5                   10                  15

Leu Gly Ser His Leu Cys Glu Arg Leu Val Glu Leu Gly His Asp Val
            20                  25                  30

Leu Cys Val Asp Asn Tyr Phe Thr Gly Thr Lys Gln Asn Val Ala Thr
        35                  40                  45

Leu Leu Gly Asn Pro Ser Phe Glu Ala Leu Arg His Asp Val Thr Phe
    50                  55                  60

Pro Leu Tyr Val Glu Val Asp Glu Ile Tyr Asn Leu Ala Cys Pro Ala
65                  70                  75                  80

Ser Pro Ile His Tyr Gln Phe Asp Pro Val Gln Thr Thr Lys Thr Ser
                85                  90                  95
```

```
Val Met Gly Ala Ile Asn Met Leu Gly Leu Ala Lys Arg Thr His Ala
                100                 105                 110

Arg Val Leu Gln Thr Ser Thr Ser Glu Val Tyr Gly Asp Pro Asp Val
                115                 120                 125

His Pro Gln Pro Glu Ser Tyr Arg Gly Asn Val Asn Pro Leu Gly Pro
                130                 135                 140

Arg Ala Cys Tyr Asp Glu Gly Lys Arg Cys Ala Glu Thr Leu Phe Phe
145                 150                 155                 160

Asp Tyr His Arg Gln Gln Asn Val Arg Ile Lys Val Val Arg Ile Phe
                165                 170                 175

Asn Thr Tyr Gly Pro Arg Met His Pro Asn Asp Gly Arg Val Val Ser
                180                 185                 190

Asn Phe Ile Val Gln Ala Leu Arg Gly Glu Asp Ile Thr Leu Tyr Gly
                195                 200                 205

Asp Gly Ser Gln Thr Arg Ala Phe Cys Tyr Val Asp Asp Met Val Asp
                210                 215                 220

Gly Leu Ile Arg Met Met Ala Thr Pro Ala Glu Leu Thr Gly Pro Ile
225                 230                 235                 240

Asn Leu Gly Asn Pro His Glu Ile Ala Val Ser Glu Leu Ala Gln Ile
                245                 250                 255

Ile Leu Arg Leu Thr Gly Ser Lys Ser Arg Leu Val Phe Arg Pro Leu
                260                 265                 270

Pro Lys Asp Asp Pro Thr Gln Arg Cys Pro Asp Ile Ser Leu Ala Arg
                275                 280                 285

Thr His Leu Asp Trp Glu Pro Thr Ile Gly Leu Glu Ala Gly Leu Gln
                290                 295                 300

Arg Thr Ile Asp Tyr Phe Cys Ser Thr Leu Ala Ala
305                 310                 315

<210> SEQ ID NO 21
<211> LENGTH: 239
<212> TYPE: PRT
<213> ORGANISM: Burkholderia contaminans
<220> FEATURE:
<221> NAME/KEY: MISC_FEATURE
<222> LOCATION: (1)..(239)
<223> OTHER INFORMATION: putative thioesterase

<400> SEQUENCE: 21

Met Arg Leu Ile Cys Phe Pro Tyr Ala Gly Gly Ser Ala Ala Val Tyr
1               5                   10                  15

Arg Thr Leu Gln Ala Ser Leu Pro Gly Ile Glu Val Cys Arg His Glu
                20                  25                  30

Leu Ala Gly Arg Gly Ser Arg Leu Ser Glu Pro Ala Val Arg Asp Met
                35                  40                  45

Ala Thr Leu Val Asp Thr Leu Leu Cys Asp Leu Asp Asp Cys Phe Asp
            50                  55                  60

Arg Pro Phe Ala Leu Leu Gly His Ser Met Gly Ala Ala Ile Ala Ala
65                  70                  75                  80

Glu Leu Ala Leu Arg Leu Pro Ala His Ala Arg Pro Asn Leu Arg His
                85                  90                  95

Leu Phe Val Ser Ala Arg Ala Ala Pro Gly Lys Glu Arg His Asp Arg
                100                 105                 110

Arg Met Gln Ala Leu Asp Asp Arg Ala Phe Ile Asp Ala Leu Arg Glu
                115                 120                 125
```

```
Met Gly Gly Thr Pro Lys Ala Val Leu Asp Asn Ser Glu Leu Met Ala
    130                 135                 140

Leu Leu Met Pro Ala Leu Arg Ala Asp Phe Thr Met Ile Glu Asn His
145                 150                 155                 160

Arg Pro Val Pro Gly Pro Arg Leu Ala Val Asp Ile Thr Ala Phe Ala
                165                 170                 175

Gly Arg Ala Asp Lys Glu Ile Pro Val Asp Ala Val Ala Gly Trp Gly
                180                 185                 190

Ala Ala Thr Thr Gly Arg Phe Asp Phe His Val Ile Glu Gly Asp His
                195                 200                 205

Phe Phe Leu Arg Asn Glu Met Arg Thr Met Ala Gly Ile Ile Ala Ala
    210                 215                 220

Arg Met Arg Arg Pro Glu His Ala Ala Ser Ser Ala Leu Gln Ala
225                 230                 235

<210> SEQ ID NO 22
<211> LENGTH: 95
<212> TYPE: PRT
<213> ORGANISM: Burkholderia contaminans
<220> FEATURE:
<221> NAME/KEY: MISC_FEATURE
<222> LOCATION: (1)..(95)
<223> OTHER INFORMATION: hypothetical protein

<400> SEQUENCE: 22

Met Gln His Arg Gln Lys Ala Val Pro Thr Gln Val Ala Asn Glu
1               5                   10                  15

Arg Val Ile Val Thr Glu Trp Arg Phe Ala Pro Gly Ala Glu Thr Gly
                20                  25                  30

Trp His Val His Arg His Asp Tyr Val Val Pro Gln Thr Asp Gly
                35                  40                  45

Gln Leu Leu Leu Glu Thr Ala Gln Gly Asn Arg Glu Ser Gln Leu His
            50                  55                  60

Ala Gly Arg Ser Tyr Ala Gly Leu Lys Gly Val Glu His Asn Val Val
65                  70                  75                  80

Asn Ala Thr Asp His Glu Val Val Phe Val Glu Val Glu Ile Leu
                85                  90                  95

<210> SEQ ID NO 23
<211> LENGTH: 58101
<212> TYPE: DNA
<213> ORGANISM: Burkholderia contaminans

<400> SEQUENCE: 23
aattcctgca gcacggtgcg cgaccagccc cagatgtccc cgctgagcgt gagtgcgaga    60
ccggccgtcg tgatggccag ctgcgtctgg ccgaacagcg cgtcaatgc gccttcgccg    120 ccgatcacga tccgcttgac gagatccgag atggactgcg agatcgaatc ggagaacgga   180
tagttgtacg gctgcgtgac ggcgcgcgac aggaacggct gctgggcgt cggcgtccag    240 accttgagcc acggcttggt cgtgaacggg aaccagatgg cttccacccg gcccgagccg    300
tcgagaaacg atgcgatcgt gcggcccgtc gtgccgggcg cggcgaacag ttcggaggcc    360
ggaatatcga cgtagctctg gcagcgtagc cgctggttcg gccctgccgt cagcgtgact    420
tcgacgacga gcgctcgccc gatgtgcgcg aggaacgcgc cgatctcggg atcgctgcgc    480
tcgaaccggc gcagcacgta ttgctgccgg gccggatcga acacgaccgc cgtgagcgcg    540
accacgagat tgctcagcga gccgtaggta tggcccggtt gcaaggtttc accggccgcg    600
```

```
ggcacggcgg tgccgtgtgc atcgatcgcg agcgcgccgc cgagcgtgat gtcgcccggt    660
gccggcgcgg caatcacgcc gaggccaacc tgctcgagcg tcgcgagcag cgactccagc    720
gagacgcccg tttgggcggt gacgcgcgcc ggacgcgccg acgtgtcgac ggagacggcc    780
gtcagcgact tcgtcgtatc gagcagcacg aggttcgcgg cgccggcgcc cgggtccagc    840
gtcagcggcg accagttgtg cgtgtagccg cgcgggcgta tccgatagcc gtttgcgcgc    900
gcccagttga cggttgcgac gacgtcgtcg gcggagcgcg gcgcggcggt ccatacgtcc    960
tgcacggcga tctcgccgct ccagttcagg aacgcctgct tgtaaagctg gatgtcggcc   1020
gggaagccgg gcggtgtctc gccggccgtt cgcgcgtgcg ccgcaacctg gtagagcggt   1080
gtccagccgg tgacgatgcc ggccgccgcg agcttcgcca tgtcggccag gaaggcgcga   1140
cgcggcgcag gttcgtctct gaagtcgtga ctcatggtgt gctccaattt ttcggaattg   1200
ttttgcagat tggaaagacg acaaatgacg cgttgagact cgtgtggcaa ttcgagcagg   1260
tgcgacgcgc gggaagtgtt gcgcgtgggt gggccaggat tgaaaaaaga cggtgcgttc   1320
ggcaatgcgc ggccgcacat catcacggac gtctaatagg aaatcggaaa accgcctggc   1380
gattgcttta attggccgtc ggccggttct gtcggcaagc agataggag attcgacgga    1440 atcgcgcgcg gcgaagcgct agccgtggcg atcgataaaa gatgatttca cgtgaatatt   1500
aatcttcatg tttcgatttt taaataaacc cggccgcagt tcaaggttga ttgacgatgc   1560
gtcatgcatt tcggtcgaaa gcgtagcaat ttatctatcg ggtgacaagc ggcggagttg   1620
acgaattccg agtcatttaa tatggaaatt ttatgacggg aaatggcttc gtccgttgtg   1680
ggtattttgc aacgcggctg ccggtgtcgc gccacgtggg cttggagcgc aaattatgct   1740
ttgccgtcgc gtatattgaa tcgattgttg agcgaatcga ataacgtcc ggaagacaat    1800 agctgaagcc gggtcgatga gcgggaggta gggtgaaatc cgataattcc tctctcgaat   1860
aacgctcctg gatgaaaatt cgtggtatgc gtcgcccggg tgattattac aaaagttcgt   1920
ggtaaacgga tgtcgattta tcggtgtatt cataataatg ccaatgagcg gctcgcgaat   1980
tgattgattt ccggttcgtg aaagatgtgt tttaaaaaaa tagatgtcgg gctgactgca   2040
aatgtctgaa tcgtcgctat catacgcggc tgggatatac atggatcaaa ttcaatggaa   2100
agaatcgttt cgcttttga tcgcgatttt tctttgaatt cgccgggaac gcgcccgctt    2160
cgagccggcg ccgggttttc cgattcaggt ttcaggcacg tccggcggcg gcgcgttttc   2220
atccggcaac gcgaatcggc cgaaatggac gtttcagcct tttgcggctt cgcgagtcgc   2280
ccgcatcggg ctgaactggg aacggcacgc cgtcgtctcg catgagccgg acgcatcggc   2340
gcgcgctggc ggcggcgcgt tgcccgcctg aaaaaggcgc gcgacgcagc gcgacccgac   2400
gcgcgccgcg caaaccgtgc cggttcgccg gcgcttgcgt tgtgccaggt cctcaagcac   2460
gcacaacaag gagagtcaga tgttcgcgaa gctcgggaag gtgatttcga gcgcaggcag   2520
tgagcggttc gcatccgaca tgcatgcatt gctggtcgag tcgattccgc tcacgatcac   2580
ccggatgact gaatggacgc tcgacgagcc ggcgggcgaa gtcgtccgcg tgcaatcgct   2640
cggcgcggac ggcgcgccgg gcgatgacgg gcgcggcgcg ccggccgcgc acggcgagcg   2700
ggaaccggca gcgcatccgc cgttgaaccg gatcctggcg gcctgcgacc ggcagctcat   2760
tcacatcaat ccgctgatgc ggcgcggcaa tggcggcgaa gtcgcgccgt cgcgcgggcc   2820
gggcggcgga tttcagtgcc atctcgtgtc gggcaaggcg aatcgccgtt acgtgatctc   2880
gctgcatcgc acggcatcgc atcgcgactt ctcgttgcgt gagatgtcgt tcctgaagaa   2940
tttcgccgat acgctgctgc cgctcgtcga gtggcatgcg tcgacgtgcc ggcacggcga   3000
```

```
gcgggaaggt gcgacggcac ccggtgcgac ggcaggcatg cccggcgtcg aggcgctgcg   3060
ccacgagttc gaatcgcggc tcgcgcgcgc gagggtcgtg ttgtcggcgc gtgaaaacga   3120
agtgtgcctc ggcctgctcg cgggcaagat gctgcgcgaa atggccggcg agctcggtgt   3180
gaaggagagc acgatcgaga cgtacatcaa gcgagccgcg gtgaagctcg gcatcagcgg   3240
ccggcacggg ctcacgaaat ggatgatcga cgattccgta ccgtgcgcgt cggcggcgtg   3300
acaccgtcac gccatcacgc cgcggacgcg cgacgcatgc cgcccgggcat gcgcgttcgg   3360
gccgcgggcc ctcaggttcc gaggcgcggc gacgcgtagt cgcgccgcat gcttctcatg   3420
tcgcccccag cagcttccgt cgcggccccg gccgtctcgt cgagcatcca gcgcgtcagg   3480
ccatgacgcc cgctgaagcc cagcttgacg gccgcccgct tcaggtaggt ttcgacggtg   3540
cttcgcgca gcgcgaagcg catggcgatg gcaggcaccg tgtcaccggc caggagtgcc   3600
gtgcatgcct cgatctcgcg cgtcgacagc ttgacgcccg cttgctgcag gcgatcggcg   3660
aatcgccgcg ccacgcgctc ccggcccgat tgcgtcgccg gcggcgcggc ggtcgtcaca   3720
cgagcggccg gcggagccga atcgagcgcc gcgacatggc tctcgacgat cggaaacagc   3780
acgtgcgaga gttccttgag gaaggtccgc tcctgcggcg agaaatcgtc gaacgtacag   3840
gtgcgataca acgagatcac gtaacagtgg ccccgcttgc gggtcacgag gtggaattgc   3900
gcgtagcgcg gcgacacgat cgccgcctgc atgaggatga agcggtcgag ctgcgcgtgg   3960
atcgggccgt ggccggcgag cgtgtcgtcg acgtgcaggg ggctcgtgcc cgggcgcggc   4020
ggcatctgcg gcccgcaaca gacagcggcc gcgccggtct tcgcgagcgc cgcgccgacc   4080
gcgccgaggc tgcgcacctc gggagggccg tccggcacgt cgtcgatcgc aagctccgaa   4140
atgcggatct cgtcgacggg gaccgccgcg gcgatcaggt tgtacatcat ccggggaaaa   4200
cgtcggctcc cgctgctcga gatcgcttcg ccgacgtgtg cgaacaatct gctgaactcc   4260
atgaagggat tcctgatgag acgttgaagc tgcgcttgtg cgcatgaatg ccgacatgat   4320
ttaaacaccc ggttgcgaac gcgtctgtaa cggattgccg ggacagacgc aacattgccg   4380
gccgtcgaag ccggtacggc gcacggcgac cgttgcgccc gtctgcgacg gatggcgcgc   4440
accttgtccg agtccggatc gctgctcatc cggctgcctc ggcccggacg gcacacatgg   4500
ccgtatcgga gaagatgcgg ccgctatcca ggcgaatgac ccgatccgcc agcttgaagt   4560
actgatcgtc gtgggtgatg atgacaacgc atttcccgcg tgatttcaga tcggaacca   4620
gcacttcata ggaaaatcgc ttgaacaccg gatcctgatc ggcggcccat tcgtccagga   4680
tataaatcgg acgatcctcg atgtacgcgc aaagcagcgc caagcgcttg cgttgccctg   4740
tcgataacgc gcgggtggtc gagtaggtcc ggccggaaat ctcgatcttg tccgccagtt   4800
tcagggtggc gaggtatttc cggcaagct cgatgctttc attgccccga tccggtccga   4860
tgatgcgatt gaacaaatgg aaatcggtga agacggcgga aaacaggttt cggtagcgtt   4920
ccctcgcagc gtcgtcaacg acttttccgt cgagggaaat cgtgccgccg gtaggcgcat   4980
agaggccgct gaggaccttg ccaagcgtgc tcttgccgct gccgtttccg ccgatcacgt   5040
agacgagttc tccggcatga atcgtcatgt cgatggggcc gagcacgaag tcgaccgatg   5100
cttcattgtc acggtagttc atcgtcacgt cttcaactc gatgaccttc catgacttgg   5160
ccgacagggt ttccacgttg cccgcagggc gcggttcctc gtgtgaggcc tgcgtgtcgt   5220
cgatcagaaa gccgaattcc gccagccggg cgagcgcggt cttgccttcg gccaccaccg   5280
gcagaacatt gatcagcatg gtcaagggcc ccatcatgta gagcacggcc agaatgctcg   5340
```

```
ccgtgagtac ggagggatcc acgacgccca gagaaggtac gccgaacagc aggcatccga   5400
gcaggaccgc tacggtgatc tggccgatgc tgtcgccgct catgaaccag aagcgttcta   5460
tgtaattgaa tcccgccacg cgcttcgacg acaattcgat cgcggcgcgg gtaaaccagc   5520
gtcgcctggc ccggttgagc ttgagctcct tgatgccgaa cacgaggcca tgtgtgtatt   5580
cgttgaactg gacgaattca tcgcgaaccc gctccgtaaa attgaccgcc ttccgataga   5640
aaaacagata aagcaccagg ccgacgaggg tcaggatgat cgtcgacgcg aacacgatcc   5700
acgagagata ggcgagatag gcgatgctgc agatcaggac gactgattga acgatgatcg   5760 tcggatggt  cagcagggtc tggctcagtt gcggaatgtc ctgtgtcagc atggtcagca   5820 cattggggc  gccgcgtctg tcgatttcat ccagcggggt tgccaggatc cgtttgcaca   5880
ggttgacgcg caacctcgtc atgactttca tgcaggcata ggagggcatc acggcggcgc   5940
agctcctgca gaccaccgcg acgacattca ccgcgatgaa cagcagcaac agcgtctggc   6000
gatcatcctg gtcgtgcagc acggtgctga tcaacccgac gcccgcgatc gacgcgatgc   6060
cgctgacgag gcccgtcacg accgtgccca gcgtcagcca gggatgactg cgccacatca   6120
gggtggcggc ggaatgccat ggcggcgatt tgctttgagc ggaatccatg agtggccaat   6180
aggtctcagt tgatcaggtg gctgagttcg acattgcttg ccgctgatct caacctcgac   6240
gaggtttcgt gcttgcccag gaacgtgatg ctttccacga ttcccagcgg cgaatcggaa   6300
aacaggatgc agcacttcag caggcgctgc gcacgctccc agccgacgcc gtccggtgaa   6360
tcggccacgc ttcgcaacgc ggcctcgacc gaggcggccg tccagtcttc gctccgtgcc   6420
agccccgact cgatctgccg aagaaattgc aggagcgtgc ggggattgct ttcgatgctg   6480
tacatgagga tgtaatcgat ccgcagtttc ttcgtgatca gcggaaaaat caggtcgatc   6540
acgccggcgc tcgattcgca tttcccatat gccagtgaaa tcgcgtcgcc gagcttgcag   6600
tcccggtgaa gcgcatccag cgcggccttg acgaacgccg cttcgaggtc aacggtggtg   6660
agttgcatga tgttcagtgg cctgtcgagt gttggatcgc ggcgagcacg ggcggcaggc   6720
gttaccagcc gtccggaatg ggcatggaat aggtcagcgg cttctccggc atcacttcgt   6780
ccatgatgtc ggagtagccg gactcctgtc cgaccagatt cggctcgaag cagtagcaat   6840
tgaacgtctg ctgcaggacg aggttgttgc ggtcgttgat cgccggcggg ttttcgttga   6900
tcgcgatgaa tgcgtcgtaa agcgagttcc tgacgacgta cgcgtgcgcg gtgagcgtct   6960
ccacggcctt gacgatgttc ggcgcgacgg gaatcggcgg cgtgaagtga tacgcgccca   7020
ggaacagcat gtgccagtcg tccggcactt cgcgcgatga actcgggaaag cgcgcggcga   7080 aatcggcgtc gaagaacgcg tcgtcctcga agatcaggac ttctctcgca ccggcggcct   7140
tcgcctgttt caccgcggcg agatggctca tcgtgcagcc gtagtcctgc gcacgcatat   7200
ggctcaacga ttccggcacg ctcaccagcc ttgcatcgac ggcaggcagc cgttccaccg   7260
tgaggatgtt ctgctctgcg aatttcgtt gcatcgcttc ccagcggtcg gggcgccggt    7320
ccaggttgat gcagaccttg cgggcaaaag tattgtcgat cgtcggcgtt gatttcatga   7380
gggcgttttt tccagaaacg aattgacatg gcggcgagg acaccggcat gcggatcgag    7440
cagcatggtc aggtggtcgc cggggacgtc cgtcaccgcg acgggtgcg  ccgagaagcg    7500 agaccatccc caggtcgcgt ccaggcgaag ctgcgcgatc tcggacgacg gcgcgtagtc   7560
gccgggatcg cgctcggtgc tgcggaacaa cgcgatcggc acgggcagcg gggtggcgtg   7620
cggcgcgtag tgcgacttga agttggcctg atagacgcgc aggtaggcgc gcaggcggtc   7680
ggacccggcg tccgcgaacc agctgccgcg gtcgccgatc cgttcgagga tcaggccggc   7740
```

```
ctggccgtcg ggatcgagat ggacgaggtc cgctcgcgtc acctgaaggt cggtcccgag    7800
gaaggtgccg atttcgtggg cgatcgcgac cagccattcg gtgtcgtccc agtcctgcca    7860
gtaagtggcg gccgagctgt cgatgggcgc ggacgcgtcg aagatcgcca gcaatttcac    7920
gtcggcgccc ttggcgacca gttgcctgct catttcgagc gccacgtgcg cgccgaacga    7980
gtggcccgcc aggtagtacg gacccgcgcc caccagcggc cagatgcgtt cgatatgacg    8040
ggccgcgatg tcttccacgc gggtgagcgg ctcgcacgcg ccgtcgaggc cgagcgcttc    8100
cagcccgtga atcgcgtgag cgccgctcag gtggttcgcg agcgggcgga agtagaccac    8160
gttcccgccg gcgcccggca gcaggaagag cggcgcggcg gggccgccgt cgcgaatcgg    8220
cacgagcccg ccggcgggcg cggacggttc tttcgcggcc agcgccgccg ccagtttctc    8280
gatcgtcgga ttctcgaaga gacaggaaat cggcagcctg cgatcgaacg ccttctcgac    8340
atgggccatc agctggatcg cgatgatcga gtggccgccc aggtcgaaat agttgtcgct    8400
gaccgcgatg tcgtctcttt tgaagatccg ccgccagatc tccagcaacg tgctttcgtc    8460
cgccgcatgc gcgacggcgc gcgccgccgc ggccgcaccg gcagcggctt cgatggccgg    8520 cccgccccg ctgcgcggcg cgctcggccg gccgtcggcg gccggcggat cggcgagctg    8580
gccggtcaac tggcccgggt tctcggcgaa tcgctcgagc aacgtgcgga gggtatcgag    8640
catctgccgc acgacctccg gcgcgatgcg gtgggcatcg tgcgaaatat ggaagccgat    8700
gcgctcgttc gggtgcacgg tcagggtcag cgggtagttc gattccgcga acgcgcgggt    8760
gtcgaggatc tcgatgtcgt ccggcccgag atcggggcg gcggcaaccg ggaagttctc    8820
gaagaccagc aggctgtcga acagactgtc gccggcgggc agttcgctcc acgactggat    8880
atcgaccagc gagctgtacg aatgcggctc catcgccgtc tgggctgcgt ggacctctgc    8940
cagccattcg atgaacgggc gctcgggcgc gatccgcagg cgcagcggca gcgtgttgat    9000
gaacagcccc acgatcgact cgacgccgtc gagcatcggc gggcgaccgg acacggtgac    9060
gccgaagacg acgtcgtccg ttccggcgtg gcgccgcagc accaacgccc agaccgcgcg    9120
gatcagcacg ttgagggtga cgcgatgcgt gcgcgtgagc gtttgcagcc gcgcggccag    9180
cgcctcgtcc agcaggaatt gctgggtccg gcgcttgtcc tgccgcgggg catcgccggt    9240
cgcctgccgg gccggactgg ccgcgaccgg cgtggcggcc ttgaagccgg ccagttcggc    9300
gcgccaccac gtttcgtcgg ccgagcgagg atgacgcgcg agccagtcga tgtacgcgcg    9360
gtatcccggc gccgacgccg cgaccgcggg catgccggtg cgggcgagcg acaggtagtc    9420
gtcgaacacc tccttcatca gggtcgcggt gctccagccg tcgaggatga tgtggtgcgc    9480
gctccagcag aagcgatggc gcgtgtccgt ttcctggatc agcgtgcagc ggaacaacgg    9540
cgcgcgctgc agatcgaagc cgcgccgccg gtcgtcggcg aggaacgcat cgaaatcctg    9600
cgcgcggcgg gacgcatcgc ggtgccgcca gtcaaggaac gtccatggca ggtcgaccgt    9660
gtgccgtacg gtctggacgg gatggtgcgc atcggcccac gcgaacgcgg tgcgcagcac    9720
ggcatggcgc gcgagcgcat ggcccacgc ctgccggagc gccggcacct ggagcgggcc    9780
gctgacgaca aagctgaact gctggaagta ggcggcagga tccaggtcgt acagcgaatg    9840
gaacaggatg ccctgttgca gcgacgagag cggatagctg tcctcgatat cgtccgctgc    9900
ggtgtcgggg accgacgccg cgaagtcgag caaccggtcc ctgaagtgcg cggccaggtt    9960
ctcgaccgtc tgccgccggt ggagccgctc gccgtagcgc cagtccacct ggagcttgcc   10020
gtcggcaacg gccgcgacga tctcgaaggc atgcgtgcgc tgcgaccgcc cggcgcgcag   10080
```

-continued

```
cgaaccgagg tcttcggccg ccgggcgcca gccatcggat tgccgcaata cggtatcgag    10140
ctgcccgtga tagttgaaga ggatatcggc cttcggcaac gcggcgagac tgtcgcgcac    10200
ggcggcgtcg gggctctggt agcggagcag cgaataaccg agaccgtcgg ccggaatccg    10260
gcgcagctgc tgccgtgcgg cacgcagcgc ttgctccggc gcgtgcatcg cgtcggcgtc    10320
gagcacgacg gggtagatgg acgtgaacca gcccaccgtc cgggtgaggt cgagcggcgc    10380
atccgacacg tggcggccgt gactctcgag atcgatccgc gtgcgggtgt tacccgtgac    10440
catgctgcag gcttgcgcga gcgcgacgag caggacgtcg ttgatgcggg tgtcgtaggc    10500
ccgcggcagc cggcgcagca acgcggtggt atcggcttcg cccagctcga atgaaacgga    10560
cgacgcgtcg tcgactgcgt tgttggccgc gcccgtgcct ggatagtcaa ccggcatcgg    10620
ctcgacgggc tgcgcgagga gggcttgcca cagccgtgct tcgtcgccga tggcgggcga    10680
ccgggccagt tgctgcagat gcaacgccca ttcgcggaac gaagtcgtct tcccgggcaa    10740
cggctggccg tggtaagcgg catgcaggtc ctcgagaagc acgcgccatg acacgccgtc    10800
caccgccagg tgatggatcg acacgaacag gcgggcgagc ggctcgtcgg ccaggcagaa    10860
gagccgggcc gccagcaacg ggccatgcgt gatgtcgatg ccgcgctccg cgtcagcggc    10920
ggcggcacgc atcgccgcca ggcgctcgcc tgcgtcgtcg gcgatcacct gtttcgcaaa    10980
gagcgccggc atctcgccgc cggcgacgac ctgctgggtc cagcggcccg catcgtgcga    11040
gaaacgcagt cgcaacgcat cgtgatgttc gtagacctgc cggaacgcgt cggccagcct    11100
cgatgcgtcg atatccgccg gcacctggat caggaccgtc tggttgtagt gcgacggcgc    11160
atcgatctcc tgttcgaaga accagtgctg caccggcgta agcggcgcat cgcccagcgg    11220
gctcaaggtc ggcgcgcagg ctgcccgctc ctcgggcgcg gcggccagct gcgcgatcgt    11280
ctgatactgg aacagctgct cgccgtcac gcgcagccct gcctgattgg cgcgcgcgat    11340
cacctggatg ctcaggatcg agtcgccgcc gagttcgaag aaattgtcgt ggatgccgac    11400
ggaaggcaac tgcagcacgt ctatgcagat cgacgccagc aggatttccc gcggcgtgac    11460
ggcaggtgca tgcggctggg ccgcgtcgcc ccgatccgcc ggaagcggca gcgccttgcg    11520
gttgatcttg ccgttgggca gcatcggcaa ggattcaagg gcgaagaact gcgacggcac    11580
catgtagtcg gcgagcttgc cgcccagata gccgcgcaga tcggcgatgt ccggcgcggc    11640
ggtcgcgaca taggcgatca ggaacgttcg ggctccttcg gttttcgcga tcacgacgca    11700
gtcgtcgacc gacggatgcg cgcgcagcgc cgcctcgatt tcaccgggtt cgatgcgcag    11760
gccgcgcagc ttgatctggt gatcgatgcg gccgaggaac tcgatgttgc cgtcgggccg    11820
gtagcgcgcg aggtcgccgg tgcggtagag gcgcgcgagc gggtcggccg agaacggatc    11880
ggcgatgaac ttttcggcgc tcagttcggg ttcgccgtgg tagccgcgcc cgaccggtgt    11940
gccgccgatc agcaattcgc cggccacgcc gatcggcgtg gctgcatct gcgcgtcgac    12000
gatgtagagg cgggtgttgg cgatgggccg gccgatcggc acgatgcggt gcggatcgtc    12060
gcgccggcat tcccacgcgg tcacgtcgac ggcggcctcg gtggggccgt agaggttgta    12120
gagcttgacg tccaggcgct cgaggcaacg ctgctgcagg tcatggggca aggcctcgcc    12180
gctgcacacg acgcggcgca gcgacgcgca gtgcgcgtcg aggtccggat gatcgaggaa    12240
cgcgcgcagc atcgacggca cgaaatggat cgtggtgatg cgttcgcgct cgatgagctc    12300
gaccaggtag tcggtctcgc gctgccgcc ggggcgggcg aacacgaggc gcgcgccggt    12360
gacgagcggc cagaagagtt cccagaccga gacgtcgaag ctgaacgggg tcttctgcag    12420
cacggcatcg tcggcgtcga gcgcataggc gtgctgcatc cagaggatgc ggttggtgat    12480
```

```
cgcgcgatgg gtgttgagcg cgcccttggg gcggccggtc gagccggacg tgtagatcat    12540
gtaggcgagg ttgtcgccgt tcagcgcggg tgcggggttg gacgtcgccg cggcgtcgag    12600
gtcgagcgag tcgcgatcga cgacgatcac gtgcgcgtcg gtgtcgggca gcgcgtcgtg    12660
cagatgctgc tgggtgagga gccagcgcaa ctgcgcgtgg tcgatcatga agcgcacgcg    12720
ctcggcgggg tagtcggggt cgacggggac gtaggcgccg ccggccttga ggatcgcgag    12780
cagggcaacg ctcatgtcga gcgaacgctc catggcgacg ccgacgagcg agtcggggcc    12840
gacgccgagc gcgacgaggt ggtgggcgag gcggttggcg cgcaggttga gttcggcgta    12900
ggtgagcgcg cgtgtcatcga agacgatcgc gacggcatcg ggcgtgcgct cgacctgctg    12960
ctcgaacagg cggtgcagcg gttgcgcggc gtcctcgccg aaatccgtgt cggtgcggtt    13020
ccactcgacg gtcagcaggt tccgctccgc gtcattcgac aacgacagcg cgccgagcgg    13080
ccggtccgga tcggcgatca cggcatcgac gagcgtgcgg aagtgttccg ccatgcgatc    13140
gatcgtggcg gcgtcgaaca gatccaggtt gtattccagc gagcccgcga ggccgtcgtc    13200
ggcatcctga acatgaagcg tgaggtcgaa cttcgcggtg tgggtctcca ccgccaccgg    13260
cgtggccacg agaccgggga agctcactgc ccggggttgc gctttctcgt atgcgaacac    13320
gacctggaac accggcgtgc ggcccaggtt gcgttcgagc tcgagcgagt ccaccacctg    13380
ctcgaacgga atctcctggc ggctgtagcc gtccagcgcg acgcgcttca cgcgcgccag    13440
caggtcgccg aaggtcggat tgcccgacag gtccacgcgc agcgcgagca tgttcgcgaa    13500
gaagccgatc agcggctcgg tcatgctgga acgccgattg gcgatcgggg agccgatgac    13560
gaggtcctgc tggttgctgt atcgcgacag gagcagcgca tacgcggcga gcacgaccat    13620
gaacgtgctg gtgccggacg cacgggcaat cgcgcgcagg ccgtcggcgc gttcggcgct    13680
cagctggaac ggcaggaccg cgccgcggaa ctgctggacg gcgggccggg ggcggtcggt    13740
gggcagttcg atcaggtccg gcgcgtccgc cagcgcggcg ctcaggagcg ccagctcccg    13800
atgcgtgtcg gcggacgcca ggcgctcgtg ctgccacacg gcgtagtccg cgtactgcac    13860
ggccagttcc ggcagcgact cgccggcata gagcgcggcc agttcgccga tgaggatgcc    13920
tgacgaccat gcatcggaaa cgatgtgatg catcacgatg ccgaagacgt gcaggcgctc    13980
atggacgcga tacagcacga cgcgatagag cggcccggcg gcgagatcga acgggcggtc    14040
ggcttcctcc gcgagcagcg cgagcgtgtc ggattcgctg gcgacgtcga cgacgtcgag    14100
cgcgaccggc gccggcggcg caatgcgttg aaccccgcgg ccgtcgacgg cgggaaacgt    14160
cgtgcgcagg atctcgtgac gccggctgat ctcggacacg gcaaaccgca ggcgcgcgac    14220
gtcgagttcg ccttcgaagc gcagcgcgct cgagatgttg taggtggccg acgggccttc    14280
cagttgcgcg aggaaccaca gccgctgctg cggaaaggac agcggcaggt cgttcgcgcg    14340
cgagcggggc gggatggcgc cggccgtcga gccggggtgg ggcgacgacg cttcgatcag    14400
gtcggacacc gcgctgatgg tctggagttc gaagatcgcg tcgatgccga tctcgacgga    14460
gaagctgctc cagatccgcg agaccagttg catggcttgc agcgaatcgc cgccgtagtc    14520
gaagaagcgg ccggcgagat cgacggccgg attgtcgagc acgtcgcgcc agatgcgcac    14580
cagttcgcgc tgaatcggcg tggcgtcgag aggggcttcc tcgggcgcgg cggcaggctc    14640
cagggccagg agcgccgggc gatccagctt gccgttggcg ttgagcggga attcggcgat    14700
cgggatgatg tcgacgggga ccatgtagtc cggcagcttc ccggccaggt aggcccgcag    14760
gttcggcacg ctcaggctcg cggcgccctt gacgtaggcc gccagcttgc gcaccccgtg    14820
```

```
ggcggattcg cgcagcatga ccgccgcgcc gacgacgtcc tcgtgcgcgg cgatcgcggc   14880
ctcgatctcg ccgagttcga cacggtgccc gcggatcttg acctggtggt cgacgcgtcc   14940
gtagcactgg atacgtccgt cgggcagcca ccggccgatg tcgccggtgc gatagatgcg   15000
cgcttcgccg ggaaacggat gctcgacgaa tttcgcggcg gtgacgtcgg gccgctggtg   15060
gtagccgcgt gcaaggccgg cgccggcgag gcagatttcc ccgggcacgc cgagcggaac   15120
cggccgcagc gcgtcgtcga gcatgtacac ccgggtgtcg cgatgggac ggccgatcag    15180 caccgtgggc ggcgcgtcct cgacgcgctc gacgatgcag ccgaccgtcg cctcggtggg   15240
accgtactcg ttgtagattt cgatcgcggg atcgatcttg cgcagcgtgg cgatgtgctg   15300
gggcgtcagt tcctcgccgc ccacgatcac cttgcgcacg ccggagcgtg ccaggttcat   15360
gtattccagc aggtgaatgt gggtgggcgt gagcttgagg gtgtcgacgc cgctgccggg   15420
ctggaacatc cgggccagga tggtgtcgat gctttccgac tgcggataga tgcgcagcgt   15480
cttgccgcgc accagcgggc agaagatgtt ggtgagcgtg aagtcgaagc agagcgagct   15540
gtacaggccg aaactgccgg tcgtgctttc cggaaagtaa tacccggcgg cccacgcgat   15600
gtagtgggcc aggttccggt gttcgagcag gcagcctttg ggtttccgg tcgagcccga    15660 cgtgtagagc acgtaggcca ggtgcgccgg ttcggcacgg tgcggcgggt tgtccggcag   15720
cggctgccag ccggggagtt cctggtccag cagcagcgtc acgccggaga attcatacca   15780
ctgcgcgagc tgactcgact gggtcaccag cagcgacagg cccgtgtcgc cgaggatgtg   15840
attgatccgc tcggccggat acgcggggtc cagcggaacg aacgccgccc ccgccttcag   15900
gatgccgaga atcgcgacga tcatccattc ggaacggtcg agcatgatgc cgaccagcga   15960
ttccggcccg acgccgtggt gttcgcgcaa gtgatgcgcg aggctgttgg cccgcgcgtt   16020
caggtcggcg taggtcatca gcgaactgtc ggtgaccagg gccggcgccg tcggcgtgcg   16080
tgcgacctgg gcttcgaaca tggcgacgac cgtcgggtgg ctgggccgg ccgtcgcggt    16140 ttcgttgaac gcggccagca gcgggccctg ttccggcggg gccgcttcga tgtcgccgac   16200
ggcgccgtcg aggtgttcga atgcctccag caccgcggcg aggctgccgg cgaaaccgtc   16260
gatgatgaaa ggctcgatgg ccccgctgta acgaagctcg atttcgccgc gcgcgagccg   16320
caggtgcaac tgcagatcgt cgtcccgacc ggtcggtgcg tggtgcacgc ggtcgtccgc   16380
cagcgcgact tcgtgagct gcgcgagcgc catgtccttt tcgttgcgca cgagcgtttc     16440
cagcgggaat cgaggctcgg cgtagctgtc ttccacgatc ccggccacgc gcgacaggta   16500
gtcctcgatg cgctcgtcgg ggcggacctc gatgatcagc ggaacgatgg cggcccgggc   16560
cgacggatgc ccggccagcc ccggcgtgcc gagcaccgtg accggaatcc ggaagtattt   16620
ccagagcagg aacgcgatgc ccgccgccgc gacggcgaat cggcaagct cgccgtcgcc    16680 gatgcgccgc aacaggtcga gcgacgcggg cgtgagccgc accgagcggg tcagcgggcg   16740
acccggctgc tggctcgggg cgtacgccgc gattccgtac acgccggcga cccgggaaag   16800
gctttcgcgc cagaaacgcg cggtggctgc atagcgatgg tcggtgacca gcacgttatt   16860
gtcttgcaca ggaaactcct tgagacgttt tgttcacctg aaacaacctg aagcagcacg   16920
cacgcgcgcg gccgctcgaa ccccggcggg cgcgcatcac gtcttctcct cgagcgcgtc   16980
gtcggccgtg accgcgggcg cgcgcttcag gcgcaggccg cccggactc gcgggccggc    17040 ggcgggcgcc tcgtcggaga gcgggatgcg atcgaccggc gtggccggat cgcgacggaa   17100
gacgtcgtgg atcgcgagca gtcgatcgcg catcgcggcg atggtcgacg ggcggaacag   17160
gtgggtgttg tagatgaact ggatcaggtg ccggccttcg ctttccacga cctggaagga   17220
```

```
caggtcgaac ttggccgtcg tgtccgccgg cgagatgtcc gtgatgcgaa ggcctggctg    17280
cggcgccggc atcgacacgt ggttcacctg aatgtcgaag atcggaaat ggttcgccgg     17340 cgtgcggatc ttcaggtctt ccagcaacac gtcgaacgga taggacgcat gctccagcgc    17400
ttgcgcggag gctttcgcca ccccgtcgat cacctccgcg accgtcgcgg atttccgcac    17460
cggcacgcgc agcacgacgg tgttgaggta cacgccgacc tgcgattcga gctgctcgct    17520
gtcgcgcccg gccgacacgc tgccgatgac gatgtcctca cgccccgtgt agcggtgcat    17580
cagcacgcag aacgacgcca gtagcaccgc gtggagcgac gtgtggtgag cgcgggccag    17640
cgtcgcgagt tccgccgcgt gcggctgcgg cagttcgact tcgagcgtct gcccggcatg    17700
accgagccgc tcgggacgcg ggaagtcgga tgccagttgc aggcggggca gcggcggcgc    17760
cagttgctcg agccagtacg cgcgatgcgc ggcggcgcgc ggaccccgcga ggctcgcgtt    17820 gtgccacgcg gcgtagtcgc gatactggat cgacagcggc ggcaggtcgc gccccgcata    17880
cagcgcatgc aggtcgtcgg tcagcacgcg gatcgaccat gcatccgaga tcacgtggtg    17940
catgttcagc agcaacagat gcttctcctg cgacagccgg accagcttga cgcgaaagag    18000
cgggcccgac gcgagatcga acggctgctc gcattccgcg cgaatcagcg catcgatcgc    18060
ttgcggcccg gcatcgtccg cgagatcgcg ctgctcgacc cggaatccgg acgcttcgcg    18120
gctgaggacg cgttgccgca actcgccttc gatcatcgcg aacacggtgc gcaggctctc    18180
gtggcgatcg accagcgtgt cgaatgcacg gacgaggcgc gccgtatcga cggcgccgtc    18240
cagctgcagc gcgcccgcca tgttgtacgt ggacggatcc gcgccgcggc tggcgagcca    18300
gatccgcttc tgtgcacgag acaccgcgta ggacggttgc gcggccagcg ccgggatgat    18360
cgcgtcgtcg tcggcggcgc cgtcgacggg catggcagcc agcctttgtg cgagcgcgcg    18420
cggcgtcggc gcatggaaga tgtcggcgac cgcgacgttc agtgcagccc gggggatccg    18480
gctgaccatc tggatcgcct tgaggctttg gcctccgtgc tcgaagaaat cgtcgtcgac    18540
gccgttcggc cggcggccga gcacctcggc gaagaggcgc agcagcgccg cttcgaccgg    18600
cgtgcgcggt tcggcccgca cgccgtcggg cacggacgcg gcatccggca gcggcagcgc    18660
ggcgcggttg atcttgccgt tcggcatgac gggcagcgcc ggcagcagca tcacggtgtc    18720
gggcaccatg tgcgccggca gcgtgtcgcg cagtgcgtcg cgcacgcgct ggggcgtcca    18780
gccggttccc gacgcgtagc cgcacagggt catttcggca tccgacgttt ccgggcgac    18840 caccacggcg tgggaaatgc cggcaagact ggtcagcgcg gcttcgattt ccccgagctc    18900
gatgcggtag ccacggatct tgacctggaa gtcgcggcgg ccgaagaagt gcagattgcc    18960
gtccgccccg aagcagccga tgtcgccggt gcgatacagg cgcgcgcctg gttccggact    19020
gaacggatcg tcgcggaaca ccgcccgggt gcgggcttcg tcgaacaggt agccgcgccc    19080
gacgccgacg ccccgatgc agatctcgcc cttgacgccg gccgggcacg gattcatgtc     19140
ggcatccacg acgtagaggc gcaggttctc gatcggccgg ccgatcggaa tgccggcc     19200 atccggcgcg cgcgtcaggc agtaatgcgc gacggagtcc gacgcttcgg tcggcccata    19260
ggcgttgatg agccggacgg ccggattcag gcggaaccac gcttgcgcgg tggcgggctg    19320
cagcgtttcg ccgatcgtca gcaacgtgtc gaggtgaggg aaggccggtg ccgcgtgccg    19380
ttccagttcg ccgagaaagg tcgcgagata ggacggtacg aattgcattg ccgtgatgcg    19440
gtcgcggtgc aggctgtcga tcaggcgcgc gggctcgagg atcacggcat cgggatagat    19500
caccgtcgtg ccgcccgacg ccagcgccgc gaagcattgc cagaccgaaa tatcggagca    19560
```

```
gtgcgaagcg gtctgggcga ccgcgctctg cgcgccgagc ccgacccggc gcgccatcgc    19620
gagcacgtga ttgagcatgc cgcgatgttc gaccatcgcg cccttcggct ggccggtcga    19680
acccgacgtg aagatcacgt aggcgaggtc cgcgggccgg cagcgcggcg tcaccggcgc    19740
cggcgcttcg gcgccgcgac ggtcgggcag gcgggccgga tcgaccagcg ggatcgacgc    19800
cagcgccggc ggcggcacgc agtccgtcgt gacgatgacg gccggccgcg ccagcgtcag    19860
gatggtctcg acccgctggg ccgggtaggc cggatcgacc ggaacgtacg ccgcgccgca    19920
cttccagatg gccaggatcg tttccagcat cagcggcgag cgcggcatcc agacggcgat    19980
ccggtcgtcc ggctgcagcg gcgccgtctg cagaagatgc gcggcgatcc ggttggcgcc    20040
ttcgacgagg tcacggtagg tgcgaacctc cgtgccgcag cgaaccgcca cgcgctcggg    20100
gtgcgctgcg gcgacggcct cgatcagttc gggcagcgtc cggtcggacg gaaccggcgc    20160
gaacgtgtcg ttccagccga gcaggatggc gtcccgctcg gcggcagcga aagcggcac    20220 gctgcggttc gggcgatctt ccgcgccggc caggccggtg agcagggtct cgacatggcg    20280
cagcaggcgg acgatcgtgt cgcgatcgaa ccggccgtcg tcgtacagca cctgcagcga    20340
caggcgcttg cccggcgtca cgaccagcgt cagcgggtaa ttgttcggat cggacacctc    20400
gaatgcgccg atccgcaggc cgggcagcgc atcggccagc gcttcttcca ccggataatt    20460
ctggaagatg agcaggcttt cgaagagcgg cacgccgggt ggcaggccgg cgaatttctg    20520
gatgtcggcc agcggatagt gcgcatagtc ctcctgctgc gcgagatcca tctgcaattg    20580
cgccagccac gctgacgtcg ggcgtgcgtc gatgcgcacc cgcaccggca gcgtgttgat    20640
gaacagcccg accatttcgt cggatgccgg cagcgacgcc gggcggccgg aaacgatcgt    20700
gccgaacacg acgtccgatt cgccgctgta gcggctcagc aactgcgccc atgcgccctg    20760
cgcgagcgtg ttcagggtga ggcggcggga ttgcgcgaat gcgacgagcc gttgcgtgtc    20820
gctttcggag agcagcagcg gctcttccac gtaggcgccc ggcgcggccg tgccgtcgag    20880
ttcggggcgg cccagcacga gcggcgtcgt cgccgggaaa tccgccagct tcgtcttcca    20940
gaaacgttgc gcggcggcgg cgtcctggcg tgccagccag cgcacgtaac cggcgaaggc    21000
aggcggcgcg tcccgctgcg gcgcgccttc ggccggcggc gcctgatagg cggcggccac    21060
gtcgctcagc aaccgggcgg agctccaccc gtcgagcagg atgtggtgat ggctccaatg    21120
gaagcgccat gcgtgctcgc ccacgcggaa cagcgcgagc cgcatcagcg gcgcgcgggt    21180
aaagtcgaag ccgcgcgccc ggtcttgcgc cacgtaggct tcccagcgct gttcggcctc    21240
cgcggcggac gccgcgcgca gatcctcgtc gtgccacggc aagtcgatcc ggcgatgcac    21300
gacctgcacg gggctttcga tgtcttccca gtgaaacgac gtacgcagga tgtcgtgccg    21360
gtgcgccacg gtctcccacg cgcggcgaaa ccgttcgacg tcgagcgccc cgtcgatacg    21420
gaaattcagg ctgctgaagt acgcatccga cgcgggttcg tacaggctgt ggaacagcat    21480
gccctgctgg gtcggcgtca gcgggtagac gtcggcgatc tcgtccggac tcaccgacgc    21540
cggcgccggc gcctgcggca acgcagtcgc gggccgggtc gatgcggacg ggacagcgtg    21600
gccggcgacc agggtttcga gccgcgcgat gtaggcttgc gcgacgcgca ggatggtggc    21660
cgtgtcgtgg caggcccggc tgaattccca cgcaacgtgc aggcgattac cggtcacgta    21720
cgcgttgatg tcgagcaggt gctcgcgcaa ctggttcgcg ttgcggccgt ccccgctcgg    21780
ctccgcggcc tgtttccagt ccgtgcggc ggtgaacagc tggtcggtct gccccaggta    21840
gttgaactgc agtcgcggct gcggaagcgg gccgtcgagc cggtctagca gcaggccgta    21900
ggtgatgccc gcgttcggca ccgcgcgcag ccgcgtcctg accgatgcga cgaggctggc    21960
```

```
cggatcgtgc gaaccggcat cgaccgtcag caagaccggg aaaaccgacg taaaccagcc  22020
caccgtgcgc gagatgtcga gcgcgtcgat cagttcctcg cgcccgtgcg cttcgagatc  22080
cagcagcacg tcggcgcatc cgctccattc gctgacggca cgcgcgagcg cggcgagcag  22140
cacgtcgttg acctgcgcgt cgtaggcgcg gggcgcggcg cccagcaagg ccgtcgtcgc  22200
ggcttcgccc aactcgacga cgatcgtgtc ggcggacgac acggtattgg cgtcggcagg  22260
cgcatcgcga tcgagcggca ggccgggcag ggcggcacgc gcgagggcct gccaatgggc  22320
gaggtcggcg tcggcggcgc cggagccggc ccaggtcgag atcgcccggg tccatgcggt  22380
ccaggtcgcg ctgccgcctg cgaattcggg cgccttgccg ttgcgcagcc gggtataggc  22440
gtcgtacacg gtttcgagca gcgcgcccca cgacacgccg tcgacgacca gatgatgggc  22500
gaccagcagc aggcggagcg aacggccttc gtcgacgcgg aacaggtccg cgcgcacgac  22560
ggggccgtcc gcgagattca ggctcgcatg cgactgcgcg acgtactgcg cgagctgatc  22620
gcgcgcaatg tcggacacga cgacgggat ctccgggtcg tcgacgactt cctgggtcca  22680
gccgctctcg ccctcgcgaa agcgcagccg cagcgcgtca tgccatttga ccgcatgccg  22740
cagcgcctgg cgcagcaaga ccggatcgag gtcggccggc acgtcgagca ggaccgcctg  22800
gttgtactgg tccgggtcgt gcttgccctg cgcgaagaaa cgcttctgga tgggcgtcag  22860
cggcagcggg ccggacgatg cgacgaacgc cgccgcgccg accgtgccgc gcgtcgccac  22920
ggcggcgagt tcggccaccg tcggatgctg gaagatgagc cgggtggtga gcttcaggcc  22980
cgccttcgcg gccagcgaca cgatgcgcat gctcagaatc gaatcgccgc ccagcgcgaa  23040
gaggttgtcg tggatgccgg gcgacggaat gcccagcgct tcgccccaga tgcggcacag  23100
cagcgtctcg gtaggcgtgc ggggcggcgt cggcgcgtgt gccgtggcgg cgagtcgcgc  23160
gcggtccagc ggcggcagcg cgttgcggtc gatcttgccg ttgccgctca ggggcagcgc  23220
gtcgagcacc acgtagatgc cgggcaccat gtagtccggc agcgtggcgg acagcgcggc  23280
ggcgatcccg gcgtcgctca gcgacgcgcc gtcgcggaac gcgacgtacg cgcacagcgc  23340
ggcgcggccg gcctcgtcgc gatagtcgag cgcggcggcc tggcggagtt ccgcgaatg   23400 gtcggccagt cgtcgttggt cgatctcccc gagctcgatg cggtagccgc ggatcttcag  23460
ctggtggtcc ttgcggccgt gcagcacgat cgttccgtcg ggcaggtagc agccgatgtc  23520
gcgggtgcgg tacaggcgga cgccgcgctg aggatggaac ggatcctcga cgaacgcgtc  23580
ctgcgtggcg gcttcattgt tcagatagcc gcgaccgacg gcgacgccgg acacgcacag  23640
ctcgccggga atcccgatcg ggcacaggtt catctgcggg tcgacgacgt agaggcgaac  23700
gttgcggatc ggcttgccga ccggtacgta aggcgtggac ggcgcgcccg tcatgcggtg  23760
ctgtgcgacg tcgtcggacg cttcggccgg gccgtacgcg ttcaccagcg ggatcgccgg  23820
gaacacgtcg aaccactgtt tcaccagcgc cgggctgacc atctcgccgg tgacgagcag  23880
gtgccgcaga tgccgcatca gcgccggccg ttccgacgcg cggtcgagca ggcggacag   23940 ataggacggc accagttcga ggatgctgat ccgggtggtt tccaggtacg cgacgaaacg  24000
cgcgggatcg cgaatgcagt cgtcgtcgac gatcacggtc ttgccgccga cgagcggcgc  24060
cgtgaaaaat tgccagaccg aaatatcgaa gcaatgcggc gcggtttgcg cgatcaccga  24120
cgacgccgag atcgagaact cgtcgatctc ggcgagcatg tggttcagca tgccggcgtg  24180
ctcgaccatc gcgcctttgg gcttgccggt ggagccggac gtgtagatca cgtaggcgag  24240
gctgtcgggc gacacggggc ggccgggatt ggagtcgtcg acggcgtcgg tggcggcgtc  24300
```

```
gagcgacacg accagcgcga tcccggccag ctccgggggc aggagcccgt cgcaggtgat    24360
cacgagggcg gcgccggaat cctcgaggat ggtgcggatg cgggccaccg gataattcgg    24420
gtcgaccgga atataggcgg cgccgcactt ccagaccgcg aggatcgcct ccatcagctg    24480
ggcggaccgg tgcatgcaga ttgcgaccag cgcgtccggg cccaggtcgg cggcggcgag    24540
caggcggtgc gcgatgcggt tggcgcgcgc gttcagttcg cccgcgctca ggacgccatc    24600
ccggtactcg accgcgggcc gctcggggtg gtccgcggcg gcctgctcca ggcgatgcac    24660
cacggtgagc gcggcgtcga acggcacggc ggtgtcgttg aaggtctcca gcaactgccg    24720
gcgttccgcg tcgggcaaga tcggcacgcg gccgagcagc cggttcggat cggccgcgaa    24780
cgcgtcgagc gtcgcggcca cgtggcccag catccgctgc atcgtgtctt catcgaagcg    24840
ccgcgggtcg aacgacagtt ccatcttcca gtcgtcgcgc gccgtcacca cgaattcgag    24900
cggaatgtcg gcgcggttgt agagctgcac ctcgtcgacc gccagcccgt gcgcgccatg    24960
cgtgagcgac gcgtcgagcg ggtaattcat gaacgtgatg ttgctctcga acagcggcgc    25020
cgtcggcggc acgtcgctgc agcgctgaat gtcgggcaac ggggtgtgct cgaacggcgc    25080
gcgggcggcc acgcgcgcct ggatcatctt cagccacggc accagcggct gcctcgggtc    25140
gacccgcacc cgcaccggca ccgtattgat gaacaggccg agcatggttt cgatccccgg    25200
caggttggcg ccccgcccgg acacgacggc gccgaacacc acgtcggttt ccccgctgta    25260
acgcgacagc acgagcgccc acgccgcttg cgcgagggta ttgagggtga cgtgatggcg    25320
ggccgcgaat tgccgcaggc gcgcgctcag gtcggccgac aggtcggcct gcacttgcgc    25380
gaggccctgg ccgaagcgtt cgtccgcgcc cgcgcgcgcg gccgtgggca gcggggtcgg    25440
tgtgcggaac ccttcgagat agcgcgtcca gtattgctgc gcggcttgcg gctcgtgctg    25500
ctgcagccac tggatatagt cgcgataggg gcgcaccggc gggagcgccg gcgacacgcc    25560
gcgcgcgagc gcgccataga cctcgaagat ctcctcgatg acgagcgaca ggcaccagcc    25620
atcggccagg atgtgatggt ggctccagct gaacaggtag gcgtcggcgg cgacgcgcac    25680
caggcgacag cgcacgagcg gcgcgcgatc gagcgcgaag ccctcggcca ggtcgttgtc    25740
gagatgcgcg cgccaccgtg agcgctgttc gtgttccggc aggtcgagcc agtcgtcctg    25800
cacccacggc agcgtggcgc gcgcgtgcac gacctgcatc ggcttgtcga actcctccca    25860
atggaacgac gtgcgcatca ccggatgccg atcgatgagc tgctgccacg cggcatgaaa    25920
cagcgcggga tcgaggctgc cggtgatccg gcaactgagc tggttgaagc tgcttctcga    25980
gccgggctcg tgcacggcat gaaagagcat cccctcctgc atcggggaga gctcgtagat    26040
atcggcgatg gtgggggatg tcacgatttg atccttgaga caagggcgtc cagcgcttcc    26100
tggctgatgc gcgcggccgg aaagtccgac gggctcagcg cgcgcgggcc gtcgccgccg    26160
gccgcgacga tcgacagcag gcggctgcgg tagcactgcg tcagctgttc gatgacgccg    26220
ggtgcgcagg cctcgcggtt gtagtgccag gtcaggcgca gacggccgtc gaacaccatc    26280
ccgtcgatct cgaacagatg gccgcgacgt gcgcgcgggc tgtgctcggg gctctggaag    26340
tcgagtaccg gcttccagcc cgtgtcgtcg ggcagcacgc gatcgacctg gccgagatag    26400
ttgaagcgca ccgcgccgg cggctgccgt tcgagcgccg ccgcgatgcc ggcgtcgtgg    26460
ccgaggtagc gggcgatgcc gtagccgagc ccgcgcatcg gaaccgcgcg cagctgctcc    26520
ttgacgtggc gcagcgcgtc gaccgccacg gtggcgtcgc cggcgttcag gcacaccgga    26580
tagtgggtgg tgaaccagcc gatcgtgcgc gacgtatcga cgccgtcgaa aatgtcctcg    26640
cggccgtggc cttcgagatc gacgaccagc gacgcgttgc cggtccagtc gccgaacgcg    26700
```

```
agcagcaggg ccgtcagcag gacttcgttg atctgcgtgt tgaacgcacg cggcacgtcc   26760
tgcaacagcg cgagtgtctg ctgcgcatcg aactcgacga tcgtcgagcc cgcttcggcg   26820
acggtgccgg ccggcatgtc gtcgaagcac gccggctcgc cggcgttgcc ctggagccag   26880
tagtccagcc ccaggccgtc gagcgcggtc gcgccgagtc cggacaggcg cgtcgaccag   26940
tcgcgccagg ccgtcgtcct ggccgggagc tgtaccgcgt cgcccgcttc gagctggcga   27000
catgcggtgt acaggtcttc gaacaggatg cgccacgaca cgccgtcgat caccaggtga   27060
tgcgcgaccg cgagcaggcg ctgcggcgcg tcgggaccga actggaacag gtgcgcgcgc   27120
agcagcggcg gcgccgacag cgtgaagctt tcctgcatgc cggtggcggt cgcgagcatc   27180
gcggcctgcc gtgcggcagg cgccgcgtcc gccagcgacg tgacgccgag cggaatggcc   27240
agcggcggcg cggcatgcga ttgctgccac acgccggcga cgcacgcgaa actcagccgc   27300
agcgcgtcgt gatgcgtcgc gacggccgcc agcgcgcgct cgatcgtgtc cggccgcagc   27360
gatgcgggca cctcgatcat cgtcgactgg ttgtagtggt gcggatcggc gacgtcttgc   27420
gcgaagaacc agtgctggat cggcgtcagc ggggcggggc cgaccaccgg ctcctgcgcg   27480
atccggatcg acgcgcctc cgtcgcgacc tgggcgagct cggcgatggt cgggtgtgcg   27540
aagaactggt cggcggtgaa cttgagcccg acttgctggg ccagcgacat cacctggatg   27600
atcaggatcg agtcgccgcc cagttcgaag aaattgtcgt gcacgccgat cggctcgcgg   27660
cccagcacgt cgcaccagat cctgcccagg cgcgcctcga cgtcattggc cggtgcgacg   27720
taggcggttt cgctcggcgc gggcgccagt tccagcgcgg cgagcgcctt gcggtcgggc   27780
ttgccgttcg gcgtcagcgg caggcgttcg agcgtcacga tcgacgccgg caccatgaac   27840 tcggcaggc gttccttcag gtgttcccgc aggctggcga cgctggccgt cgccgtcgcg   27900
acgcaggcca ccagctgctt gtgctgcggc gtgtcctcgc gcacgaacac gatcgcgtcg   27960
gcgacgccgg cgtgctgcct gagcgccgcc tcgatctcgc ccatttcgat ccggtagccg   28020
cgaatcttca cctgcgtgtc gcgccgcccg gtgacttcca ggttgccgtc cggcagccag   28080
acgccgaggt cgccggtgcg atagaggcgc tcgcccgcct cgaacgggtg ggcgacgaac   28140
gcggcggccg tcaggtcgtc gcggccgaca tagccgcgcg ccagcgcgat gccggacacg   28200
cagatctcgc ccgcgcaacc ctcggggggcc agcgccccgt gctcgtcgag caggtacagg   28260
tgcgtgttgt ggatcgggcg gcccaccggc agacgggcgc cgtaggtgat ggccgggtcg   28320
accacgtagt ccgcgatgca cacggttgcc tcggtcgggc cgtacgagtt gtggcacgtg   28380
cgggtccggg ccagctcgcg cagatccgcc acgcgggcgc tgtcgcccgc gctgatgacc   28440
cgtttcacgg cgccgagcgc atgccagtcg agcgcggcaa ggtaggccgg cgtcgcgttg   28500
acggtggtga cgccctgctg tgcgatgtag tcgacgaaac gcggcacgtc ccggatcacg   28560
gcggtctttg ccagcaccag gcgggcgccc gcgagcagcg tgacgaagat ttccatgatc   28620
gagccgtcga agcccgggga gtagaactgg acgaagcggt cggcggaatc gaaaccgaat   28680
gcgtccacgt ggtactgcgc catgttcagg agccctgcgt gttcgagcac gacgcccttg   28740
ggcacgcccg tggagccgga cgtgtagatg atgtatgccg cgtcgtccgg ccgcaccctcg   28800 acctgcgcca tgccgacgc gggtgccagc gtgtcgagct ggaagtcgag ggcgaacatc   28860
gggatcgccc agaaatcggc gagcaacggc aggtgttccg agtgcgtcag cagcgccttg   28920
accttcgcgt cctcgatcat gaagcgcagg cgctcccgcg gaaattccgg gtcgagcggc   28980
agatacaccg cgcccgcctt gagggcgccg agcatgccga cgatccagcg ctcggaacgg   29040
```

```
tcggccacca cgcccaccac gtcgccgcgt tcgatcgcgt attccgcgag caggaagctc    29100
gccagccggg acgcctggtc gtcgagttcg gcataggtca gcgatgcgtc ggcggtcacc    29160
accgcgacgc tgtccggcgc ggccgcgacc cgttgcgcga actgctccag gaaggtgccc    29220
tgtaccgcga cgggcgccgc atgcgaacgc aggcgcgcgc gctcttcgtc gtcgagcagc    29280
gagacggtgt cgagcggcgc atccagtgcg ccgaagccgg ccacgacgtt gcgcaggtgc    29340
cgtgcgacat gctggagata gtgcagcgtg aacaccgtcg gccggcccgt cagcacgatc    29400
tcgtagcgct cccgatgccg gatctcgatc gacaggtcgt agtcggccgc tgcccaggct    29460
tcgtgaaggc cgtcgaagcg cacgccgacg ttggtcgcgc gccgttcgcc atgcagcttg    29520
tgcgcgaggg cggcgatcgg gaaatcctgg tacgaatagc tgcgctgcac gctgtcgcgc    29580
agctggttca ggtacgcgcg aaccgtgggg ccgggctcgc cggcgtcgag cagcgggaca    29640
ggctcggcgc agccgctcgc gggttcgacg atcagctgcg gcgacgccac gaacaggccg    29700
gccgcgccgt tgtagcgccc cagcacgcgg aacagcgcgg ccagcagcac gacgaacgcg    29760
cccagctcgt tgccggcggc gagccgctcc agcacctgcg ccgcgtcgcc gtcgagcgcg    29820
aacgtcagtg ccggctcggg gccgagcggc agcgcatacg cctgccacgc ctgctgaagg    29880
cggaaatctt catcgatgcg accgagcgcg tcgttccaga acgccacgtg ttcctggtat    29940
tgcccgctgg tcgagagcgc gttgagattc agttctgaca aagcacgatc tccctcgtcg    30000
cgtacaggat ttcggaagcg atgccccttgg ccttgcagtg cgccgacgaac tgggtggact    30060 ggatgtggct gggcgagttt cgtcgaagg tgttgtcgag gaggtggttc agccagggct    30120
cctgacccat cgcatagaca tacgccgcgt tgaacgcgaa atcgtccacc agcgcggcgg    30180
cctcgccgaa ctggcagccg cgcgcccggc gtgattgatc gatgtcgcgc ggcagcgcct    30240
tgggaaacag cgggccgtag acccatgacg gcggcgcgcc ctcggtttcc atcccgacga    30300
acagggtgtc cggcttgccg gcgaggcgga agacatgctc gtagaggcgc gggtccaggt    30360
tgcacgaatc ggcgatgcac agcaccgagc gcgagccgaa gcggatcatg aagctctgct    30420
tgctgtggat cgccaggtcg ttgtgttcgc ccatgaacgg aatggcggtg atggcgccgc    30480
cgggcacctt gatttcctgc gcatcccgaa cttccagcac gtcgtcgaag ccgagcttgc    30540
gcaacgccag ctccatcgac ggatcttgcg gaaagccgtc gagattcctg ccgaccacca    30600
cggtcttgac cttgtggcga agctgcagca gcgtttcgag gacgatgtga tcgtgatggc    30660
tgtgcgtgat cagcacgtag tcgatctggt ccggcaggtc ggcgaacgta tagcgcggca    30720
gcgcggtgtc gtagccgtag ctgatcaccg gatcgatcag gatgctcacg ccccggctct    30780
ggatcagcac gcacgcgtgg ccgtagtagc ggatgcggat gtcgtcgccg tcgaacgaac    30840
gatccggttt cggcgccggc gcctcctcga cgaagaacga gcggaacagc ggctcgtcct    30900
tctcctccac gcgcatcagg tcgacgatct tcgcgtagct gccgggcgtg tcgcgcatgc    30960
ggaacagcgt gtcgagcgcg cggtcgtcga aggccatgtt gctgaacacc gtgcgctcgt    31020
cgcggagccg gggcgtgctg aggatgaacg gccgcggcgt gtgctcctcg atcgccgaca    31080
gcgcgatgct ctgcgcatcg cgcgcataga acgggctcgc gtacagcagg ctttcgaaca    31140
cccgaaggga cggggttgtgg ttcaggtcgt agtagatctc gacatagccc ttcagcacct    31200
ccggaatctc ggggtagagc gggtccgacg ccatccccgt ggcccgttcc agcagcagcg    31260
tggagaacgc cttgtatgcc ttcgccagtt ccagttgccg gtcgcgcgt tgggtggtct    31320 gctcgatcag cgtgcggatt tcgtcgacgc gctggccgcc caggtcgagg aacgccgc    31380 cgcgcatcgc gggatccttg caggccgccg catgcatcat cggcgatgcg gcataggact    31440
```

```
tcagcagcgg caggaaccgc tccgccacgt tgagggcggc ggtcaacggc ggaagcgtgt   31500
gataccacgc gtaccagctg ttgatcagcg gttcgaactg gatgttttgg cgcaggtaga   31560
cctgcgcgct ggacgaaata gtcaacgaag gctccttaga atgcgctgag ttcgacggtg   31620
ggctggcggg cttcggcgtg cagcgcgcgt tgtcccaggg tcaggttccg gatgcgaacg   31680
cccggattgg cgagcacctc gccgatgacg gacgtcagct cgttggcgag gccttgcacc   31740
agggcttcgc tgaaccgccc cgcgtgatag acgacgcgga tcgcgagacc ctcggcgtgc   31800
ggctcggcca ggaaccagaa atcggttgcg gcttccgtgt ccgcgcgctg cgggtcgtgg   31860
tccggcagct cggcgatatg cacttgtccc gcgtagcgat cgacggggcc gtgtcgctgg   31920
ttctgcagcg tcaggccgat gtcgaagagc ggattgcgtc ccgccacgcg tttgatgtgc   31980
agctcgtcga gcaggcgatc cagcgggtac agcgggtgcg agaacgcttc gagcgtggtg   32040
tcccgcaccc gggtcagcag cgtgtcgaac cggtcgtcgc ccgcgacacg atcgcgcagc   32100
gccagcacgt tcaggtaggg gccgacctgc gactcgagtt cggcgagttc gcggcccgcg   32160
accggcgtgc cgacgacgat gtcctcctgg ccggagcggc ggtagaacag cgccttgatg   32220
gcggacagca gcgcgatgaa caaggtcgcg ccgtggcgct tgccgagcga ttccagcgcg   32280
gccgtctcgg cggcgggcag gtcgaatcgc caggatttcc agctcggcgc ggccggctgc   32340
tcgacgtcgc ccggcagttc cagtgcgcgc aggccgccgc ccagtttggt cagccagtag   32400
tccttcatgc gcgcgccgtc cggcccggcg agcaggcggt tcagccagcc ggcgtaatcc   32460
ttgtactgga tcgggagggc gggcagcgga tcgtcgcgac gctggacgaa tgcgtcatag   32520
agcgcggaca ggtcgtcgag cagtacctcc gtggaccagc cgtcgctcac gatgtgatgc   32580
atcgtgcaga ggcagacgtg acggacttcg gagagcctca gcagcttgac gcggaacagc   32640
gggccggtcg cgagatccat cggcacgagc cgttcgctcg cctggatcgc cgctgcctgg   32700
gcatcgcggt cctcggcatc ctgcagatcc acgatctcga ccgggaacgc ggcttcgccg   32760
ggcggcagca cgtgctggac cggctggttg ccttccagca cgaaacgcgt gcgcaggatc   32820
tcgtgacgct cgctcaacgc gcggaacgcc cgcacgagcg catccacgtc cagcacgccc   32880
tcgaacagca gcgacgtggg cagcggcccc tcggcttgcg ccgcatggag acgatcctgg   32940
acccacagcc gcgtctgtgc gggagagagc gcgtagcttg cctgcgccgg cagcggcgtc   33000
accggcgcgt aatcgatcgg ctgcgtatcg gcgatgcgct tcgcgaggct cgagatggtt   33060
gggagtgcga acaggctgcg gatttccagc ttcacatgca gatcgcgccg gatgcgcgcg   33120
acgaccttcg tcgccagcag cgaattgccg cccagatcga agaaattgcc ggtcgtgctg   33180
atccgcgcct ggccgagcac ttcctgccag atggcagcca actgcgcttc gagtgcgttg   33240
acgggcgcaa cgtggtccag gccgtcgccg ggttcgggca gcctggtgcg atcgagcttg   33300
ccgttgggca gatgctcgaa cgcgctcacg acgacgaacg cggagggcac catgtaatcc   33360
ggcagccgct gccgcaggtg gccgcgcacc gcttcgatca gttctgcttc ggggtgcgac   33420
gagcacagcc atccgaccag tctcgcgccg tcgtccacgc cgcgcagcgc gacgacggcg   33480
gcatcgacca gcgggtgcga cgtcagcgcc gcctcgattt caccgggttc gatgcgcagg   33540
ccgcgcagct tgatctggtg atcgatgcgg ccgaggaact cgatgttgcc gtcgggccgg   33600
tagcgcgcga ggtcgccggt gcggtagagg cgcgcgagcg ggtcggccga gaacggatcg   33660
gcgatgaact tttcggcgct cagttcgggt tcgccgtggt agccgcgccc gaccggtgtg   33720
ccgccgatca gcaattcgcc ggccacgccg atcggcgtgg gctgcatctg cgcgtcgacg   33780
```

-continued

```
atgtagaggc gggtgttggc gatgggccgg ccgatcggca cgatgcggtg cggatcgtcg    33840
cgccggcatt cccacgcggt cacgtcgacg gcggcctcgg tggggccgta gaggttgtag    33900
agctcgacgt ccaggcgctc gaggcaacgc tgctgcaggt catggggcaa ggcctcgccg    33960
ctgcacacga cgcggcgcag cgacgcgcag tgcgcgtcga ggtccggatg atcgaggaac    34020
gcgcgcagca tcgacggcac gaaatggatc gtggtgatgc gttcgcgctc gatgagctcg    34080
accaggtagt cggtctcgcg ctggccgccg gggcgggcga acacgaggcg cgcgccggtg    34140
acgagcggcc agaagagttc ccagaccgag acgtcgaagc tgaacggggt cttctgcagc    34200
acggcatcgt cggcgccgag ggcgtaggcg tgctgcatcc agaggatgcg gttggtgatc    34260
gcgcgatggg tgttgagcgc gcccttgggg cggccggtcg agccggacgt gtagatcatg    34320
taggcgaggt tgtcgccgtt cagcgcgggt gcggggttgg acgtcgccgc ggcgtcgagg    34380
tcgagcgagt cgcgatcgac gacgatcacg tgcgcgtcgg tgtcgggcag cgcgtcgtgc    34440
agatgctgct gggtgaggag ccagcgcaac tgcgcgtggt cgatcatgaa gcgcacgcgc    34500
tcggcggggt agtcggggtc gacggggacg taggcgccgc cggccttgag gatcgcgagc    34560
agggcaacgc tcatgtcgag cgaacgctcc atggcgacgc cgacgagcga gtcggggccg    34620
acgccgagcg cgacgaggtg gtgggcgagg cggttggcgc gcaggttgag ttcggcgtag    34680
gtgagcgcgg tgtcatcgaa gacgatcgcg acggcatcgg gcgtgcgctc gacctgctgc    34740
tcgaacaggg ggtgcagcgg ttgcgcggcg tcctcgccga aatccgtgtc ggtgcggttc    34800
cactcgacgg tcagcaggtt ccgctccgca tcgctcgaca acggcagacg ggcaacggcg    34860
gccgacgcat cgtccgcgag atgcgtcagt agggtccggt agatgtcgag gaaacgctgc    34920
accgtgctcg cgtcgaacag atcggtgttg tagtcgcaat cgatcaggag tgcttgcccc    34980
gcgtcgagca cgttgacgtt caggtcgaac gcggtatggc ggatcagcgg cgccacgagg    35040
ccgaccgtca ggccgggcag ttcgggcagc gccgacacgg gttcgaggtt gaagaccgcc    35100
gataccagcg gcgcggcgtt gagatcgcgc tgtgcgccga tttcgcggac cagttcggcg    35160
aacggataat cctggtgctc gagcgcgtcg agcaggttct gccgggtgcc ggccaggaaa    35220
ctggccacgg tggcctgctc cggcagcgtg gagtgcagcg gcagcagatg cgtgcagtag    35280
ccggcgaggc gatcgctgcc ggccaccgag cggccggtca ccggaatgcc ggtgacgatc    35340
tcctgctggc cggcgacgcg gtgcaggaac agattgaagc cggcgagcag caccatgtag    35400
agcgtgcagc cgttctgacg ggccgcggtg cgcagcgtcg cggccgtcgc cgcgtccaga    35460
tgcagggaca cgcgctcgcc gtgaaacgtc ttcaccgcgg gccgcgggta gtccaccgga    35520
agattcagcg gtgcggcctg acgcgcgcat tgcgccagcc agtactcgcg attcgccttc    35580
gtttccgggc tgtggcgctg gccgtcgagc tgcttcaggt acgcgcgaaa ctgcagcggc    35640
gcgtcggccg gcgccgcacc ggcatacgcg cgggccagat cctcgagcag cacgccgaac    35700
gtcgagccgt cacagatgat gtgatgggcc gtcatcacca gcaggtgacg ctcgctgccg    35760
aggcgcacga gcgcggcccg aaagagcggc ccgttcacca ggtcgaacgg ctggcggctt    35820
tcctgctccc gccacgcgtt cgggtccgtg tcgatcagcg gaatctcgag tgtcagcgac    35880
gggtgcacga tctggcccga cccgtccgcc atcaccgtgg tgcgcagtgc ctcgtgccga    35940
tcgacgaggc tctggacggc cgcgcgcatc gcggcttcgt cgagccggcc gttcagttcg    36000
agcgtggtgt tgacgttgta ggcgagcgat ccttcgggat cgatttccga caacacccac    36060
agctggcgtt gcgcttcgct cagcgcggcc accgtgccgt gtttcgagtg cggccggatg    36120
aagccgcccc ggcgcaggtc ggcgacgctg tccttcaccg cccggatgaa gcggtcgata    36180
```

```
tcggcatcgg tatgcgcggt ggacaggaag caggtgcgcc attcccagat gtagatgccc    36240
ttttcgagca tgtgatagaa gaacaggtcg aggttctcgg tgaattcgaa gcggaacatc    36300
gagccgaacc acgtgacctt gatcggcgcc tcggcctccg cgaagaatgc attcagcgtg    36360
ccggcgatct gcgcggtgcg ttcgttgagc gcggcctgca gcgccggccc ctcctgttcg    36420
atcttctcga gcacggccag cgccgccgcc atcgcgagcg gatactggca gaaggtgccg    36480
ccgaacgcgg tgcggtccgc cgcggggaac gagtggtcgc cgtaggtcca catgccgccg    36540
tcgatggcat ccatgaagcg gctggtgccg gcgatcacgc ccagcggcag gccgccgccg    36600
atgatcttgc cgtacgtcgc gagatcggcc ctgatgccga acatggcttg cgagccgccc    36660
ggatggacgc ggaaaccggt gatcatttcg tcgaagatca gtgcgacgcc ggcctcctcg    36720
gtgatgcgac gcagttcctt gaggaatgcg acgggctgca gggaagggtt gcggctctgc    36780
accggctcca ccatcacggc ggcgagggtc gacgccatcc cgcgaatggc ctcgagcgcg    36840
gcgtcgctgc cgtagtcgag caggatcatg ttctcgacgg agccgaacgg tacgcccggg    36900
gcgatggttt ccgtcacgcc ttccgcgttc gccgcggcga gcgtgccgtc ggcatggccg    36960
tgatacgaat gcgtgaacat cacgatcttg tcgcgcccgg tcacggcgcg cgcgagccgc    37020
atcgcggtca tgacggcctc ggtgccggtg ttcgagaacg ccacgcgatc gaggccggtc    37080
acgcgggcaa agcgcgcggc gacttcgccg acgaggctgg agcgcgcacc cagttcgagc    37140
gggcgctgcc attcccgcgt gacctgctgc tggatgaaat ccggcgtgtg gccgaacagg    37200
tgcacgccga agcccatcgt gaaatcgatg tactcgttgc cgtcgatgtc ccacagccgc    37260
gaaccggccg cgcgatcgcc gacgatcgga tacagcatct ccttggtcga aaagcggaag    37320
ccgaccgtgg cgcggctgtc ggccagcacc gggcgcgacg cctgcaccga gtccttcgat    37380
ttccgggtgc gcgtcgtgta gcgcacgatc agcgcctcga gatgctcctg ctgcgcggcg    37440
gacagcccgc gcgcccgctg ctggaccggg ctgcccacg gcatcatcgg cttgggcggc    37500
gggttgtcgg ccgcgggcgc ggcggcagct gcaggcgcgg gcttcgccgc gggtgcggcg    37560
gccggggccg cgctcgccgc tttgggtgcg acgctcgccg tgctcgcgac ggcttgcacg    37620
gcggccgtcg ccggccggac gccgggctgg ccggtcagcg acgtgcgcag cagttccatc    37680
tgctggctca tcacgtgcga cagcagctga ttctgctccc gcagcacgcg ctcgaccgtc    37740
gagccgcctt cggccgccac ccattccgcg ggggcggccg cgagcggcgc aagccccgcc    37800
gcggacggcg tgaccgcgac cgccggcgtg gacggttccg ccgcggccac ggctacggct    37860
acggcctcgg ccccggacgg tgcggcggct gccggcaggt tgtccgcgac atattcggcg    37920
agcgcctgca ccgtcgcgag gtcttcgaag aagcggcgca tggccagctt cacgccgtac    37980
tccgcctcga tgtgccggat ggcctcgatc agcacgatcg agtcggcgcc catctcgagg    38040
aagggcagtt cgatgttgat ggtggcggga tcggcctgga tcaattcgcc gatcttgccg    38100
cgaagccatt cgagaatctc gccgctgcga ttgtgcgtcg gtgctgcggc gatgggtgat    38160
gcgcttgtct gagtcatgga cgtgtccgct ttctggaacc aggtacggct gcgttggaag    38220
ggataggacg gcaatgcgat gcgcgcgggc gcgggtgttt cggtcggggc ccagtcgaca    38280
tcgacgccgc gggcatacag gctcgacagc gtttcgatca gcgcttgctg ctcgacttgc    38340
ggccgctgca gggcaaggaa ctggatcccg gcgtccggcg cacagcacgc gcgggccagg    38400
ttgacgagca ccgccttcgg gccgatttcg accagcacgt tgaaaccggc ttcggcgagg    38460
cgctcgacgc tgctcgcgaa ctgcactggc tcccggcagt ggcggcgcca gtacgtgtcg    38520
```

```
gtgggtgcct cgtccatcac ggcgcccgtg agattcgaat agaacgggat cgccgggcgt    38580
gcgacgggca cggttttcgc cgcgagctgg aagctgtcca gcatcggctc gagcagcggc    38640
gagtgaaacg cgtgcgacgt attgagcggc acggaccgga tgtcccgcgc ggcgaacgca    38700
tcgaccagca tcgcgatgcg ctcgcgcttg ccggaaatca cgatgctcgc cgggccgttg    38760
acggccgcca ccgcgacctc gtgcggccac gcgtcgatcg cgcgctcgac cgtggcgagg    38820
tcggtgaaaa tcgccgccat ctcgccgtcg cggggcaacg cctgcatcag ccggccgcgt    38880
tcggcgatca gccgcaggcc gtcttccggc gagaagacgc cggccgcgca agccgccgcg    38940
tactcgccga cgctgtggcc catcacggcg tcgggcacca cgccgaacga cgccagcaac    39000
gtggtgagcg cgtactgcag cgagaacagg gccggctggc tgtagccggt ctggtggatg    39060
tcctcgccct gggccgacag cacttcgagc aacggcttgt cgagcaacgg atcggccacc    39120
gcgcggcaac ggtcgatggc gtctcggaac accggatacg cgtcgtacag gcggcggccc    39180
atgccggcgt attgcgagcc ctggccggtg aacaggaagg ccatcttcac gcgggggcg    39240 ggctgcgccg cgccggccgg ttccttcgcg tggaaggcgc gcagcttgtc gatggcgtcg    39300
tcgagcgacg tcaccggcca tgccagccga tgcgcgaaat gcgagcggcc ggtcgccgcc    39360
gaaaaggcca cggccgcgat gtcgagaccg ggttcggctt cgagccgccg ctgatagcgc    39420
ccggccagct cgcgcaacgc cgcggggtc ttggccgaca gcaccagcgg atgcaccttg    39480
tgtctcgacg gcgtcgcctg ccgcgccggc gccggcgctt cttccagcac caggtgggca    39540
ttggtgccgc tcgcgccgaa cgcgctgacg ccggctcgcc gtggccgttc gccacgcggc    39600
cacgcgctcg cctcggcgca gatctcgacg ggcattgcgt cccactgcac cagcgggctc    39660
ggctggcgga aatgcaggtg ggcgggcagg cggtcgtggt tcagcgacag cacgaccttg    39720
atgacgcccg cgatgccggc ggcggactcc gtgtggccga tgttggtttt caccgagccg    39780
acgcgcagcc gccggccgc gtcgcggcct gcgccgaaca ccgtcgccag cgcctgcaac    39840
tcgacgggat cgcccagcgg ggtgccggtg ccgtgcgctt ccacgtaatc gatgacgcg    39900 gcgggcaacc cgcccagcgc ctggcggatc acggcttcct gcgcacgacc gttcggcgcg    39960
gtaaagccgc tcgacgcgcc gtcgtggttg accgccgaac cccgcagcac ggccagcacg    40020
cgatcgcccg cggcgagcgc atcggacagg cgcttgagca ccagcgcgcc gcagccttcg    40080
ctgcgtacga agccgtccgc cgccgcgtcg aaggtcttgc agcggccgtc cggcgccagc    40140
gcccgcgtgc gcgagacggc gatggagttg tccggcgaca ggatcaggtt gacgccgccc    40200
gcgatgcgca gatcgcactc gccgctgcgc aggttctggc tggcggtatg gatcgccgtg    40260
agcgacgacg agcaggcggt gtcgatcgcc atgcttggcc cctgcacgcc gagtccgtag    40320
gagatgcggc cggccgccgt gttcagcggg ttgccggtga agaaatagcc gtcgatgccg    40380
ctgccgccgc cgttgcgaag ctgcaggttc gcgtaatcgt tggtggtgat gccgacgaac    40440
acgccggtgc ggctgcccctt gagactgtcg accggaatgc cggcatgctc cagcgcttcg    40500
tgactgacct cgagcaacag gcgctgctgc gggtccatcg cggccgcttc gcgcggcgtg    40560
atgcggaaga acgccggatc gaactggtcg acgtcgtcga gaaaaccgcc gaagcggctg    40620
tacatacgcc ccggcgcttc cggatcggga tcgtagtacg cgtcgacatc ccagcgctcg    40680
cgcggcactt cggagatcgc atccacgccg tcgttcagca ggttccagta ggcgtcgaga    40740
tcgtgcgcgg cgcccggaaa ccggcagctc atgccgacga tcgcgatcgg ctccggcgtg    40800
ccggcgtcgc gggcctcgat ggccggcgcg atcggccgcg gctgctgctg cggcggcacg    40860
gtctgcgcct gcgccgtgcc ggacgcctgc tccgccagga aatccgcgag ggcgttgacc    40920
```

```
gtcggatgat cgaacaacag cgcgaccgac agcgggatgc ccagcgcatt ttcgaggtgc    40980
gtgcgcacgt ccagtgccat cagcgaatcc atgcccatct cgaagaagcc gagatcgcga    41040
tccagcgtcc ccgcgtcgta gcccagcacc tgggccaccg cgcgatcgat gctgtccgcc    41100
agcagccgct ttcgctcgcg cggcgatgcg tcgctcagcg ccggcattgc cggcgcgctc    41160
ggcgcgcttt tggccacccg cacgtggtcg aggaacggct tgggtccgcg cgcctcgtag    41220
gagccctgga acagcgccag gtcgatatcg acgaccgcga cctggggcac ggcggggaga    41280
cgattcagca cgtcgagcgc gcgatccgcc gccagcgacc ggatgccgac acgccgcagc    41340
agcgcttccg cctcggggaa cgtcatgccg ccttccgccc agggcccca gttcacgctc    41400 agcgccggca ggccctggcc gcggcgatga tgcgcgagcg cgtcgaggaa acggttcgct    41460
gcactgtagt gcgcctgctc acgcgagccc cacgcggacg cgatcgacga aaacaggagg    41520
aagaaatcga gcgggaagtg ctcgctctgc tgatggagca gccacgcgcc ggcgaccttc    41580
ggttgcagga ccgcgtccag ttcgtcgcgc tcgacctgca tgatcggctt gtagccgacg    41640
atgccggccg cgtgcacgat gcctttcagc ggcacgccgt cgcgccgcag cgcggcgaag    41700
aaagcggcga ccgctgcggg gtcggcgata tcgaggcgct cgcagcgcag cgtgacgttc    41760
cgctcacgca gctcggcgat cgcccgctgg ctctcgtcgc tcgcggcccc ttgccggccg    41820
accaggatca gcgtgcccgc accgcgcgcc gccagccatc gggcggtgtg cagcccgagc    41880
gcgccgaacc cgccggtgat caggtaggcc gcgtccgggt cgaccggcag cgcggccgtt    41940
tcggctggcg cgagcgggct caggcgcgcg acatggcgcg cgccgtgccg caacgccacc    42000
tgctcctcgc ggctctcgcc gagcatctcc tgaagcagtg cctgcgtctc gttctccggc    42060
gcggccggat cgagatcgat cgcggtgccg aaccattccg gatgctcgat cattgccccg    42120
cgtgcgaggc ccgacagcgc agcctgggcg agcccggata cgtgcggcgc ttcgccggct    42180
tccaccgcgt cgcgcgtgac caccgagatc ctgggccggg tcgaaggcgt ccactcgcgc    42240
tcgctgccga ccagcgcgtg cacgagatgc agcagggcgg cggacatgcg cgtttcgccg    42300
acggcttcgt ccagcgccca taaaaagacg atgcgctggc cggaagcggc ggtttcgttc    42360
agcaagcgga cgaaatcgtc cggccgctcg ggcgcgacct gccagcccgc ttccgcgccg    42420
gtgacatagt cgatgccggg gcggaccagc gagcaggatg cgccgcgcgc gcgcagcagc    42480
gctgcaagcc gctcgccgac accgctcgca tccgcgaaga tcagccacgg ggacgcgtcg    42540
gcggcggccg gtgccgccgg catcgcggcc tgctgctccc acaccacgtg atagagcggg    42600
tgtgcgttcg acgcgacggt ctcggcggcg gcgaatgcag tcctgagcag gtccggaaac    42660
gcgttcagca tgtcctccgg gtacttgccg gacgacttga ggtgccgcaa cgctgcgtcg    42720
atgctgccgg catccatgcc gacgatcggc gacggaatct tctccaggct gaagcgctgc    42780
cgctcgaacg ggtagttcgg cagggtcgtg gcgggctggg cgggcgccgg aaacagcgcg    42840
cgccagtcga actgcgcgcc ctgcacgtac agcgccgcga gtgcgcgctc cagtgcatcg    42900
cccgcgcagg gcggcggcag ccagccgtcg gcgagcccct ccggcgggtg cgatgcgtcg    42960
gcctgatccg acgcgccagc cagttgcaac cagtactgcg ggtgcgtcac ctcgtcggtc    43020
acgtcggtgc cgagatagcc cgaaatcagg cggaccgacg gccgtgcgag cggcatgtcc    43080
cgaagcacgg cgcgcaacgc ttcggcatcc gaacgggcgg ccacgaggcg cagcgcgtcg    43140
gccacgctca cgacgcccgc cacgcaggcc gcgacatatt cgccgatgcc atggcccgac    43200
acgacggccg ggcggaggcc ccatccctcc cacagttccg cccacgcgaa ctggatcgcg    43260
```

```
aaccggcccg cgtcggtctc gagtgcgtcc agcggcaccg agcaacgcgc gaacgcgtcg    43320
cggaacagcg gttccgacgc gtggagcgcg tgcgcgacgc cggtgtccgg cacaccgaac    43380
ccgaagccca tgcgcaacgc cttgcccgtg cgcggcgcgg ccgccgacgc taccctcgcg    43440
cccgatacat aggcggcgcg aaacggatag tgactccgcc cggtggcggc ggcacggcag    43500
atcgcggcta gctcctgcgg cgtcgcgccg gcgatcgcgc gctcgtagcg tggcacgagc    43560
gccgccagcg ccgcttcgga ccttgccgac agcagcagca acgcgcgctg cgcggcgtgt    43620
gccggcgcga cgggcggttc ctcgacgatg gcgtgggcat tggtgccgct gaatccgaac    43680
gcgctcaccc cggcgatgcg cctgcgttcc ccgcgccgcc acgcgaccgg atcggccgcg    43740
acgcggatcg ggatgtcctg ccacggcgta tgcggattgg gttgcgtgaa atgcaggtgc    43800
gccggaatcc ggtcgtgctc gaacgacagc agcaccttga tcaggccggc gatgccggag    43860
gccgactcca gatgcccgat attggtcttg accgaaccga tcacgagcgg ctcgttcgcc    43920
gcgcgcccgg ggccatagac gccggccagc gcttcgacct cgatcgggtc gccgagggac    43980
gtgccggtgc cgtgggcctc gacgtaggac acgtcgccgg gcgcgaggcc ggcctggttc    44040
agtgcgcggc ggatcacccg ttcctgcgaa tcgcggctcg gcacggtcag cccgccgccc    44100
gcgccgccct ggtcgaccgc cgtgccgcgc acgatgccga gcaccggtc gccgtcggcg    44160
agcgcgtcgg cgaggcgctt gagcaccacc atgccgcacc cttcgccgcg cacatagccg    44220
tccgccgccg cgtcgaaggt cttgcagcgt ccgtccggcg acagcatgcg cgcctgcgag    44280
aagctgacca tgacctcggg cgacagcatc aggttgacgc cgcccgcgag cgccatgttg    44340
ctttcgcgcg agcgcaggct ttcgcaggcg aggtgcaggc acaccagcga agacgagcag    44400
gcggtgtcga tcgccatgct cgggccggtg aggcccagca cgaacgacag ccggcccgcg    44460
gccatgttca gcgcgctgcc cgtgccggca tagctgctcg acggcatcga cgcattggac    44520
acctggatcg cgtggtcgaa gcaggtgatg ccgacgtaca cgcccgtggc ggactgccgg    44580
aagcgttcgg gcgcgagatg ggcgttctcg agcgcctccc acgccacttc gagcaggagc    44640
cgttgttgcg gatcgaggta ggtcgcttcg cgcggcgcga tcccgaagaa cgccgcgtcg    44700
aattgatcca cgccgttcgag aaaggcgccg tggcgggtcg ccatcttgcc gggcgtggac    44760
ggatcggggt cgtagtagcg atcgatgtcc cagcgttcgc cgggcacttc ggtgacggca    44820
tcgtgcgcgc cgtcgagcaa ttgccagaac gcgtccggcg tatcgctgcg tccggggaag    44880
cggcaagcca tgccgatgac ggcgatcggc tcgttgcggt cagaacgcag cgccgcgatt    44940
tccgcgcgcc gcaggcgcag ttcgtcgagc gcggctttca gtgcatgcgt ggccttggcg    45000
ttcattgggc gccgatctcc tgggcgatca gttcggaaag gtcgtcctcg tcgaggtcgt    45060
cggatgcttc gtcgacgacc ggcgcgggga gcgacggcga cagttcgttg agcacgtact    45120
gggcgagcgt ctgcaggttc ggataggaaa agaacaacgt cgcgcgaaac ggtcttccga    45180
ataccttggt gaggcggtcc gtcagttcga gcgcgaccag cgaatccagg ccagatcga    45240
gcagcgattg ctcgggcgcg atggcatcgg ggccggaaag gcgcaaggtt tcagccagca    45300
tcgccgcgag cgtgtcggtg atgcgctcga cccgttcgcg cggcgcgcac gcatgcagct    45360
ggcgcagcaa cgccgtctcc tgctgcgccg gctgcgcggc cggttgcgtc agctcggaaa    45420
acagcgcgga cccggcggcc ggcgcatcga cccggaacag ggtcggccag tcgatccgcg    45480
cgactccgga ctgggcgacg ccggacgcca tcagccgttc cagcgtcgcg atggccagtt    45540
cgggcggcag cgtgccgacg ccgagcgcgc cgagttgttc gtgcgcgcgc cgtccgtagt    45600
cggtggcggc gtggccgatc tccgcccacg gcccccaatt gacgctgagc cccggtttcc    45660
```

```
cctgcgcgcg ccgatgctgg gcgagcgcgt cgaggaagct gttcgccgcc gcgtagttgc  45720
cctggcccgg catggtgatc agcgcggcca tcgacgagaa caggacgaaa tggtccagcg  45780
gcaagccggc cgtcagctcg tgcagatacc acgcgccgtc ggccttgccg ctgccggcgc  45840
gatggaagaa gtcgtcgtcc tggcgtgtca gcagcgcatc gtcgagcgcg ccggcgaggt  45900
gaaagatccc tttgagcggc ggcatcgaat gcgcgatttc accgagcgcc tgcccgacgt  45960
cctcgcgacg cgacaagtcg gcgcgaatga accgtgcgtc gagcgtgcgc aggattttcc  46020
cggctgcggc ggaaggttcg ccgcgcccca gcagcacgat tttcccggcg ccgttgtcgg  46080
caagccagga cgcgagccgc aggccgagcc cgccgagccc gccggtcaca agataggtcg  46140
cgtcaccgtg gaaccggatc ggccggtggc tgacgtattc gcgattgtcg cgggcgatgc  46200
gcgcgacgta gcgctggtcg cggcgaaacg cgatcatgtc ttcacggccg ccagcctgta  46260
ccgcttgcat gatgtccgct gccgacggct gctcgggatc gaggtcgacg agcccgcccc  46320
acagcgccgc atgctccacc gcgatcgcgc ggcccaatcc ccacagcggc gcctgtgcca  46380
ccgcgatcga ttcgccatcc agaacattca tcgcacccga cgtcaccagc cacaggcgag  46440
cctgccgggc cgacgcgcg cgtgacgcaa gcgccctgac caggtgcagc acgctcgcgc  46500
tggcacgccg tctcgccgcg atgtcagagg gtgcgagatc gagactccac aggtggatga  46560
cgcccttcag cgggcggtcg gccgcgggca gttccggcgt cgcgtcggcg aagcgcagcg  46620
tgcacgtatc gccgtgggct tccagcagag ctgacagctg ggcgcccacg ccgccgcggt  46680
ccgcgagaat cagccactcg ccgtgcgccc aaccgccggt tgccgcgtcg acgttcgacg  46740
gtctccagac gcgttgataa agcagcgcgg cgaagtcgtg ccgctcgacg gcgcgcgccg  46800
cgcgaacctg ttgcaaccgc agtgcatcga tctcgatcag cagtcggcca gcaaggtcat  46860
ggacgcggat gtcgccctcc agcgcgccct gtccgatcgg cgtgcgcagc gtggcgtgac  46920
tccatgcctc ggtcgacgcc ggcggctgat ggaccgtac cgccgccgatc gagctgggca  46980 ggtacaggtc gcccgactcc agcgcgtccg gatcgatggc ggcggcgagc acgcggctgc  47040
atgcgtcgag aaaggcgggg tgtacctggt acggcgacga cgccagcgca tctgccggca  47100
ggctgatttt ccccagcgcc tcgccggtcg tgcgccagat ctgccggatc gcgtcgaaca  47160
cgccgtcgat ctgcacgccg tgctgccgaa tttcgccgtt gaagtccgcg cccgacgtcg  47220
tttcggtgca gcgggcctgc acctcggcgg catcgaatcg cgtcggcgcg gcggatcgcc  47280 gggggggcaca catttcccgg agccggcgca gctgcggaag attgccgagg atccgctcga  47340
ccggcggacc gaaatcgagc aggcaggcca cttcatccac gccgatcgac tcgagatccc  47400
gcaccagttc gacgcaggtt tccggcgtgc cgatgagccc gcgcgattgc gcgaagcgtt  47460
catagagaaa ctcgacgaac tcgtccagct cgcgtgcgcc catcgcgcgc acgtcgaccg  47520
actggccgcg actctgcgcc agcccgttca atagcccgat attgctgcgg atgtagttgc  47580
agaacggcac acgcgcctgt tcgcgcgcct gcgccgcatc gtcgccgacg aacgtatgca  47640
gcatcacgga aacggtgccg gccgccggat cgaagccatg cttcgcacgc gcctcgcggt  47700
agagcgcgat cttgtgcgcg agctggtcac gatcctggtc gagcacgtgg gtcagcaggt  47760
tggcgccggc ttcgccggca cgcacgaatg tctgcgcgatt gctcgcggcg gtcacccaga  47820
cgggcagctc cggctgcacc ggcgtcggat agacacgcaa ccgcaccggc ttgccgacac  47880
cgttcgtcgc atccagcgtg ccgccgcgcc acagatgctg gacggcgcgc atcgtggtca  47940
gcatgtcgtc ctgccgggtc gcatatttgt ccggggcaaa cacgaagtcg tcaggattcc  48000
```

```
atccggaggc gaacgacacg cccacgcggc cgttcgacag gttgtccacc atcgaccatt    48060
cttccgcgat ccggatcggg ttgtgcagcg ccgcgaccac gctgcccgcg accagcttca    48120
cgcgctgggt ggccgcggcg agcgcggcgt gcaggacggc gggattcggg taaagcgagc    48180
cgaattcggt gaaatggcgc tccggcaccc agacgctgga gaacccgttc gcatcggcga    48240
aacgcgcgct ctccatcacg agctggtact tgttgccgga cagcgcctct tcactgctgg    48300
cgaagaacat cagtccgaat ttcatgcgtg gctccgatcc gattcgtgaa tttcggcact    48360
cgcgcacatc tgccacgtcg cggcggcgcg ggtgtcgtcg atccggtgat agacggcaaa    48420
cgaaaacggt ccccaggacc ggcggctcag cacggtctgc acggtgtgcg attcgtgcgg    48480
atgcagcggc aacggcgcat gcagtgcgag gtccttcaac gtcgtatggc cggctgcgcc    48540
gatttccgac gttgccgaca cgccatttc cacgaaggcg aatagggca ggacgggcga     48600 ccccttgacg cgatgaccgt cgagaaagtt ggttgccggc gcatcgagac gcgattgcca    48660
gatccacgtg gccggcgcat gcgcgtgctg ctccatgagg cgcccgagca acggatgccg    48720
acgcgcatgt ggcctgatcc agaagccgcg ccgctcgaac gggtaggtcg gcagggcgag    48780
ccggcggtgc ggtgcacctt gctccacggc atcccagtcg atggatgcgc cgcgtacgta    48840
gagcgcggcg agcgtgtgca ggatcgcgtc ccacgcggcc gtgtgcgcgc cgatgtcgat    48900
cacgatgccg gggtgtcctg ccgcaccgct gtccggcgcc tgcggcacgc cggcccacgc    48960
ggctgcggcg cgctgcccgt cgccggtgct gctgaccgca tccggtgcga tgccgaagga    49020
catccacagt tgcgcgagcg cgcgctggaa tctcgtgaac ccggcttcgt cggggggcgag   49080 cgcgggcgcg ccggatgcgt cggactgccg ctgcatcagc gcgtcgaaag cggggctggc    49140
cgcgcgcaat tgccgaaccg cgtcggcgct ggcgccgtcg tcggcgcaaa agtggaacgt    49200
caccgcgggc ggtgtttcgg caggctcccc ggacgaaacg gaatcaagtt gcgcacgcaa    49260
cgaatcgcga ctcggtgcga cgatggccgc gcgctgcgtg aagtgggtgc gcccggtatt    49320
ggccgtgaac gcgacatccc gcacaccggc ctcgggatgg gcgtcgagat aggccgcata    49380
ggacgcagcg agcgcttgca acgcgtccgg cgtgcgcgcg gagagcgtca cgacgcgcgc    49440
cgcgggtgca accggttcgg cttcgatctc cgggagcccg ggtgcttctg acaggatcag    49500
gtgcgcgttg gtgccgccga agccgaacga gctcacccct gccaggcgcg gcccgtgttc    49560
cgaatgccag ggcgtgacct gccgaggaat ccggaagggc gtgccgtcga gcgcgatttg    49620
cggattgatc gaccggaaat ggaggttcgg cggaatcgcg cgatggtgta gtgcaagggc    49680
ggtcttgatc aggctggcga tgcccgcggc cgattccagg tggccgatgt tggtcttgac    49740
cgacccgatc cagcagagat cgtccgggcg gcgggattcg ttcaggacgg ccgccagcga    49800
gttcaactcg atcgggtcgc cgagcggcgt gcccgtcccg tgcgtctcga cgaagccgat    49860
gtcctgcgcg cgtacaccgg catcgcgcag cgcgccgtga atcacggcct gctgggccgg    49920
gccattcggc gcggtcaggc cgttgctgcg cccatcctga ttcaccgcgg agccgcggat    49980
cacggcgaac acggtgtcgc cgttctcgag cgcatcgtcg agccgcttga gcagcaccat    50040
gcccacgcct tcgccgcgaa cataaccgtt cgctgccgcg tcgaacgcct tgcatcggcc    50100
gtccggcgac agcatgcccg cttgcgtgaa ggacgcgctc aattgcggcg ccagaatcag    50160
gttgaccccg ccggccagcg ccgcatcgga ctcgccgcgc tgcagcgcgc ggcacgcctg    50220
gtgaaccgcg acgagcgagg acgaacacgc ggtgtcgacc gcccagctcg ggccgcgcaa    50280
atcgagcgcg taggaaatgc ggttggcggc gacgctgagc gcattgcccg tcgcgacata    50340
agggccgacg tccgcgactt cgtcctgcgc cagacggatg tagtccgaat tgctgatgcc    50400
```

```
gacgatgacc gcggtgcgtc cgccggcgag gctgcggggt gcgatcccccg catgctcgag    50460 cgtctcccag gccacctcca gcagcaggcg ctgttgcgga tccatcgatt cggcttcgcg    50520
ggcgctgatg ccgaagaaag ccgcatcgaa ttgatcgacc tgatccagca gtccggcgag    50580
cggaaggtcg gccgcgcgct gcgtcgccgc accgaccgcg tcccggccct ccagcagaag    50640
ctgccagaat gcgtcgggat tgccggcgcc ggggaagcgg catcccatcc cgacgatcgc    50700
gatatccgcg cgtgcttcgg ccgagcccgg cgcctggtcc ggcatggcac tcccggtgcc    50760
gctcaaatgg cgcgccagca gggaaatact cggaaaatca tagacgacgg tcgggaaac    50820 cggccgcccg agccagtcct gcagctcgcc cgagagcatg atggcgtcct tcgaatcgag    50880
cccgtggacg ctgaacggcg cgtcggggtc gatcttgccg gaagcgattc ccgacagacg    50940
cgagacacgc tcgatgcacc attgcaccag cgcttgcgtg tcgcgtggct cggcagtctg    51000
cgggggggct ggcggcgcgg agaacgcacg ccgccattcg cccgcgatcg cgagcccctg    51060
ttcatcgagg aatgcctgcc tgatccggct ccgctggatt tttccgctgg acgtgcgcag    51120
gatcgtggca ggtttcaaca ggactgccgc atacagatcg acgtcgtgca cttcggcgag    51180
cgtgtgccga atctcggcgg ccacggcttc cgcgtccagc gtgttgagcg cttcccggcg    51240
cacttcacag gcgacgacga cccgctccac gttatcgacg tggatcgaga aagccgccga    51300
tgcgttcggc gccagcgcgg ggtggctgcc ctccgcggat tgctcgagat cctgcgggta    51360
gtgattgcgg ccggcgacga tgatgaggtc tttcaagcgg ccggtaacga agagatcctc    51420
gccatcgacg aagccgagat cgcccgtgcg caggtaacgc gcgtcatcgc cgtccagctt    51480
cgcgcggaag gtgcgctccg tttcgtcgat acggttccag tagccgacgc cgacactcgg    51540
gccggtcagc cagatttcgc cgatccggcc gggcgcgcag cgctcaccgg tatccggatt    51600
cacgatgcgc acgcggtgct cagcccaggt ccggccgcat gagaccagcg cgtggcgctt    51660
gccggagtcg tttctcgtcg ccacgccttg tgccagcgcg tcggcatcgt agtccgccac    51720
gcgcggcagc gagcgtgccg gctggccgga gatgaacaag gtcgcctcgg ccatcccgta    51780
gacggggcgc atggtgtgcg cgtggaagcc gcacgcggcg aatgcgcgcg aaaaacgcgc    51840
caccgactcc gcgcgcaccg gttccgcgcc gttgaatgca cccgccagc tgctcaggtc    51900 cagctgcgcg cgcgcttcat cggcgatttt gcgagcacac aggtcatacg cgaaatccgg    51960
cgcggcacaa tgcgtgccgc gatacttcgt gatggcctgc agccagcgca cgggtttctg    52020
cacgaatgcc gcgggcgcca tcagcaccga cagcacgccg agatagatcg gcagcaacac    52080
cttcccgaag aaacccatgt cgtgaaacac cgggagccag ctgacgaaca ccgtcgacgc    52140
atcggcatcg ctcgcctcgg cgatgaccgc catattgctc aggatgttcg cgtggctgat    52200
catcacgcct ttgggcgtac cggtggagcc tgacgtgtat tgcagaagcg ccagcgtctg    52260
cggcgtgatg tccggtgcgc gccattgttc ggccggggcg tcgaagcgct ggtccgtcgc    52320
caggatcttc agttccagcg tgtcggaata accgtccgcg tgatgcgcga tgccgtcgag    52380
cgtcgcggcg tccgtcagcg cgacgaccgg cgtggcgtcg gcgacgatgg ccttgagacg    52440
atcggcggga cgatgcctgc gcggtggata cgcgggtacg ccgatcaggc cggcgtacag    52500
gcatcccacc catgcgcaga tgaattccag cccgggcgga taaaccagaa ggacgcgatc    52560
gcccggttga gcgatggctt gcagcctggc ggcgatgccg cgagcccgct tgtccaggtc    52620
gccgaacgtg aggcgggtca gctccgcttc gccgttctcg agaaaaatga atgcggtctt    52680
ctccggttcg accttgccgc gaaacaacaa aatttctgta acagtcctga attttgtatc    52740
```

```
gggaagcatg ctcaaccttc gttgtcttct aaacgttgaa tatctcagga ccggttgtgg    52800
cgatcccgcc aagcgtgctt catcggacgg tatcgaaatt agagcattgc tctaatccgg    52860
cgtctgcccc gtaatccaag gacacggcgt ttcgcgcact ggatcaatac ggcttgtcat    52920
tgatgtgcac gctcgctaac gatcggcgat tccttcgatg tcgggcgtgt acgggtccag    52980
cagcgacacg acgaccttgc gctcgccttc gaacgggttg cggccatgcg cgaagcgcat    53040
gttgtcgacc agcaggacgt cgcctcgttg ccacggaaac gtgatcgcgc attcgcggaa    53100
cgcgtggcgg atctgctcga ggtcggcgag atcgaacgga ctcccgtcgc catggcaggc    53160
attgcgcgga atgcgatcct cgccgaacag gctgacgatc gaactggcga gcgatgcttc    53220
caggttcgag atatggaaca gatgggcctg attgaagaac accgctcgc cggtgaccgg     53280 atggtaggcc acgccctggt tgatctgcgc ggtgcgcaac gtgtcgtcgt cgagccattc    53340
gagcgcgatg ccgttatccg cgcagaaggc tgcaacctgg ttgcggtcgc tggtctggaa    53400
cacggtctcc cacggaatgt cgacgtgccg ccggtagtgc ctgacatagc ggacctgtct    53460
cgcctcgaag tgatccagga tgcgcggtcc gatcctgcgg ctcacctccc gcatgtcggc    53520
aatcggcgtt tcgccgccgg tcgcggccgg cgtcaggcaa cagaaggcca ctcgcagcgg    53580
ccagcttcgt tgatacgcgt tttcgcaatg aagggcgatc gtctcgctcg gcggatactc    53640
ggttgcggtg aagatgccgt tgccgatcga ggtgcgcggc gtggaacggt aaacgtagtc    53700
ggactgatgg gccgaaatcg cgcgagcaaa cgcttcgaag ccgcccacgg atgaaacgtc    53760
gaagccacga aacaggagta cgccgtgttc cagaagccgg gattcgagtg ccgcccggtt    53820
gtcgttcacc gcctgcgcca gatcgcgtcc attcgataca ggctccagca gccacggcgt    53880
gcttccctcg gcaagcaact tgcgttccgt catgcccagc atcgtcaata gtcctttcct    53940
gtacgtggat cacggcgaag ccgaacgggt cggcccgcgt ggtcgcgccg cggtgcggct    54000
atgcgcggca ggccgtttcc acggcatgct cgaagcgatt gagaatgtcg tggatgtccg    54060
cttccgaaac gatcagcggc ggcaggaacc ggagcaccgc gccgttgcgg ccgccggttt    54120
cgacgatgag cccgtttcgc aggcagttct gcttgatggc tcttgcccgt tccgtgtggg    54180
gcgggccggc tcgccgtgg gtgccgggca cgacgacttc ggcgccgatc atcaggccgc     54240
ggccgcgtat ctggcccagg caggggaagc gttcggcaag ctcctcgagg ccggcaacca    54300
ggagtttgcc gaccctgtcc gcgtgcgccg acagatcttc tctctcgacg atgcgcatgg    54360
tcgacaagcc ggccaccatc gcaatctggt tgcctcgaaa ggtgccggca tgcgcgccgg    54420
gcggccaggt gtccaggcgc tcgtcataga ccaccaccga taacggatag ccgccgccga    54480
atgccttcga cagcaccagt acgtccggcc ggatgccgga atgttcgatc gcgaacaggg    54540
cgccggtgcg accgagtccg gtctgcactt catcgacgat caacgggatt tcatgccgca    54600
gcgtcagctc gcgcaactcg atcaaccagg tgtcgggagc ggggatgcag cctccttcgc    54660
cttgcacgac ttcgacgatg atggccgccg gcttcgtgat cccgctctcg ggatcggaca    54720
ggacggtccg gatgtagttg atgctgagtt gatcggtcgc cgagccgtcg gtgccgaacg    54780
ggcagcgaaa ggcgtaggga tagggcagga aatgaacgtc gcgtccgttg ccgccggccg    54840
acttgggcgt gaggtttccc gacgcggcga gtgcgccgga cgtcatgccg tggtaggcgc    54900
cgtggaacgc catgatcgtc ggccggccgg tatagtgccg ggtcagcttg atcgccgctt    54960
cgacgccatc cgcgccactg gggctgcaaa actggatctt gccggattcg gcgatcttcc    55020
cgggcagaag cgagaaaagc tgctcgacga atgcgtgctt ggccggcgtc gccagatcga    55080
gtgcctgttg catctgatcg gacgacagaa accgcatcac ggcttcattg acttccgggt    55140
```

```
gattgtgtcc gagcgcgagc gtgcccgcat tcgacaggca gtcgatgtat tcctgcccgt   55200
cggcgtcgcg tacgcgtatg cctttcgcat gggtaaacag ccgcgggaag gaggttgcgt   55260
aggttcgcgc gttcgattcg acctgcttca gatactcgag tttttccatg cgcgcagatc   55320
cggcttgcaa ggcggattga tggacactgg cgcacgagaa tcgcttcatc ctggccaatg   55380
gtgtttaacg gtacgaccgg attggagcat ggtctccgta tcgcgtctgt cacgtaaaaa   55440
tgggacatcg gccatgcgac gtcaccacgt catgccgttg ccttccgatc atcgaagcgg   55500
tttccgggcg cgacgtcagg cagcgagggt cgagcagaaa taatcgatgg tccgttggag   55560
acccgcttcg agcccgatcg tcggctccca gtcgaggtgg gtgcgtgcga ggctgatgtc   55620
ggggcaacgt tgcgtcggat cgtccttcgg cagcggacgg aatacgagcc gcgacttcga   55680
gccggtcagg cgcaagatga tctgcgccag ttcgctgacc gcgatctcgt gcggattgcc   55740
gaggttgatc gggccggtga gctccgcggg cgtggccatc atccggatca aaccgtcgac   55800
catgtcgtcg acatagcaga atgcccgggt ctggctgccg tcgccataca gcgtgatgtc   55860
ctcgccccgc agcgcctgca cgatgaagtt ggacacgacg cggccgtcgt tgggatgcat   55920
gcgcggcccc tacgtgttga agatgcgtac caccttgatt cgtacgttct gctggcggtg   55980
atagtcgaag aacagggtct ccgcgcaacg cttgccttcg tcgtagcagg cgcgcggccc   56040
gagcgggttg acgttgcccc ggtaactctc cggttgcgga tgcacatcgg ggtcgccgta   56100
cacctcgctc gtcgacgttt gcagaacgcg tgcatgcgtg cgcttggcga gcccgagcat   56160
gttgatcgcg cccatcacac tggtcttggt ggtctgcacg ggatcgaatt gatagtggat   56220
gggcgaagcc gggcaggcga ggttgtagat ctcgtccacc tccacgtaca acggaaaagt   56280
gacgtcgtgg cgcagcgcct cgaagctcgg gttgccgagc agcgtagcca cgttctgctt   56340
cgtgccggtg aaatagttgt cgacgcacaa tacgtcgtga ccgagttcga cgagacgctc   56400
gcaaagatgc gaaccgagga aacccgcgcc acccgttacg aggattcgct ttcgattacg   56460
ttgcacaatt gcactccaag tatcgcgcgc tgggaagcga cgcggcctcc ccgcacgctt   56520
gaccggcccg cggcaccggc aggggagcgg atcaggcgcg cgggcgtttg cattcgacga   56580
tcacggcgcc ggccggcacg ccgatcgcga ggatcggccc gtcatgcctg cagtgcgctc   56640
gacgcggcgt gctccgggcg ccgcatgcgc gccgcgatga tgccggccat cgttcgcatt   56700
tcgtttctca aaagaaatg atcccctttcg atgacgtgaa aatcgaagcg cccggtcgtc   56760
gcggcgcccc agcctgcaac ggcatcgacg gggatctctt tatccgcccg gcccgcgaac   56820
gcggtgatgt ccaccgccag cctgggcccg ggcacgggcc ggtggttttc gatcatcgtg   56880
aaatccgcac gcagcgccgg catcagcagc gccatcagtt cgctgttgtc cagcaccgcc   56940
ttcggtgtgc cgcccatttc gcgcagcgca tcgatgaagg cgcggtcgtc cagcgcctgc   57000
atgcgccgat cgtggcgctc cttgcccggt gcggcacgcg cgctcacgaa cagatgccgc   57060
aggttcggtc gtgcgtgggc gggaagccga agggccagtt cggccgcaat ggccgcgccc   57120
atgctgtgtc cgagcagtgc gaagggacga tcgaagcagt cgtccaggtc gcacagcaac   57180
gtgtcgacca gcgtcgccat gtctcggacg gcaggctcgg acaggcggct gcctcggcct   57240
gcaagttcat gacggcacac ttcgatgccc ggtaacgacg cttgcagcgt gcgatagacg   57300
gcggccgagc cgcccgcata gggaaaacag atcagacgca tgcgggcggg tactcgagcg   57360
gctcatctgc tgccggcgcg caggcgatgg cgctgtggaa attcatgtgt tcggcgtttt   57420
tcaccattca ggttccagat ccggttgggc gtgagttaaa cacgaggctg cgtggatgta   57480
```

```
tgtcgtagga agaggggacg cgttgtcggc catgtcgaag cggttcgtct ctgaatggat    57540
cccggcgcgg acacggtatc ggcgaaaaca gatgcgcggg aaatcgcgac gcatctgagt    57600
gtgtcgaacg atgcgcttcg tctttagaat gggcagcgag catggcgagc catcagaatt    57660
gcggcatccg atggtgccgc cgcgctaccc gataagttgg agacatacta tgcaacaccg    57720
tcagaaagcc gtcccgaccc agcaagtcgc gaacgagcgc gtgatcgtca ccgaatggcg    57780
attcgcgccc ggcgccgaga ccggctggca tgttcaccgg catgactatg tcgtggtgcc    57840
gcaaacggac ggtcagcttc tcctcgaaac cgcacaaggc aaccgcgagt cgcaattgca    57900
cgccgggcgc agctatgcgg ggctgaaggg cgtcgagcat aacgtcgtca acgcgacgga    57960
ccacgaagtg gtgttcgtcg aagtcgagat tctctaaggg gcgtcaggcc ccgcgagcaa    58020
ggccacgaca gggagcagca ggatgaaaat gaccgacatc ccgtttggca cgaccgactg    58080
gcgcaccgtt gaaccgaccg a                                              58101
```